(12) United States Patent
Pons et al.

US011939393B2

(10) Patent No.: US 11,939,393 B2
(45) Date of Patent: *Mar. 26, 2024

(54) ANTIBODIES AGAINST SIGNAL-REGULATORY PROTEIN ALPHA AND METHODS OF USE

(71) Applicant: ALX Oncology Inc., South San Francisco, CA (US)

(72) Inventors: Jaume Pons, San Francisco, CA (US); Bang Janet Sim, South San Francisco, CA (US); Hong Wan, Foster City, CA (US); Tracy Chia-Chien Kuo, San Carlos, CA (US)

(73) Assignee: ALX Oncology Inc., South San Francsico, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/677,873

(22) Filed: Feb. 22, 2022

(65) Prior Publication Data

US 2022/0324996 A1 Oct. 13, 2022

Related U.S. Application Data

(63) Continuation of application No. 16/359,799, filed on Mar. 20, 2019, now Pat. No. 11,292,850.

(60) Provisional application No. 62/646,210, filed on Mar. 21, 2018.

(51) Int. Cl.
*C07K 16/28* (2006.01)
*A61P 35/00* (2006.01)
*A61K 45/06* (2006.01)

(52) U.S. Cl.
CPC ......... *C07K 16/2896* (2013.01); *A61P 35/00* (2018.01); *C07K 16/2818* (2013.01); *C07K 16/2827* (2013.01); *A61K 45/06* (2013.01)

(58) Field of Classification Search
None
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 5,122,469 A | 6/1992 | Mather et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,894 A | 11/1996 | Wels et al. |
| 5,587,458 A | 12/1996 | King et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,731,168 A | 3/1998 | Carter et al. |
| 5,869,046 A | 2/1999 | Presta et al. |
| 6,075,181 A | 6/2000 | Kucherlapati et al. |
| 6,143,559 A | 11/2000 | Michael et al. |
| 6,150,584 A | 11/2000 | Kucherlapati et al. |
| 6,180,370 B1 * | 1/2001 | Queen ................. C07K 16/087 435/69.6 |
| 6,248,516 B1 | 6/2001 | Winter et al. |
| 7,575,893 B2 | 8/2009 | Simmons |
| 8,088,896 B2 | 1/2012 | Tesar et al. |
| 8,475,792 B2 * | 7/2013 | Dall'Acqua ..... C07K 14/70503 530/387.9 |
| 8,592,644 B2 | 11/2013 | Harriman et al. |
| 9,151,760 B2 | 10/2015 | Weissman et al. |
| 9,352,037 B2 | 5/2016 | van den Berg |
| 9,380,769 B2 | 7/2016 | Leighton et al. |
| 9,399,682 B2 | 7/2016 | Jaiswal et al. |
| 9,493,575 B2 | 11/2016 | Jaiswal et al. |
| 9,605,076 B2 | 3/2017 | Jaiswal et al. |
| 9,611,329 B2 | 4/2017 | Jaiswal et al. |
| 9,623,079 B2 | 4/2017 | Willingham et al. |
| 9,624,305 B2 | 4/2017 | Jaiswal et al. |
| 9,765,143 B2 | 9/2017 | Jaiswal et al. |
| 9,771,428 B2 | 9/2017 | Weiskopf et al. |
| 9,790,275 B2 | 10/2017 | van den Berg |
| 9,920,122 B2 | 3/2018 | van den Berg |
| 10,064,925 B2 | 9/2018 | Tseng et al. |
| 10,081,680 B2 * | 9/2018 | Weiskopf ................ A61P 35/00 |

(Continued)

FOREIGN PATENT DOCUMENTS

| | | |
|---|---|---|
| EP | 2242512 B1 | 4/2016 |
| EP | 3482772 A1 | 6/2017 |

(Continued)

OTHER PUBLICATIONS

Zhang, Jing, Su-Bee Tan, and Zhi-Gang Guo. World journal of diabetes 11.6 (2020): 239). (Year: 2020).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Almagro and Fransson (2008). "Humanization of antibodies," Front. Biosci. 13:1619-1633.
Araghi et al., (2014). "Flow cytometric immunophenotyping of feline bone marrow cells and haematopoietic progenitor cells using anti-human antibodies," J. Feline Med. Surg. 16(4):265-74.
Baca et al. (1997). "Antibody humanization using monovalent phage display," J. Biol. Chem., 272(16):10678-10684.

(Continued)

*Primary Examiner* — Michael Szperka
*Assistant Examiner* — Lia E Taylor
(74) *Attorney, Agent, or Firm* — MORRISON & FOERSTER LLP

(57) ABSTRACT

Provided herein, inter alia, are isolated, humanized antibodies that bind an extracellular domain of a human SIRP-α polypeptide. Also provided are polynucleotides, vectors, host cells, and methods of production and use related thereto.

24 Claims, 22 Drawing Sheets

Specification includes a Sequence Listing.

(56) References Cited

U.S. PATENT DOCUMENTS

| | | |
|---|---|---|
| 10,184,004 B2 | 1/2019 | Weiskopf et al. |
| 10,301,387 B2 | 5/2019 | Willingham et al. |
| 10,329,354 B2 | 6/2019 | Leeper et al. |
| 10,344,094 B2 | 7/2019 | Weissman et al. |
| 10,611,842 B2 | 4/2020 | Liu et al. |
| 10,618,976 B2 | 4/2020 | Weissman et al. |
| 10,723,803 B2 | 7/2020 | Weiskopf et al. |
| 10,780,117 B2 | 9/2020 | Weissman et al. |
| 10,781,256 B2 | 9/2020 | Weiskopf et al. |
| 10,851,164 B2 | 12/2020 | Van Eenennaam et al. |
| 11,242,404 B2 | 2/2022 | Pons et al. |
| 11,292,850 B2 | 4/2022 | Pons et al. |
| 11,401,338 B2 | 8/2022 | Pons et al. |
| 2002/0114807 A1 | 8/2002 | Berg et al. |
| 2003/0026803 A1 | 2/2003 | Barclay |
| 2003/0054415 A1 | 3/2003 | Buhring et al. |
| 2004/0147731 A1 | 7/2004 | Parkos |
| 2004/0213792 A1 | 10/2004 | Clemmons et al. |
| 2006/0263356 A1 | 11/2006 | Endl et al. |
| 2008/0160013 A1 | 7/2008 | Clemmons et al. |
| 2010/0215640 A1 | 8/2010 | Clemmons et al. |
| 2010/0239578 A1 | 9/2010 | Danska et al. |
| 2013/0189253 A1 | 7/2013 | Danska et al. |
| 2014/0065169 A1 | 3/2014 | Jaiswal et al. |
| 2014/0161825 A1 | 6/2014 | Jaiswal et al. |
| 2014/0242095 A1 | 8/2014 | Wang et al. |
| 2016/0186150 A1 | 6/2016 | Deming et al. |
| 2016/0333093 A1 | 11/2016 | Weiskopf et al. |
| 2017/0114134 A1 | 4/2017 | Clemmons et al. |
| 2017/0151282 A1 | 6/2017 | Discher et al. |
| 2017/0247464 A1 | 8/2017 | Poirier et al. |
| 2018/0105600 A1 | 4/2018 | Pons et al. |
| 2018/0155424 A1 | 6/2018 | van den Berg |
| 2018/0214524 A1 | 8/2018 | Weissman et al. |
| 2018/0244748 A1 | 8/2018 | Gill et al. |
| 2018/0312587 A1 | 11/2018 | Van Eenennaam et al. |
| 2018/0312600 A1 | 11/2018 | Poirier et al. |
| 2019/0119396 A1 | 4/2019 | Liu et al. |
| 2019/0127477 A1 | 5/2019 | Poirier et al. |
| 2019/0134089 A1 | 5/2019 | Liu et al. |
| 2019/0153095 A1 | 5/2019 | Matozaki et al. |
| 2019/0233515 A1 | 8/2019 | Jaiswal et al. |
| 2019/0275150 A1 | 9/2019 | Pincetic et al. |
| 2019/0322986 A1 | 10/2019 | Keller et al. |
| 2019/0352419 A1 | 11/2019 | Pons et al. |
| 2019/0359707 A1 | 11/2019 | Pincetic et al. |
| 2020/0102387 A1 | 4/2020 | Abbasian et al. |
| 2020/0129557 A1 | 4/2020 | Shizuru et al. |
| 2020/0223923 A1 | 7/2020 | Schnorr et al. |
| 2020/0262918 A1 | 8/2020 | Liu et al. |
| 2020/0297842 A1 | 9/2020 | Puro et al. |
| 2020/0354469 A1 | 11/2020 | Weiskopf et al. |
| 2022/0002434 A1 | 1/2022 | Pons et al. |
| 2023/0018821 A1 | 1/2023 | Pons et al. |

FOREIGN PATENT DOCUMENTS

| | | | |
|---|---|---|---|
| EP | | 3308641 B1 | 7/2019 |
| EP | | 2931752 B1 | 8/2019 |
| EP | | 3180363 B1 | 9/2019 |
| EP | | 3186395 B1 | 9/2019 |
| EP | | 3421601 B1 | 12/2019 |
| EP | | 3043181 B1 | 4/2020 |
| EP | | 3209691 B1 | 7/2020 |
| EP | | 3209769 B1 | 8/2020 |
| WO | WO-1987/000195 A1 | | 1/1987 |
| WO | WO-1990/003430 A1 | | 4/1990 |
| WO | WO-1991/010741 A1 | | 7/1991 |
| WO | WO-1993/016185 A2 | | 8/1993 |
| WO | WO-1994/004690 A1 | | 3/1994 |
| WO | WO-1996/033735 A1 | | 10/1996 |
| WO | WO-1996/034096 A1 | | 10/1996 |
| WO | WO-1997/048723 A2 | | 12/1997 |
| WO | WO-1998/024893 A2 | | 6/1998 |
| WO | WO-1999/040940 A1 | | 8/1999 |
| WO | WO-2005/014653 A2 | | 2/2005 |
| WO | WO-2009/111014 A2 | | 9/2009 |
| WO | WO-2011/019844 A1 | | 2/2011 |
| WO | WO-2012/162422 A2 | | 11/2012 |
| WO | WO-2013/056352 A1 | | 4/2013 |
| WO | WO-2013/059159 A1 | | 4/2013 |
| WO | WO-2015/138600 A2 | | 9/2015 |
| WO | WO-2016/063233 A1 | | 4/2016 |
| WO | WO-2017/178653 A2 | | 10/2017 |
| WO | WO-2017178653 A2 * | | 10/2017 ............. A61P 35/00 |
| WO | WO-2018/057669 A1 | | 3/2018 |
| WO | WO-2018057669 A1 * | | 3/2018 ................ A61P 1/04 |
| WO | WO-2018190719 A2 | | 10/2018 |
| WO | WO-2018/210793 A2 | | 11/2018 |
| WO | WO-2018210795 A1 | | 11/2018 |
| WO | WO-2020013170 A1 | | 1/2020 |
| WO | WO-2020099653 A1 | | 5/2020 |

OTHER PUBLICATIONS

Barclay et al., (2014). "The interaction between signal regulatory protein alpha (SIRPα) and CD47: structure, function, and therapeutic target," Annu. Rev. Immunol., 32:25-50.

Barclay, A.N. and Brown, M.H. (2006). "The SIRP family of receptors and immune regulation," Nat. Rev. Immunol., 6(6):457-464.

Barnes et al. (1980). "Methods for growth of cultured cells in serum-free medium," Anal. Biochem. 102:255-70.

BioLegend. (2016). "Purified anti-human CD172a/b (SIRPa/b) Antibody," https://www.biolegend.com/en-gb/global-elements/pdf-popup/purified-anti-human-cd172a-b-sirpalpha-beta-antibody-4028?filename=Purified%20anti-human%20CD172ab%20SIRPalphabeta%20Antibody.pdf&pdfgen=true, Retrieved: Dec. 15, 2017.

Boerner et al. (1991). "Production of antigen-specific human monoclonal antibodies from in vitro-primed human splenocytes," J. Immunol., 147(1):86-95.

Bravman, T. et al. (2006). "Exploring "one-shot" kinetics and small molecule analysis using the ProteOn XPR36 array biosensor," Anal. Biochem., 358(2):281-288.

Brennan et al. (1985). "Preparation of bispecific antibodies by chemical recombination of monoclonal immunoglobulin G1 fragments," Science, 229(4708):81-3.

Bruggemann et al. (1993). "Designer mice: the production of human antibody repertoires in transgenic animals," Year in Immunol., 7:33-40.

Carter et al. (1992). "High level Escherichia coli expression and production of a bivalent humanized antibody fragment," Biotechnology, 10(2):163-167.

Carter et al. (1992). "Humanization of an anti-p185HER2 antibody for human cancer therapy," Proc. Natl. Acad. Sci. USA, 89(10):4285-9.

Champe et al. (1995). "Monoclonal antibodies that block the activity of leukocyte function-associated antigen 1 recognize three discrete epitopes in the inserted domain of CD11a," J. Biol. Chem., 270(3):1388-1394.

Chin et al., (2008). "Immune intervention with monoclonal antibodies targeting CD152 (CTLA-4) for autoimmune and malignant diseases," Chang Gung Med J., 31(1):1-15.

Chothia and Lesk, (1987). "Canonical structures for the hypervariable regions of immunoglobulins," J. Mal. Biol., 196(4):901-917.

Clackson et al. (1991). "Making antibody fragments using phage display libraries," Nature, 352: 624-628.

Fellouse (2004). "Synthetic antibodies from a four-amino-acid code: a dominant role for tyrosine in antigen recognition," Proc. Natl. Acad. Sci. USA, 101(34):12467-12472.

Fishwild et al. (1996). "High-avidity human IgG kappa monoclonal antibodies from a novel strain of minilocus transgenic mice," Nature Biotechnol., 14(7):845-851.

George et al. (1998). "Differential effects of anti-beta2-glycoprotein I antibodies on endothelial cells and on the manifestations of experimental antiphospholipid syndrome," Circulation, 97:900-906.

(56) References Cited

OTHER PUBLICATIONS

Glanville, J. et al. (2009). "Precise determination of the diversity of a combinatorial antibody library gives insight into the human immunoglobulin repertoire," Proc. Natl. Acad. Sci., 106(48):20216-20221.
Graham et al. (1977). "Characteristics of a human cell line transformed by DNA from human adenovirus type 5," J. Gen Viral., 36(1):59-74.
Griffiths et al. (1993). "Human anti-self antibodies with high specificity from phage display libraries," EMBO J, 12(2):725-734.
Gruber et al. (1994). "Efficient tumor cell lysis mediated by a bispecific single chain antibody expressed in Escherichia coli," J. Immunol, 152(11):5368-74.
Ham et al. (1979). "Media and growth requirements," Meth. Enz., 58:44-93.
Hamers-Casterman et al. (1993). "Naturally occurring antibodies devoid of light chains," Nature, 363(6428):446-448.
Hatherley, D. et al. (2007). "The structure of the macrophage signal regulatory protein alpha (SIRPalpha) inhibitory receptor reveals a binding face reminiscent of that used by T cell receptors," J. Biol. Chem., 282(19):14567-75.
Hatherley, D. et al. (2008). "Paired receptor specificity explained by structures of signal regulatory proteins alone and complexed with CD47," Mal. Cell, 31(2):266-77.
Hatherley, D. et al. (2009). "Structure of signal-regulatory protein alpha: a link to antigen receptor evolution," J. Biol. Chem., 284(39):26613-9.
Hlavacek et al. (1999). "Steric Effects on Multivalent Ligand-Receptor Binding: Exclusion of Ligand Sites by Bound Cell Surface Receptors," Biophysical Journal, vol. 76, Issue 6, pp. 3031-3043.
Hollinger et al. (1993). "'Diabodies': small bivalent and bispecific antibody fragments," Proc. Natl. Acad. Sci. USA, 90(14):6444-6448.
Hongo et al. (1995). "Development and characterization of murine monoclonal antibodies to the latency-associated peptide of transforming growth factor beta 1," Hybridoma, 14(3):253-260.
Hoogenboom and Winter (1992). "By-passing ignalingon. Human antibodies from synthetic repertoires of germline VH gene segments rearranged in vitro," J. Mol. Biol., 227(2):381-388.
Hoogenboom, H.R. (2002). "Overview of antibody phage-display technology and its applications," Methods in Molecular Biology, 178:1-37.
Hudson et al. (2003). "Engineered antibodies," Nat. Med., 9(1):129-134.
International Search Report and Written Opinion directed to PCT Application No. PCT/US2017/052592, dated Dec. 20, 2017, 22 pages.
International Search Report and Written Opinion directed to PCT Application No. PCT/US2019/023238, dated May 20, 2019, 6 pages.
Jakobovits et al. (1993). "Analysis of homozygous mutant chimeric mice: deletion of the immunoglobulin heavy-chain joining region blocks B-cell development and antibody production," Proc. Natl. Acad. Sci. USA, 90(36):2551-5.
Jakobovits et al. (1993). "Germ-line transmission and expression of a human-derived yeast artificial chromosome," Nature, 362(6417):255-258.
Janeway et al. (2001). "Immunobiology: the immune system in health and disease." 5th Editions, New York, Garland Science, 5 pages.
Jayaram, N. et al. (2012). "Germline VH/VL pairing in antibodies," Protein Eng. Des. Sel., 25(10):523-529.
Jiang et al., (2005). "A Novel Peptide Isolated from a Phage Display Peptide Library with Trastuzumab Can Mimic Antigen Epitope of HER-2," J. Biol. Chem., 280(6):4656-4662.
Jones et al. (1986). "Replacing the complementarity-determining regions in a human antibody with those from a mouse," Nature, 321(6069):522-525.

Kharitonenkov, A. et al. (1997). "A family of proteins that inhibit ignaling through tyrosine kinase receptors," Nature, 386(6621):181-6.
Kim, E.J. et al. (2013). "SHPS-1 and a synthetic peptide representing its ITIM inhibit the MyD88, but not TRIF, pathway of TLR signaling through activation of SHP and PI3K in THP-1 cells," Inflammation Research, 62(4):377-86.
Kipriyanov et al. (2004). "Generation and production of engineered antibodies." Molecular biotechnology, 26(1):39-60.
Kohler and Milstein, (1975). "Continuous cultures of fused cells secreting antibody of predefined specificity," Nature, 256(5517):495-97.
Kostelny et al. (1992). "Formation of a bispecific antibody by the use of leucine zippers." J. Immunol., 148(5):1547-1553.
Krieg et al. (2005). "Functional analysis of B and T lymphocyte attenuator engagement on CD4+ and CD8+ T cells," Journal of Immunology (Baltimore, MD. : 1950), vol. 175, No. 10, pp. 6420-6427, ISSN: 0022-1767.
Lee et al. (2004). "Bivalent antibody phage display mimics natural immunoglobulin," J. Immunol. Methods, 284(1-2):119-132.
Lee et al. (2004). "High-affinity human antibodies from phage-displayed synthetic Fab libraries with a single framework scaffold," J. Mol. Biol., 340(5):1073-1093.
Lee, W. Y. et al. (2010). "The role of cis dimerization of signal regulatory protein alpha (SIRPalpha) in binding to CD47," J. Biol. Chem., 285(49):37953-63.
Lee, W.Y. et al. (2007). "Novel structural determinants on SIRP alpha that mediate binding to CD47," J. Immunol., 179(11):7741-50.
Li et al. (2006). "Optimization of humanized IgGs in glycoengineered Pichia pastoris," Nat. Biotech., 24(2):210-215.
Liu et al., (2007). "Functional elements on SIRPalpha IgV domain mediate cell surface binding to CD47," J. Mol. Biol., 365(3):680-93.
Lloyd, C. et al. (2009). "Modelling the human immune response: performance of a 1011 human antibody repertoire against a broad panel of therapeutically relevant antigens," Protein Eng. Des. Sel., 22(3):159-168.
Lonberg (2008). "Fully human antibodies from transgenic mouse and phage display platforms," Curr. Opin. Immunol., 20(4):450-459.
Lonberg and Huszar (1995) "Human antibodies from transgenic mice," Intern. Rev. Immunol., 13(1):65-93.
Lonberg et al. (1994). "Antigen-specific human antibodies from mice comprising four distinct genetic modifications," Nature, 368(6474):856-859.
Ludwig et al. (2017). "Mechanisms of Autoantibody-Induced Pathology," Front Immunol, 8: 603.
Majeti, R. et al. (2009). "CD47 is an adverse prognostic factor and therapeutic antibody target on human acute myeloid leukemia stem cells," Cell, 138(2):286-99.
Marks et al. (1992). "By-passing immunization. Human antibodies from V-gene libraries displayed on phage," J. Mol. Biol., 222(3):581-597.
Marks et al. (1992). "By-passing immunization: building high affinity human antibodies by chain shuffling," Biotechnology, 10(7):779-783.
Mather (1980). "Establishment and characterization of two distinct mouse testicular epithelial cell lines," Biol. Reprod., 23(1):243-252.
Mather et al. (1982). "Culture of testicular cells in hormone-supplemented serum-free medium," Annals N.Y. Acad. Sci., 383:44-68.
Mettler Izquierdo, S. et al. (2016). "High-efficiency antibody discovery achieved with multiplexed microscopy," Microscopy (Oxf), 341-52.
Morimoto et al. (1992). "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, 24(1-2):107-117.
Morrison (1994). "Immunology. Success in specification," Nature, 368(6474):812-813.

(56) References Cited

OTHER PUBLICATIONS

Morrison et al. (1984). "Chimeric human antibody molecules: mouse antigen-binding domains with human constant region domains," Proc. Natl. Acad. Sci. USA, 81(21):6851-6855.
Murata, Y. et al. (2014). The CD47-SIRPα signaling system: its physiological roles and therapeutic application, The Journal of Biochemistry, 155(6):335-344.
Nakaishi, A. et al. (2008). "Structural insight into the specific interaction between murine SHPS-1/SIRP alpha and its ligand CD47," J. Mal. Biol. 375:650-60.
Nettleship, J. et al. (2013). "Crystal structure of signal regulatory protein gamma (SIRPg) in complex with an antibody Fab fragment", BMC Structural Biology, 13(13):1-8.
Neuberger (1996). "Generating high-avidity human Mabs in mice," Nature Biotechnol., 14(7):826.
Ochi, F. et al. (1997). "Epidermal growth factor stimulates the tyrosine phosphorylation of SHPS-1 and association of SHPS-1 with SHP-2, a SH2 domain-containing protein tyrosine phosphatase," Biochem. Biophys. Res. Commun., 239(2):483-7.
Plückthun et al. (1997). "New protein engineering approaches to multivalent and bispecific antibody fragments," Immunotechnology, 3(2):83-105.
Presta (1992). "Antibody engineering," Curr. Op. Struct. Biol. 2:593-596.
Presta et al. (1993). "Humanization of an antibody directed against IgE," J. Immunol., 151(5):2623-32.
Riechmann et al. (1988). "Reshaping human antibodies for therapy," Nature, 332(6162):323-327.
Riemer et al., (2005). "Matching of trastuzumab (Herceptin) epitope mimics onto the surface of Her-2/neu—a new method of epitope definition," Mol. Immunol., 42:1121-1124.
Rudikoff et al. (1982). "Single amino acid substitution altering antigen-binding specificity," Proc. Nat. Acad. Sci., vol. 79, pp. 1979-1983, Immunology.
Seiffert, M. et al. (1999). "Human Signal-Regulatory Protein Is Expressed on Normal, But Not on Subsets of Leukemic Myeloid Cells and Mediates Cellular Adhesion Involving Its Counterreceptor CD47," Blood, 94(11):3633-3643.
Seiffert, M. et al. (2001). "Signal-regulatory protein a (SIRPa) but not SIRPb is involved in T-cell activation, binds to CD47 with high affinity, and is expressed on immature CD34+CD38− hematopoietic cells," Blood, 97(9):2741-2749.
Sheriff et al. (1996). "Redefining the minimal antigen-binding fragment," Nature Struct. Biol., 3(9):733-736.
Sidhu et al. (2004). "Phage-displayed antibody libraries of synthetic heavy chain complementarity determining regions," J. Mol. Biol., 338(2): 299-310.
Sim et al. (2019). "Discovery of high affinity, pan-allelic, and pan-mammalian reactive antibodies against the myeloid checkpoint receptor SIRPα," MAbs. 11(6):1036-1052.
Sims et al. (1993). "A humanized CD18 antibody can block function without cell destruction," J. Immunol., 151(4):2296-308.
Spiess, C. et al. (2015). "Alternative molecular formats and therapeutic applications for bispecific antibodies," Mal. Immunol., 67(2 Pt A):95-106.
Takenaka, K. et al. (2007). "Polymorphism in Sirpa modulates engraftment of human hematopoietic stem cells," Nat. Immunol., 8(12):1313-23.

Treffers et al., (2018). "Genetic variation of human neutrophil Fcγ receptors and SIRPα in antibody-dependent cellular cytotoxicity towards cancer cells," European Journal of Immunology 48(2):344-354.
Urlaub et al. (1980). "Isolation of Chinese hamster cell mutants deficient in dihydrofolate reductase activity," Proc. Natl. Acad. Sci. USA, 77(7):4216-20.
Van Der Heijden, J. (Jul. 1, 2014). "Genetic Variation in Human Fc Gamma Receptors: Functional Consequences of Polymorphisms and Copy Number Variation," located at <https://dare.uva.nl/search?identifier=54e3332e-a8c8-4fec-a49d-833b35617f2f> last visited on Sep. 7, 2017, pp. 115-135, 22 pages.
Vollmers and Brandlein, (2005). "Death by stress: natural IgM-induced apoptosis," Methods and Findings in Experimental and Clinical Pharmacology, 27(3):185-91.
Vollmers and Brandlein, (2005). "The 'early birds': natural IgM antibodies and immune surveillance," Histology and Histopathology, 20(3):927-937.
Weiskopf, K. et al. (2013). "Engineered SIRPα variants as immunotherapeutic adjuvants to anticancer antibodies," Science, 341(6141):88-91.
Willingham, S.B. et al. (2012). "The CD47-signal regulatory protein alpha (SIRPa) interaction is a therapeutic target for human solid tumors," 109(17):6662-7.
Winkler et al. (2000). " Changing the antigen binding specificity by single point mutations of an anti-p24 (HIV-1) antibody," J Immunol. 165(8):4505-14.
Winter et al. (1994). "Making antibodies by phage display technology," Ann. Rev. Immunol., 12:433-455.
Yanagita, T. et al. (2017). "Anti-SIRPα antibodies as a potential new tool for cancer immunotherapy," JCI Insight, 2(1):e89140.
Yi. Et al (2015). "Splenic dendritic cells survey red blood cells for missing self-CD47 to trigger adaptive immune responses," Immunity, 433(4):764-775.
Zhang et al. (2020). "CD47 decline in pancreatic islet cells promotes macrophage mediated phagocytosis in type | diabetes," World J Diabetes, 11(6): 239-251.
Zhao, X.W. et al. (2011). "CD47-signal regulatory protein-α (SIRPα) interactions form a barrier for antibody-mediated tumor cell destruction," Proc. Natl. Acad. Sci., 108(45):18342-7.
Padlan (1994). "Anatomy of the antibody molecule," Mol. Immunol., 31: 169-217.
Ratnikova et al. (2017). "CD47 receptor as a primary target for cancer therapy. Molecular Biology," 51(2):251-261 (translation of abstract only, in p. 261).
U.S. Appl. No. 17/337,180, filed Jun. 2, 2021, titled "Antibodies Against Signal-Regulatory Protein Alpha and Methods of Use," inventor Pons et al., Applicant ALX Oncology Inc. (Copy not submitted herewith pursuant to the waiver of 37 C.F.R. § 1.98(a)(2)(iii)).
Bostrom et al. (2009). "Improving antibody binding affinity and specificity for therapeutic development," Methods Mol Biol, 525:353-376.
Gonzales et al. (2005). "Minimizing the immunogenicity of antibodies for clinical application," Tumour Biol, 26(1): 31-43.
Kunik et al. (2012). "Structural consensus among antibodies defines the antigen binding site," 8(2):e1002388, 12 pages.
Wark et al. (2006). " Latest technologies for the enhancement of antibody affinity," Adv Drug Deliv Rev, 58(5-6): 657-670.

\* cited by examiner

| Parental VL | IGLV3 | IGLV1 | IGLV3 | IGLV1 | IGLV2 | IGLV1 |
|---|---|---|---|---|---|---|
| | 25 | 25 | 66 | 66 | 25 | 21 |
| Human framework | Hum1 | Hum2 | Hum3 | Hum4 | Hum5 | Hum6 |
| Protein yield | + | - | + | - | + | - |
| Human v1 | | | | | | |
| Human v2 | | | | | ▓ | |
| Cyno SIRPα | | | | | ▓ | |
| BALBc SIRPα | | | | ▓ | ▓ | ▓ |
| Human SIRPγ | | | | | | |

A821_Heavy Chain

*Protein Yield (mg/mL)*
"+" — no change
"-" — reduced expression

*Binding affinity (Koff 1/s)*
• No change □
• Reduced by 1-2log ▓

FIG. 2

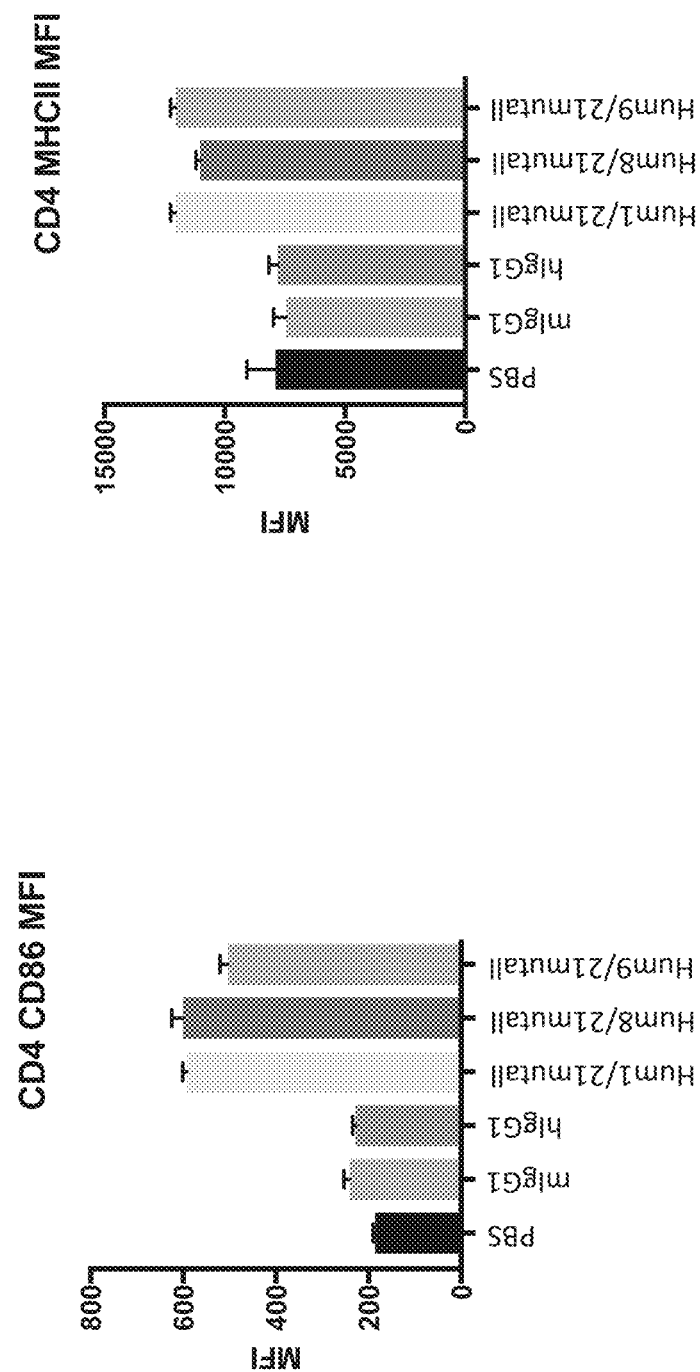

Proposed engineering

```
Original  - FGGGTKLTVL identical to IGLJ2
Version 1 - FGTGTKVTVL identical to IGLJ1
Version 2 - FGGGTQLTVL identical to IGLJ7
Version 3 - FGGGTRLTVL
```

FIG. 9

```
                                                                                    43
Hum1  (1)  SYELTQPPSVSVSPGQTARITC SGGSYSSYYYA YQQKPGQAP
v1+DS (1)  SYELTQPPSVSVSPGQTARITC SGGSYSSYYYA YQQKPGQAP
v1+SD (1)  SYELTQPPSVSVSPGQTARITC SGGSYSSYYYA WQQKPGQAP
v2+DS (1)  SYELTQPPSVSVSPGQTARITC SGGSYSSYYYA YQQKPGQAP
v2+SD (1)  SYELTQPPSVSVSPGQTARITC SGGSYSSYYYA WQQKPGQAP
v3+DS (1)  SYELTQPPSVSVSPGQTARITC SGGSYSSYYYA YQQKPGQAP
v3+SD (1)  SYELTQPPSVSVSPGQTARITC SGGSYSSYYYA WQQKPGQAP
                                     L1

86
Hum1  (44) VTLIY DDKRPS NIPERFSGSSSGTTVTLTITSGVQAEDEADYY
v1+DS (44) VTLIY DDKRPS NIPERFSGSSSGTTVTLTITSGVQAEDEADYY
v1+SD (44) VTLIY DDKRPS NIPERFSGSSSGTTVTLTITSGVQAEDEADYY
v2+DS (44) VTLIY DDKRPS NIPERFSGSSSGTTVTLTITSGVQAEDEADYY
v2+SD (44) VTLIY DDKRPS NIPERFSGSSSGTTVTLTITSGVQAEDEADYY
v3+DS (44) VTLIY DDKRPS NIPERFSGSSSGTTVTLTITSGVQAEDEADYY
v3+SD (44) VTLIY DDKRPS NIPERFSGSSSGTTVTLTITSGVQAEDEADYY
                 L2

K104                          129
Hum1  (87) CGGYDQSSYTNPF GGGT Q LTVLGQPKANPTVTLFPPSSEELQA
v1+DS (87) CGGYDQSSYTNPF GGGT K VTVLGQPKANPTVTLFPPSSEELQA
v1+SD (87) CGGYDQSSYTNPF GGGT K VTVLGQPKANPTVTLFPPSSEELQA
v2+DS (87) CGGYDQSSYTNPF GGGT Q LTVLGQPKANPTVTLFPPSSEELQA
v2+SD (87) CGGYDQSSYTNPF GGGT Q LTVLGQPKANPTVTLFPPSSEELQA
v3+DS (87) CGGYDQSSYTNPF GGGT R LTVLGQPKANPTVTLFPPSSEELQA
v3+SD (87) CGGYDQSSYTNPF GGGT R LTVLGQPKANPTVTLFPPSSEELQA
             L3                  *                    **
```

FIG. 10

```
                    130                                                       172
Hum1   (130) NKATLVCLISDFYPGAVTVAWKADGSPVKAGVETTKPSKQSNN
v1+DS  (130) NKATLVCLISDFYPGAVTVAWKADGSPVKAGVETTKPSKQSDS
v1+SD  (130) NKATLVCLISDFYPGAVTVAWKADGSPVKAGVETTKPSKQSSD
v2+DS  (130) NKATLVCLISDFYPGAVTVAWKADGSPVKAGVETTKPSKQSDS
v2+SD  (130) NKATLVCLISDFYPGAVTVAWKADGSPVKAGVETTKPSKQSSD
v3+DS  (130) NKATLVCLISDFYPGAVTVAWKADGSPVKAGVETTKPSKQSDS
v3+SD  (130) NKATLVCLISDFYPGAVTVAWKADGSPVKAGVETTKPSKQSSD
                                                                               *

173                                                       214
Hum1   (173) KYAASSYLSLTPEQWKSHRSYSCQVTHEGSTVEKTVAPTECS
v1+DS  (173) KYAASSYLSLTPEQWKSHRSYSCQVTHEGSTVEKTVAPTECS
v1+SD  (173) KYAASSYLSLTPEQWKSHRSYSCQVTHEGSTVEKTVAPTECS
v2+DS  (173) KYAASSYLSLTPEQWKSHRSYSCQVTHEGSTVEKTVAPTECS
v2+SD  (173) KYAASSYLSLTPEQWKSHRSYSCQVTHEGSTVEKTVAPTECS
v3+DS  (173) KYAASSYLSLTPEQWKSHRSYSCQVTHEGSTVEKTVAPTECS
v3+SD  (173) KYAASSYLSLTPEQWKSHRSYSCQVTHEGSTVEKTVAPTECS
```

FIG. 11

ANTIBODIES AGAINST SIGNAL-REGULATORY PROTEIN ALPHA AND METHODS OF USE

CROSS REFERENCE TO RELATED APPLICATIONS

This application is a continuation of U.S. patent application Ser. No. 16/359,799, filed Mar. 20, 2019, issued as U.S. Pat. No. 11,292,850 on Apr. 5, 2022, which claims the priority benefit of U.S. Provisional Application Ser. No. 62/646,210, filed Mar. 21, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name 757972000601SEQLIST.TXT, dated recorded: Feb. 22, 2022, size: 234,738 bytes).

FIELD

The present disclosure relates to isolated, humanized antibodies that bind an extracellular domain (e.g., the D1 domain) of a human SIRP-α polypeptide, as well as polynucleotides, vectors, host cells, and methods related thereto.

BACKGROUND

Signal-regulatory protein alpha (SIRP-α) is part of a family of cell-surface receptors that plays critical roles in the regulation of the immune system (see. e.g., Barclay, A. N. and Brown, M. H. (2006) *Nat. Rev. Immunol.* 6:457-64). SIRP-α is expressed on the surface of various cells, including leukocytes such as dendritic cells, eosinophils, neutrophils, and macrophages. SIRP-α includes an extracellular domain that interacts with external stimuli such as ligands and an intracellular domain that mediates a variety of intracellular signals.

One of the major roles of SIRP-α is its regulation of the immune response through interactions with CD47. CD47 is expressed on the surface of a variety of cell types. When the IgSF domain of CD47 binds the extracellular domain (e.g., the D1 domain) of SIRP-α expressed on an immune cell (e.g., a macrophage), this transduces a SIRP-α-mediated signal in the immune cell that prevents phagocytosis of the CD47-expressing cell. Thus, CD47 serves to convey what has been termed a "don't eat me" signal to the immune system that prevents phagocytosis of healthy cells (see, e.g., WO2015/138600 and Weiskopf, K. et al. (2013) *Science* 341:88-91). However, CD47 has also been shown to be highly expressed by a variety of cancers, and its interaction with SIRP-α in this context is thought to allow tumors to mimic the healthy "don't eat me" signal in order to evade immune surveillance and phagocytosis by macrophages (see, e.g., Majeti, R et al. (2009) *Cell* 138:286-99; Zhao, X. W. et al. (2011) *Proc. Natl. Acad. Sci.* 108:18342-7). As such, antibodies that block this interaction are highly desirable.

SIRP-α is known to be a highly polymorphic protein in humans, monkeys, and mice. For example, polymorphic differences have been identified between SIRP-α proteins in the NOD and C57BL/6 mouse strains, and these polymorphisms lead to functional consequences related to CD47 binding and engraftment of human hematopoietic stem cells in these mouse strains. In humans, two prevalent alleles of the SIRPA gene have been reported (Treffers, L W. et al. (2018), *Eur. J. Immunol.* 48:344-354; Zhao, X. et al. (2011), *PNAS.* 108:18342-47; van der Heijden, J. (2014). Genetic variation in human Fc gamma receptors: Functional consequences of polymorphisms and copy number variation (Doctoral dissertation)).

Due to the importance of the SIRP-α-CD47 interaction in normal immune function and tumorigenesis, the identification of antibodies that bind human SIRP-α is of great interest for development of clinical candidates.

All references cited herein, including patent applications, patent publications, non-patent literature, and UniProtKB/Swiss-Prot Accession numbers are herein incorporated by reference in their entirety, as if each individual reference were specifically and individually indicated to be incorporated by reference.

SUMMARY

To meet these and other needs, provided herein, inter alia, are isolated antibodies that bind an extracellular domain of a human SIRP-α polypeptide. Advantageously, these antibodies possess one or more of many useful in vitro and/or in vivo properties, such as binding to multiple SIRP-α polypeptides with high affinity, cross-reactivity against multiple mammalian SIRP-α polypeptides (e.g., human v1, human v2, cynomolgus, and/or multiple murine SIRP-α proteins), the ability to enhance macrophage phagocytosis, the ability to enhance dendritic cell activation, and/or the ability to inhibit in vivo growth of a tumor that expresses CD47. In addition, the present disclosure provides antibodies with variant light chains that have been engineered to remove potential liabilities, such as residues that may be modified by deamidation or glycation, resulting in antibodies with more desirable characteristics for manufacturing, storage, and/or drug development.

In certain aspects, the present disclosure provides antibodies (e.g., isolated antibodies) that bind an extracellular domain of a human SIRP-α polypeptide, where the antibodies comprise: a heavy chain comprising a heavy chain variable (VH) domain that comprises the amino acid sequence of SEQ ID NO:26; and a light chain comprising a light chain variable (VL) domain that comprises an amino acid sequence according to the formula SYELTQPPSVSVSPGQTARITCSGGSYS-SYYYAWYQQKPGQAPVTLIYSDDKRPSNI PERFSGSSSGTTVTLTISGVQAEDEADYYCGGYDQSS YTNPFGX$_1$GTX$_2$X$_3$TVL (SEQ ID NO:71), wherein X$_1$ is G or T; X$_2$ is K, Q, or R; and X$_3$ is L or V, and wherein the VL domain does not comprise the sequence of SEQ ID NO:25.

In some embodiments, the VL domain comprises an amino acid sequence selected from the group consisting of SEQ ID NOs:39-41. In some embodiments, the light chain further comprises a light chain constant (CL) domain sequence that comprises an amino acid sequence according to the formula GQPKANPTVLFPPS-SEELQANKATLVCLISDFYPGAVTVAWKADGSPVK-AGVETT KPSKQSX$_4$X$_5$KYAASSYLSLTPEQWKSHRSY SCQVTHEGSTVEKTVAPTECS (SEQ ID NO:72), wherein X$_4$X$_5$ is ND, DN, DS, or SD. In some embodiments, the light chain further comprises a light chain constant (CL) domain sequence that comprises an amino acid sequence selected from the group consisting of SEQ ID NOs:43-46. In some embodiments, the light chain further comprises a kappa light chain constant (CL) domain. In some embodiments, the light chain comprises the amino acid sequence of SEQ ID NO:36. In some embodiments, the light chain further comprises a lambda light chain constant (CL) domain. In some embodiments, the light chain comprises the amino acid sequence of SEQ ID NO:37 or SEQ ID NO:38. In some embodiments, the light chain comprises an amino acid sequence selected from the group consisting of SEQ ID NOs:48-57.

In some embodiments, the antibody is a scFv-Fc, single domain antibody, single heavy chain antibody, or single light chain antibody. In some embodiments, the antibody is a monoclonal antibody. In some embodiments, the antibody comprises a heavy chain comprising a heavy chain constant domain that comprises an Fc region. In some embodiments, the Fc region is a human Fc region selected from the group consisting of an IgG1 Fc region, an IgG2 Fc region, and an IgG4 Fc region. In some embodiments, the Fc region is a human IgG1 Fc region. In some embodiments, the Fc region is a human IgG1 Fc region comprising L234A, L235A, and G237A substitutions, amino acid position numbering according to EU. In some embodiments, the Fc region is a human IgG2 Fc region. In some embodiments, the Fc region is a human IgG2 Fc region comprising A330S and P331S substitutions, amino acid position numbering according to EU. In some embodiments, the Fc region further comprises an N297A substitution, amino acid position numbering according to EU. In some embodiments, the Fc region is a human IgG2 Fc region comprising an N297A substitution, amino acid position numbering according to EU. In some embodiments, the Fc region is a human IgG4 Fc region, and wherein the heavy chain comprises an S228P substitution, amino acid position numbering according to EU. In some embodiments, the heavy chain comprises a heavy chain constant domain that comprises an amino acid sequence selected from the group consisting of SEQ ID NOs:31-35. In some embodiments, the heavy chain comprises a heavy chain constant domain that comprises an amino acid sequence selected from the group consisting of SEQ ID NOs:33, 34, and 137. In some embodiments, the heavy chain comprises a heavy chain constant domain that comprises an amino acid sequence selected from the group consisting of SEQ ID NOs:132-139.

In some embodiments, the heavy chain comprises an amino acid sequence selected from the group consisting of SEQ ID NOs:58-62. In some embodiments, the heavy chain comprises an amino acid sequence selected from the group consisting of SEQ ID NOs:60, 61, and 129. In some embodiments, the heavy chain comprises an amino acid sequence selected from the group consisting of SEQ ID NOs:124-131.

In certain aspects, the present disclosure provides antibodies (e.g., isolated antibodies) that bind an extracellular domain of a human SIRP-α polypeptide, wherein: the heavy chain comprises the amino acid sequence of SEQ ID NO:62, and the light chain comprises the amino acid sequence of SEQ ID NO:52; the heavy chain comprises the amino acid sequence of SEQ ID NO:62, and the light chain comprises the amino acid sequence of SEQ ID NO:53: the heavy chain comprises the amino acid sequence of SEQ ID NO:62, and the light chain comprises the amino acid sequence of SEQ ID NO:54; the heavy chain comprises the amino acid sequence of SEQ ID NO:62, and the light chain comprises the amino acid sequence of SEQ ID NO:55: the heavy chain comprises the amino acid sequence of SEQ ID NO:62, and the light chain comprises the amino acid sequence of SEQ ID NO:56; or the heavy chain comprises the amino acid sequence of SEQ ID NO:62, and the light chain comprises the amino acid sequence of SEQ ID NO:57.

In certain aspects, the present disclosure provides antibodies (e.g., isolated antibodies) that bind an extracellular domain of a human SIRP-α polypeptide, wherein: the heavy chain comprises the amino acid sequence of SEQ ID NO:58, and the light chain comprises the amino acid sequence of SEQ ID NO:52: the heavy chain comprises the amino acid sequence of SEQ ID NO:59, and the light chain comprises the amino acid sequence of SEQ ID NO:52: the heavy chain comprises the amino acid sequence of SEQ ID NO:60, and the light chain comprises the amino acid sequence of SEQ ID NO:52; the heavy chain comprises the amino acid sequence of SEQ ID NO:61, and the light chain comprises the amino acid sequence of SEQ ID NO:52; the heavy chain comprises the amino acid sequence of SEQ ID NO:58, and the light chain comprises the amino acid sequence of SEQ ID NO:53; the heavy chain comprises the amino acid sequence of SEQ ID NO:59, and the light chain comprises the amino acid sequence of SEQ ID NO:53; the heavy chain comprises the amino acid sequence of SEQ ID NO:60, and the light chain comprises the amino acid sequence of SEQ ID NO:53; the heavy chain comprises the amino acid sequence of SEQ ID NO:61, and the light chain comprises the amino acid sequence of SEQ ID NO:53; the heavy chain comprises the amino acid sequence of SEQ ID NO:58, and the light chain comprises the amino acid sequence of SEQ ID NO:54; the heavy chain comprises the amino acid sequence of SEQ ID NO:59, and the light chain comprises the amino acid sequence of SEQ ID NO:54: the heavy chain comprises the amino acid sequence of SEQ ID NO:60, and the light chain comprises the amino acid sequence of SEQ ID NO:54; the heavy chain comprises the amino acid sequence of SEQ ID NO:61, and the light chain comprises the amino acid sequence of SEQ ID NO:54; the heavy chain comprises the amino acid sequence of SEQ ID NO:58, and the light chain comprises the amino acid sequence of SEQ ID NO:55: the heavy chain comprises the amino acid sequence of SEQ ID NO:59, and the light chain comprises the amino acid sequence of SEQ ID NO:55; the heavy chain comprises the amino acid sequence of SEQ ID NO:60, and the light chain comprises the amino acid sequence of SEQ ID NO:55: the heavy chain comprises the amino acid sequence of SEQ ID NO:61, and the light chain comprises the amino acid sequence of SEQ ID NO:55; the heavy chain comprises the amino acid sequence of SEQ ID NO:58, and the light chain comprises the amino acid sequence of SEQ ID NO:56; the heavy chain comprises the amino acid sequence of SEQ ID NO:59, and the light chain comprises the amino acid sequence of SEQ ID NO:56: the heavy chain comprises the amino acid sequence of SEQ ID NO:60, and the light chain comprises the amino acid sequence of SEQ ID NO:56; the heavy chain comprises the amino acid sequence of SEQ ID NO:61, and the light chain comprises the amino acid sequence of SEQ ID NO:56; the heavy chain comprises the amino acid sequence of SEQ ID NO:58, and the light chain comprises the amino acid sequence of SEQ ID NO:57; the heavy chain comprises the amino acid sequence of SEQ ID NO:59, and the light chain comprises the amino acid sequence of SEQ ID NO:57; the heavy chain comprises the amino acid sequence of SEQ ID NO:60, and the light chain comprises the amino acid sequence of SEQ ID NO:57; the heavy chain comprises the amino acid sequence of SEQ ID NO:61, and the light chain comprises the amino acid sequence of SEQ ID NO:57; the heavy chain comprises the amino acid sequence of SEQ ID NO:57, and the light chain comprises the amino acid sequence of SEQ ID NO:55: the heavy chain comprises the amino acid sequence of SEQ ID NO:61, and the light chain comprises the amino acid sequence of SEQ ID NO:55: the heavy chain comprises the amino acid sequence of SEQ ID NO:129, and the light chain comprises the amino acid sequence of SEQ ID NO:55; the heavy chain comprises the amino acid sequence of SEQ ID NO:124, and the light chain comprises the amino acid sequence of SEQ ID NO:52; or the heavy chain comprises the amino acid sequence of SEQ ID NO:124, and the light chain comprises the amino acid sequence of SEQ ID NO:55.

In some embodiments, the antibody enhances phagocytosis by a macrophage expressing a human SIRP-α polypeptide. In some embodiments, the antibody enhances activation of a dendritic cell expressing a human SIRP-α polypeptide. In some embodiments, the antibody inhibits in vivo growth of a tumor that expresses CD47.

In some embodiments of any of the above embodiments, the antibody is conjugated to an agent. e.g., a cytotoxic agent, label, or moiety that modules the immune system.

In some embodiments of any of the above embodiments, the antibody is a bispecific antibody. In some embodiments, the antibody comprises a first antigen binding domain that binds an extracellular domain of a human SIRP-α polypeptide and a second antigen binding domain that binds an antigen expressed by a cancer cell. In some embodiments, the antigen expressed by the cancer cell is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PD-L1, PTK7, STEAP1, Endothelin B Receptor, mesothelin, EGFRvIII, ENPP3, SLC44A4, GNMB, nectin 4, NaPi2b, LIV-1A. Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. In some embodiments, the antibody comprises a first antigen binding domain that binds an extracellular domain of a human SIRP-α polypeptide and a second antigen binding domain that binds an antigen expressed by an immune cell. In some embodiments, the antigen expressed by the immune cell is selected from the group consisting of BDCA2, BDCA4, ILT7, LILRB1, LILRB2, LILRB3, LILRB4, LILRB5, Siglec-3, Siglec-7, Siglec-9, Siglec-15, FGL-1, CD200, CD200R, CSF-1R, CD40, CD40L, CD163, CD206, DEC205, CD47, CD123, arginase, IDO, TDO, AhR, EP2, COX-2, CCR2, CCR-7, CXCR1, CX3CR1, CXCR2, CXCR3, CXCR4, CXCR7, TGF-β RI, TGF-β RII, c-Kit, CD244, L-selectin/CD62L, CD11 b, CD11c, CD68, 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, TNFR2, PVRIG, DNAM, and ICOS. In some embodiments, the antibody comprises a first antigen binding domain that binds an extracellular domain of a human SIRP-α polypeptide and a second antigen binding domain that binds an antigen expressed by a natural killer (NK) cell. In some embodiments, the antigen expressed by the NK cell is selected from the group consisting of NKR-P1A, CD94, KLRG1, KIR2DL5A, KIR2DL5B, KIR2DL1, KIR2DL2, KIR2DL3, KIR2DS2, KIR2DS3, KIR2DS4, KIR2DS5, KIR3DS1, KIR2DS1, CD94, NKG2D, CD160, CD16, NKp46, NKp30, NKp44, DNAM1, CRTAM, CD27, NTB-A, PSGL1, CD96, CD100, NKp80, SLAMF7, and CD244.

In certain aspects, the present disclosure provides a polynucleotide encoding the antibody according to any one of the above embodiments. In certain aspects, the present disclosure provides a vector comprising the polynucleotide according to any one of the above embodiments. In certain aspects, the present disclosure provides a host cell comprising the polynucleotide or vector according to any one of the above embodiments. In certain aspects, the present disclosure provides a method of producing an antibody, the method comprising culture the host cell according to any one of the above embodiments such that the antibody is produced. In some embodiments, the method further comprises recovering the antibody from the host cell.

In certain aspects, the present disclosure provides a method of treating or delaying progression of cancer in an individual, the method comprising administering to the individual an effective amount of the antibody according to any one of the above embodiments. In some embodiments, the method further comprises administering to the individual an effective amount of a second antibody that binds an antigen expressed by the cancer. In some embodiments, the antigen expressed by the cancer is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA. TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. In some embodiments, the method further comprises administering to the individual an effective amount of an immunotherapeutic agent. In some embodiments, the immunotherapeutic agent comprises a second antibody. In some embodiments, the second antibody binds to an antigen selected from the group consisting of BDCA2, BDCA4, ILT7, LILRB1, LILRB2, LILRB3, LILRB4, LILRB5, Siglec-3, Siglec-7, Siglec-9, Siglec-15, FGL-1, CD200, CD200R, CSF-1R, CD40, CD40L, CD163, CD206, DEC205, CD47, CD123, arginase, IDO, TDO, AhR, EP2, COX-2, CCR2, CCR-7, CXCR1, CX3CR1, CXCR2, CXCR3, CXCR4, CXCR7, TGF-β RI, TGF-β RII, c-Kit, CD244, L-selectin/CD62L, CD11b, CD11c, CD68, 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, TNFR2, PVRIG, DNAM, and ICOS. In some embodiments, the second antibody binds to PD-1. In some embodiments, the second antibody binds to PD-L1. In some embodiments, the immunotherapeutic agent comprises a vaccine, oncolytic virus, adoptive cell therapy, cytokine, or small molecule. In some embodiments, the method further comprises administering to the individual an effective amount of a second antibody that binds an antigen expressed by a natural killer (NK) cell. In some embodiments, the antigen expressed by the NK cell is selected from the group consisting of NKR-P1A, CD94, KLRG1, KIR2DL5A, KIR2DL5B, KIR2DL1, KIR2DL2, KIR2DL3, KIR2DS2, KIR2DS3, KIR2DS4, KIR2DS5, KIR3DS1, KIR2DS1, CD94, NKG2D. CD160. CD16, NKp46, NKp30, NKp44, DNAM1, CRTAM, CD27, NTB-A, PSGL1, CD96, CD100, NKp80, SLAMF7, and CD244. In some embodiments, the method further comprises administering to the individual an effective amount of a chemotherapeutic agent or small molecule anti-cancer agent. In some embodiments, the method further comprises administering to the individual an effective amount of a targeted small molecule inhibitor. In some embodiments, the targeted small molecule inhibitor is a VEGFR and/or PDGFR inhibitor, EGFR inhibitor, ALK inhibitor, CDK4/6 inhibitor, PARP inhibitor, mTOR inhibitor, KRAS inhibitor, TRK inhibitor, BCL2 inhibitor, IDH inhibitor, PI3K inhibitor, DNA damage response (DDR) inhibitor, or hypomethylation agent.

In certain aspects, the present disclosure provides a method of treating or delaying progression of an autoimmune disease or an inflammatory disease in an individual, the method comprising administering to the individual an effective amount of the antibody according to any one of the above embodiments. In some embodiments, the autoimmune disease or inflammatory disease is selected from the group consisting of multiple sclerosis, rheumatoid arthritis, a spondyloarthropathy, systemic lupus erythematosus, an antibody-mediated inflammatory or autoimmune disease, graft versus host disease, sepsis, diabetes, psoriasis, psoriatic arthritis, atherosclerosis, Sjogren's syndrome, progressive systemic sclerosis, scleroderma, acute coronary syndrome, ischemic reperfusion, Crohn's Disease, ulcerative colitis, endometriosis, glomerulonephritis, IgA nephropathy, polycystic kidney disease, myasthenia gravis, idiopathic pulmonary fibrosis, fibrotic disease (e.g., pulmonary fibrosis, liver cirrhosis, atrial fibrosis, endomyocardial fibrosis, myelofibrosis, or retroperitoneal fibrosis), asthma, atopic dermatitis, acute respiratory distress syndrome (ARDS), vasculitis, and inflammatory autoimmune myositis.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 2 compares expression yield and binding affinity of antibodies having the AB21 human heavy chain and the indicated humanized light chains. The antibodies were produced by expression in FreeStyle™ 293-FS cells (Thermo Fisher).

FIGS. 4A & 4B show the results of in vivo dendritic cell activation assays with the indicated anti-SIRP-α antibodies. Mice were intravenously injected with the indicated antibody at 10 mg/kg, and spleens were harvested five hours after injection. Activation markers CD86, MHCII and CCR7 on CD4+ dendritic cells were measured by flow cytometry.

FIG. 9 shows a fragment of the Hum1 light chain with the K104 residue subject to glycation (SEQ ID NO:67; "Original"), along with 3 variants (SEQ ID NOs:68-70; versions 1-3, respectively) engineered to remove the glycation site. Glycation site is underlined.

FIGS. 10 & 11 show an alignment of the original Hum1 light chain (with Hum1 VL and IGCL1 constant domain) with 6 variants. Variants each include 1 of the 3 glycation site variants (v1, v2, and v3) and either DS or SD mutations to replace the N171/N172 deamidation site. Shown from top to bottom are SEQ ID NOs:47 and 52-57, respectively. Asterisks indicate sequence differences. CDRs are depicted in boxes (representing SEQ ID NOs:22, 23, and 24, respectively). CDR delineations are according to Kabat. Amino acid numbering is based on sequential numbering of residues.

FIGS. 13A & 13B show the depletion of lin− HLADR+ dendritic cells (DCs) and represent the results of experiments performed using PBMCs obtained from different donors. FIG. 13C shows the lack of depletion of CD3+ T cells by anti-SIRP-α antibodies and isotype controls. FIG. 13D shows the lack of depletion of CD14+ monocytes by anti-SIRP-α antibodies and isotype controls. FIG. 13E shows the lack of depletion of CD20+ B cells by anti-SIRP-α antibodies and isotype controls.

DETAILED DESCRIPTION

Figure 1:
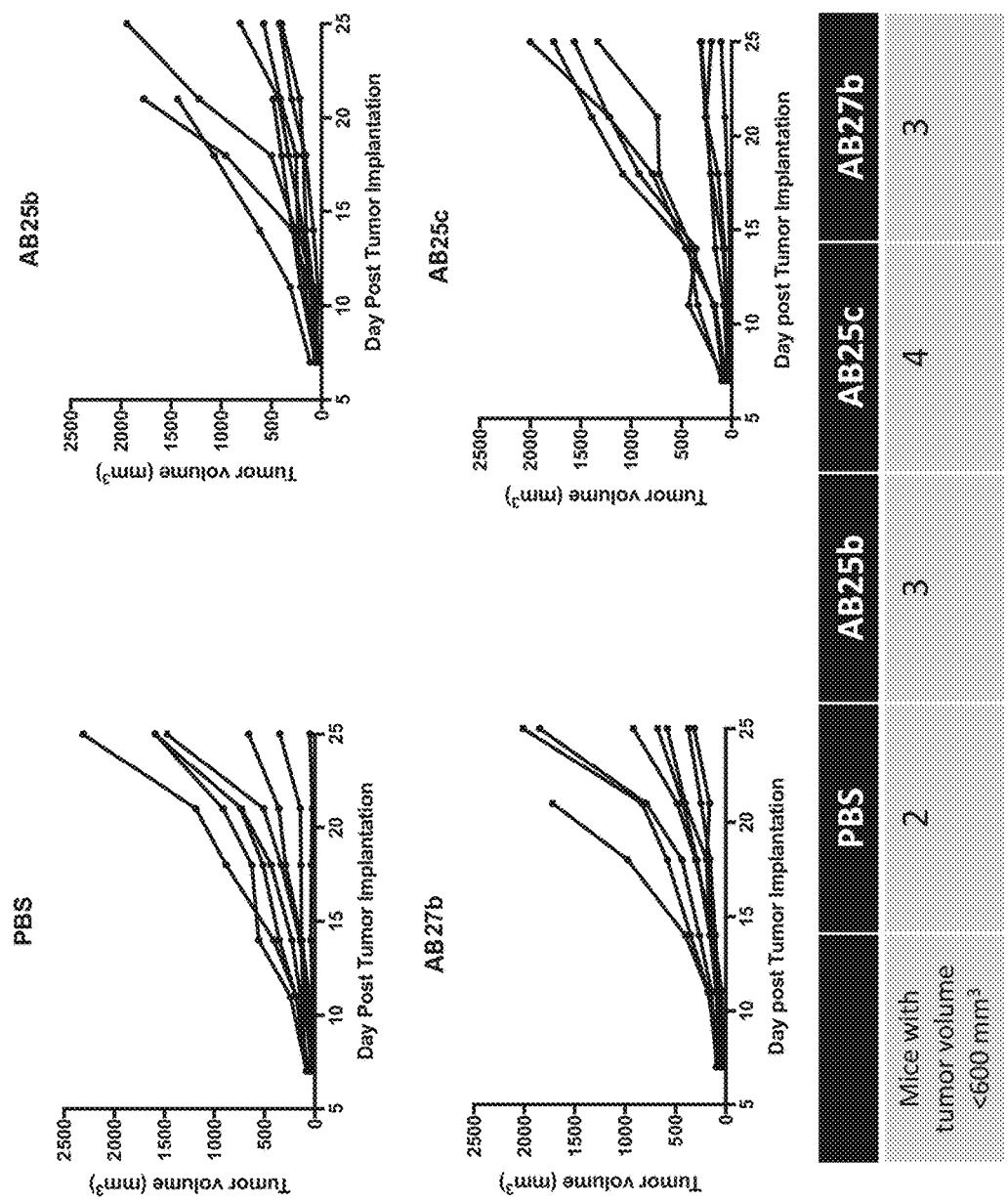
FIG. 1 shows the results of an in vivo syngeneic mouse colon carcinoma model to assess single agent activity. MC38 cells were implanted subcutaneously in C57BL/6 mice and randomized into groups (8 mice/group). Mice were treated with vehicle (PBS), CD47 blocking anti-SIRP-α antibody AB27b, CD47 blocking anti-SIRP-α antibody AB25b, or CD47 blocking anti-SIRP-α antibody AB25c. Treatment was initiated when tumors were an average of 60 mm³, day 7 post implant. Mice were dosed intraperitoneally (IP) at 10 mg/kg twice a week for three weeks with anti-SIRPα antibodies. Animals were sacrificed when tumors reached a volume of ~2000 mm³.

The present disclosure describes antibodies that bind the extracellular domains (e.g., the D1 domains) of one or more human SIRP-α polypeptides and have a variety of SIRP-α binding profiles of potential interest. In addition, the present disclosure describes anti-SIRP-α antibodies with one or more in vitro and/or in vivo biological properties of interest, such as binding to multiple SIRP-α polypeptides with high affinity and the ability to enhance macrophage phagocytosis, enhance dendritic cell activation, and/or inhibit in vivo growth of a tumor that expresses CD47. These antibodies have a light chain derived from chicken, which provides unique opportunities to generate antibodies that cross-react across multiple mammalian SIRP-α polypeptides. Indeed, these antibodies were found to cross-react with human SIRP-α v1 and v2, cynomolgus SIRP-α, and murine SIRP-α from multiple strains, making them highly advantageous for both pre-clinical testing and clinical application across a large human population. Importantly, these antibodies have also been engineered to remove potential liabilities, such as residues that may be modified by deamidation or glycation, resulting in antibodies with more desirable characteristics for manufacturing, storage, and/or drug development.

In one aspect, provided herein are isolated antibodies that bind the extracellular domain (e.g., the D1 domain) of a human SIRP-α polypeptide. Further provided herein are polynucleotides and vectors encoding the antibodies of the present disclosure, as well as methods of antibody production related thereto.

In another aspect, provided herein are methods for treating or delaying progression of cancer in an individual, comprising administering to the individual an effective amount of an antibody of the present disclosure.

In another aspect, provided herein are methods for treating or delaying progression of an autoimmune or inflammatory disease in an individual, comprising administering to the individual an effective amount of an antibody of the present disclosure.

Definitions

Before describing the disclosed embodiments in detail, it is to be understood that the present disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the present disclosure include "comprising," "consisting," and "consisting essentially of" aspects and embodiments.

A "SIRP-α polypeptide" as used herein may refer to any endogenous or naturally occurring SIRP-α polypeptide encoded by a genome from any vertebrate, including mammals such as humans, monkeys, rodents (e.g., mouse or rat), and birds, such as chickens. The term also includes naturally occurring variants, e.g., alternatively spliced variants, allelic variants, or polymorphisms (e.g., those described herein). The term may further refer to full-length, unprocessed SIRP-α polypeptides as well as SIRP-α polypeptides that result from cellular processing. e.g., removal of a signal sequence, etc. Exemplary SIRP-α polypeptide sequences are described herein. In some embodiments, a human SIRP-α poly peptide is one encoded by a human SIRPA gene, e.g., as described by NCBI Gene ID No. 140885. As described herein, SIRP-α polypeptides are highly polymorphic within and among species, including, for example, multiple human variants with amino acid polymorphisms in the extracellular domain.

SIRP-α polypeptides include an extracellular domain that binds ligands/partners, e.g., CD47. SIRP-α polypeptides comprise 3 highly homologous immunoglobulin (Ig)-like extracellular domains-D1, D2, and D3. The SIRP-α D1 domain ("D1 domain") refers to the membrane distal, extracellular domain of SIRP-α and mediates binding of SIRP-α to CD47 (see, e.g., Hatherley, D. et al. (2008) *Mol. Cell* 31:266-77; Hatherley, D. et al. (2007) *J. Biol. Chem.* 282:14567-75; Hatherley, D. et al. (2009) *J. Biol. Chem.* 284:26613-9; and Lee, W. Y. et al. (2010) *J. Biol. Chem.* 285:37953-63). The extracellular domain generally refers to the entire extracellular portion of SIRP-α, e.g., as expressed on a cell surface, and may include distinct SIRP-α domains, such as the D1 domain. The D1 domain contains residues shown to be critical for mediating CD47 binding (see. e.g., Lee, W. Y. et al. (2007)*J. Immunol.* 179:7741-50). In some embodiments, an antibody that binds an extracellular domain of a SIRP-α polypeptide binds one or more residues of the D1 domain.

As used herein, "CD47" (also known as integrin associated protein (IAP), MER6, and OA3) refers to a polypeptide that, among other roles, serves as a binding partner for SIRP-α polypeptides. In some embodiments, CD47 refers to a human CD47 polypeptide, e.g., a polypeptide encoded by a human CD47 gene, such as that described by NCBI Ref Seq ID No. 961. Exemplary human CD47 amino acid sequences are known (see, e.g., NCBI Reference Sequence Accession No. NP_001768). In particular, the IgSF domain of CD47 refers to the N-terminal extracellular domain of CD47 that is known to be critical for SIRP-α binding (see, e.g., Barclay, A. N. and Brown, M. H. (2006) *Nat. Rev. Immunol.* 6:457-64 and Hatherley, D. et al. (2009) *J. Biol. Chem.* 284:26613-9). The term "CD47" may also include modified CD47 polypeptides that are able to bind SIRP-α, e.g., a polypeptide comprising an IgSF domain of CD47 conjugated to another polypeptide or other moiety, e.g., an Ig Fc region.

As used herein "modulating SIRP-α signaling" may refer to antagonizing, agonizing, or otherwise interfering with one or more aspects of SIRP-α signaling in a cell expressing a SIRP-α polypeptide. SIRP-α signaling may refer to one or more intracellular signaling events mediated by activation of a SIRP-α polypeptide, including without limitation tyrosine phosphorylation of the intracellular region of SIRP-α, phosphatase (e.g., SHP1) binding, adaptor protein binding (e.g., SCAP2, FYB, and/or GRB2), cytokine production (e.g. IL-10, IL-1J, IFN or TNF), and nitric oxide production; and/or one or more intercellular phenotypes, including without limitation macrophage phagocytosis and other activating or suppressive phenotypes of macrophages, eosinophils, neutrophils, dendritic cells, and myeloid-derived suppressor cells (MDSCs).

As used herein, the term "antibody" may refer to intact antibodies; antibody fragments (including without limitation Fab, F(ab')2, Fab'-SH, Fv, diabodies, scFv, scFv-Fc, single domain antibodies, single heavy chain antibodies, and single light chain antibodies), provided that they exhibit the desired biological activity (e.g. epitope binding); monoclonal antibodies; polyclonal antibodies; monospecific antibodies; multi-specific antibodies (e.g., bispecific antibodies); and antibody-like proteins.

As used herein, the term "bispecific" when used in reference to an antibody or antibody fragment includes an antibody or antibody fragment that possesses two different binding specificities. For example, each binding specificity may recognize a different antigen, or each binding specificity may recognize the same antigen with different affinity and/or precise epitope. In some embodiments, each different binding specificity comprises one or more different antibody antigen binding domains (e.g., variable domains), such that the bispecific antibody or antibody fragment comprises at least a first antigen binding domain with a first binding specificity and a second antigen binding domain with a second binding specificity. A variety of exemplary bispecific antibody formats are described herein and known in the art.

An "isolated" antibody may refer to an antibody that has been separated and/or recovered from a component of its natural environment, e.g., a host cell or organism. In some embodiments, an antibody is purified to a desired purity by weight (e.g., at least 95%); and/or homogeneity by SDS-PAGE using, for example, staining by silver, Coomassie, etc. In some embodiments, an isolated antibody is obtained following one or more purification steps.

As is known in the art, "native" antibodies refer to typically heterotetrameric complexes including two identical light (L) chains and two identical heavy (H) chains. Variable numbers of disulfide bonds connect the two heavy chains, and one connects each light chain to a heavy chain, in addition to intrachain disulfide bridges. The heavy chains include a variable domain (VH) followed (N-terminus to C-terminus) by three or four constant domains. The light chains include a variable domain (VL) followed by a constant domain (CL). Typically, mammalian light chains fall into one of two categories based on amino acid sequence: kappa and lambda.

A "constant domain" may refer to the more conserved portion of the antibody or fragment, e.g., outside the variable domains. The term may include the CL domain as well as heavy chain constant domains CH1, CH2, and CH3, along with the heavy chain hinge region. Optionally, a heavy chain constant domain may further comprise a CH4 heavy chain constant domain.

Constant domains of the heavy chain can be assigned to one of 5 major types: IgA, IgD, IgE, IgG, and IgM. Several subtypes exist for many of these major types. The subunit structures and three-dimensional configurations of different classes of immunoglobulins are well known and described generally in, for example, Abbas et al. *Cellular and Mol. Immunology*, 4th ed. (W.B. Saunders, Co., 2000).

As used herein, the term "antibody variable domain" refers to the portions of the light and heavy chains of an antibody that include the complementary determining regions (CDRs, e.g., CDR L1, CDR L2, CDR L3, CDR H1, CDR H2, and CDR H3) and framework regions (FRs).

The term "variable" refers to the fact that subsequences of the variable domains differ substantially in sequence between antibodies and are critical to the binding specificity of a particular antibody for its antigen. Variability is concentrated in three hypervariable regions (HVRs) in both VH and VL domains. The more conserved portions of variable domains are called the framework regions (FR) in which the HVRs are interspersed. The variable domains of native heavy and light chains each comprise four FR regions connected by three HVRs that form loops (see Kabat et al., *Sequences of Proteins of Immunological Interest*, Fifth Edition, National Institute of Health, Bethesda, Md. (1991)).

The term "hypervariable region (HVR)" may refer to the subregions of the VH and VL domains characterized by enhanced sequence variability and/or formation of defined loops. These include three HVRs in the VH domain (H1, H2, and H3) and three HVRs in the VL domain (L1, L2, and L3). H3 is believed to be critical in imparting fine binding specificity, with L3 and H3 showing the highest level of diversity. See Johnson and Wu, in *Methods in Molecular Biology* 248:1-25 (Lo, ed., Human Press, Totowa. N.J., 2003).

A number of HVR delineations are known. The Kabat Complementarity Determining Regions (CDRs) are based on sequence variability and are the most commonly used (Kabat et al., *Sequences of Proteins of Immunological Interest*, 5th Ed. Public Health Service. National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below. "Framework" or "FR" residues are those variable domain residues other than the HVR residues.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

"Extended" HVRs are also known: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH (Kabat numbering).

"Numbering according to Kabat" may refer to the numbering system used for heavy chain variable domains or light chain variable domains of the compilation of antibodies in Kabat et al., supra. The actual linear amino acid sequence may contain fewer or additional amino acids corresponding to a shortening of, or insertion into, a FR or HVR of the variable domain. The Kabat numbering of residues may be determined for a given antibody by alignment at regions of homology of the sequence of the antibody with a "standard" Kabat numbered sequence. Typically, the Kabat numbering is used when referring to a residue in the variable domains (approximately residues 1-107 of the light chain and residues 1-113 of the heavy chain), whereas the EU numbering system or index (e.g., the EU index as in Kabat, numbering according to EU IgG1) is generally used when referring to a residue in the heavy chain constant region.

"Full length" or "intact" antibodies typically include heavy chains with an Fc region, e.g., as opposed to an antibody fragment. Antigen-binding "Fab" fragments with a single antigen binding site may be released from the residual Fc fragment by papain digestion. F(ab')2 fragments include two antigen-binding sites produced by pepsin treatment of an antibody. Antibody fragments will, however, include one or more antibody variable regions.

An "Fv" fragment contains a complete antigen-binding site. A single chain Fv (scFv) can include a VH and a VL domain linked by a peptide linker such that the VH and VL domains associate, e.g., as in an antibody or Fab fragment, such that the HVRs form an antigen binding site. See Pluckthün, in *The Pharmacology of Monoclonal Antibodies*, vol. 113, Rosenburg and Moore eds., (Springer-Verlag, New York, 1994), pp. 269-315. In some embodiments, the scFv is fused to an antibody Fc domain (e.g., scFv-Fc). While six HVRs typically comprise an antigen binding site, a single variable domain with three HVRs is still capable of binding an antigen, albeit at a lower affinity. See Hamers-Casterman et al., *Nature* 363:446-448 (1993), Sheriff et al., *Nature Struct. Biol.* 3:733-736 (1996). Single domain antibodies (e.g., camelid antibodies) typically include a single, monomeric variable domain for antigen binding. Single heavy chain (VHH) and single light chain antibodies are also known. A Fab' fragment typically includes a few more residues at the C-terminal end than a Fab fragment. A Fab'-SH includes cysteine residues with a free thiol. Various chemical couplings of antibody fragments are known in the art.

A "diabody" includes antibody fragments with two antigen-binding sites. These include a VH and VL domain connected by a linker, which is typically too short to facilitate pairing of domains in the same chain. Diabodies may be bivalent or bispecific. Tribodies and tetrabodies, or other numbers of VH/VL domains are known. See Hudson et al., *Nat. Med.* 9:129-134 (2003).

As used herein, a "monoclonal" antibody refers to an antibody obtained from a population of substantially homogeneous antibodies, e.g., substantially identical but allowing for minor levels of background mutations and/or modifications. "Monoclonal" denotes the substantially homogeneous character of antibodies, and does not require production of the antibody by any particular method. In some embodiments, a monoclonal antibody is selected by its HVR, VH, and/or VL sequences and/or binding properties, e.g., selected from a pool of clones (e.g., recombinant, hybridoma, or phage-derived). A monoclonal antibody may be engineered to include one or more mutations, e.g., to affect binding affinity or other properties of the antibody, create a humanized or chimeric antibody, improve antibody production and/or homogeneity, engineer a multispecific antibody, resultant antibodies of which are still considered to be monoclonal in nature. A population of monoclonal antibodies may be distinguished from polyclonal antibodies as the individual monoclonal antibodies of the population recognize the same antigenic site. A variety of techniques for production of monoclonal antibodies are known; see. e.g., the hybridoma method (e.g., Kohler and Milstein, *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992): Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see. e.g., WO 1998/24893: WO 1996/34096; WO 1996/33735: WO 1991/10741; Jakobovits et al., *Proc. Natl. Acad. Sci. USA* 90: 2551 (1993); Jakobovits et al., *Nature* 362: 255-258 (1993); Bruggemann et al, *Year in Immunol*. 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol*. 14: 845-851 (1996); Neuberger, *Nature Biotechnol*. 14: 826 (1996); and Lonberg and Huszar, *Intern. Rev. Immunol*. 13: 65-93 (1995).

"Chimeric" antibodies may refer to an antibody with one portion of the heavy and/or light chain from a particular isotype, class, or organism and another portion from another isotype, class, or organism. In some embodiments, the variable region will be from one source or organism, and the constant region will be from another.

"Humanized antibodies" may refer to antibodies with predominantly human sequence and a minimal amount of non-human (e.g., mouse or chicken) sequence. In some embodiments, a humanized antibody has one or more HVR sequences (bearing a binding specificity of interest) from an antibody derived from a non-human (e.g., mouse or chicken) organism grafted onto a human recipient antibody framework (FR). In some embodiments, non-human residues are further grafted onto the human framework (not present in either source or recipient antibodies), e.g., to improve antibody properties. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See Jones et al., *Nature* 321:522-525 (1986): Riechmann et al., *Nature* 332:323-329 (1988); and Presta, *Curr. Op. Struct. Biol.* 2:593-596 (1992).

A "human" antibody may refer to an antibody having an amino acid sequence which corresponds to that of an antibody produced by a human and/or has been made using any of the techniques for making human antibodies as disclosed herein. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991); preparation of human monoclonal antibodies as described in Cole et al., *Monoclonal Antibodies and Cancer Therapy*, Alan R. Liss, p. 77 (1985); Boemer et al., *J. Immunol.*, 147(1):86-95 (1991); and by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENO-MOUSE™ technology) or chickens with human immunoglobulin sequence(s) (see. e.g., WO2012162422, WO2011019844, and WO2013059159).

As used herein, the term "linker" refers to a linkage between two elements, e.g., protein domains. In some embodiments, a linker can be a covalent bond or a spacer. The term "spacer" refers to a moiety (e.g., a polyethylene glycol (PEG) polymer) or an amino acid sequence (e.g., a 1-200 amino acid sequence) occurring between two polypeptides or polypeptide domains to provide space or flexibility (or both space and flexibility) between the two polypeptides or polypeptide domains. In some embodiments, an amino acid spacer is part of the primary sequence of a polypeptide (e.g., joined to the spaced polypeptides or polypeptide domains via the polypeptide backbone).

The term "cytotoxic agent" as used herein may refer to any agent that inhibits cellular proliferation or induces cell death. Cytotoxic agents include, but are not limited to, chemotherapeutic agents; radioactive isotopes: growth inhibitory agents; and toxins such as small molecule toxins or enzymatically active toxins, including fragments and/or variants thereof. Exemplary cytotoxic agents include without limitation metabolic inhibitors, anti-microtubule agents, platinum containing compounds, alkylating agents, proteasome inhibitors, topoisomerase II inhibitors, antimetabolites, topoisomerase I inhibitors, signal transduction pathway inhibitors, non-receptor tyrosine kinase angiogenesis inhibitors, hormones and hormonal analogues, proapoptotic agents, inhibitors of LDH-A, cell cycle inhibitors, HDAC inhibitors, and antibiotic agents.

As used herein, a "label" may include any moiety that serves as a detection agent, e.g., of binding between a labeled antibody of the present disclosure and a macromolecule or cell. Exemplary labels include without limitation fluorescent (e.g., compounds or proteins), radioactive, or enzymatic moieties, as well as affinity purification tags.

As used herein, an antibody may be said to "bind" an antigen with an affinity sufficient to render the antibody useful for in vitro and/or in vivo manipulation of the antigen. In some embodiments, an antibody that "binds" an antigen has a dissociation constant ($K_D$) for the antigen that is less than or equal to 1 µM at 25° C.

As used herein, the term "affinity" or "binding affinity" refers to the strength of the binding interaction between two molecules. Generally, binding affinity refers to the strength of the sum total of non-covalent interactions between a molecule and its binding partner, such as a high affinity SIRP-α D1 variant and CD47. Unless indicated otherwise, binding affinity refers to intrinsic binding affinity, which reflects a 1:1 interaction between members of a binding pair. The binding affinity between two molecules is commonly described by the dissociation constant ($K_D$) or the association constant ($K_A$). Two molecules that have low binding affinity for each other generally bind slowly, tend to dissociate easily, and exhibit a large $K_D$. Two molecules that have high affinity for each other generally bind readily, tend to remain bound longer, and exhibit a small $K_D$. In some embodiments, the $K_D$ of two interacting molecules is determined using known methods and techniques, e.g., surface plasmon resonance (SPR). $K_D$ can be calculated as the ratio of $k_{off}/k_{on}$.

As used herein, the term "$K_D$ less than" refers to a numerically smaller $K_D$ value and an increasing binding affinity relative to the recited $K_D$ value. As used herein, the term "$K_D$ greater than" refers to a numerically larger $K_D$ value and a decreasing binding affinity relative to the recited $K_D$ value.

As used herein, "treatment" may refer to therapeutic administration of a molecule, compound, formulation, composition. etc. so as to alter one or more pathological symptoms in an individual or cell being treated. Desirable effects of treatment can include without limitation decelerating disease progression, ameliorating or palliating a pathological symptom or disease state, improving prognosis, and/or achieving disease remission. For example, an individual's cancer is successfully "treated" if one or more symptoms associated with cancer are mitigated or abolished, such as, without limitation, reducing the proliferation of cancer cells, eliminating cancer cells or tumor burden, decreasing symptoms resulting from the cancer, increasing the quality of life of the individual, lessening the dose of other medication(s), and/or prolonging survival of the individual. As another example, an autoimmune or inflammatory disease may be successfully "treated" if one or more symptoms associated with the autoimmune or inflammatory disease are mitigated or abolished, such as, without limitation, reducing autoreactive immune cells and/or inflammatory immune cells or cytokines, decreasing immune activation and/or inflammation, slowing or mitigating organ damage resulting from the disease, decreasing symptoms resulting from the disease, increasing the quality of life of the individual, lessening the dose of other medication(s), and/or prolonging survival of the individual.

As used herein, "delaying progression" of a disease may refer to slowing, retarding, deferring, postponing development of, stabilizing, or otherwise hindering the pathological course of the disease. In some embodiments, the term may refer to a delay sufficient to effectively encompass prevention, e.g., in preventing the individual from developing the disease. In some embodiments, e.g., an advanced cancer, delaying progression may include delaying metastasis. One of skill in the art will appreciate that the precise length of delay may depend. e.g., upon the specific disease, condition of the individual, and the like.

The terms "cancer" and "cancerous" may describe dysregulated or unregulated cell growth/proliferation by a cell or cells in a mammal. Any cancer type known in the art may be included, such as but not limited to carcinoma, sarcoma, lymphoma, leukemia, lymphoma, and blastoma. More particular examples of such cancers include, but are not limited to, lung cancer, squamous cell cancer, brain tumors, glioblastoma, head and neck cancer, hepatocellular cancer, colorectal cancer (e.g., colon or rectal cancers), liver cancer, bladder cancer, gastric or stomach cancer, pancreatic cancer, cervical cancer, ovarian cancer, cancer of the urinary tract, breast cancer, peritoneal cancer, uterine cancer, salivary gland cancer, kidney or renal cancer, prostate cancer, vulval cancer, thyroid cancer, anal carcinoma, penile carcinoma, melanoma, multiple myeloma and B-cell lymphoma (including non-Hodgkin's lymphomas (NHL)): acute lymphoblastic leukemia (ALL): chronic lymphocytic leukemia (CLL); acute myeloid leukemia (AML); Merkel cell carcinoma: hairy cell leukemia; chronic myeloblastic leukemia (CML); and associated metastases.

As used herein, the term "effective amount" may refer to an amount of an antibody of the present disclosure or a pharmaceutical composition containing an antibody of the present disclosure that is sufficient and effective in achieving a desired therapeutic effect in treating or delaying progression of a patient having a disease, such as a cancer, e.g., solid tumor or hematological cancer. In some embodiments, a therapeutically effective amount will avoid adverse side effects, and/or such side effects will be outweighed by beneficial effects. An effective amount may depend upon the individual being treated, e.g., age, weight, sex, disease state, as well as the ability of the agent to produce a desired response. An effective amount can be administered in one or more administrations. As in the clinical context, an effective amount of a drug, compound, or pharmaceutical composition may or may not be achieved in conjunction with another drug, compound, or pharmaceutical composition, such as another therapeutic agent. Thus, an "effective amount" may also be considered in the context of administering one or more additional therapeutic agents, and a single agent may be considered to be given in an effective amount if, in conjunction with one or more other agents, a desirable result may be or is achieved.

As used herein, the term "pharmaceutical composition" may refer to a medicinal or pharmaceutical formulation that includes an active ingredient as well as excipients or diluents (or both excipients and diluents) and enables the active ingredient to be administered by suitable methods of administration. In some embodiments, the pharmaceutical compositions disclosed herein include pharmaceutically acceptable components that are compatible with one or more antibodies of the present disclosure. In some embodiments, the pharmaceutical composition is in tablet or capsule form for oral administration or in aqueous form for intravenous or subcutaneous administration, for example by injection.

As used herein, the terms "subject," "individual," and "patient" are used interchangeably to refer to a vertebrate, for example, a mammal. Mammals include, but are not limited to, murines, simians, humans, farm animals, sport animals, and pets.

As used herein, "in conjunction with" or "in combination with" may refer to administration of one therapeutic in addition to (e.g., before, during, and/or after) another therapeutic.

Antibodies

Certain aspects of the present disclosure relate to antibodies that bind the extracellular domain (e.g., the D1 domain) of a human SIRP-α polypeptide. In some embodiments, the antibody is a humanized antibody. In some embodiments, the antibody is a monoclonal antibody.

In some embodiments, an antibody of the present disclosure comprises a heavy chain comprising a VH domain shown in Table 2 and/or a light chain comprising a VL domain that comprises an amino acid sequence according to the formula SYELTQPPSVSVSPGQTARITCSGGSYS-SYYYAWYQQKPGQAPVTLIYSDDKRPSNI PERFSGSSSGTTVTLTISGVQAEDEADYYCGGYDQS-SYTNPFGX$_1$GTX$_2$X$_3$TVL (SEQ ID NO:71), where X$_1$ is G or T; X$_2$ is K, Q, or R; and X$_3$ is L or V. In some embodiments, an antibody of the present disclosure comprises a heavy chain comprising a VH domain shown in Table 2 and a light chain comprising a VL domain that comprises an amino acid sequence according to the formula SYELTQPPSVSVSPGQTARITCSGGSYS-SYYYAWYQQKPGQAPVTLIYSDDKRPSNI PERFSGSSSGTTVTLTISGVQAEDEADYYCGGYDQS-SYTNPFGX$_1$GTX$_2$X$_3$TVL (SEQ ID NO:71), where X$_1$ is G or T; X$_2$ is K, Q, or R; and X$_3$ is L or V. In some embodiments of any of the above embodiments, the VL domain does not comprise the sequence of SEQ ID NO:25. In certain embodiments, an antibody of the present disclosure comprises a heavy chain comprising a VH domain that comprises the amino acid sequence of SEQ ID NO:26 and a light chain comprising a VL domain that comprises an amino acid sequence according to the formula SYELTQPPSVSVSPGQTARITCSGGSYS-SYYYAWYQQKPGQAPVTLIYSDDKRPSNI PERFSGSSSGTTVTLTISGVQAEDEADYYCGGYDQS-SYTNPFGX$_1$GTX$_2$X$_3$TVL (SEQ ID NO:71), where X$_1$ is G or T; X$_2$ is K, Q, or R; and X$_3$ is L or V. In some embodiments, the VL domain does not comprise the sequence of SEQ ID NO:25. In some embodiments, an antibody of the present disclosure comprises a heavy chain comprising a VH domain shown in Table 2 and/or a light chain comprising a VL domain shown in Table 1. In some embodiments, an antibody of the present disclosure comprises a heavy chain comprising a VH domain shown in Table 2 and a light chain comprising a VL domain shown in Table 1.

In some embodiments, an antibody of the present disclosure comprises a heavy chain comprising a VH domain that comprises the amino acid sequence of SEQ ID NO:26 and/or a light chain comprising a VL domain that comprises an amino acid sequence selected from SEQ ID NOs:39-41. In some embodiments, an antibody of the present disclosure comprises a heavy chain comprising a VH domain that comprises the amino acid sequence of SEQ ID NO:26 and a light chain comprising a VL domain that comprises an amino acid sequence selected from SEQ ID NOs:39-41.

In some embodiments, an antibody of the present disclosure comprises a heavy chain comprising a VH domain shown in Table 2 and/or a light chain comprising an amino acid sequence selected from SEQ ID NOs:48-57. In some embodiments, an antibody of the present disclosure comprises a heavy chain comprising a VH domain shown in Table 2 and a light chain comprising an amino acid sequence selected from SEQ ID NOs:48-57. In some embodiments, an antibody of the present disclosure comprises a heavy chain comprising a VH domain that comprises the amino acid sequence of SEQ ID NO:26 and/or a light chain comprising an amino acid sequence selected from SEQ ID NOs:48-57. In some embodiments, an antibody of the present disclosure comprises a heavy chain comprising a VH domain that comprises the amino acid sequence of SEQ ID NO:26 and a light chain comprising an amino acid sequence selected from SEQ ID NOs:48-57. In some embodiments, an antibody of the present disclosure comprises a heavy chain comprising a VH domain that comprises the amino acid sequence of SEQ ID NO:81 and a light chain comprising an amino acid sequence selected from SEQ ID NOs:48-57. In some embodiments, an antibody of the present disclosure comprises a heavy chain comprising a VH domain that comprises the amino acid sequence of SEQ ID NO:83 and a light chain comprising an amino acid sequence selected from SEQ ID NOs:48-57. In some embodiments, an antibody of the present disclosure comprises a heavy chain comprising a VH domain that comprises an amino acid sequence selected from SEQ ID NOs:77-111 and a light chain comprising an amino acid sequence selected from SEQ ID NOs:48-57. In some embodiments, an antibody of the present disclosure comprises a heavy chain comprising a VH domain that comprises an amino acid sequence selected from SEQ ID NOs:77-111 and a light chain that comprises an amino acid sequence selected from SEQ ID NOs:48-51. In some embodiments, an antibody of the present disclosure comprises a heavy chain comprising a VH domain shown in Table 2 and a constant domain that comprises an amino acid sequence selected from the group consisting of SEQ ID NOs:33, 34, and 137 and/or a light chain comprising an amino acid sequence selected from SEQ ID NOs:48-57. In some embodiments, an antibody of the present disclosure comprises a heavy chain comprising an amino acid sequence selected from the group consisting of SEQ ID NOs:60, 61, and 129 and/or a light chain comprising an amino acid sequence selected from SEQ ID NOs:48-57.

In some embodiments, an antibody of the present disclosure comprises a heavy chain comprising a VH domain that comprises an amino acid sequence selected from SEQ ID NOs:26, 81, or 83 and a light chain that comprises an amino acid sequence selected from SEQ ID NOs:48-57. In some embodiments, an antibody of the present disclosure comprises a heavy chain comprising a VH domain that comprises an amino acid sequence selected from SEQ ID NOs:26, 81, or 83 and a light chain comprising a VL domain that comprises an amino acid sequence selected from SEQ ID NOs:39-41. In some embodiments, an antibody of the present disclosure comprises a heavy chain comprising a VH domain that comprises the amino acid sequence of SEQ ID NO:26 and a light chain comprising a VL domain that comprises an amino acid sequence selected from SEQ ID NOs:39-41.

In some embodiments, an antibody of the present disclosure comprises a heavy chain comprising a VH domain that comprises an amino acid sequence selected from SEQ ID NOs:26, 81, or 83 and a light chain that comprises a VL domain sequence selected from SEQ ID NOs:39-41 and a CL domain comprising a sequence selected from SEQ ID NOs:36-38. In some embodiments, an antibody of the present disclosure comprises a heavy chain comprising a VH domain that comprises the amino acid sequence of SEQ ID NO:26 and a light chain that comprises a VL domain sequence selected from SEQ ID NOs:39-41 and a CL domain comprising a sequence selected from SEQ ID NOs: 36-38.

In some embodiments, an antibody of the present disclosure comprises a heavy chain comprising a VH domain that comprises an amino acid sequence selected from SEQ ID NOs:26, 81, or 83 and a light chain comprising a VL domain comprising the sequence of SEQ ID NO:25 and a CL domain sequence selected from SEQ ID NOs:43-46. In some embodiments, an antibody of the present disclosure comprises a heavy chain comprising a VH domain that comprises the amino acid sequence of SEQ ID NO:26 and a light chain that comprises a VL domain comprising the sequence of SEQ ID NO:25 and a CL domain sequence selected from SEQ ID NOs:43-46.

In some embodiments, an antibody of the present disclosure comprises a heavy chain that comprises a VH domain comprising the amino acid sequence of SEQ ID NO:83 and a light chain that comprises a VL domain sequence selected from SEQ ID NOs:39-41. In some embodiments, an antibody of the present disclosure comprises a heavy chain that comprises a VH domain comprising the amino acid sequence of SEQ ID NO:83 and a light chain that comprises a VL domain comprising the amino acid sequence of SEQ ID NO:40. In some embodiments, an antibody of the present disclosure comprises a heavy chain that comprises a VH domain comprising the amino acid sequence of SEQ ID NO:83 and a light chain that comprises the amino acid sequence of SEQ ID NO:55.

In some embodiments, an antibody of the present disclosure comprises a heavy chain comprising an amino acid sequence selected from the group consisting of SEQ ID NOs:119-123 and a light chain that comprises a VL domain sequence selected from SEQ ID NOs:39-41. In some embodiments, an antibody of the present disclosure comprises a heavy chain comprising an amino acid sequence selected from the group consisting of SEQ ID NOs:119-123 and a light chain that comprises a VL domain comprising the amino acid sequence of SEQ ID NO:40. In some embodiments, an antibody of the present disclosure comprises a heavy chain comprising an amino acid sequence selected from the group consisting of SEQ ID NOs:119-123 and a light chain that comprises the amino acid sequence of SEQ ID NO:55. In some embodiments, an antibody of the present disclosure comprises a heavy chain that comprises the amino acid sequence of SEQ ID NO:119 and a light chain that comprises the amino acid sequence of SEQ ID NO:55. In some embodiments, an antibody of the present disclosure comprises a heavy chain that comprises the amino acid sequence of SEQ ID NO:120 and a light chain that comprises the amino acid sequence of SEQ ID NO:55. In some embodiments, an antibody of the present disclosure comprises a heavy chain that comprises the amino acid sequence of SEQ ID NO:121 and a light chain that comprises the amino acid sequence of SEQ ID NO:55. In some embodiments, an antibody of the present disclosure comprises a heavy chain that comprises the amino acid sequence of SEQ ID NO:122 and a light chain that comprises the amino acid sequence of SEQ ID NO:55. In some embodiments, an antibody of the present disclosure comprises a heavy chain that comprises the amino acid sequence of SEQ ID NO:123 and a light chain that comprises the amino acid sequence of SEQ ID NO:55.

In some embodiments, an antibody of the present disclosure comprises a heavy chain that comprises a VH domain comprising the amino acid sequence of SEQ ID NO:26 and a constant domain sequence selected from the group consisting of SEQ ID NOs:132-139; and/or a light chain comprising a VL domain that comprises the amino acid sequence of SEQ ID NO:40. In some embodiments, an antibody of the present disclosure comprises a heavy chain that comprises a VH domain comprising the amino acid sequence of SEQ ID NO:26 and a constant domain sequence selected from the group consisting of SEQ ID NOs:33,34, and 137; and/or a light chain comprising a VL domain that comprises the amino acid sequence of SEQ ID NO:40. In some embodiments, an antibody of the present disclosure comprises a heavy chain that comprises a VH domain comprising the amino acid sequence of SEQ ID NO:26 and a constant domain sequence selected from the group consisting of SEQ ID NOs:132-139; and/or a light chain comprising the amino acid sequence of SEQ ID NO:55. In some embodiments, an antibody of the present disclosure comprises a heavy chain that comprises a VH domain comprising the amino acid sequence of SEQ ID NO:26 and a constant domain sequence selected from the group consisting of SEQ ID NOs:33,34, and 137; and/or a light chain comprising the amino acid sequence of SEQ ID NO:55.

In some embodiments, an antibody of the present disclosure comprises a heavy chain that comprises an amino acid sequence selected from the group consisting of SEQ ID NOs:124-131; and/or a light chain comprising a VL domain that comprises the amino acid sequence of SEQ ID NO:40. In some embodiments, an antibody of the present disclosure comprises a heavy chain that comprises an amino acid sequence selected from the group consisting of SEQ ID NOs:60, 61, and 129; and/or a light chain comprising a VL domain that comprises the amino acid sequence of SEQ ID NO:40. In some embodiments, an antibody of the present disclosure comprises a heavy chain that comprises an amino acid sequence selected from the group consisting of SEQ ID NOs:124-131; and/or a light chain comprising the amino acid sequence of SEQ ID NO:55. In some embodiments, an antibody of the present disclosure comprises a heavy chain that comprises an amino acid sequence selected from the group consisting of SEQ ID NOs:60, 61, and 129; and/or a light chain comprising the amino acid sequence of SEQ ID NO:55. In some embodiments, the heavy chain comprises the amino acid sequence of SEQ ID NO:60, and the light chain comprises the amino acid sequence of SEQ ID NO:55. In some embodiments, the heavy chain comprises the amino acid sequence of SEQ ID NO:61, and the light chain comprises the amino acid sequence of SEQ ID NO:55. In some embodiments, the heavy chain comprises the amino acid sequence of SEQ ID NO:137, and the light chain comprises the amino acid sequence of SEQ ID NO:55.

In some embodiments, an antibody of the present disclosure comprises a heavy chain that comprises an amino acid sequence selected from SEQ ID NOs:58-62 and/or a light chain comprising a VL domain that comprises an amino acid sequence according to the formula SYELTQPPSVSVSPGQTARITCSGGSYS-SYYYAWYQQKPGQAPVTLIYSDDKRPSNI PERFSGSSSGTTVTLTISGVQAEDEADYYCGGYDQS-SYTNPFGX$_1$GTX$_2$X$_3$TVL (SEQ ID NO:71), where X$_1$ is G or T; X$_2$ is K, Q, or R; and X$_3$ is L or V. In some embodiments, an antibody of the present disclosure comprises a heavy chain that comprises an amino acid sequence selected from SEQ ID NOs:58-62 and a light chain comprising a VL domain that comprises an amino acid sequence according to the formula SYELTQPPSVSVSPGQ-TARITCSGGSYS-SYYYAWYQQKPGQAPVTLIYSDDKRPSNI PERFSGSSSGTTVTLTISGVQAEDEADYYCGGYDQS-SYTNPFGX$_1$GTX$_2$X$_3$TVL (SEQ ID NO:71), where X$_1$ is G or T; X$_2$ is K, Q, or R; and X$_3$ is L or V. In some embodiments of any of the above embodiments, the VL domain does not comprise the sequence of SEQ ID NO:25.

In some embodiments, an antibody of the present disclosure comprises a heavy chain that comprises an amino acid sequence selected from SEQ ID NOs:58-62 and a light chain comprising a VL domain shown in Table 1. In some embodiments, an antibody of the present disclosure comprises a heavy chain that comprises an amino acid sequence selected from SEQ ID NOs:58-62 and a light chain comprising a VL domain that comprises an amino acid sequence selected from SEQ ID NOs:39-41. In some embodiments, an antibody of the present disclosure comprises a heavy chain that comprises an amino acid sequence selected from SEQ ID NOs:58-62 and a light chain comprising an amino acid sequence selected from SEQ ID NOs:48-57. In some embodiments, an antibody of the present disclosure comprises a heavy chain that comprises an amino acid sequence selected from SEQ ID NOs:58-62 and a light chain comprising a VL domain that comprises an amino acid sequence selected from SEQ ID NOs:39-41 and a CL domain that comprises an amino acid sequence selected from SEQ ID NOs:36-38. In some embodiments, an antibody of the present disclosure comprises a heavy chain that comprises an amino acid sequence selected from SEQ ID NOs:58-62 and a light chain comprising a VL domain that comprises the amino acid sequence of SEQ ID NO:25 and a CL domain that comprises an amino acid sequence selected from SEQ ID NOs:43-46.

In some embodiments, an antibody of the present disclosure comprises a heavy chain that comprises the amino acid sequence of SEQ ID NO:62 and a light chain that comprises the amino acid sequence of SEQ ID NO:52. In some embodiments, an antibody of the present disclosure comprises a heavy chain that comprises the amino acid sequence of SEQ ID NO:62 and a light chain that comprises the amino acid sequence of SEQ ID NO:53. In some embodiments, an antibody of the present disclosure comprises a heavy chain that comprises the amino acid sequence of SEQ ID NO:62 and a light chain that comprises the amino acid sequence of SEQ ID NO:54. In some embodiments, an antibody of the present disclosure comprises a heavy chain that comprises the amino acid sequence of SEQ ID NO:62 and a light chain that comprises the amino acid sequence of SEQ ID NO:55. In some embodiments, an antibody of the present disclosure comprises a heavy chain that comprises the amino acid sequence of SEQ ID NO:62 and a light chain that comprises the amino acid sequence of SEQ ID NO:56. In some embodiments, an antibody of the present disclosure comprises a heavy chain that comprises the amino acid sequence of SEQ ID NO:62 and a light chain that comprises the amino acid sequence of SEQ ID NO:57.

In some embodiments, an antibody of the present disclosure comprises a heavy chain that comprises the amino acid sequence of SEQ ID NO:58 and a light chain that comprises the amino acid sequence of SEQ ID NO:52. In some embodiments, an antibody of the present disclosure comprises a heavy chain that comprises the amino acid sequence of SEQ ID NO:59 and a light chain that comprises the amino acid sequence of SEQ ID NO:52. In some embodiments, an antibody of the present disclosure comprises a heavy chain that comprises the amino acid sequence of SEQ ID NO:60 and a light chain that comprises the amino acid sequence of SEQ ID NO:52. In some embodiments, an antibody of the present disclosure comprises a heavy chain that comprises the amino acid sequence of SEQ ID NO:61 and a light chain that comprises the amino acid sequence of SEQ ID NO:52.

In some embodiments, an antibody of the present disclosure comprises a heavy chain that comprises the amino acid sequence of SEQ ID NO:58 and a light chain that comprises the amino acid sequence of SEQ ID NO:53. In some embodiments, an antibody of the present disclosure comprises a heavy chain that comprises the amino acid sequence of SEQ ID NO:59 and a light chain that comprises the amino acid sequence of SEQ ID NO:53. In some embodiments, an antibody of the present disclosure comprises a heavy chain that comprises the amino acid sequence of SEQ ID NO:60 and a light chain that comprises the amino acid sequence of SEQ ID NO:53. In some embodiments, an antibody of the present disclosure comprises a heavy chain that comprises the amino acid sequence of SEQ ID NO:61 and a light chain that comprises the amino acid sequence of SEQ ID NO:53.

In some embodiments, an antibody of the present disclosure comprises a heavy chain that comprises the amino acid sequence of SEQ ID NO:58 and a light chain that comprises the amino acid sequence of SEQ ID NO:54. In some embodiments, an antibody of the present disclosure comprises a heavy chain that comprises the amino acid sequence of SEQ ID NO:59 and a light chain that comprises the amino acid sequence of SEQ ID NO:54. In some embodiments, an antibody of the present disclosure comprises a heavy chain that comprises the amino acid sequence of SEQ ID NO:60 and a light chain that comprises the amino acid sequence of SEQ ID NO:54. In some embodiments, an antibody of the present disclosure comprises a heavy chain that comprises the amino acid sequence of SEQ ID NO:61 and a light chain that comprises the amino acid sequence of SEQ ID NO:54.

In some embodiments, an antibody of the present disclosure comprises a heavy chain that comprises the amino acid sequence of SEQ ID NO:58 and a light chain that comprises the amino acid sequence of SEQ ID NO:55. In some embodiments, an antibody of the present disclosure comprises a heavy chain that comprises the amino acid sequence of SEQ ID NO:59 and a light chain that comprises the amino acid sequence of SEQ ID NO:55. In some embodiments, an antibody of the present disclosure comprises a heavy chain that comprises the amino acid sequence of SEQ ID NO:60 and a light chain that comprises the amino acid sequence of SEQ ID NO:55. In some embodiments, an antibody of the present disclosure comprises a heavy chain that comprises the amino acid sequence of SEQ ID NO:61 and a light chain that comprises the amino acid sequence of SEQ ID NO:55.

In some embodiments, an antibody of the present disclosure comprises a heavy chain that comprises the amino acid sequence of SEQ ID NO:58 and a light chain that comprises the amino acid sequence of SEQ ID NO:56. In some embodiments, an antibody of the present disclosure comprises a heavy chain that comprises the amino acid sequence of SEQ ID NO:59 and a light chain that comprises the amino acid sequence of SEQ ID NO:56. In some embodiments, an antibody of the present disclosure comprises a heavy chain that comprises the amino acid sequence of SEQ ID NO:60 and a light chain that comprises the amino acid sequence of SEQ ID NO:56. In some embodiments, an antibody of the present disclosure comprises a heavy chain that comprises the amino acid sequence of SEQ ID NO:61 and a light chain that comprises the amino acid sequence of SEQ ID NO:56.

In some embodiments, an antibody of the present disclosure comprises a heavy chain that comprises the amino acid sequence of SEQ ID NO:58 and a light chain that comprises the amino acid sequence of SEQ ID NO:57. In some embodiments, an antibody of the present disclosure comprises a heavy chain that comprises the amino acid sequence of SEQ ID NO:59 and a light chain that comprises the amino acid sequence of SEQ ID NO:57. In some embodiments, an antibody of the present disclosure comprises a heavy chain that comprises the amino acid sequence of SEQ ID NO:60 and a light chain that comprises the amino acid sequence of SEQ ID NO:57. In some embodiments, an antibody of the present disclosure comprises a heavy chain that comprises the amino acid sequence of SEQ ID NO:61 and a light chain that comprises the amino acid sequence of SEQ ID NO:57.

In some embodiments, an antibody of the present disclosure comprises a heavy chain that comprises a VH domain comprising a sequence selected from SEQ ID NOs:77-111 and a light chain that comprises a VL domain comprising the sequence of SEQ ID NO:25. In some embodiments, an antibody of the present disclosure comprises a heavy chain that comprises a VH domain comprising a sequence selected from SEQ ID NOs:77-111 and a light chain that comprises a VL domain comprising a sequence selected from SEQ ID NOs:39-41. In some embodiments, an antibody of the present disclosure comprises a heavy chain that comprises a VH domain comprising a sequence selected from SEQ ID NOs:77-111 and a light chain that comprises a VL domain comprising a sequence selected from SEQ ID NOs:39-41 and a CL domain comprising a sequence selected from SEQ ID NOs:36-38. In some embodiments, an antibody of the present disclosure comprises a heavy chain that comprises a VH domain comprising a sequence selected from SEQ ID NOs:77-111 and a light chain that comprises a VL domain comprising the sequence of SEQ ID NO:25 and a CL domain comprising a sequence selected from SEQ ID NOs:43-46. In some embodiments, an antibody of the present disclosure comprises a heavy chain that comprises a sequence selected from SEQ ID NOs:114-123 and a light chain that comprises a sequence selected from SEQ ID NOs:47-63. In some embodiments, an antibody of the present disclosure comprises a heavy chain that comprises a sequence selected from SEQ ID NOs:124-131 and a light chain that comprises a sequence selected from SEQ ID NOs:47-63. In some embodiments, an antibody of the present disclosure comprises a heavy chain that comprises a sequence selected from SEQ ID NOs:114-131 and a light chain that comprises a sequence selected from SEQ ID NOs:47-63.

In some embodiments, an antibody of the present disclosure comprises a heavy chain that comprises an amino acid sequence selected from SEQ ID NOs:114-118 and a light chain that comprises an amino acid sequence selected from SEQ ID NOs:48-57. In some embodiments, an antibody of the present disclosure comprises a heavy chain that comprises an amino acid sequence selected from SEQ ID NOs:119-123 and a light chain that comprises an amino acid sequence selected from SEQ ID NOs:48-57. In some embodiments, an antibody of the present disclosure comprises a heavy chain that comprises an amino acid sequence selected from SEQ ID NOs:114-123 and a light chain that comprises a VL domain comprising a sequence selected from SEQ ID NOs:39-41. In some embodiments, an antibody of the present disclosure comprises a heavy chain that comprises an amino acid sequence selected from SEQ ID NOs:114-123 and a light chain that comprises a VL domain comprising a sequence selected from SEQ ID NOs:39-41 and a CL domain comprising a sequence selected from SEQ ID NOs:36-38. In some embodiments, an antibody of the present disclosure comprises a heavy chain that comprises an amino acid sequence selected from SEQ ID NOs:114-123 and a light chain that comprises a VL domain comprising the sequence of SEQ ID NO:25 and a CL domain comprising a sequence selected from SEQ ID NOs:43-46.

In some embodiments, an antibody of the present disclosure comprises three CDRs from a VH domain comprising a sequence set forth in Table 2 and/or three CDRs from a VL domain comprising a sequence set forth in Table 1. In some embodiments, an antibody of the present disclosure comprises a VH domain comprising a sequence that is at least 90%, at least 91%, at least 92%, at least 93%, at least 94%, at least 95%, at least 96%, at least 97%, at least 98%, at least 99%, or 100% identical to a VH domain sequence set forth in Table 2 and optionally three CDRs from a VH domain comprising a sequence set forth in Table 2, and/or a VL domain comprising a sequence that is at least 90%, at least 91%, at least 92%, at least 93%, at least 94%, at least 95%, at least 96%, at least 97%, at least 98%, at least 99%, or 100% identical to a VL domain sequence set forth in Table 1 and optionally three CDRs from a VL domain comprising a sequence set forth in Table 1. In some embodiments, an antibody of the present disclosure comprises a heavy chain comprising a sequence that is at least 90%, at least 91%, at least 92%, at least 93%, at least 94%, at least 95%, at least 96%, at least 97%, at least 98%, at least 99%, or 100% identical to a heavy chain sequence set forth in Table 2 and optionally three CDRs from a VH domain comprising a sequence set forth in Table 2, and/or a light chain comprising a sequence that is at least 90%, at least 91%, at least 92%, at least 93%, at least 94%, at least 95%, at least 96%, at least 97%, at least 98%, at least 99%, or 100% identical to a light chain sequence set forth in Table 1 and optionally three CDRs from a VL domain comprising a sequence set forth in Table 1.

TABLE 1

Light chain antibody sequences.

| Name | Description | SEQ ID NO | Sequence |
|---|---|---|---|
| AB25 | HVR-L1 | 22 | SGGSYSSYYYA |
|  | HVR-L2 | 23 | SDDKRPS |
|  | HVR-L3 | 24 | GGYDSSYTNP |
| Hum1 | VL | 25 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPFGGGTKLTVL |
| Hum1 VL version 1 (v1) | VL | 39 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPFGTGTKVTVL |
| Hum1 VL, version 2 (v2) | VL | 40 | SYELTQPPSVSVSPGQTARITCSGGSYSSYYYAWYQ QKPGQAPVTLIYSDDKRPSNIPERFSGSSSGTTVTLTI SGVQAEDEADYYGGYDQSSYINPFGGGTQLTVL |
| Hum1 VL version 3 (v3) | VL | 41 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPFGGGTRLTVL |
| Human Kappa CL | CL | 36 | RTVAAPSVFIFPPSDEQLKSGTASVVCLLNNFYPREA KVQWKVDNALQSGNSQESVTEQDSKDSTYSLSSTL TLSKADYEKHKVYACEVTHQGLSSPVTKSFNRGEC |
| Human Lambda IGLC1 | CL | 37 | GQPKANPTVTLFPPSSEELQANKATLVCLISDFYPGA VTVAWKADGSPVKAGVETTKPSKQSNNKYAASSYL SLTPEQWKSHRSYSCQVTHEGSTVEKTVAPTECS |
| Human Lambda IGLC2 | CL | 38 | GQPKAAPSVTLFPPSSEELQANKATLVCLISDFYPGAV TVAWKADSSPVKAGVETTTPSKQSNNKYAASSYLSLT PEQWKSHRSYSCQVTHEGSTVEKTVAPTECS |
| Haman Lambda IGLC1_wt | CL | 42 | GQPKANPTVTLFPPSSEELQANKATLVCLISDFYPGA VTVAWKADGSPVKAGVETTKPSKQSNNKYAASSYL SLTPEQWKSHRSYSCQVTHEGSTVEKTVAPTECS |
| Human Lambda IGLC1_ N172D | CL | 43 | GQPKANPTVTLFPPSSEELQANKATLVCLISDFYPGA VTVAWKADGSPKAGVETTKPSKQSNDKYAASSYL SLTPEQWKSHRSYSCQVTHEGSTVEKTVAPTECS |
| Human Lambda IGLC1_ N171D | CL | 44 | GQPKANPTVTLFPPSSEELQANKATLVCLISDFYPGA VTVAWKADGSPKAGVETTKPSKQSDNKYAASSYL SLTPEQWKSHRSYSCQVTHEGSTVEKTVAPTECS |
| Human Lambda_ IGLC1_ N171D, N172S (DS) | CL | 45 | GQPKANPTVTLFPPSSEELQANKATLVCLISDFYPGA VTVAWKADGSPVKAGVETTKPSKQSDSKYAASSYL SLTPEQWKSHRSYSCQVTHEGSTVEKTVAPTECS |
| Human Lambda_ IGLC1_ N171S, N172D (SD) | CL | 46 | GQPKANPTVTLEPPSSEELQANKATLVCLISDFYPGA VTVAWKADGSPVKAGVETTKPSKQSSDKYAASSYL SLTPEQWKSHRSYSCQVTHEGSTVEKTVAPTECS |
| Human LC Original | Light chain | 47 | SYELTQPPSVSVSPGQTARITCSGGSYSSYYYAWYQ QKPGQAPVTLIYSDDKRPSNIPERESGSSSGTTVTLTI SGVQAEDEADYYCGGYDQSSYTNPFGGGTKLTVL GQPKANPTVTLFPPSSEELQANKATLVCLISDFYPGA |

TABLE 1-continued

Light chain antibody sequences.

| Name | Description | SEQ ID NO | Sequence |
|---|---|---|---|
| | | | VTVAWKADGSPVKAGVETTKPSKQSNNKYAASSYL SLTPEQWKSHRSYSCQVTHEGSTVEKTVAPTECS |
| Human LC Original_ N172D | Light chain | 48 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPFGGGTKLTVL GQPKANPTVTLFPPSSEELQANKATLVCLISDFYPGA VTVAWKADGSPVKAGVETTKPSKQSNDKYAASSYL SLTPEQWKSHRSYSCQVTHEGSTVEKTVAPTECS |
| Human LC Original_ N171D | Light chain | 49 | SYELTQPPSVSVSPGQTARITCSGGSYSSYYYAWYQQ KPGQAPVTLIYSDDKRPSNIPERESGSSSGTTVCLTISG VQAEDEADYYCGGYDQSSYTNPFGGGTKLTVL GQPKANPTVTLFPPSSEELQANKATLVCLISDFYPGA VTVAWKADGSPVKAGVETTKPSKQSDNKYAASSYL SLTPEQWKSHRSYSCQVTHEGSTVEKTVAPTECS |
| Human LC original N171D, N172S | Light chain | 50 | SYELTQPPSVSVSPGQTARITCSGGSYSSYYYAWYQQ KPGQAPVTLIYSDDKRPSNIPERFSGSSSGTTVTISG VQAEDEADYYCGGYDQSSYTNPFGGGTKLTVL GQPKANPTVTLFPPSSEELQANKATLVCLISDFYPGA VTVAWKADGSPVKAGVETTKPSKQSDKYAASSYL SLTPEQWKSHRSYSCQVTHEGSTVEKTVAPTECS |
| Human LC original N171S, N172D | Light chain | 51 | SYELTQPPSVSVSPGQTARITCSGGSYSSYYYAWYQQ KPGQAPVTLIYSDDKRPSNIPERFSGSSSGTTVTLTISG VQAEDEADYYCGGYDQSSYTNPFGGGTKLTVL GQPKANPTVTLFPPSSEELQANKATLVCLISDFYPGA VTVAWKADGSPVKAGVETTKPSKQSSDKYAASSYL SLTPEQWKSHRSYSCQVTHEGSTVEKTVAPTECS |
| Human LC- Version 1 + DS | Light chain | 52 | SYELTQPPSVSVSPGQTARITCSGGSYSSYYYAWYQ QKPGQAPVTLIYSDDKRYSNIPERFSGSSSGTTVTLTI SGVQAEDEADYYCGGYDQSSYTNPFGTGTKVTVL GQPKANPTVTLFPPSSEELQANKATLVCLISDFYPGA VTVAWKADGSPVKAGVETTKPSKQSDSKYAASSYL SLTPEQWKSHRSYSCQVTHEGSTVEKTVAPTECS |
| Human LC- Version 1 + SD | Light chain | 53 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPFGTGTKVTVL GQPKANPTVTLFPPSSEELQANKATLVCLISDFYPGA VTVAWKADGSPVKAGVETTKPSKQSSDKYAASSYL SLTPEQWKSHRSYSCQVTHEGSTVEKTVAPTECS |
| Human LC- Version 2 + DS | Light chain | 54 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPEGGGTQLTVL GQPKANPTVTLFPPSSEELQANKATLVCLISDFYPGA VTVAWKADGSPVKAGVETTKPSKQSDSKYAASSYL SLTPEQWKSHRSYSCQVTHEGSTVEKTVAPTECS |
| Human LC- Version 2 + SD | Light chain | 55 | SYELTQPPSVSVSPGQTARITCSGGSYSSYYYAWYQQ KPGQAPVTLIYSDDKRPSNIPERFSGSSSGTTVTLTISG VQAEDEADYYCGGYDQSSYTNPFGGGTQLTVL GQPKANPTVTLFPPSSEELQANKATLVCLISDFYPGA VTVAWKADGSPVKAGVETTKPSKQSSDKYAASSYL SLTPEQWKSHRSYSCQVTHEGSTVEKTVAPTECS |
| Human LC- Version 3 + DS | Light chain | 56 | SYELTQPPSVSVSPGQTARITCSGGSYSSYYYAWYQQ KPGQAPVTLIYSDDKRPSNIPERFSGSSSGTTVTLTISG VQAEDEADYYCGGYDQSSYTNPFGGGTRLTVL GQPKANPTVTLFPPSSEELQANKATLVCLISDFYPGA VTVAWKADGSPVKAGVETTKPSKQSDSKYAASSYL SLTPEQWKSHRSYSCQVTHEGSTVEKTVAPTECS |
| Human LC- Version 3 + SD | Light chain | 57 | SYELTQPPSVSVSPGQTARITCSGGSYSSYYYAWYQQ KPGQAPVTIYSDDKRPSNIPERFSGSSSGTTVTLTISG VQAEDEADYYCGGYDQSSYTNPFGGGTRLTVL GQPKANPTVTLEPPSSEELQANKATLVCLISDEYPGA VTVAWKADGSPVKAGVETTKPSKQSSDKYAASSYL SLTPEQWKSHRSYSCQVTHEGSTVEKTVAPTECS |

TABLE 1-continued

Light chain antibody sequences.

| Name | Description | SEQ ID NO | Sequence |
|---|---|---|---|
| Hum1 original in Lambda constant IGLC2 | Light chain | 63 | SYELTQPPSVSVSPGQTARITCSGGSYSSYYYAWYQ QKPGQAPVTLIYSDDKRPSNIPERFSGSSSGTTVTLTI SGVQAEDEADYYCGGYDQSSYTNPEGGGTKLTVLG QPKAAPSVTLFPPSSEELQANKATLVCLISDFYPGAV TVAWKADSSPVKAGVETTTPSKQSNNKYAASSYLS LTPEQWKSHRSYSCQVTHEGSTVEKTVAPTECS |

TABLE 2

Heavy chain antibody sequences.

| Name | Description | SEQ ID NO | Sequence |
|---|---|---|---|
| AB21 | HVR-H1<br>HVR-H2<br>HVR-H3 | 19<br>20<br>21 | SNAMS<br>GISAGGSDTYYPASVKG<br>ETWNHLFDY |
| AB21 VH MutAll | VH | 26 | EVQLVESGGGVVQPGGSLRLSCAASGFTFSSNAMS WVRQAPGKGLEWVAGISAGGSDTYYPASVKGRFTI SRDNSKNTLNLQMNSLRAEDTAVYYCARETWNHL FDYWGQGTLVTVSS |
| AB21_ VH MutAll_ IgG1 wt | Heavy chain | 58 | EVQLVESGGGVVQPGGSLRLSCAASGFTFSSNAMS WVRQAPGKGLEWVAGISAGGSDTYYPASVKGRFTI SRDNSKNTLNLQMNSLRAEDTAVYYCARETWNHL FDYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNTK VDKKVEPKSCDKTHTCPPCPAPELLGGPSVFLFPPK PKDTLMISRTPEVTCVVVDVSHEDPEVKFNWYVDG VEVHNAKTKPREEQYNSTYRVVSVLTVLHQDWLN GKEYKCKVSNKALPAPIEKTISKAKGQPREPQVYTL PPSREEMTKNQVSLTCLVKGFYPSDIAVEWESNGQ PENNYKTTPPVLDSDGSFFLYSKLTVDKSRWQQGN VFSCSVMHEALHNHYTQKSLSLSPG |
| AB21_ HC mutall_ IgG1A AA dead | Heavy chain | 59 | EVQLVESGGGVVQPGGSLRLSCAASGFTFSSNAMS WVRQAPGKGLEWVAGISAGGSDTYYPASVKGRFTI SRDNSKNTLYLQMNSLRAEDTAVYYCARETWNHL FDYWGQGTLVTVSSASTKGPSVFPLAPSSKSTSGGT AALGCLVKDYFPEPVTVSWNSGALTSGVHTFPAVL QSSGLYSLSSVVTVPSSSLGTQTYICNVNHKPSNTK VDKKVEPKSCDKTHTCPPCPAPEAAGAPSVFLFPPK PKDTLMISRTPEVTCVVVDVSHEDPEVKFNWYVDG VEVHNAKTKPREEQYASTYRVVSVLTVLHQDWLN GKEYKCKVSNKALPAPIEKTISKAKGQPREPQVYTL PPSREEMTKNQVSLTCLVKGFYPSDIAVEWESNGQ PENNYKTTPPVLDSDGSFFLYSKLTVDKSRWQQGN VESCSVMHEALHNHYTQKSLSLSPG |
| AB21_ VH MutAll_ IgG2 wt | Heavy chain | 60 | EVQLVESGGGVVQPGGSLRLSCAASGFTFSSNAMSW VRQAPCKGLEWVAGISAGGSDTYYPASVKGRFTISR DNSKNTLYLQMNSLRAEDTAVYYCARETWNHLFDY WGQGTLVTVSSASTKGPSVFPLAPCSRSTSESTAALG CLVKDYFPEPVTVSWNSGALTSGVHTFPAVLQSSG LYSLSSVVTVPSSNFGTQTYTCNVDHKPSNTKVDKT VERKCCVECPPCPAPPVAGPSVFLFPPKPKDTLMISRT PENTCVVVDVSHEDPEVQFNWYVDGVEVHNAKTKP REEQFNSTFRVVSVLTVVHQDWLNGKEYKCKVSNK GLPAPIEKTISKTKGQPREPQVYTLPPSREEMTKNQ VSLTCLVKGFYPSDIAVEWESNGQPENNYKTTPPML DSDGSFFLYSKLTVDKSRWQQGNVFSCSVMHEALH NHYTQKSLSLSPG |
| AB21_ VH MutAll_ IgG2 Da | Heavy chain | 61 | EVQLVESGGGVVQPGGSLRLSCAASGFTFSSNAMS WVRQAPGKGLEWVAGISAGGSDTYYPASVKGRFTI SRDNSKNTLYLQMNSLRAEDTAVYYCARETWNHL FDYWGQGTLVTVSSASTKGPSVFPLAPCSRSTSEST AALGCLVKDYFPEPVTVSWNSGALTSGVHTFPAVL QSSGLYSLSSVVTVPSSNFGTQTYTCNVDHKPSNTK |

TABLE 2-continued

Heavy chain antibody sequences.

| Name | Description | SEQ ID NO | Sequence |
|---|---|---|---|
| | | | VDKTVERKCCVECPPCPAPPVAGPSVFLFPPKPKDT LMISRTPEVTCVVVDVSHEDPEVQFNWTYVDGVEV HNAKTKPREEQFNSTERVVSVTTVVHQDWLNGKE YKCKVSNKGLPSSIEKTISKTKGQPREPQVYTLPPSR EEMTKNQVSLTCLVKGITYPSDIAVEWESNGQPENN YKTTPPMLDSDGSFFLYSKITVDKSRWQQGNVFSC SVMHEALHNHYTQKSLSLSPG |
| AB21_VH MutAll_ IgG4 S228P | Heavy chain | 62 | EVQLVESGGGVVQPGGSLRLSCAASGFTFSSNAMS WVRQAPGKGLEWVAGISAGGSDTYYPASVKGRFTI SRDNSKNTLYLQMNSLRAEDTAVYYCARETWNHL FDYWGQGTLVTVSSASTKGPSVFPLAPCSRSTSEST AALGCLVKDYFPEPVTVSWNSGALTSGVHTFPAVL QSSGLYSLSSVVTVPSSSLGTKTYTCNVDHKPSNTK VDKRVESKYGPPCPPCPAPEFLGGPSVFLFPPKPKD TLMISRTPEVTCVVVDVSQEDPEVQFNWYVDGVE VHNAKTKPREEQFNSTYRVVSVLTVLHQDWLNGK EYKCKVSNKGLPSSIEKTISKAKGQPREPQVYTLPP SQEEMTKNQVSLTCLVKGFYPSDIAVEWESNGQPE NNYKTTPPVLDSDGSFFLYSRLTVDKSRWQEGNVF SCSVMHEALHNHYTQKSLSLSLG |
| AB21_ HC_wt | VH | 77 | DVQLVESGGGVVRPGESLRLSCAASGFTFSSNAMS WVRQAPGKGLEWLAGISAGGSDTYYPASVKGRFTI SRDNSKNTLYLQMNTLTAEDTAVYYCARETWNHL FDYWGLGTLVTVSS |
| AB25_ HC_wt | VH | 78 | DVQLVESGGGVVRPGESLRLSCEASGFTFSSNAMS WVRQAPGKGLEWVAGISSGSDTYYGDSVKGRLTIS RDNSKNILYLQMNSLTAEDTAVYYCARETWNHLF DYWGLGTLVTVSS |
| AB27_ HC_wt | VH | 79 | DVQLVESGGGVVRPGESLRLSCAVSGFRFSSYAMS WVRQAPGKGLEWVSGISSGGDTYYVDSVKGRFTIS RDNSKNTLYLQVNSLTAEDTAIYYCARETWNHLFD YWGLGTLVFVSS |
| AB66 HC_wt | VH | 80 | DVQLVESGGGVVRPGESLRLSCAASGFTFSSYAMS WVRQAPGKGLEWLAGISAGGSDTYYIDSVKGRETI SRDNPKNSLYLQMSSLTAEDTAVYYCARETWNHL FDYWGLGTLVTVSS |
| AB25_ HC_ Mutall | VH | 81 | EVQLVESGGGVVQPGGSLRLSCAASGFTFSSNAMS WVRQAPGKGLEWVAGISSGSDTYYGDSVKGRFTIS RDNSKNTLYLQMNSLTAEDTAVYYCARETWNHLF DYWGQGTLVTVSS |
| AB25 VH MutAll M34V | VH | 82 | EVQLVESGGGVVQPGGSLRLSCAASGFTFSSNAVS WVRQAPGKGLEWVAGISSGSDTYYGDSVKGRFTIS RDNSKNTLYLQMNSLTAEDTAVYYCARETWNHLF DYWCQGTLVTVSS |
| AB27_ HC_ Mutall | VH | 83 | EVQLVESGGGVVQPGGSLRLSCAASGFRFSSYAMS WVRQAPGKGLEWVSGISSGGDTYYVDSVKGRFTIS RDNSKNTLYLQMNSLRAEDTAVYYCARETWNHLF DYWGQGTLVTVSS |
| AB27 VH MutAll M34V | VH | 84 | EVQLVESGGGVVQPGGSLRLSCAASGFRFSSYAVS WVRQAPGKGLEWVSGISSGGDTYYVDSVKGRFTIS RDNSKNTLYLQMNSLRAEDTAVYYCARETWNHLF DYWGQGTLVTVSS |
| AB21 NTH MutAll M34V | VH | 85 | EVQLVESGGGVVQPGGSLRLSCAASGFTFSSNAVS WVRQATGKGLEWVAGISAGGSDTYYPASVKGRFTI SRDNSKNTLYLQMNSLRAEDTAVYYCARETWNHL FDYWGQGTLVTVSS |
| AB21_ HC_ MutAll_ M311 | VH | 86 | EVQLVESGGGVVQPGGSLRLSCAASGFTFSSNALS WVRQAPGKGLEWVAGISAGGSDTYYPASVKGRFTI SRDNSKNCLYLQMNSLRAEDTAVYYCARETWNHL FDYWGQGTLVTVSS |

TABLE 2-continued

Heavy chain antibody sequences.

| Name | Description | SEQ ID NO | Sequence |
|---|---|---|---|
| AB25_HC_MutAll_M311 | VH | 87 | EVQLVESGGGVVQPGGSLRLSCAASGFTFSSNALS WVRQAPGKGLEWVAGISSGSDTYYGDSVKGRFTIS RDNSKNTLYLQMNSLTAELYCAVYYCARETWNHLF DYWGQGTLVTVSS |
| AB27_HC_MutAll_M34L | VH | 88 | EVQLVESGGGVVQPGGSLRLSCAASGFRFSSYALS WVRQAPGKGLEWNTSGISSGGDTYYVDSVKGRFTIS RDNSKNTLYLQMNSLRAEDTAVYYCARETWNHLF DYWGQGTLVTVSS |
| S16 | VH | 89 | DVQLVESGGGVVRPGESLRLSCAVSGFRFSSYAMSWVR QAPGKGLEWVSGISSGGDTYYVDSVKGRFTISRDNSKNT LYLQVNSLTAEDTAIYYCARETWNHLFDYWGLGTLVTV SS |
| S17 | VH | 90 | DVQLVESGGAVVRPGESLRLSCAASGFTFSSYAMSWVR QAPCKGLEWLAGISAGGSDTYNIDSVKGRFTISRDNSEN SLYLQMNSLTAEDTAVYYCARETWNHLFDYWGLGTLV TVSS |
| S22 | VH | 91 | DVQLVESGGGVVRPGESLRLSCAASGFTFSSYAMSWVR QAPGKGLEWLAGISAGGSDTYYIDSVKGRFTISRRQFQE QSLSPNEPALTAEDTAVYYCARETWNHLFDYWGLGTLV TVSS |
| S23 | VH | 92 | DVQLVESGGGVVRPGESLRLSCAASGFETSSHAMSWVR QAPGKGLEWLAGLSAGGSDTYYIDSVKGRFFISRDNSKS SLYLRMNSLTAEDTAVYYCARETWNHLFDYWGLGTLV TVSS |
| S24 | VH | 93 | DVQLVESGGGVVRPGESERLSCAASGFTFSSNAMSWVR QAPGKGLEWLAGISAGGSDTYYPASVKGRFTISRDNTKN TLYLQMNTLTAEDTAVYYCARETWNHLFDYWGLGTLV TVSS |
| S26 | VH | 94 | DVQLVESGGGVVRPGESLRLSCAASGFTFSTYAMSWVR QAPGKGLEWVSGISASGSGTYYCDSVKGRFTMSRDNSK NTLYLQMNSLTAEDTAVYYCARETWNHLFDYWGLGTL VTVSS |
| S28 | VH | 95 | DVQLVESGGGVVRPGESLRLSCAASGFSFSSNAMSWVR QAPGKGLEWVAGISASGDTYYSGSMKGRFTISRDNSKN TLYLQMNSLTAEDTAVYNCARETWNHLFDYWGLGTLV TVSS |
| S29 | VH | 96 | DVQLVESGGGVVRPGIESLRLSCAVSGFRFSSYAMSWVR QAPGKGLEWVSGISSDSDAYYVDSVKGRFTISRDNSKNT LYLQVNSLTAEDTAVYYCARETWNHLFDYWGLGTMVT VSS |
| S30 | VH | 97 | DVQLVESGGGVVRPGESLRLSCEASGFTFSSDAMSWVR QAPGKGLEWVSGISSGSSTYYGGSVKGRFTISRDNSKNT LYLQMNSILTAEDTAVYYCARETWHLALFDYWGLGTLVT VSS |
| S55 | VH | 98 | DVQLVESGGGVVRPGESLRLSCAVSGFRFSSYAMSWVR QAPGKGLEWVSGISSGGDTYYVDSVKGRFTISRDNSKNT LYLQVNSLTAEDTAIYYCARETWNHLFDYWGLGTLVTV SS |
| S56 | VH | 99 | DVQLVESGGGVVRPGESLRLSCAASGFTFSSYAMSWVR QAPGKGLEWLAGISAGGSDTYYIDSVKGRFTISRDNSKN SLYLQVNSLTAEDTAVYYCARETWNHLFDYWGLGTLV TVSS |
| S59 | VH | 100 | DVQLVESGGGVVRPGESLRLSCAVSGFRFSSHAMSWVR QAPGKGLEWVSGISSGGDTYYVDSVKGRFTSRDNSKNT LYLQVNSLTAEDTAIYYCARETWNHLFDYWGLGMVTV SS |
| S60 | VH | 101 | DVQLVDSGGGVVRPGESLRLSCAASGFTFSSYAMSWVR QAPGKGLEWLAGISAGGSDTYYIDSVKGRFTISRDNSKN SLYLQMNSLTAEDTAVYYCARETWNHLFDYWGLGTLV TVSS |

TABLE 2-continued

Heavy chain antibody sequences.

| Name | Description | SEQ ID NO | Sequence |
|---|---|---|---|
| S65 | VH | 102 | DVQLVESGGGVVRPGESLRLSCAASGFTFSSYAMSWVRQAPGKGLEWLAGISAGGSDTYYIDSVKGRETISRDNSKNSLYLQMNSLTAEDTAVYYCARETWNHLFDYWGLGTLVTVSS |
| S69 | VH | 103 | DLQLVESGGGVVRPGESLRLSCAASGFTFSSYAMSWVRQAPGKGLEWLAGISAGGSDTYYIDSVKGRFTISRDNSKNSLYLQMNSLTAEDTAVYYCARETWNHLFDYWGLGTLVTVSS |
| S70 | VH | 104 | DVQLVESGGGVVRPGESLRLSCAASGFTFSSYAMSWVRQAPGKGLEWLAGISAGGSDAYYIDSVKGRFTISRDNSKNSLYLQMNSLTAEDTAVYYCARETWNHLFDYWGLGTLVTVSS |
| S71 | VH | 105 | DVQLVESGGGVVRPGESLRLSCAASGFTFSSYAMSWVRQAPGKGLEWLAGISAGGSDTYTIDSVKGRFTISRDNSKNSLYLQMNSLTAEDTAVYYCARETWNHLFDYWGLGTLVTVSS |
| S73 | VH | 106 | DVQLVESGGGVVRPGESLRLSCAASGFTFSSYAMSWARQAPGKGLEWVAGISSGSDTYYGDSVKGRLTISRDNSKNILYLQMNSLTAEDTAVYYCARETWNHLFDYWGLGTLVTVSS |
| S74 | VH | 107 | DVQLVESGGGVVRPGESLRLSCAASGFTFSSNAMSWVRQAPGKGLEWLAGISAGDSDTYYPASVKGRFTISRDNPKNTLYLQMNTLTAEDTAVYYCARETWNHLFDYWGLGTLVTVSS |
| S76 | VH | 108 | DVQLVESGGGVVRPGESLRLSCAASGFTFSSYAMSWVRQAPGKGLEWLAGISAGGSDTYYIDSVKGRFTISRDNSKNSLYLQMNSLTAEDTAVYYCARETWNHLFDYWGLGTLVTVSS |
| S201 | VH | 109 | DVQLVESGGAVVRPGETLRLSCTASGFTFSSYAMSWVRQAPGKGLEWVSGISASGSDTYYADSVKGRSTISRDNSKNTLYLRMSSLTAEDTAVYYCARETWNHLFDYWGLGTLVTVSS |
| S202 | VH | 110 | DVQLVESGGGVVRPGESLRLSAASGFTFSSYAMSWVRQAPGKGLEWLAGISAGGSDTYTIDSVKGRFTISRDNSKNSLYLQMNSLTAEDTAVYYCARETWNHLFDYWGLGTLVTVSS |
| S206 | VH | 111 | DVQLVESGGAVVRPGETLRLSCTASGFTFSSYAMSWVRQAPGKGLEWVSGISASGSDTYYADSVKGRSTISRDNSKNTLYLRMSSLTAEDTAVYYCARETWNHLFDYWGLGGTLVTLSS |
| AB25 VH Mutall_IgG1 wt | Heavy chain | 114 | EVQLVESGGGVVQPGGSLRLSCAASGFTFSSNAMSWVRQAPGKGLEWVAGISSGSDTYYGDSVKGRFTISRDNSKNTLYLQMNSLTAEDTAVYYCARETWNHLFDYWGQMTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKTKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPG |
| AB25 VH Mutall_IgG1 dead | Heavy chain | 115 | EVQLVESGGGVVQPGGSLRLSCAASGFTFSSNAMSWVRQAPGKGLEWVAGISSGSDTYYGDSVKGRFTISRDNSKNTLYLQMNSLTAEDTAVYYCARETWNHLFDYWGQGTLYVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGAPSVFLEPPKPKDTLMISRTPEVTCVVVDVSHEDPEVKFNWYVDGVEVHNAK |

TABLE 2-continued

Heavy chain antibody sequences.

| Name | Description | SEQ ID NO | Sequence |
|---|---|---|---|
| | | | TKPREEQYASTYRVVSVLTVLHQDWLNGKEY KCKVSNKALPAPIEKTISKAKGQPREPQVYTLP PSREEMTKNQVSLTCLVKGFYPSDIAVEWESN GQPENNYKTTPPVLDSDGSFFLYSKLTVDKSR WQQGNVFSCSVMHEALHNHYTQKSLSLSPG |
| AB25 WH Mutall_ IgG2 wt | Heavy chain | 116 | EVQLNESGGGVVQPGGSLRLSCAASGFTFSSN AMSWVRQAPGKGLEWVAGISSGSDTYYGDSV KGRFTISRDNSKNTLYLQMNSLTAEDTAVYYC ARETWNMLFDYWGQGTLVTVSSASTKGPSVFP LAPCSRSTSESTAALGCLVKDYFPEPVTVSWNS GALTSGVHTFPAVLGSSGLYSLSSVVTVPSSNF GTQTYTCNVDHKPSNTKVDKTVERKCCVECPP CPAPPVAGPSVFLFPPKPKDTLMISRTPEVTCV VVDVSHEDPEVQFNWYVDGVEVHNAKTKPRE EQFNSTFRVVSVLTVVHQDWLNGKEYKCKVS NKGLPAPIEKTISKTKGQPREPQVYTLPPSREE MTKNQVSLTCLVKGFYPSDIAVEWESNGQPEN NYKTTPPMLDSDGSFFLYSKLTVDKSRWQQG NVFSCSVMHEALHNHYTQKSLSLSPG |
| AB25 VH_ Mutall_ IgG2 Da | Heavy chain | 117 | EVQLVESGGGVVQPGGSLRLSCAASGFTFSSN AMSWVRQAPGKGLEWVAGISSGSDTYYGDSV KGRFTISRDNSKNTLYLQMNSLTAEDTAVYYC ARETWNHLFDYWGQGTLVTVSSASTKGPSVFP LAPCSRSTSESTAALGCLYKDYFPEPVSWNS GALTSGVHTFPAVLGSSGLYSLSSVVTVPSSNF GTQTYTCNVDHKPSNTKVDKTVERKCCVECPP CPAPPVAGPSVFLFPPKPKDTLMISRTPEVTCV VVDVSHEDPEVQFNWYVDGVEVHNAKTKPRE EQFNSTFRVVSVLTVVHQPWLNGKEYKCKVS NKGLPSSIEKTISKTKGQPREPQVYTLPPSREEM TKNQVSLTCLVKGFYPSDIAVEWESNGQPENN YKTTPPMLDSDGSFFLYSKLTVDKSRWQQGN VFSCSVMHEALHNHYTQKSLSLSPG |
| AB25 VH Mutall_ IgG4_ S228_ P | Heavy chain | 118 | EVQLVESGGGVVQPGGSLRLSCAASGFTFSSN AMSWVRQAPGKGLEWVAGISSGSDTYYGDSV KGRFTISRDNSKNTLYLQMNSLTAEDTAVYYC ARETWNHLFDYWGQGTLVTVSSASTKGPSVFP LAPCSRSTSESTAALGCLVKDYFPEPVTVSWNS GALTSGVHTFPAVLQSSGLYSLSSVVTVPSSSL GTKTYTCNVDHKPSNTKVDKRVESKYGPPCPP CPAPEFLGGPSVFLFPPKPKDTLMISRTPEVTCV VVDVSQEDPEVQFNWYVDGVEVHNAKTKPRE EQFNSTYRVVSVLTVLHQDWLNGKEYKCKNS NKGLPSSIEKTISKAKGQPREPQVYTEPPSQEE MTKNQVSLTCLVKGFYPSDIAVEWESNGQPEN NYKTTPPVLDSDGSFFLYSRLTVDKSRWQEGN VFSCSVMHEALHNHYTQKSLSLSLG |
| AB27 VH_ Mutall IgG1 wt | Heavy chain | 119 | EVQLVESGGGVVQPGGSLRLSCAASGFRFSSY AMSWVRQAPGKGLEWVSGISSGGDTYYVDSV KGRFTISRDNSKNTLYLQMNSLRAEDTAVYYC ARETWNHLFDYWGQGTLVTVSSASTKGPSVFP LAPSSKSTSGGTAALGCLVKDYFPEPVTVSWN SGALTSGVHTFPAVLQSSGLYSLSSVVTVPSSS LGTQTYICNVNHKPSNTKVDKKVEPKSCDKTH TCPPCPAPELLGGPSVFLFPPKPKDTLMISRTPE VTCVVVDVSHEDPEVKFNWYVDGVEVHNAK TKPREEQYNSTYRVVSVLTVLHQDWLNGKEY KCKVSNKALPAPIEKTISKAKGQPREPQVYTLP PSREEMTKNQVSLTCLVKGFYPSDIAVEWESN GQPENNYKTTPPVLDSDGSTFLYSKLTVDKSR WQQGNVFSCSVMHEALHNHYTQKSLSLSPG |
| AB27 VH_ Mutall_ IgG1 dead | Heavy chain | 120 | EVQLVESGGGVVQPGGSLRLSCAASGFRFSSY AMSWVRQAPGKGLEWVSGISSGGDTYYVDSV KGRFTISRDNSKNTLYLQMNSLRAEDTAVYYC ARETWNHLFDYWGQGTLVTVSSASTKGPSVFP LAPSSKSTSGGTAALGCLVKDYFPEPVTVSWN SGALTSGVHTFPAVLQSSGLYSLSSVVTVPSSS LGTQTYICNVNHKPSNKVDKKVEPKSCDKTH TCPPCPAPEAAGAPSVFLFPPKPKDTLMISRTPE VTCVVVDVSHEDPEVKFNWYVDGVEVHNAK |

TABLE 2-continued

Heavy chain antibody sequences.

| Name | Description | SEQ ID NO | Sequence |
|---|---|---|---|
| | | | TKPREEQYASTYRVVSVLTVLHQDWLNGKEY
KCKVSNKALPAPIEKTISKAKGQPREPQVYTLP
PSREEMTKNQVSLTCLVKGFYPSDIAVEWESN
GQPENNYKTTPPVLDSDGSFFLYSKLTVDKSR
WQQGNVFSCSVMHEALHNHYTQKSLSLSPG |
| AB27 VH_Mutal1_IgG2 wt | Heavy chain | 121 | EVQLVESGGGVVQPGGSLRLSCAASGFRFSSY
AMSWVRQAPGKGLEWVSGISSGGDTYYVDSV
KGRFTISRDNSKNTLYLQMNSLRAEDTAVYYC
ARETWNHLFDYWGQGTLVTVSSASTKGPSVFP
LAPCSRSTSESTAALGCLVKDYFPEPVTVSWNS
GALTSGVHTFPAVLQSSGLYSLSSVVTVPSSNF
GTQTYTCNVDHKPSNTKVDKTVERKCCVECPP
CPAPPVAGPSVFLFPPKPKDTLMISRTPEVTCV
VVDVSHEDPEVQFNWYVDGVEVHNAKTKPRE
EQFNSTFRVVSVLTVVHQDWLNGKEYKCKVS
NKGLPAPIEKTISKTKGQPREPQVYTLPPSREE
MTKNQVSLTCLVKGFYPSDIAVEWESNGQPEN
NYKTTPPMLDSDGSFFLYSKLTVDKSRWQQG
NVFSCSVMHEALHNHYTQKSLSLSPG |
| AB27 VH_Mutal1_IgG2 Da | Heavy chain | 122 | EVQLVESGGGVVQPGGSLRLSCAASGFRFSSY
AMSWVRQAPGKGLEWVSGISSGGDTYYVDSV
KGRFTISRDNSKNTLYLQMNSLRAEDTAVYYC
ARETWNHLFDYWGQGTLVTVSSASTKGPSVFP
LAPCSRSTSESTAALGCLVKDYFPEPVTVSWNS
GALTSGVHTFPAVLQSSGLYSLSSVVTVPSSNF
GTQTYTCNVDHKPSNTKVDKTVERKCCVECPP
CPAPPVAGPSVFLFPPKPKDTLMISRTPEVTCV
VVDVSHEDPEVQFNWYVDGVEVHNAKTKPRE
EQFNSTFRVVSVLTVVHQDWLNGKEYKCKVS
NKGLPSSIEKTISKTKGQPREPQVYTLPPSREEM
TKNQVSLTCLVKGFYPSDIAVEWESNGQPENN
YKTTPPMLDSDGSFFLYSKLTVDKSRWQQGN
VFSCSVMHEALHNHYTQKSLSLSPG |
| AB27 VH_Mutal1_IgG4_S228P | Heavy chain | 123 | EVQLVESGGGVVQPGGSLRLSCAASGFRFSSY
AMSWVRQAPGKGLEWVSGISSGGDTYYVDSV
KGRFTISRDNSKNTLYLQMNSLRAEDTAVYYC
ARETWNHLFDYWGQGTLVTVSSASTKGPSVFP
LAPCSRSTSESTAALGCLVKDYFPEPVTVSWNS
GALTSGVHTFPAVLQSSGLYSLSSVVTVPSSSL
GTKTYTCNVDHKPSNTKVDKRVESKYGPPCPP
CPAPEFLGGPSVELFPPKPKDTLMISRTPEVTCV
VVDVSQEDPEVQFNWYVDGVEVHNAKTKPRE
EQFNSTYRVVSVLTVLHQDWLNGKEYKCKVS
NKGLPSSIEKTISKAKGQPREPQVYTLPPSQEE
MTKNQVSLTCLVKGFYPSDIAVEWESNGQPEN
NYKTTPPVLDSDGSFFLSRLTVDKSRWQEGN
VFSCSVMHEALHNHYTQKSLSLSLG |
| AB21_MutAll_IgG1_AAA | Heavy chain | 124 | EVQLVESGGGVVQPGGSLRLSCAASGFTFSSN
AMSWVRQAPGKGLEWVAGISAGGSDTYYPAS
VKGRFTISRDNSKNTLYLQMNSLRAEDTAVYY
CARETWNHLFDYWGQGTLVTVSSASTKGPSV
FPLAPSSKSTSGGTAALGCLVKDYFPEPVTVSW
NSGALTSGVHTFPAVLQSSGLYSLSSVVTVPSS
SLGTQTYICNVNHKPSNTKVDKKVEPKSCDKT
HTCPPCPAPEAAGAPSVFLFPPKPKDTLMISRTP
EVTCVVVDVSHEDPEVKFNWYVDGVEVHNA
KTKPREEQYNSTYRVVSVLTVLHQDWLNGKE
YKCKVSNKALPAPIEKTISKAKGQPREPQVYTL
PPSREEMTKNQVSLTCLVKGFYPSDIAVEWES
NGQPENNYKTTPPVLDSDGSFFLYSKLTVDKS
RWQQGNVFSCSVMHEALHNHYTQKSLSLSPG |
| AB21_MutAll_IgG2 wildtype_C232S | Heavy chain | 125 | EVQLVESGGGVVQPGGSLRLSCAASGFTFSSN
AMSWVRQAPGKGLEWVAGISAGGSDTYYPAS
VKGRFTISRDNSKNTLYLQMNSLRAEDTAVYY
CARETWNHLFDYWGQGTLVTVSSASTKGPSV
FPLAPCSRSTSESTAALGCLVKDYFPEPVTVSW
NSGALTSGVHTFPAVLQSSGLYSLSSVVTVPSS
NFGTQTYTCNVDHKPSNTKVDKTVERKSCVE
CPPCPAPPVAGPSVFLFPPKPKDTLMISRTPEVT
CVVVDVSHEDPEVQFNWYVDGVEVHNAKTK |

TABLE 2-continued

Heavy chain antibody sequences.

| Name | Description | SEQ ID NO | Sequence |
|---|---|---|---|
| | | | PREEQFNSTFRVVSVLTVVHQDWLNGKEYKC KVSNKGLPAPIEKTISKTKGQPREPQVYTLPPSR EEMTKNQVSLTCLVKGFYPSDIAVEWESNGQP ENNYKTTPPMLDSDGSFFLYSKLTVDKSRWQQ GNVFSCSVMHEALHNHYTQKSLSLSPG |
| AB21_ MutAll_ IgG2_ wildtype_ C2 33S | Heavy chain | 126 | EVQLVESGGGVVQPGGSLRLSCAASGFTFSSN AMSWVRQAPGKGLEWVAGISAGGSDTYYPAS VKGRFTISRDNSKNTLYLQMNSLRAEDTAVYY CARETWNHLFDYWGQGTLVTVSSASTKGPSV FPLAPCSRSTSESTAALGCLVKDYFPEPVTVSW NSGALTSGVHTFPAVLQSSGLYSLSSVVTVPSS NTGTQTYTCNVDHKPSNTKVDKTVERKCSVE CPPCPAPPVAGPSVFLFPPKPKDTLMISRTPEVT CVVVDVSHEDPEVQFNWYNDGVEVHNAKTK PREEQFNSTFRVVSVLTVVHQDWLNGKEYKC KVSNKGLPAPIEKTISKTKGQPREPQVYTLPPSR EEMTKNQVSLTCLVKGFYPSDIAVEWESNGQP ENNYKTTPPMLDSDGSFFLYSKLTVDKSRWQQ GNVFSCSVMHEALENHYTQKSLSLSPG |
| AB21_ MutAll_ IgG2Da_ C2 32S | Heavy chain | 127 | EVQLVESGGGVVQPGGSLRLSCAASGFTFSSN AMSWVRQAPGKGLEWVAGISAGGSDTYYPAS VKGRFTISRDNSKNTLYLQMNSLRAEDTAVYY CARETWNHLFDYWGQGTLVTVSSASTKGPSV FPLAPCSRSTSESTAALGCLVKDYFPEPVTVSW NSGALTSGVHTFPAVLQSSGLYSLSSVVTVPSS NFGTQTYTCNVDHKPSNTKNDKTVERKSCVE CPPCPAPPVAGPSVFLFPPKPKDTLMISRTPEVT CVVVDVSHEDPEVQFNWYVDGVEVHNAKTK PREEQFNSTFRVVSVLTVVHQDWLNGKEYKC KVSNKGLPSSIEKTISKTKGQPREPQVYTLPPSR EEMTKNQVSLTCLVKGFYPSDIAVEWESNGQP ENNYKTTPPMLDSDGSFFLYSKLTTVDKSRWQQ GNVFSCSVMHEALHNHYTQKSLSLSPG |
| AB21_ MutAll_ IgG2Da_ C2 33S | Heavy chain | 128 | EVQLVESGGGVVQPGGSLRLSCAASGFTFSSN AMSWVRQAPGKGLEWVAGISAGGSDTYYPAS VKGRFTISRDNSKNTLYLQMNSLRAEDTAVYY CARETWNHLFDYWGQGTLVTVSSASTKGPSV FPLAPCSRSTSESTAALGCLVKDYFPEPVTVSW NSGALTSGVHTFPAVLQSSGLYSLSSVVTVPSS NFGTQTYTCNVDHKPSNTKVDKTVERKCSVE CPPCPAPPVAGPSVFLFPPKPKDTLMISRTPEVT CVVVDVSHEDPEVQFNWYNDGVEVHNAKTK PREEQFNSTFRVVSVETVVHQDWLNGKEYKC KVSNKGLPSSIEKTISKTKGQPREPQVYTLPPSR EEMTKNQVSLTCLVKGFYPSDIAVEWESNGQP ENNYKTTPPMLDSDGSFFLYSKLTVDKSRWQQ GNVFSCSVMHEALHNHYTQKSLSLSPG |
| AB21_ MutAll_ IgG2_ N297 A | Heavy chain | 129 | EVQLVESGGGVVQPGGSLRLSCAASGFTFSSN AMSWVRQAPGKGLEWVAGISAGGSDTYYPAS VKGRFTISRDNSKNTLYLQMNSLRAEDTAVYY CARETWNHLFDYWGQGTLVTVSSASTKGPSV FPLAPCSRSTSESTAALGCLVKDYFPEPVTVSW NSGALTSGVHTFPAVLQSSGLYSLSSVVTVPSS NFGTQTYTCNVDHKPSNTKVDKTVERKCCVE CPPCPAPPVAGPSVFLFPPKPKDTLMISRTPEVT CVVVDVSHEDPEVQFNWYVDGVEVENAK PREEQFASTFRVVSVLTVVHQDWLNGKEYKC KVSNKGLPAPIEKTISKGQPREPQVYTLPPSR EEMTKNQVSLTCLVKGFYPSDIAVEWESNGQP ENNYKTTPPMLDSDGSFFLYSKLTVDKSRWQQ GNVFSCSVMHEALHNHYTQKSLSLSPG |
| AB21_ MutAll_ IgG2_ N297A_ C23 2S | Heavy chain | 130 | EVQLVESGGGVVQPGGSLRLSCAASGFTFSSN AMSWVRQAPGKGLEWVAGISAGGSDTYYPAS VKGRFTISRDNSKNTLYLQMNSLRAEDTAVYY CARETWNHLMYWGQGTLVTVSSASTKGPSV FPLAPCSRSTSESTAALGCLVKDYTFPEPVTVSW NSGALTSGVHTFPAVLQSSGLYSLSSVVTVPSS NFGTQTYTCNVDHKPSNTKVDKTVERKSCVE CPPCPAPPVAGPSVFLFPPKPKDTLMISRTPEVT CVVVDVSHEDPENTQFNWYNDGVEVHNAKTK |

TABLE 2-continued

Heavy chain antibody sequences.

| Name | Description | SEQ ID NO | Sequence |
|---|---|---|---|
| | | | PREEQFASTFRVVSVLTVVHQDWLNGKEYKC KVSNKGLPAPIEKTISKTKGQPREPQVYTLPPSR EEMKNQVSLTCLVKGFYPSDIAVEWESNGQP ENNYKTTPPMLDSDGSFFLYSKLTVDKSRWQQ GNVFSCSVMHEALHNHYTQKSLSLSPG |
| AB21_ MutAll_ IgG2_ N297A_ C23 3S | Heavy chain | 131 | EVQLVESGGGVVQPGGSLRLSCAASGFTFSSN AMSWVRQAPGKGLEWVAGISAGGSDTYYPAS VKGRFTISRIASKNTLYLQMNSLRAEDTAVYY CARETWNHLFDYWGQGTLVTVSSASTKGPSV FPLAPCSRSTSESTAALGCLVKDYFPEPVTVSW NSGALTSGVHTFPAVLQSSGLYSLSSVVTVPSS NFGTQTYTCNVDHKPSNTKVDKTVERKCSVE CPPCPAPPVAGPSVFLFPPKPKDTLMISRTPEVT CVVVDVSHEDPEVQFNWYNDGVEVHNAKTK PREEQFASTFRVVSVLTVVHQDWLNGKEYKC KVSNKGLPAPIEKTISKTKGQPREPQVYTLPPSR EEMKNQVSLTCLVKGFYPSDIAVEWESNGQP ENNYKTTPPMLDSDGSFFLYSKLTVDKSRWQQ GNVFSCSVMHEALHNHYTQKSLSLSPG |

As described supra, various techniques for delineating hypervariable regions (HVRs) or complementarity determining regions (CDRs) are known in the art and can be applied to the variable domain sequences described herein. In some embodiments, an antibody of the present disclosure comprises HVRs as defined by Chothia, Kabat, IMGT, or a combination thereof (e.g., one or more HVRs as defined by one delineation and one or more HVRs as defined by a different delineation). As used herein, unless otherwise specified, the numbering of HVR or CDR residues is defined by Kabat numbering.

In some embodiments, an antibody of the present disclosure binds an extracellular domain (e.g., the D1 domain) of a human SIRP-α v1 polypeptide comprising the amino acid sequence of EEELQVIQPDKSVLVAAGETATLRCTATSLIPVGPIQWFRGAGPGRELIYNQKEGHFP RVTTVSDLTKRNNMDFSIRIGNIT-PADAGTYYCVKFRKGSPDDVEFKSGAGTELSVR AKPS (SEQ ID NO:5). In some embodiments, an antibody of the present disclosure binds an extracellular domain (e.g., the D1 domain) of a human SIRP-α v2 poly peptide comprising the amino acid sequence of EEELQVIQPDKSVSVAAGESAILHCTVTSLIPVG-PIQWFRGAGPARELIYNQKEGHFPR VTTVSES-TKRENMDFSISISNIT-PADAGTYYCVKFRKGSPDTEFKSGAGTELSVRAKPS (SEQ ID NO:6). In some embodiments, an antibody of the present disclosure binds an extracellular domain (e.g., the D1 domain) of a human SIRP-α v1 polypeptide comprising the amino acid sequence of EEELQVIQPDKSVLVAAG-ETATLRCTATSLIPVGPIQWFRGAGPGRELIYNQKEG-HFP RVTTVSDLTKRNNMDFSIRIGNIT-PADAGTYYCVKFRKGSPDDVEFKSGAGTELSVR AKPS (SEQ ID NO:5) and an extracellular domain (e.g., the D1 domain) of a human SIRP-α v2 polypeptide comprising the amino acid sequence of (SEQ ID NO: 6)
EEELQVIQPDKSVSVAAGESAILHCTVTSLIPVGPIQWERGAGPARELIY

NQKEGHFPRVTTVSESTKRENMDFSISISNITPADAGTYYCVKFRKGSPD

TEFKSGAGTELSVRAKPS.

In some embodiments, an antibody of the present disclosure binds an extracellular domain (e.g., the D1 domain) of a monkey SIRP-α polypeptide (e.g., the D1 domain of a monkey SIRP-α polypeptide). In some embodiments, an antibody of the present disclosure binds an extracellular domain (e.g., the D1 domain) of a cynomolgus SIRP-α polypeptide (e.g., found in the organism Macaca fascicularis). In some embodiments, the antibody binds the extracellular domains (e.g., the D1 domains) of at least two different monkey SIRP-α variant polypeptides. In some embodiments, the antibody binds the extracellular domains (e.g., the D1 domains) of at least two different cynomolgus SIRP-α variant polypeptides. For example, in some embodiments, the antibody binds an extracellular domain (e.g., the D1 domain) of a cynomolgus SIRP-α polypeptide comprising the amino acid sequence of EEELQVIQ-PEKSVSVAAGESATLNCTATSLIPVG-PIQWFRGVGPGRELIYHQKEGHFP RVTPVSDPTKRNNMDFSIRISNIT-PADAGTYYCVKFRKGSPDVELKSGAGTELSVRAK PS (SEQ ID NO:11), an extracellular domain (e.g., the D1 domain) of a cynomolgus SIRP-α polypeptide comprising the amino acid sequence of EEELQVIQPEKSVSVAAGD-SATLNCTVSSLIPVGPIQWFRGAGPGRELIYNLKEG-HFP RVTAVSDPTKRNNMDFSIRISNIT-PADAGTYYCVKFRKGSPDVELKSGAGTELSVRA KPS (SEQ ID NO:12), or both.

In some embodiments, an antibody of the present disclosure binds an extracellular domain of a murine or mouse SIRP-α polypeptide (e.g., found in the organism Mus musculus; e.g., the D1 domain of a murine or mouse SIRP-α polypeptide). In some embodiments, the antibody binds the extracellular domains (e.g., the D1 domains) of two or more different murine SIRP-α variant polypeptides. A variety of murine SIRP-α variant polypeptides from different mouse strains are known. In some embodiments, the murine SIRP-α variant polypeptide comprises an amino acid sequence selected from (SEQ ID NO: 7; from 129 mouse strain)
KELKVTQPEKSVSVAAGDSTVLNCTLTSLLPVGPIKWYRGVGQSRLLIYS

FTGEHFPRVTNVSDATKRNNMDFSIRISNVTPEDAGTYYCVKFQKGPSEP

DTEIQSGGGTEVYVLAKPS, (SEQ ID NO: 8; from NOD mouse strain)
TEVKVIQPEKSVSVAAGDSTVLNCTLTSLLPVGPIRWYRGVGQSRQLIYS

FTTEHFPRVTNVSDATKRSNLDFSIRISNVTPEDAGTYYCVKFQRGSPDT

EIQSGGGTEVYVLAK, (SEQ ID NO:9; from C57BL/6 mouse strain)
KELKVTQPEKSVSVAAGDSTVLNCTLTSLLPVGPIRWYRGVGPSRLLIYS

FAGEYVPRIRNVSDTTKRNNMDFSIRISNVTPADAGIYYCVKFQKGSSEP

DTEIQSGGGTEVYVLAK,
and (SEQ ID NO: 10; from BALB/c mouse strain)
TEVKVTQPEKSVSVAAGDSTILNCTVTSLLPVGPIRWYRGVGQSRLLIYS

FTGEHFPRIRNVSDTTKRNNMDFSIRISNVTPEDAGTYYCVKFQRGSSEP

DTEIQSGGGTEVYVLAK.

In some embodiments, an antibody of the present disclosure binds an extracellular domain (e.g., the D1 domain) of a human SIRP family protein. In some embodiments, an antibody of the present disclosure binds an extracellular domain (e.g., the D1 domain) of a human SIRP-β polypeptide. In some embodiments, a human SIRP-β polypeptide refers to a polypeptide encoded by a human SIRPB1 gene, e.g., as described by NCBI Ref Seq ID No. 10326. In some embodiments, the extracellular domain (e.g., the D1 domain) of the human SIRP-β polypeptide comprises the amino acid sequence of (SEQ ID NO: 13)
EDELQVIQPEKSVSVAAGESATLRCAMTSIAPVGPIMWFRGAGAGRELIY

NQKEGHFPRVTTVSELTKRNNLDFSISISNLITADAGTYYCVKFRKGSPD

DVEFKSGAGTELSVRAKPS
or (SEQ ID NO: 14)
EEELQVIQPDKSISVAAGESATLHCTVSLIPVGPIQWFRGAGPGRELIYN

QKEGHFPRVTTVSDLTKRNNMDFSIRISNITPADAGTYYCVKFRKGSPDH

VEFKSGAGTELSVRAKPS.

In some embodiments, an antibody of the present disclosure binds an extracellular domain (e.g., the D1 domain) of a human SIRP-γ polypeptide. In some embodiments, a human SIRP-γ polypeptide refers to a polypeptide encoded by a human SIRPG gene, e.g., as described by NCBI Ref Seq ID No. 55423. In some embodiments, the extracellular domain (e.g., the D1 domain) of the human SIRP-γ polypeptide comprises the amino acid sequence of (SEQ ID NO: 15)
EEELQMIQPEKLLLVTVGKTATLHCTVTSLLPVGPVLWFRGVGPGRELIY

NQKEGHFPRVTTSDLTKRNNMDFSIRISSITPADVGTYYNCVKFRKGSPE

NVEFKSGPGTEMALGAKPS.

In some embodiments, an antibody of the present disclosure binds an IgSF domain of CD47 (e.g., human CD47). In some embodiments, an antibody of the present disclosure binds a polypeptide comprising the amino acid sequence of (SEQ ID NO: 16)
QLLFNKTKSVEFTFSNDTVVIPCFVTNMEAQNTTEVYVKWKFKGRDIYTF

DGALNKSTVPTDFSSAKIEVSQLLKGDASLKMDKSDAVSHTGNYTCEVTE

LTREGETIIELKYRVVS.

In some embodiments, an antibody of the present disclosure modulates SIRP-signaling in a cell expressing a human SIRP-α polypeptide. In some embodiments, an antibody of the present disclosure antagonizes SIRP-α signaling in a cell expressing a human SIRP-α polypeptide. In some embodiments, an antibody of the present disclosure interferes with SIRP-α signaling in a cell expressing a human SIRP-α polypeptide. In some embodiments, an antibody of the present disclosure agonizes SIRP-α signaling in a cell expressing a human SIRP-α polypeptide. In some embodiments, SIRP-α signaling includes one or more intracellular signaling events mediated by activation of a SIRP-α polypeptide, including without limitation tyrosine phosphorylation of the intracellular region of SIRP-α, phosphatase (e.g., SHP1) binding, adaptor protein binding (e.g., SCAP2, FYB, and/or GRB2), and nitric oxide production. Various assays for measuring SIRP-α signaling in a cell include without limitation SIRP-α phosphorylation, SHP1 and SHP2 co-immunoprecipitation, PI3-kinase signaling, cytokine production (both inflammatory IL-12, IL-23, TNFα, IFN and suppressive cytokines IL-10, IL-4, IL-13, cell surface markers levels for M1 and M2 macrophage markers) or dendritic cell activation and function; Kharitonenkov, A. et al. (1997) *Nature* 386: 181-6; Ochi, F. et al. (1997) *Biochem. Biophys. Res. Commun.* 239:483-7; Kim, E. J. et al. (2013) *Inflammation Research* 62:377-86; Yi, T. et al. (2015) *Immunity* 43:764-75.

In some embodiments, the cell expressing a human SIRP-α polypeptide is a leukocyte. In some embodiments, the cell is a macrophage, dendritic cell, neutrophil, eosinophil, or myeloid-derived suppressor cell (MDSC). In some embodiments, an antibody of the present disclosure decreases or antagonizes SIRP-α signaling in a cell expressing a human SIRP-α polypeptide by at least 20%, at least 30%, at least 40%, at least 50%, at least 60%, at least 70%, at least 80%, or at least 90%, e.g., using one or more of the SIRP-α signaling assays described herein or otherwise known in the art. In some embodiments, an antibody of the present disclosure increases or agonizes SIRP-α signaling in a cell expressing a human SIRP-α polypeptide by at least 20%, at least 30%, at least 40%, at least 50%, at least 60%, at least 70%, at least 80%, or at least 90%, e.g., using one or more of the SIRP-α signaling assays described herein or otherwise known in the art.

In some embodiments, an antibody of the present disclosure modulates an intercellular phenotype mediated by SIRP-α. In some embodiments, an antibody of the present disclosure enhances phagocytosis by a macrophage expressing a human SIRP-α polypeptide. For example, phagocytic activity of a macrophage treated or contacted with an antibody of the present disclosure can be compared with phagocytic activity of a macrophage not treated or contacted with the antibody, or phagocytic activity of a macrophage that expresses a human SIRP-α polypeptide and is treated or contacted with an antibody of the present disclosure can be compared with phagocytic activity of a macrophage that does not express a human SIRP-α polypeptide and is treated or contacted with the antibody. Exemplary phagocytosis assays may be found, e.g., in Wieskopf, K. et al(2013) *Science* 341: 88 and Willingham, S. B. et al. (2012) *Proc. Natl. Acad. Sci.* 109:6662-7. In some embodiments, an antibody of the present disclosure increases phagocytosis by a macrophage expressing a human SIRP-α polypeptide by at least 20%, at least 30%, at least 40%, at least 50%, at least 60%, at least 70%, at least 80%, or at least 90%, e.g., using one or more of the phagocytosis assays described herein or otherwise known in the art.

In some embodiments, an antibody of the present disclosure enhances activation of dendritic cell(s) expressing a human SIRP-α polypeptide (e.g., an increased level of activation of individual dendritic cells, or an increased proportion of dendritic cells that are activated within a sample population). For example, activation of dendritic cell(s) treated or contacted with an antibody of the present disclosure can be compared with activation of dendritic cell(s) not treated or contacted with the antibody, or activation of dendritic cell(s) that express a human SIRP-α polypeptide and are treated or contacted with an antibody of the present disclosure can be compared with activation of dendritic cell(s) that do not express a human SIRP-α polypeptide and are treated or contacted with the antibody. Exemplary dendritic cell activation assays are described herein. In some embodiments, an antibody of the present disclosure increases dendritic cell (e.g., expressing a human SIRP-α polypeptide) activation by at least 20%, at least 30%, at least 40%, at least 50%, at least 60%, at least 70%, at least 80%, or at least 90%, e.g., using one or more of the dendritic cell activation assays described herein or otherwise known in the art.

In some embodiments, an antibody of the present disclosure inhibits in vivo growth of a tumor that expresses CD47. For example, in vivo growth of a tumor that expresses CD47 and is treated with an antibody of the present disclosure can be compared against in vivo growth of a tumor that expresses CD47 and is not treated with an antibody of the present disclosure. Exemplary in vivo tumor growth assays are described herein. In some embodiments, an antibody of the present disclosure inhibits in vivo growth of a tumor that expresses CD47 by at least 20%, at least 30%, at least 40%, at least 50%, at least 60%, at least 70%, at least 80%, or at least 90%, e.g., using one or more of the in vivo tumor growth assays described herein or otherwise known in the art.

In some embodiments, an antibody of the present disclosure blocks binding between an extracellular domain (e.g., the D1 domain) of a human SIRP-α polypeptide and an IgSF domain of a human CD47 polypeptide (e.g., a "blocking" antibody). For example, the antibody and the CD47 polypeptide may "compete" for the same SIRP-α epitope, and/or antibody binding to SIRP-α may be mutually exclusive with CD47 binding to SIRP-α. The binding interface between SIRP-α and CD47, as well as residues of both proteins that participate in binding, are known; see Hatherley, D. et al. (2007) *J. Biol. Chem.* 282:14567-75 and Nakaishi, A. et al. (2008) *J. Mol. Biol.* 375:650-60. In some embodiments, an antibody of the present disclosure blocks binding between an extracellular domain (e.g., the D1 domain) of a human SIRP-α polypeptide and an IgSF domain of a human CD47 polypeptide in an in vitro assay such as an ELISA or SPR assay, e.g., using purified SIRP-α and/or CD47 polypeptides.

Antibody Production and Other Antibody Properties

An antibody of the present disclosure may be produced by any means known in the art. Exemplary techniques for antibody production are described below; however these exemplary techniques are provided for illustrative purposes only and are not intended to be limiting. In addition, exemplary antibody properties contemplated for use with the antibodies described herein are further described.

In some embodiments, an antibody that "binds" an antigen has a dissociation constant ($K_D$) for the antigen that is less than or equal to 1 µM at 25° C. In some embodiments, an antibody of the present disclosure has a dissociation constant ($K_D$) for human v1 and/or v2 SIRP-α polypeptides that is less than or equal to 1 µM at 25° C., less than or equal to 500 nM at 25° C., less than or equal to 400 nM at 25° C., less than or equal to 300 nM at 25° C., less than or equal to 250 nM at 25° C. less than or equal to 200 nM at 25° C., less than or equal to 200 nM at 25° C., less than or equal to 100 nM at 25° C., or less than or equal to 50 nM at 25° C. In some embodiments, an antibody that binds a human SIRP-α polypeptide and one or more non-human SIRP-α polypeptides binds the human SIRP-α polypeptide at a higher affinity (e.g., 10-fold or 100-fold higher) than the non-human SIRP-α polypeptide, though it still considered to "bind" both polypeptides. In some embodiments, an antibody that binds a non-human SIRP-α polypeptide and one or more human SIRP-α polypeptides binds the non-human SIRP-α polypeptide at a higher affinity (e.g., 10-fold or 100-fold higher) than the human SIRP-α polypeptide, though it still considered to "bind" both polypeptides. Assays for determining binding affinity are known in the art and include without limitation surface plasmon resonance (SPR), e.g., as described herein; radiolabeled antigen binding assay (RIA), e.g., using a Fab version of an antibody and its antigen; and the like.

To prepare an antigen, the antigen may be purified or otherwise obtained from a natural source, or it may be expressed using recombinant techniques. In some embodiments, the antigen may be used as a soluble protein. In some embodiments, the antigen may be conjugate to another polypeptide or other moiety. e.g., to increase its immunogenicity. For example, an antigen described herein may be coupled with an Fc region. In some embodiments, a cell expressing the antigen on its cell surface may be used as the antigen.

Polyclonal antibodies can be raised in an animal by multiple subcutaneous (sc) or intraperitoneal (ip) injections of the antigen and an adjuvant. For example, descriptions of chicken immunization are described herein. In some embodiments, the antigen is conjugated with an immunogenic protein, e.g., keyhole limpet hemocyanin, serum albumin, bovine thyroglobulin, or soybean trypsin inhibitor using a bifunctional or derivatizing agent. Exemplary methods for immunization of chickens are provided herein. Relevant methods suitable for a variety of other organisms, such as mammals, are well known in the art.

As described supra, monoclonal antibodies may be produced by a variety of methods. In some embodiments, a monoclonal antibody of the present disclosure is made using the hybridoma method first described by Kohler et al., *Nature,* 256:495 (1975), and further described in Hongo et al., Hybridoma, 14 (3): 253-260 (1995); Harlow et al., *Antibodies: A Laboratory Manual*, (Cold Spring Harbor Laboratory Press, 2nd ed. 1988); and Hammerling et al., in: *Monoclonal Antibodies and T-Cell Hybridomas* 563-681 (Elsevier, N.Y., 1981). Human hybridoma technology (Trioma technology) is described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005). A culture medium in which hybridoma cells are grown may be screened for the presence of an antibody of interest, e.g., by in vitro binding assay, immunoprecipitation, ELISA, RIA, etc.; and the binding affinity may be determined, e.g., by Scatchard analysis. A hybridoma that produces an antibody with desired binding properties can be subcloned and grown using known culture techniques, grown in vivo as ascites tumors in an animal, and the like.

In some embodiments, a monoclonal antibody is made using a library method, such as a phage display library. See, e.g., Hoogenboom et al. in *Methods in Molecular Biology* 178:1-37 (O'Brien et al., ed., Human Press, Totowa, NJ, 2001). In some embodiments, repertoires of VH and VL genes are cloned by polymerase chain reaction (PCR) and recombined randomly in phage libraries, which are then screened for antigen-binding phage, e.g., as described in Winter et al., *Ann. Rev. Immunol.*, 12: 433-455 (1994). Phage typically display antibody fragments, either as single-chain Fv (scFv) fragments or as Fab fragments. Alternatively, the naive repertoire can be cloned (e.g., from human) to provide a single source of antibodies to a wide range of non-self and also self-antigens without any immunization as described by Griffiths et al., *EMBO J.* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992).

In some embodiments, an antibody of the present disclosure is a chicken antibody. Chicken antibodies can be produced using various techniques known in the art: see, e.g., U.S. Pat. Nos. 6,143,559; 8,592,644; and 9,380,769.

In some embodiments, an antibody of the present disclosure is a chimeric antibody. See, e.g., U.S. Pat. No. 4,816,567 and Morrison et al., *Proc. Natl. Acad. Sci. USA*, 81:6851-6855 (1984). In some embodiments, a chimeric antibody comprises a non-human variable region (e.g., a variable region derived from a chicken, mouse, rat, hamster, rabbit, or non-human primate, such as a monkey) and a human constant region. In some embodiments, a chimeric antibody is a "class switched" antibody in which the class or subclass has been changed from that of the parent antibody. Chimeric antibodies include antigen-binding fragments thereof.

In some embodiments, a chimeric antibody is a humanized antibody. A non-human antibody can be humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody (e.g., a chicken antibody), and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity. Humanized antibodies and methods of making them are reviewed, e.g., in Almagro and Fransson. *Front. Biosci.* 13:1619-1633 (2008). Methods of humanizing a chicken antibody have also been described, e.g., in WO2005014653.

Human framework regions useful for humanization include but are not limited to: framework regions selected using the "best-fit" method; framework regions derived from the consensus sequence of human antibodies of a particular subgroup of light or heavy chain variable regions; human somatically mutated framework regions or human germline framework regions; and framework regions derived from screening FR libraries. See, e.g., Sims et al. *J. Immunol.* 151:2296 (1993); Carter et al. *Proc. Natl. Acad. Sci. USA*, 89:4285 (1992); Presta et al. *J. Immunol.*, 151:2623 (1993); Almagro and Fransson, *Front. Biosci.* 13:1619-1633 (2008); and Baca et al., *J. Biol. Chem.* 272:10678-10684 (1997).

In some embodiments, an antibody of the present disclosure is a human antibody. Human antibodies can be produced using various techniques known in the art. In some embodiments, the human antibody is produced by a non-human animal, such as the genetically engineered chickens (see, e.g., U.S. Pat. Nos. 8,592,644; and 9,380,769) and/or mice described herein. Human antibodies are described generally in Lonberg, *Curr. Opin. Immunol.* 20:450-459 (2008).

In some embodiments, an antibody of the present disclosure is generated by or derived from a chicken, e.g., using the methods described herein.

In some embodiments, an antibody of the present disclosure is an antibody fragment, including without limitation a Fab, F(ab')2, Fab'-SH, Fv, or scFv fragment, or a single domain, single heavy chain, or single light chain antibody. Antibody fragments can be generated, e.g., by enzymatic digestion or by recombinant techniques. In some embodiments, Proteolytic digestion of an intact antibody is used to generate an antibody fragment, e.g., as described in Morimoto et al., *Journal of Biochemical and Biophysical Methods* 24:107-117 (1992) and Brennan et al., *Science*, 229:81 (1985). In some embodiments, an antibody fragment is produced by a recombinant host cell. For example, Fab, Fv and ScFv antibody fragments are expressed by and secreted from *E. coli*. Antibody fragments can alternatively be isolated from an antibody phage library.

Fab'-SH fragments can be directly recovered from *E. coli* and chemically coupled to form F(ab')$_2$ fragments. See Carter et al., *Bio/Technology* 10:163-167 (1992). F(ab')$_2$ fragments can also be isolated directly from a recombinant host cell culture. Fab and F(ab')$_2$ fragment with increased in vivo half-life comprising salvage receptor binding epitope residues are described in U.S. Pat. No. 5,869,046.

In some embodiments, an antibody is a single chain Fv fragment (scFv). See WO 93/16185 and U.S. Pat. Nos. 5,571,894 and 5,587,458. scFv fusion proteins can be constructed to produce a fusion of an effector protein at either the amino or the carboxy terminus of an scFv. The antibody fragment may also be a "linear antibody", e.g., as described in U.S. Pat. No. 5,641,870, for example. Such linear antibodies may be monospecific or bispecific.

In some embodiments, an antibody of the present disclosure is a multispecific antibody. Multispecific antibodies possess binding specificities against more than one antigen (e.g., having two, three, or more binding specificities). In some embodiments, the antibody is a bispecific antibody. In some embodiments, a bispecific antibody comprises two different binding specificities for the same antigen (e.g., having different binding affinity and/or specific epitope of the same antigen). In some embodiments, a bispecific antibody comprises binding specificities for two distinct antigens. In some embodiments, the bispecific antibody is a full-length or intact antibody. In some embodiments, the bispecific antibody is an antibody fragment of the present disclosure.

Bispecific or multispecific antibodies with a variety of combinations of binding specificities are contemplated herein. In some embodiments, the bispecific antibody has a first binding specificity for one or more SIRP-α polypeptides as described herein. In some embodiments, the bispecific antibody has a second binding specificity for an antigen expressed by a cancer cell, e.g., on the cell surface. Exemplary such antigens include without limitation CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, PD-L1, STEAP1, Endothelin B Receptor, mesothelin, EGFRvIII, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. Without wishing to be bound by theory, it is thought that combining such a binding specificity with a binding specificity against a SIRP-α is particularly advantageous, e.g., to direct FcR-expressing leukocytes to target a tumor cell with the second binding specificity while also inhibiting the responsiveness of SIRP-α expressed by the leukocyte to any CD47 expressed by the tumor cell with the first binding specificity.

In some embodiments, the bispecific antibody has a second binding specificity for an antigen expressed by an immune cell, e.g., on the cell surface. Exemplary such antigens include without limitation BDCA2, BDCA4, ILT7, LILRB1, LILRB2, LILRB3, LILRB4, CSF-1R, CD40, CD40L, CD163, CD206, DEC205, CD47, CD123, IDO, TDO, 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, PVRIG, DNAM, and ICOS. In some embodiments, the antigen is expressed on a myeloid cell. Such antigens can include without limitation BDCA2, BDCA4, ILT7, LILRB1, LILRB2, LILRB3, LILRB4, CSF-1R, CD40, CD40L, CD163, CD206, DEC205, CD47, CD123, IDO, and TDO. In some embodiments, the antigen is expressed on a T cell. Such antigens can include without limitation 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, TNFR2, PVRIG, DNAM, and ICOS.

In some embodiments, the bispecific antibody has a second binding specificity for an antigen expressed by an NK cell, e.g., on the cell surface. Exemplary such antigens include without limitation NKR-PIA (KLRB1), CD94 (NKG2A), KLRG1, KIR2DL5A, KIR2DL5B, KIR2DL1, KIR2DL2, KIR2DL3, KIR2DS2, KIR2DS3, KIR2DS4, KIR2DS5, KIR3DS1, KIR2DS1, CD94 (NKG2C/E), NKG2D, CD160 (BY55), CD16 (FcγRIIIA), NKp46 (NCR1). NKp30 (NCR3), NKp44 (NCR2), DNAM1 (CD226), CRTAM, CD27, NTB-A (SLAMF6), PSGL1, CD96 (Tactile), CD100 (SEMA4D), NKp80 (KLRF1, CLEC5C), SLAMF7 (CRACC, CS1, CD319), and CD244 (2B4, SLAMF4).

Various methods are known in the art for generating and purifying a bispecific antibody. Numerous approaches have been described. One approach is the "knobs-into-holes" or "protuberance-into-cavity" approach (see, e.g., U.S. Pat. No. 5,731,168). In some embodiments, heterodimerization of Fc domain monomers is promoted by introducing different, but compatible, substitutions in the two Fc domain monomers, such as "knob-into-hole" residue pairs and charge residue pairs. The knob and hole interaction favors heterodimer formation, whereas the knob-knob and the hole-hole interaction hinder homodimer formation due to steric clash and deletion of favorable interactions. A hole refers to a void that is created when an original amino acid in a protein is replaced with a different amino acid having a smaller side-chain volume. A knob refers to a bump that is created when an original amino acid in a protein is replaced with a different amino acid having a larger side-chain volume. For example, in some embodiments, an amino acid being replaced is in the CH3 antibody constant domain of an Fc domain monomer and involved in the dimerization of two Fc domain monomers. In some embodiments, a hole in one CH3 antibody constant domain is created to accommodate a knob in another CH3 antibody constant domain, such that the knob and hole amino acids act to promote or favor the heterodimerization of the two Fc domain monomers. In some embodiments, a hole in one CH3 antibody constant domain is created to better accommodate an original amino acid in another CH3 antibody constant domain. In some embodiments, a knob in one CH3 antibody constant domain is created to form additional interactions with original amino acids in another CH3 antibody constant domain.

In some embodiments, a hole is constructed by replacing amino acids having larger side chains such as tyrosine or tryptophan with amino acids having smaller side chains such as alanine, valine, or threonine, for example a Y407V mutation in the CH3 antibody constant domain. Similarly, in some embodiments, a knob is constructed by replacing amino acids having smaller side chains with amino acids having larger side chains, for example a T366W mutation in the CH3 antibody constant domain. In some embodiments, one Fc domain monomer includes the knob mutation T366W and the other Fc domain monomer includes hole mutations T366S, L358A, and Y407V. In some embodiments, a polypeptide of the disclosure including a high affinity SIRP-α D1 variant is fused to an Fc domain monomer including the knob mutation T366W to limit unwanted knob-knob homodimer formation. Examples of knob-into-hole amino acid pairs are included, without limitation, in Table 3.

TABLE 3

Knob-into-hole amino acid pairs.

| Fc domain monomer 1 | Y407T | Y407A | F405A | T394S | T366S L358A Y407V | T394W Y407T | T394S Y407A | T366W T394S |
|---|---|---|---|---|---|---|---|---|
| Fc domain monomer 2 | T366Y | T366W | T394W | F405W | T366W | T366Y F405A | T366W F405W | F405W Y407A |

Another approach uses antibody variable domains with the desired binding specificities (antibody-antigen combining sites) fused to immunoglobulin constant domain sequences, e.g., with an immunoglobulin heavy chain constant domain, comprising at least part of the hinge, CH2, and CH3 regions. In some embodiments, the bispecific antibody has a hybrid immunoglobulin heavy chain with a first binding specificity in one arm and a hybrid immunoglobulin heavy chain-light chain pair (providing a second binding specificity) in the other arm. See WO 94/04690. Another approach uses cross-linking (see. e.g., U.S. Pat. No. 4,676,980) to produce a heterconjugate antibody. In some embodiments, bispecific antibodies can be prepared using chemical linkage (see, e.g., Brennan et al., *Science,* 229: 81 (1985)) to proteolytically cleave an intact antibody into F(ab')$_2$ fragments that are reduced in the presence of a dithiol complexing agent and converted to thionitrobenzoate (TNB) derivatives, one of which is reconverted to the Fab'-thiol by reduction and mixed with the other Fab'-TNB derivative to form the bispecific antibody. In some embodiments, Fab'-SH fragments are chemically coupled. In some embodiments, bispecific antibody fragments are produced in cell culture using leucine zippers, as in Kostelny et al., *J. Immunol.,* 148(5):1547-1553 (1992). For other bispecific antibody formats, see, e.g., Spiess, C. et al. (2015) *Mol. Immunol.* 67:95-106.

In some embodiments, an antibody of the present disclosure is a diabody. See. e.g., Hollinger et al., *Proc. Natl. Acad. Sci. USA.* 90:6444-6448 (1993). In a diabody, the $V_H$ and $V_L$ domains of one fragment pair with complementary $V_L$ and $V_H$ domains of another fragment, thus forming two antigen-binding sites. Another strategy for making bispecific antibody fragments by the use of single-chain Fv (sFv) dimers has also been reported. See Gruber et al, *J. Immunol,* 152:5368 (1994).

In some embodiments, an antibody of the present disclosure is a single-domain antibody. A single-domain antibody refers to a single polypeptide chain comprising all or a portion of the heavy chain variable domain or all or a portion of the light chain variable domain of an antibody. In certain embodiments, a single-domain antibody is a human single-domain antibody (see, e.g., U.S. Pat. No. 6,248,516 B1). In one embodiment, a single-domain antibody includes all or a portion of the heavy chain variable domain of an antibody. Camelid antibodies are also known.

Antibodies can be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

An antibody of the present disclosure can be produced recombinantly as a fusion polypeptide with a heterologous polypeptide, e.g., a signal sequence or other polypeptide having a specific cleavage site at the N-terminus of the mature protein or polypeptide. The heterologous signal sequence selected can be one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from alkaline phosphatase, penicillinase, lpp, or heat-stable enterotoxin II leaders. For yeast secretion the native signal sequence may be substituted by, e.g., the yeast invertase leader, a factor leader (including *Saccharomyces* and *Kluyveromyces* α-factor leaders), or acid phosphatase leader, the *C. albicans* glucoamylase leader, etc. In mammalian cell expression, mammalian signal sequences as well as viral secretory leaders, for example, the herpes simplex gD signal, are available.

Both expression and cloning vectors contain a nucleic acid sequence that enables the vector to replicate in one or more selected host cells, e.g., to allow the vector to replicate independently of the host chromosomal DNA. This sequence can include origins of replication or autonomously replicating sequences. Such sequences are well known for a variety of bacteria, yeast, and viruses. Generally, the origin of replication component is not needed for mammalian expression vectors (the SV40 origin may be used because it contains the early promoter).

Expression and cloning vectors can contain a selection gene or selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media. Examples of dominant selection use the drugs neomycin, mycophenolic acid and hygromycin. Another example of suitable selectable markers for mammalian cells are those that enable the identification of cells competent to take up antibody-encoding nucleic acid, such as DHFR, glutamine synthetase (GS), thymidine kinase, metallothionein-I and -II, preferably primate metallothionein genes, adenosine deaminase, ornithine decarboxylase, and the like. For example, a Chinese hamster ovary (CHO) cell line deficient in endogenous DHFR activity transformed with the DHFR gene is identified by culturing the transformants in a culture medium containing methotrexate (Mtx), a competitive antagonist of DHFR.

Alternatively, host cells (particularly wild-type hosts that contain endogenous DHFR) transformed or co-transformed with DNA sequences encoding an antibody of interest, wild-type DHFR gene, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418.

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoter sequences are known for eukaryotes. Yeast promoters are well known in the art and can include inducible promoters/enhancers regulated by growth conditions. Virtually all eukaryotic genes have an AT-rich region located approximately 25 to 30 bases upstream from the site where transcription is initiated. Examples include without limitation the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Antibody transcription from vectors in mammalian host cells can be controlled, for example, by promoters obtained from the genomes of viruses. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Alternatively, the Rous Sarcoma Virus long terminal repeat can be used as the promoter.

Transcription of a DNA encoding an antibody of the present disclosure by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus.

Expression vectors used in eukaryotic host cells (yeast, fungi, insect, plant, animal, human, or nucleated cells from other multicellular organisms) will also contain sequences necessary for the termination of transcription and for stabilizing the mRNA.

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, etc. In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. Certain fungi and yeast strains may be selected in which glycosylation pathways have been "humanized," resulting in the production of an antibody with a partially or fully human glycosylation pattern. See, e.g., Li et al., *Nat. Biotech.* 24:210-215 (2006).

Plant cell cultures of cotton, corn, potato, soybean, petunia, tomato, duckweed (Leninaceae), alfalfa (*M. truncatula*), and tobacco can also be utilized as hosts.

Suitable host cells for the expression of glycosylated antibody are also derived from multicellular organisms (invertebrates and vertebrates). Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified.

Vertebrate cells may be used as hosts, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065): mouse mammary tumor (MMT 060562, ATCC CCL51): TRI cells (Mather et al., *Annals N. Y. Acad Sci.* 383:44-68 (1982)): MRC 5 cells; FS4 cells; and a human hepatoma line (Hep G2). Other useful mammalian host cell lines include Chinese hamster ovary (CHO) cells, including DHFR-CHO cells (Urlaub et al., *Proc. Natl. Acad. Sci. USA* 77:4216 (1980)); and myeloma cell lines such as NS0 and Sp2/0. For a review of certain mammalian host cell lines suitable for antibody production, see, e.g., Yazaki and Wu, *Methods in Molecular Biology*. Vol. 248 (B. K. C. Lo, ed., Humana Press, Totowa, N.J., 2003), pp. 255-268.

The host cells of the present disclosure may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM). Sigma) are suitable for culturing the host cells. In addition, any of the media described in Ham et al., *Meth. Enz.* 58.44 (1979). Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to one of skill in the art.

When using recombinant techniques, the antibody can be produced intracellularly, in the periplasmic space, or directly secreted into the medium. If the antibody is produced intracellularly, as a first step, the particulate debris, either host cells or lysed fragments, are removed, for example, by centrifugation or ultrafiltration. Carter et al., *Bio/Technology* 10:163-167 (1992) describe a procedure for isolating antibodies which are secreted to the periplasmic space of *E. coli*.

The antibody composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps.

In some embodiments, an antibody of the present disclosure comprises a light chain comprising a light chain constant (CL) domain sequence that comprises an amino acid sequence according to the formula GQPKANPTVTLFPPS-SEELQANKATLVCLISDFYPGAVTVAWKADGSPVK-AGVETTK PSKQSX$_4$X$_5$KYAASSYLSLTPEQWKSHR-SYSCQVTHEGSTVEKTVAPTECS (SEQ ID NO:72), where X$_4$X$_5$ is ND, DN, DS, or SD. In certain embodiments, the CL domain comprises an amino acid sequence selected from SEQ ID NOs:43-46.

In some embodiments, an antibody of the present disclosure comprises a light chain variable (VL) domain comprising one, two, three, or four IGLV3 framework sequences, including without limitation SYELTQPPSVSVSPGQ-TARITC (SEQ ID NO:27), WYQQKPGQAPVTLIY (SEQ ID NO:28), NIPERFSGSSSGTTVTLTISGVQAEDEAD-YYC (SEQ ID NO:29), and FGGGTKLTVL (SEQ ID NO:30). In some embodiments, an antibody of the present disclosure comprises a light chain variable (VL) domain comprising the structure FW1-HVR-L1-FW2-HVR-L2-FW3-HVR-L3-FW4, wherein FW1 comprises the sequence SYELTQPPSVSVSPGQTARITC (SEQ ID NO:27), FW2 comprises the sequence WYQQKPGQAPVTLIY (SEQ ID NO:28), FW3 comprises the sequence NIPERFSGSSSGTTVTLTISGVQAEDEADYYC (SEQ ID NO:29), and FW4 comprises the sequence FGGGTKLTVL (SEQ ID NO:30).

In some embodiments, an antibody of the present disclosure comprises a light chain comprising a kappa or lambda light chain constant (CL) domain. In some embodiments, an antibody of the present disclosure comprises a light chain comprising a light chain constant domain comprising the amino acid sequence of one of SEQ ID NOs:36-38. In some embodiments, an antibody of the present disclosure comprises a light chain comprising a light chain constant domain comprising the amino acid sequence of one of SEQ ID NOs:43-46. In some embodiments, an antibody of the present disclosure comprises a light chain comprising a light chain constant domain sequence shown in Table 1. In some embodiments, an antibody of the present disclosure comprises a light chain that comprises a VL domain comprising the sequence of SEQ ID NO:25 and a CL domain sequence selected from SEQ ID NOs:36-38 and 43-46. In some embodiments, an antibody of the present disclosure comprises a light chain that comprises a VL domain comprising the sequence of SEQ ID NO:25 and a CL domain sequence selected from SEQ ID NOs:43-46. In some embodiments, an antibody of the present disclosure comprises a light chain that comprises an amino acid sequence selected from SEQ ID NOs:48-51. In some embodiments, an antibody of the present disclosure comprises a light chain that comprises a VL domain sequence selected from SEQ ID NOs:39-41 and a CL domain comprising a sequence selected from SEQ ID NOs:36-38. Any of the above light chains can be combined with a heavy, chain shown in Table 2 or an antibody heavy chain comprising a VH domain shown in Table 2.

In some embodiments, an antibody of the present disclosure includes a heavy, chain comprising a heavy, chain constant domain that comprises an Fc region. For example, in some embodiments, the Fc region is a human Fc region, e.g., IgG1, IgG2, or IgG4 and subtypes thereof. Exemplary and non-limiting Fc regions are provided within the heavy chain constant domains comprising the amino acid sequences of SEQ ID NOs:31-35 and 132-139, as shown in Table 4. In some embodiments, an Fc region within one or more of the heavy chain constant domain amino acid sequences of SEQ ID NOs:31-35 and 132-139 comprises one or more of the mutations described herein. e.g., infra. In some embodiments, an antibody, of the present disclosure comprises a heavy chain that comprises a heavy chain chain constant domain sequence shown in Table 2.

TABLE 4

Exemplary constant region sequences

| Name | SEQ ID NO | Sequence |
|---|---|---|
| IgG1 wildtype | 31 | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSCDKTHTCPPCPAPELLGGPSVFLFPPK<br>PKDTLMISRTPEVTCVVVDVSHEDPEVKFNWYVDGVEVHNA<br>KTKPREEQYNSTYRVVSVLTVLHQDWLNGKEYKCKVSNKAL<br>PAPIEKTISKAKGQPREPQVYTLPPSREEMTKNQVSLTCLVKGF<br>YPSDIAVEWESNGQPENNYKTTPPVLDSDGSEFLYSKLTVDKS<br>RWQQGNVFSCSVMHEALHNHYTQKSLSLSPG |
| IgG1_AAA_N297A | 32 | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSCDKTHTCPPCPAPEAAGAPSVFLFPPK<br>PKDTLMISRTPEVTCVVVDVSHEDPEVKFNWYVDGVEVHNA<br>KTKPREEQYASTYRVVSVLTVLHQDWLNGKEYKCKVSNKAL<br>PAPIEKTISKAKCQPREPQVYTLPPSREEMTKNQVSLTCLVKGF<br>YPSDIAVEWESNGQPENNYKTTPPVLDSDGSFFLYSKLTVDKS<br>RWQQGNVESCSVMHEALHNHYTQKSLSLSPG |
| IgG2 | 33 | ASTKGPSVFPLAPCSRSTSESTAALGCLVKDYFPEPVTVSWNS<br>GALTSGVHTFPAVLQSSGLYSLSSVVTVPSSNFGTQTYTCNVD<br>HKPSNTKVDKVERKCCVECPPCPAPPVAGPSVFLEPPKPKDT<br>LMISRTPEVTCVVVDVSHEDPEVQFNWYVDGVEVHNAKTKP<br>REEQFNSTFRVVSVLTVVHQDWLNGKEYKCKVSNKGLPAPIE<br>KTISKTKGQPREPQVYTLPPSREEMTKNQVSLTCLVKGFYPSDI<br>AVEWESNGQPENNYKTTPRMLDSDGSFFLYSKLTVDKSRWQ<br>QGNVFSCSVMHEALHNHYTQKSLSLSPG |
| IgG2Da | 34 | ASTKGPSVFPLAPCSRSTSESTAALGCLVKDYFPEPVTVSWNS<br>GALTSGVHTEPAVLQSSGLYSLSSVVTVPSSNFGTQTYTCNVD<br>HKPSNTKVDKTVERKCCVECPPCPAPPVAGPSVFLFPPKPKDT<br>LMISRTPEVTCVVVDVSHEDPEVQFNWYVDGVEVHNAKTKP<br>REEQFNSTFRVVSVLTVVHQDWLNGKEYKCKVSNKGLPSSIE<br>KTISKTKOQPREPQVYTLPPSREEMTKNQVSLTCLKGFYPSDI<br>AVEWESNGQPENNYKTTPPMLDSDGSFFLYSKLTVDKSRWQ<br>QGNVFSCSVMHEALHNHYTQKSLSLSPG |
| IgG4_S228P | 35 | ASTKGPSVFPLAPCSRSTSESTAALGCLVKDYFPEPVTVSWNS<br>GALTSGVHTFPAVLQSSGLYSLSSVVTVPSSSLGTKTYTCNVD<br>HKPSNTKVDKRVESKYGPPCPPCPAPEFLGGPSVFLEPPKPKDT<br>LMISRTPEVTCVVVDVSQEDPEVQFNWYVDGVEVHNAKTKP |

TABLE 4-continued

Exemplary constant region sequences

| Name | SEQ ID NO | Sequence |
|---|---|---|
| | | REEQFNSTYRVVSVLTVLHQDWLNGKEYKCKVSNKGLPSSIE KTISKAKGQPREPQVYTLPPSQEEMTKNQVSLTCLVKGFYPSD IAVEWESNGQPENNYKTTPPVLDSDGSFFLYSRLTVDKSRWQ EGNVFSCSVMHEALHNHYTQKSLSLSLG |
| Human Kappa | 36 | RTVAAPSVFIFPPSDEQLKSGTASVVCLLNNFYPREAKVQWKV DNALQSGNSQESVTEQDSKDSTYSLSSTLTLSKADYEKHKVY ACEVTHQGLSSPVTKSFNRGEC |
| Human Lambda IGLC1 | 37 | GQPKANPTVTLFPPSSEELQANKATLVCLISDFYPGAVTVAWK ADSSPVKAGVETTKPSKQSNNKYAASSYLSLTPEQWKSHRSY SCQVTHEGSTVEKTVAPTECS |
| Human Lambda IGLC2 | 38 | GQPKANPSTLFPPSSEELQANKATLVCLISDFYPGAVTVAWK ADSSPVKAGVETTTPSKQSNNKYAASSYLSLTPEQWKSHRSY SCQVTHEGSTVEKTVAPTECS |
| IgG1_AAA | 132 | ASTKGPSVFPLAPSSKSTSGGTAALGCLVKDYFPEPVTVS WNSGALTSGVHTFPAVLQSSGLYSLSSVVTVPSSSLGTQ TYICNVNHKPSNTKVDKKVEPKSCDKTHTCPPCPAPEAA GAPSVFLFPPKPKDTLMISRTPEVTCVVVDVSHEDPEVKF NWYNDGVEVHNAKTKPREEQYNSTYRVVSVLTVLHQD WLNGKEYKCKVSNKALPAPIEKTISKAKGQPREPQVYTL PPSREEMTKNQVSLTCLVKGFYPSDIAVEWESNGQPENN YKTTPPVLDSDGSFFLYSKLTVDKSRWQQGNVFSCSVM HEALHNHYTQKSLSLSPG |
| IgG2 C232S | 133 | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKSCVECPPCPAPPVAGPS VFLFPPKPKDTLMISRTPEVTCVVVDVSHEDPEVQPNWY VDGVEVHNAKTKPREEQFNSTFRVVSVLIVVHQDWLN GKEYKCKVSNKGLPAPIEKTISKTKGQPREPQVYTLPPSR EEMTKNQVSLTCLVKGFYPSDIAVEWESNGQPENNYKT TPPMLDSDGSFFLYSKLTVDKSRWQQGNVESCSVMHEA LHNHYTQKSLSLSPG |
| IgG2 C233S | 134 | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKSCVECPPCPAPPVAGPS VFLFPPKPKDTLMISRTPEVTCVVVDVSHEDPEVQFNWY VDGVEVHNAKTKPREEQFNSTFRVVSVLTVVHQDWLN GKEYKCKVSNKGLPAPIEKTISKTKGQPREPQVYTLPPSR EEMTKNQVSLTCLVKGFYPSDIAVEWESNGQPENNYKT TPPMLDSDGSFFLYSKLTVDKSRWQQGNVFSCSVMHEA LHNHYTQKSLSLSPG |
| IgG2Da C232S | 135 | ASTKGPSVFPLAPCSRSTSESTAALGCLNIKDYFPEPVINS WNSGALTSGVHTFPAVLQSSGLYSLSSVVTVPSSNFGTQ TYTCNVDFIKPSNTKVDKTVERKSCVECPPCPAPPVAGPS VFLFPPKPKDTLMISRTPEVTCVVVDVSHEDPEVFNWY VDGVEVHNAKTKPREEQFNSTFRVVSVLTVVEQDWLN GKEYKCKVSNKGLPSSIEKTISKTKGQPREPQVYTLPPSR EEMTKNQVSLTCLVKGFYPSDIAVEWESNGQPENNYKT TPPMLDSDGSFFLYSKLTVDKSRWQQGNVFSCSVMHEA LHNHYTQKSLSLSPG |
| IgG2Da C233S | 136 | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKSCVECPPCPAPPVAGPS VFLFPPKPKDTLMISRTPEVFCVVVDVSHEDPEVQFNWY VDGVEVHNAKTKPREEQFNSTFRVVSVLTVVHQDWLN GKEYKCKVSNKGLPSSIEKTISKTKGQPREPQVYTLPPSR EEMTKNQVSLTCLVKGFYPSDIAVEWESNGQPENNYKT TPPMLDSDGSFFLYSKLTVDKSRWQQGNVFSCSVMHEA LHNHYTQKSLSLSPG |
| IgG2 N297A | 137 | ASTKGPSVFPLAPCSRSTSESTAALGCLVKDYFPEPVTVS WNSGALTSGVHTFPAVLQSSGLYSLSSVVTVPSSNFGTQ TYTCNVDHKPSNTKVDKTVERKSCVECPPCPAPPVAGPS VFLFPPKPKDTLMISRTPEVTCVVVDVSHEDPEVQFNWY VDGVEVHNAKTKPREEQFASTFRVVSVLTVVHQDWLN |

TABLE 4-continued

Exemplary constant region sequences

| Name | SEQ ID NO | Sequence |
|---|---|---|
| | | GKEYKCKVSNKGLPAPIEKTISKTKGQPREPQVYTLPPSR<br>EEMTKNQVSLTCLVKGFYPSDIAVEWESNGQPENNYKT<br>TPPMLDSDGSFFLYSKLTVDKSRWQQGNVFSCSVMHEA<br>LHNHYTQKSLSLSPG |
| IgG2 N297A C232S | 138 | ASTKGPSVFPLAPCSRSTSESTAALGCLVKDYFPEPVTVS<br>WNSGALTSGVHTFPAVLQSSGLYSLSSVVTVPSSNFGTQ<br>TYTCNVDHKPSNTKVDKTVERKSCVECPPCPAPPVAGPS<br>VFLFTPKPKDTLMISRTPEVTCVVVDVSHEDPEVQFNWY<br>VDGVEVHNAKTKPREEQFASTFRVVSVLTVVHQDWLN<br>GKEYKCKVSNKGLPAPIEKTISKTKGQPREPQVYTLPPSR<br>EEMTKNQVSLTCLVKGTYPSDIAVEWESNGQPENNYKT<br>TPPMLDSDGSFFLYSKLTVDKSRWQQGNVFSCSVMHEA<br>LHNHYTQKSLSLSPG |
| IgG2 N297A C233S | 139 | ASTKGPSVFPLAPCSRSTSESTAALGCLVKDYFPEPVTVS<br>WNSGALTSGVHTFPAVLQSSGLYSLSSVVTVPSSNFGTQ<br>TYTCNVDHKPSNTKVDKTVERKCSVECPPCPAPPVAGPS<br>VFLFPPKPKDTLMISRTPEVTCVVVDVSHEDPEVQFNWY<br>VDGVEVHNAKTKPREEQFASTFRVVSVLTVVHQDWLN<br>GKEYKCKVSNKGLPAPIEKTISKTKGQPREPQVYTLPPSR<br>EEMTKNQVSLTCLVKGFYPSDIAVEWESNGQPENNYKT<br>TPPMLDSDGSFFLYSKLTVDKSRWQQGNVFSCSVMHEA<br>LHNHYTQKSLSLSPG |

In some embodiments, the Fc region includes one or more mutations that influence one or more antibody properties, such as stability, pattern of glycosylation or other modifications, effector cell function, pharmacokinetics, and so forth. In some embodiments, an antibody of the present disclosure has reduced or minimal glycosylation. In some embodiments, an antibody of the present disclosure has ablated or reduced effector function. In some embodiments, an antibody of the present disclosure has improved stability (e.g., improved stability of the hinge domain and/or reduced monomer exchange of IgG4 antibodies through use of the S228P mutation).

Exemplary Fc mutations (e.g., that influence one or more of the properties described supra) include without limitation (i) a human IgG1 Fc region mutations L234A, L235A, G237A, and optionally N297A; (ii) a human IgG2 Fc region mutations A330S, P331S and optionally N297A; and (iii) a human IgG4 Fc region mutations S228P and optionally E233P, F234V, L235A, delG236, and N297A (EU numbering). In some embodiments, the human IgG1 Fc region comprises L234A. L235A, and G237A mutations. In some embodiments, the human IgG1 Fc region comprises L234A, L235A, G237A, and N297A mutations. In some embodiments, the human IgG2 Fc region comprises A330S and P331S mutations. In some embodiments, the human IgG2 Fc region comprises A330S, P331S, and N297A mutations. In some embodiments, the human IgG4 Fc region comprises an S288P mutation. In some embodiments, the human IgG4 Fc region comprises S288P and L235E mutations.

Antibodies that target cell surface antigens can trigger immunostimulatory and effector functions that are associated with Fc receptor (FcR) engagement on immune cells. There are a number of Fc receptors that are specific for particular classes of antibodies, including IgG (gamma receptors), IgE (eta receptors), IgA (alpha receptors) and IgM (mu receptors). Binding of the Fc region to Fc receptors on cell surfaces can trigger a number of biological responses including phagocytosis of antibody-coated particles (antibody-dependent cell-mediated phagocytosis, or ADCP), clearance of immune complexes, lysis of antibody-coated cells by killer cells (antibody-dependent cell-mediated cytotoxicity, or ADCC) and, release of inflammatory mediators, placental transfer, and control of immunoglobulin production. Additionally, binding of the C1 component of complement to antibodies can activate the complement system. Activation of complement can be important for the lysis of cellular pathogens. However, the activation of complement can also stimulate the inflammatory response and can also be involved in autoimmune hypersensitivity or other immunological disorders. Variant Fc regions with reduced or ablated ability to bind certain Fc receptors are useful for developing therapeutic antibodies and Fc-fusion polypeptide constructs which act by targeting, activating, or neutralizing ligand functions while not damaging or destroying local cells or tissues.

In some embodiments, a Fc domain monomer refers to a polypeptide chain that includes second and third antibody constant domains (e.g., CH2 and CH3). In some embodiments, an Fc domain monomer also includes a hinge domain. In some embodiments, the Fc domain monomer is of any immunoglobulin antibody isotype, including IgG, IgE, IgM, IgA, and IgD. Additionally, in some embodiments, an Fc domain monomer is of any IgG subtype (e.g., IgG1, IgG2, IgG2a, IgG2b, IgG2c, IgG3, and IgG4). In some embodiments, Fc domain monomers include as many as ten changes from a wild-type Fc domain monomer sequence (e.g., 1-10, 1-8, 1-6, 1-4 amino acid substitutions, additions or insertions, deletions, or combinations thereof) that alter the interaction between an Fc domain and an Fc receptor.

In some embodiments, an Fc domain monomer of an immunoglobulin or a fragment of an Fc domain monomer is capable of forming an Fc domain with another Fc domain monomer. In some embodiments, an Fc domain monomer of an immunoglobulin or a fragment of an Fc domain monomer is not capable of forming an Fc domain with another Fc domain monomer. In some embodiments, an Fc domain monomer or a fragment of an Fc domain is fused to a polypeptide of the disclosure to increase serum half-life of the polypeptide. In some embodiments, an Fc domain monomer or a fragment of an Fc domain monomer fused to a polypeptide of the disclosure dimerizes with a second Fc domain monomer to form an Fc domain which binds an Fc receptor, or alternatively, an Fc domain monomer binds to an Fc receptor. In some embodiments, an Fc domain or a fragment of the Fc domain fused to a polypeptide to increase serum half-life of the polypeptide does not induce any immune system-related response. An Fc domain includes two Fc domain monomers that are dimerized by the interaction between the CH3 antibody constant domains.

A wild-type Fc domain forms the minimum structure that binds to an Fc receptor, e.g., FcγRI, FcγRIIa, FcγRIIb, FcγRIIIa, FcγRIIIb, and FcγRIV. In some embodiments, the Fc domain in an antibody of the present disclosure comprises one or more amino acid substitutions, additions or insertions, deletions, or any combinations thereof that lead to decreased effector function such as decreased antibody-dependent cell-mediated cytotoxicity (ADCC), decreased complement-dependent cytolysis (CDC), decreased antibody-dependent cell-mediated phagocytosis (ADCP), or any combinations thereof. For example, an antibody of the present disclosure can exhibit decreased binding (e.g., minimal binding or absence of binding) to a human Fc receptor and decreased binding (e.g., minimal binding or absence of binding) to complement protein C1q; decreased binding (e.g., minimal binding or absence of binding) to human FcγRI, FcγRIIA, FcγRIIB, FcγRIIIB, FcγRIIIB, or any combinations thereof, and C1q; altered or reduced antibody-dependent effector function, such as ADCC, CDC, ADCP, or any combinations thereof; and so forth. Exemplary mutations include without limitation one or more amino acid substitutions at E233, L234, L235, G236, G237, D265, D270, N297, E318, K320, K322, A327, A330, P331, or P329 (numbering according to the EU index of Kabat (Sequences of Proteins of Immunological Interest, 5th Ed. Public Health Service, National Institutes of Health, Bethesda. MD (1991)).

In some embodiments, an antibody of the present disclosure has reduced or ablated binding to CD16a, CD32a, CD32b, CD32c, and CD64 Fcγ receptors. In some embodiments, an antibody with a non-native Fc region described herein exhibits at least a 5%, 10%, 15%, 20%, 30%, 40%, 50%, 60%, 70%, 80%, 90% or greater reduction in C1q binding compared to an antibody comprising a wild-type Fc region. In some embodiments, an antibody with a non-native Fc region as described herein exhibit at least a 5%, 10%, 15%, 20%, 30%, 40%, 50%, 60%, 70%, 80%, 90% or greater reduction in CDC compared to an antibody comprising a wild-type Fc region.

In some embodiments, the Fc variants herein are minimally glycosylated or have reduced glycosylation relative to a wild-type sequence. In some embodiments, deglycosylation is accomplished with a mutation of N297A, or by mutating N297 to any amino acid which is not N.

In some embodiments, variants of antibody IgG constant regions (e.g., Fc variants) possess a reduced capacity to specifically bind Fcγ receptors or have a reduced capacity to induce phagocytosis. In some embodiments, variants of antibody IgG constant regions (e.g., Fc variants) possess a reduced capacity to specifically bind Fcγ receptors and have a reduced capacity to induce phagocytosis. For example, in some embodiments, an Fc domain is mutated to lack effector functions, typical of a "dead" Fc domain. For example, in some embodiments, an Fc domain includes specific amino acid substitutions that are known to minimize the interaction between the Fc domain and an Fcγ receptor. In some embodiments, an Fc domain monomer is from an IgG1 antibody and includes one or more of amino acid substitutions L234A, L235A, G237A, and N297A (amino acid position numbering as designated according to the EU numbering system per Kabat et al., 1991). In some embodiments, one or more additional mutations are included in such IgG1 Fc variant. Non-limiting examples of such additional mutations for human IgG1 Fc variants include E318A and K322A. In some instances, a human IgG1 Fc variant has up to 12, 11, 10, 9, 8, 7, 6, 5 or 4 or fewer mutations in total as compared to wild-type human IgG1 sequence. In some embodiments, one or more additional deletions are included in such IgG1 Fc variant. For example, in some embodiments, the C-terminal lysine of the Fc IgG1 heavy chain constant region is deleted, for example to increase the homogeneity of the polypeptide when the polypeptide is produced in bacterial or mammalian cells. In some instances, a human IgG1 Fc variant has up to 12, 11, 10, 9, 8, 7, 6, 5 or 4 or fewer deletions in total as compared to wild-type human IgG1 sequence.

In some embodiments, an Fc domain monomer is from an IgG2 antibody and includes amino acid substitutions A330S, P331S, or both A330S and P331S. The aforementioned amino acid positions are defined according to Kabat, et al. (1991). The Kabat numbering of amino acid residues can be determined for a given antibody by alignment at regions of homology of the sequence of the antibody with a "standard" Kabat numbered sequence. In some embodiments, the Fc variant comprises a human IgG2 Fc sequence comprising one or more of A330S, P331S and N297A amino acid substitutions (amino acid position numbering as designated according to the EU numbering system per Kabat, et al. (1991). In some embodiments, one or more additional mutations are included in such IgG2 Fc variants. Non-limiting examples of such additional mutations for human IgG2 Fc variant include V234A, G237A, P238S, V309L and H268A (as designated according to the EU numbering system per Kabat et al. (1991)). In some instances, a human IgG2 Fc variant has up to 12, 11, 10, 9, 8, 7, 6, 5, 4, 3 or fewer mutations in total as compared to wild-type human IgG2 sequence. In some embodiments, one or more additional deletions are included in such IgG2 Fc variant.

When the Fc variant is an IgG4 Fc variant, in some embodiments, such Fc variant comprises a S228P, E233P, F234V, L235A, L235E, or delG236 mutation (amino acid position numbering as designated according to Kabat, et al. (1991)). In some instances, a human IgG4 Fc variant has up to 12, 11, 10, 9, 8, 7, 6, 5, 4, 3, 2 or 1 mutation(s) in total as compared to wild-type human IgG4 sequence.

In some embodiments, the Fc variant exhibits reduced binding to an Fc receptor of the subject compared to the wild-type human IgG Fc region. In some embodiments, the Fc variant exhibits ablated binding to an Fc receptor of the subject compared to the wild-type human IgG Fc region. In some embodiments, the Fc variant exhibits a reduction of phagocytosis compared to the wild-type human IgG Fc region. In some embodiments, the Fc variant exhibits ablated phagocytosis compared to the wild-type human IgG Fc region.

Antibody-dependent cell-mediated cytotoxicity, which is also referred to herein as ADCC, refers to a form of cytotoxicity in which secreted Ig bound onto Fc receptors (FcRs) present on certain cytotoxic cells (e.g., Natural Killer (NK) cells and neutrophils) enabling these cytotoxic effector cells to bind specifically to an antigen-bearing target cell and subsequently kill the target cell. Antibody-dependent cell-mediated phagocytosis, which is also referred to herein as ADCP, refers to a form of cytotoxicity in which secreted Ig bound onto Fc receptors (FcRs) present on certain phagocytic cells (e.g., macrophages) enabling these phagocytic effector cells to bind specifically to an antigen-bearing target cell and subsequently engulf and digest the target cell. Ligand-specific high-affinity IgG antibodies directed to the surface of target cells can stimulate the cytotoxic or phagocytic cells and can be used for such killing. In some embodiments, polypeptide constructs comprising an Fc variant as described herein exhibit reduced ADCC or ADCP as compared to a polypeptide construct comprising a wild-type Fc region. In some embodiments, polypeptide constructs comprising an Fc variant as described herein exhibit at least a 5%, 10%, 15%, 20%, 30%. 40%, 50%, 60%, 70%, 80%, 90% or greater reduction in ADCC or ADCP compared to a polypeptide construct comprising a wild-type Fc region. In some embodiments, antibodies comprising an Fc variant as described herein exhibit ablated ADCC or ADCP as compared to a polypeptide construct comprising a wild-type Fc region.

Complement-directed cytotoxicity, which is also referred to herein as CDC, refers to a form of cytotoxicity in which the complement cascade is activated by the complement component C1q binding to antibody Fc. In some embodiments, polypeptide constructs comprising an Fc variant as described herein exhibit at least a 5%, 10%, 15%, 20%, 30%, 40%, 50%, 60%, 70%, 80%, 90% or greater reduction in C1q binding compared to a polypeptide construct comprising a wild-type Fc region. In some cases, polypeptide constructs comprising an Fc variant as described herein exhibit reduced CDC as compared to a polypeptide construct comprising a wild-type Fc region. In some embodiments, polypeptide constructs comprising an Fc variant as described herein exhibit at least a 5%, 10%, 15%, 20%, 30%, 40%, 50%, 60%, 70%, 80%, 90% or greater reduction in CDC compared to a polypeptide construct comprising a wild-type Fc region. In some cases, antibodies comprising an Fc variant as described herein exhibit negligible CDC as compared to a polypeptide construct comprising a wild-type Fc region.

Fc variants herein include those that exhibit reduced binding to an Fcγ receptor compared to the wild-type human IgG Fc region. For example, in some embodiments, an Fc variant exhibits binding to an Fcγ receptor that is less than the binding exhibited by a wild-type human IgG Fc region to an Fcγ receptor. In some instances, an Fc variant has reduced binding to an Fcγ receptor by a factor of 10%, 20% 30%, 40%, 50%, 60%, 70%, 80%, 90%, 95%, 96%, 97%, 98%, 99% or 100% (fully ablated effector function). In some embodiments, the reduced binding is for any one or more Fcγ receptors, e.g., CD16a, CD32a, CD32b, CD32c, or CD64.

In some instances, the Fc variants disclosed herein exhibit a reduction of phagocytosis compared to its wild-type human IgG Fc region. Such Fc variants exhibit a reduction in phagocytosis compared to its wild-type human IgG Fc region, wherein the reduction of phagocytosis activity is e.g., by a factor of 10%, 20%, 30%, 40%, 50%, 60%, 70%, 80%, 90%, 95%, 96%, 97%, 98%, 99% or 100%. In some instances, an Fc variant exhibits ablated phagocytosis compared to its wild-type human IgG Fc region.

In some embodiments, an antibody of the present disclosure is conjugated to an agent. In some embodiments, the agent is a cytotoxic agent, including but not limited to the exemplary cytotoxic agents described herein. In some embodiments, the agent is a label, including but not limited to the exemplary labels described herein.

In some embodiments, the agent is a moiety that modulates the immune system. For example, the moiety may target and/or modulate the function of a cell expressing SIRP-α on its surface, such as a small molecule that modulates a cellular signaling pathway of the cell expressing SIRP-α, e.g., an IDO/TDO inhibitor, AhR inhibitor, arginase inhibitor, A2a R inhibitor. TLR agonists, STING agonist, or Rig-1 agonist. In some embodiments, the moiety may recruit another macromolecule or cell into proximity with a cell expressing SIRP-α on its surface. In some embodiments, the moiety comprises a cytokine, e.g., IL2, IL7, IL-10, IL15, or IFN. In some embodiments, the moiety (e.g., a small molecule) modulates the activity of a cytokine, e.g., IL2. IL7, IL-10, IL15, or IFN. In some embodiments, the moiety comprises a cancer vaccine (comprising, e.g., DNA, RNA, peptide, or other cellular component(s)). In some embodiments, the moiety comprises an adjuvant. In some embodiments, the moiety comprises a CpG oligonucleotide. In some embodiments, the moiety affects antibody purification, screening, and/or display. In some embodiments, the moiety also affects the degree of binding to Fc receptors or the degree of phagocytosis reduction.

In some embodiments, fusion partners are linked to the Fc variant sequence via a linker sequence. In some embodiments, the linker sequence generally comprises a small number of amino acids, such as less than ten amino acids, although longer linkers are also utilized. In some cases, the linker has a length less than 10, 9, 8, 7, 6, or 5 amino acids or shorter. In some cases, the linker has a length of at least 10, 11, 12, 13, 14, 15, 20, 25, 30, or 35 amino acids or longer. Optionally, in some embodiments, a cleavable linker is employed.

In some embodiments, a fusion partner is a targeting or signal sequence that directs an Fc variant protein and any associated fusion partners to a desired cellular location or to the extracellular media. In some embodiments, certain signaling sequences target a protein to be either secreted into the growth media, or into the periplasmic space, located between the inner and outer membrane of the cell. In some embodiments, a fusion partner is a sequence that encodes a peptide or protein that enables purification or screening. Such fusion partners include, but are not limited to, polyhistidine tags (His-tags) (for example His6 and His10) or other tags for use with Immobilized Metal Affinity Chromatography (IMAC) systems (e.g., Ni+2 affinity columns), GST fusions, MBP fusions, Strep-tag, the BSP biotinylation target sequence of the bacterial enzyme BirA, and epitope tags which are targeted by antibodies (for example c-myc tags, flag-tags, and the like).

In some embodiments, such tags are useful for purification, for screening, or both. For example, in some embodiments, an Fc variant is purified using a His-tag by immobilizing it to a Ni+2 affinity column, and then after purification the same His-tag is used to immobilize the antibody to a Ni+2 coated plate to perform an ELISA or other binding assay.

Various fusion partners that enable a variety of selection methods are available. For example, by fusing the members of an Fc variant library to the gene III protein, phage display can be employed. In some embodiments, fusion partners enable Fc variants to be labeled. Alternatively, in some embodiments, a fusion partner binds to a specific sequence on the expression vector, enabling the fusion partner and associated Fc variant to be linked covalently or noncovalently with the nucleic acid that encodes them.

In some embodiments, when a fusion partner is a therapeutic moiety, the therapeutic moiety is, e.g., a cytotoxic agent, a peptide, a protein, an antibody, a siRNA, or a small molecule.

In some embodiments, an antibody of the present disclosure is bound to various carriers or labels and used to detect the presence of specific antigen expressing cells. Examples of carriers include glass, polystyrene, polypropylene, polyethylene, dextran, nylon, amylases, natural and modified celluloses, polyacrylamides, agaroses, and magnetite. The nature of the carrier can be either soluble or insoluble. Various different labels and methods of labeling are known. Examples of labels include enzymes, radioisotopes, fluorescent compounds, colloidal metals, chemiluminescent compounds, and bio-luminescent compounds. Various techniques for binding labels to antibodies disclosed herein are available. In some embodiments, the antibodies are coupled to low molecular weight haptens. These haptens are then specifically detected by means of a second reaction. For example, in some embodiments, the hapten biotin is used with avidin or the haptens dinitrophenol, pyridoxal, or fluorescein are detected with specific anti-hapten antibodies (e.g., anti-dinitrophenol antibodies, anti-pyridoxal antibodies, and anti-fluorescein antibodies respectively). In some embodiments, the antibodies described herein are utilized in vitro for binding assays, such as immune assays. For example, in some embodiments, the antibodies are utilized in liquid phase or bound to a solid phase carrier. In some embodiments, antibodies utilized for immunoassays are detectably labeled in various ways.

Methods of Treatment

Certain aspects of the present disclosure relate to treating a disease or disorder using an antibody described herein. In some embodiments, the disease is cancer. In some embodiments, the disease is an autoimmune or inflammatory disease.

For example, provided herein are methods of treating or delaying progression of cancer in an individual by administering an effective amount of an antibody of the present disclosure. Without wishing to be bound to theory, it is thought that the antibodies described herein may be useful in the treatment of cancer, e.g., by abrogating the cancer's ability to inhibit phagocytosis and immune surveillance through the CD47. SIRP-α signaling axis, or by otherwise enhancing activation of the immune system (such as by activation of dendritic cells).

In some embodiments, an antibody of the present disclosure is administered in combination with a second antibody, e.g., an antibody that binds an antigen expressed by the cancer (e.g., an effective amount of the second antibody, which in some embodiments as described above may be considered in the context of administering an anti-SIRP-α antibody of the present disclosure). Exemplary antigens expressed by cancers are known in the art and include without limitation CD19, CD20, CD22, CD30, CD33, CD38, CD52, CD56, CD70, CD74, CD79b, CD123, CD138, CS1/SLAMF7, Trop-2, 5T4, EphA4, BCMA, Mucin 1, Mucin 16, PTK7, PD-L1, STEAP1, Endothelin B Receptor, mesothelin, EGFRvIII, ENPP3, SLC44A4, GNMB, nectin 4, NaPi2b, LIV-1A, Guanylyl cyclase C. DLL3, EGFR, HER2, VEGF, VEGFR, integrin αVβ, integrin α5β1, MET, IGF1R, TRAILR1, TRAILR2, RANKL, FAP. Tenascin, Le$^y$, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, MAGE-A3, gp100/pmel17, Melan-A/MART-1, gp75/TRP1, tyrosinase. TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7. For example, in some embodiments, an antibody of the present disclosure is administered in combination with a monoclonal antibody that binds CD123 (also known as IL-3 receptor alpha), such as talacotuzumab (also known as CSL362 and JNJ-56022473). In some embodiments, an antibody of the present disclosure is administered in combination with a monoclonal antibody that binds EGFR (such as cetuximab). In some embodiments, the second antibody includes one or more effector functions, e.g., effector functions that are associated with Fc receptor (FcR) engagement on immune cells including without limitation ADCC or ADCP, and/or complement-dependent cytotoxicity (CDC). Without wishing to be bound to theory, it is thought that combining such an antibody with an antibody of the present disclosure is particularly advantageous, e.g., to direct FcR-expressing leukocytes to target a tumor cell to which the second antibody is bound while also inhibiting the responsiveness of SIRP-α expressed by the leukocyte to any CD47 expressed by the tumor cell with the SIRP-α antibody.

In some embodiments, an antibody of the present disclosure is administered in combination with a second antibody that binds an antigen expressed by an NK cell. Exemplary antigens expressed by an NK cell include, without limitation, NKR-P1A (KLRB1), CD94 (NKG2A), KLRG1, KIR2DL5A, KIR2DL5B, KIR2DL1, KIR2DL2, KIR2DL3, KIR2DS2, KIR2DS3. KIR2DS4, KIR2DS5, KIR3DS1, KIR2DS1, CD94 (NKG2C/E), NKG2D, CD160 (BY55), CD16 (FcγRIIIA), NKp46 (NCR1), NKp30 (NCR3), NKp44 (NCR2), DNAM1 (CD226), CRTAM, CD27, NTB-A (SLAMF6). PSGL1, CD96 (Tactile). CD100 (SEMA4D), NKp80 (KLRF1, CLEC5C), SLAMF7 (CRACC, CS1, CD319), and CD244 (2B4, SLAMF4).

In some embodiments, an antibody of the present disclosure is administered in combination with an immunotherapeutic agent (e.g., an effective amount of the immunotherapeutic agent, which in some embodiments as described above may be considered in the context of administering an anti-SIRP-α antibody of the present disclosure). An immunotherapeutic agent may refer to any therapeutic that targets the immune system and promotes a therapeutic redirection of the immune system, such as a modulator of a costimulatory pathway, cancer vaccine, recombinantly modified immune cell, etc. Exemplary and non-limiting immunotherapeutic agents are described infra. Without wishing to be bound to theory, it is thought that the antibodies of the present disclosure are suitable for use with immunotherapeutic agents due to complementary mechanisms of action, e.g., in activating both macrophages and other immune cells such as T$_{effector}$ cells to target tumor cells.

In some embodiments, the immunotherapeutic agent comprises an antibody. Exemplary antigens of immunotherapeutic antibodies are known in the art and include without limitation BDCA2, BDCA4, ILT7, LILRB1, LILRB2, LILRB3, LILRB4, LILRB5, Siglec-3, Siglec-7, Siglec-9, Siglec-15, FGL-1, CD200, CD200R, CSF-1R, CD40, CD40L, CD163, CD206, DEC205, CD47, CD123, arginase, IDO, TDO, AhR, EP2, COX-2, CCR2, CCR-7, CXCR1, CX3CR1, CXCR2, CXCR3, CXCR4, CXCR7, TGF-β RI, TGF-β RII, c-Kit, CD244, L-selectin/CD62L, CD11b, CD11c, CD68, 41BB, CTLA4, PD1, PD-L1, PD-L2, TIM-3, BTLA, VISTA, LAG-3, CD28, OX40, GITR. CD137, CD27, HVEM, CCR4, CD25, CD103, KIrg1, Nrp1, CD278, Gpr83, TIGIT, CD154, CD160, TNFR2, PVRIG, DNAM, and ICOS. Immunotherapeutic agents that are approved or in late-stage clinical testing include, without limitation, ipilimumab, pembrolizumab, nivolumab, atezolizumab, avelumab, durvalumab, and the like. In certain embodiments, an antibody of the present disclosure is administered in combination with an inhibitor of the PD-L1/PD-1 pathway. e.g., an anti-PD-L1 or anti-PD-1 antibody. As demonstrated herein, combined administration of an anti-SIRP-α antibody of the present disclosure and an inhibitor of the PD-L1/PD-1 pathway can result in synergistic anti-tumor activity.

In some embodiments, the immunotherapeutic agent comprises a vaccine, oncolytic virus, adoptive cell therapy, cytokine, or small molecule immunotherapeutic agent. Examples of such immunotherapeutic agents are known in the art. For example, adoptive cell therapies and therapeutics can include without limitation chimeric antigen receptor T-cell therapy (CAR-T), tumor infiltrating lymphocytes (TILs), TCR engineered NK cell, and macrophage cell products. Vaccines can include without limitation polynucleotide vaccines, polypeptide vaccines, or cell-based (e.g., tumor or dendritic cell-based) vaccines. Various cytokines useful for the treatment of cancer are known and include without limitation IL-2, IL-15, IL-7, IL-10, IL-12, IL21, TNFα, IFNs, GM-CSF, and engineered cytokine mutants. Small molecule immunotherapeutic agents can include without limitation IDO/TDO inhibitors, AhR inhibitors, arginase inhibitors, A2a R inhibitors, TLR agonists, STING agonists, and Rig-1 agonists.

In some embodiments, an antibody of the present disclosure is administered in combination with a chemotherapeutic agent or small molecule anti-cancer agent. In some embodiments, an antibody of the present disclosure is administered in combination with an immunotherapeutic agent and a chemotherapeutic agent or small molecule anti-cancer agent. For example, it is thought that kinase inhibitors or other inhibitors of signaling pathways (e.g., PAK4, PI3K, etc.) may be useful in combination with modulation of the immune system for treating cancer. As such, the antibodies of the present disclosure may find use in combination with one or more chemotherapeutic agents and/or small molecules (e.g., kinase inhibitors) for treating cancer. Non-limiting examples of chemotherapeutic agents and/or anti-cancer agents contemplated for use in combination with an antibody of the present disclosure are provided infra.

In some embodiments, an antibody of the present disclosure is administered in combination with a therapeutic agent (e.g., a chemotherapeutic/cytotoxic agent) including and not limited to methotrexate (RHEUMATREX®, Amethopterin) cyclophosphamide (CYTOXAN®), thalidomide (THALIDOMID®), acridine carboxamide, Actimid®, actinomycin, 17-N-allylamino-17-demethoxygeldanamycin, aminopterin, amsacrine, anthra-cycline, antineoplastic, antineoplaston, 5-azacytidine, azathioprine, BL22, bendamustine, biricodar, bleomycin, bortezomib, b ostatin, busulfan, calyculin, camptothecin, capecitabine, carboplatin, cetuximab, chlorambucil, cispla-tin, cladribine, clofarabine, cytarabine, dacarbazine, dasatinib, daunorubicin, decitabine, dichloroacetic acid, discode olide, docetaxel, doxorubicin, epirubicin, epothilone, eribulin, estramustine, etoposide, exatecan, exisulind, ferruginol, floxuridine, fludarabine, fluorouracil, fosfestrol, fotemustine, ganciclovir, gemcitabine, hydroxyurea, IT-101, idarubicin, ifosfamide, imiquimod, irinotecan, irofulven, ixabepilone, laniquidar, lapatinib, lenalidomide, lomustine, lurtotecan, mafosfamide, masoprocol, mechlorethamine, melphalan, mercaptopurine, mitomycin, mitotane, mitoxan-trone, nelarabine, nilotinib, oblimersen, oxaliplatin, PAC-1, paclitaxel, pemetrexed, pentostatin, pipobroman, pixantrone, plicamycin, procarbazine, proteasome inhibitors (e.g., bortezomib), raltitrexed, rebeccamycin, Revlimid®, rubite-can, SN-38, salinosporamide A, satraplatin, streptozotocin, swainsonine, tariquidar, taxane, tegafur-uracil, temozolo-mide, testolactone, thioTEPA, tioguanine, topotecan, tra-bectedin, tretinoin, triplatin tetranitrate, tris(2-chloroethyl) amine, troxacitabine, uracil mustard, valrubicin, vinblastine, vincristine, vinorelbine, vorinostat, zosuquidar, or the like.

In some embodiments, an antibody of the present disclosure is administered in combination with a targeted small molecule inhibitor. For example, in some embodiments, an antibody of the present disclosure is administered in combination with a VEGFR/PDGFR inhibitor (e.g., sorafenib, sunitinib, lenvatinib, vandetanib, cabozatinib, apatinib, pazopanib, axitinib, or regorafenib), EGFR inhibitor (e.g., erlotinib, gefitinib, or osimertinib), MEK inhibitor (e.g., trametinib, cobimetinib, binimetinib, or selumetinib), ALK inhibitor (e.g., crizotinib, ceritinib, alectinib, brigatinib, lorlatinib, entrectinib, TSR-011, CEP-37440, or X-396), CDK4/6 inhibitor (e.g., palbociclib, ribociclib, or abemaciclib), PARP inhibitor (e.g., olaparib, rucaparib, niraparib, talazoparib, pamiparib, veliparib, CEP 9722, or E7016), mTOR inhibitor, KRAS inhibitor, TRK inhibitor (e.g., larotrectinib), BCL2 inhibitor (e.g., venetoclax), IDH inhibitor (e.g., ivosidenib or enasidenib), hypomethylation agent (e.g., decitabine or azacitidine), PI3K inhibitor, or DDR (e.g., CHK, ATM, or ATR) inhibitor.

In some embodiments, an antibody of the present disclosure is administered in combination with a therapeutic agent including and not limited to 3F8, 8H9, Abagovomab, Abciximab, Abituzumab, Abrilumab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anetumab ravtansine, Anifrolumab, kinzumab (IMA-638), Apolizumab, Arcitumomab, Ascrinvacumab, Aselizumab, Atezolizumab, Atinumab, Atlizumab (tocilizumab), Atorolimumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Blinatumomab, Blosozumab, Bococizumab, Brentuximab vedotin, Briakinumab, Brodalumab, Brolucizumab, Brontictuzumab, Canaki-numab, Cantuzumab mertansine, Cantuzumab ravtansine, Caplacizumab, Capromab pendetide, Carlumab, Catumaxomab, cBR96-doxorubicin immunoconjugate, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Codrituzumab, Coltuximab ravtansine, Conatumumab, Concizumab, Crenezumab, CR6261, Dacetuzumab, Daclizumab, Dalotuzumab, Dapi-rolizumab pegol, Daratumumab, Dectrekumab, Demcizumab, Denintuzumab mafodotin, Denosumab, Derlotuximab biotin, Detumomab, Dinutuximab, Diridayumab, Dorlimomab aritox, Drozitumab, Duligotumab, Dupilumab, Durvalumab, Dusigitumab, Ecromeximab, Eculizumab, Edobacomab, Edrecolomab, Efalizumab, Engumab, Eldelumab, Elgemtumab, Elotuzumab, Elsilimomab, Emactuzumab, Emibetuzumab, Enavatuzumab, Enfortumab vedotin, Enlimomab pegol, Enoblituzumab, Enokizumab, Enoticumab, Ensituximab, Epitumomab cituxetan, Epratu-zumab, Erlizumab, Ertumaxomab, Etaracizumab, Etrolizumab, Evinacumab, Evolocumab, Exbivirumab, Fanolesomab, Faralimomab, Farletuzumab, Fasinunab, FBTA05, Felvizumab, Fezakinumab, Ficlatuzumab, Figitumumab, Firivumab, Flanvotumab, Fletikumab, Fontolizumab, Foralumab. Foravirumab, Fresolimumab, Fulranumab, Futuximab, Galiximab, Ganitumab, Gantenerumab, Gavilimomab, Gemtuzumab ozogamicin, Gevokizumab, Giren-tuximab, Glembatumumab vedotin, Golimumab, Gomiliximab, Guselkumab, Ibalizumab, Ibritumomab tiuxetan, Icrucumab, Idarucizumab, Igovomab, IMAB362, Imalumab, Imciromab, Imgatuzumab, Inclacumab, Indatuximab ravtansine, Indusatumab vedotin, In iximab, Intetumumab, Inolimomab, Inotuzumab ozogamicin, Ipilimumab, Iratumumab, Isatuximab. Itolizumab, Ixekizumab, Keliximab, Labetuzumab, Lambrolizumab, Lampalizumab, Lebrikizumab, Lemalesomab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Namatumab, Natalizumab, Nebacumab, Necitumumab, Nemolizumab, Nerelimomab, Nesvacumab, Nimotuzumab, Nivolumab, Nofetumomab me entan, Obiltoxaximab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Ravirumab, Ralpancizumab, Ramucirumab, Ranibizumab, Raxibacumab, Refanezumab, Regavirumab, Reslizumab, Rilotumumab, Rinucumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, SGN-CD19A, SGN-CD33A, Sifalimumab, Siltuximab, Simtuzumab, Siplizumab, Sirukumab, Sotuzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tarextumab, Te bazumab, Telimomab aritox, Tenatumomab, Teneliximab, Teplizumab, Teprotumumab, Tesidolumab, TGN1412, Ticilimumab (tremelimumab), Tildrakizumab, Tigatuzumab, TNX650, Tocilizumab (atlizumab), Toralizumab, Tosatoxumab, Tositumomab, Tovetumab, Tralokinumab, Trastuzumab, TRBS07, Tregalizumab, Tremelimumab, Tucotuzumab celmoleukin, Tuvirumab, Ublituximab, Ulocuplumab, Urelumab, Urtoxazumab, Ustekinumab, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab. Zatuximab, Ziralimumab, or Zolimomab aritox.

Combination treatments comprising an antibody of the present disclosure and multiple additional agents (e.g., as described supra) are contemplated. For example, in some embodiments, an antibody of the present disclosure is administered in combination with a chemotherapeutic/cytotoxic agent and an antibody or targeted small molecule inhibitor. In some embodiments, an antibody of the present disclosure is administered in combination with a chemotherapeutic/cytotoxic agent and an immunotherapeutic agent. In some embodiments, an antibody of the present disclosure is administered in combination with an antibody or targeted small molecule inhibitor and an immunotherapeutic agent.

Any cancer type known in the art may be included, such as but not limited to carcinoma, sarcoma, lymphoma, leukemia, lymphoma, and blastoma. More particular examples of such cancers include, but are not limited to, lung cancer, squamous cell cancer, brain tumors, glioblastoma, head and neck cancer, hepatocellular cancer, colorectal cancer (e.g., colon or rectal cancers), liver cancer, bladder cancer, gastric or stomach cancer, pancreatic cancer, cervical cancer, ovarian cancer, cancer of the urinary tract, breast cancer, peritoneal cancer, uterine cancer, salivary gland cancer, kidney or renal cancer, prostate cancer, vulval cancer, thyroid cancer, anal carcinoma, penile carcinoma, melanoma, multiple myeloma and B-cell lymphoma (including non-Hodgkin's lymphomas (NHL)); acute lymphoblastic leukemia (ALL); chronic lymphocytic leukemia (CLL): acute myeloid leukemia (AML); Merkel cell carcinoma; hairy cell leukemia; chronic myeloblastic leukemia (CML); and associated metastases.

In addition to cancer therapies, the antibodies provided herein are useful in therapies in which monoclonal antibodies are administered for the purpose of depleting cells, e.g., in the treatment of inflammatory diseases by depletion immune cells. For such purposes the an antibody provided herein is administered in combination with a second therapeutic antibody, e.g. with rituximab for depletion of B cells in inflammatory diseases and autoimmune conditions; alemtuzumab for multiple sclerosis; OKT3 for immunosuppression; others for bone marrow transplant conditioning; and the like.

Further provided herein are methods of treating or delaying progression of an autoimmune disease or an inflammatory disease in an individual by administering an effective amount of an antibody of the present disclosure. Autoimmune diseases and inflammatory diseases amenable to treatment according to the disclosure include, but are not limited to, multiple sclerosis, rheumatoid arthritis, a spondyloarthropathy, systemic lupus erythematosus, an antibody-mediated inflammatory or autoimmune disease, graft versus host disease, sepsis, diabetes, psoriasis, atherosclerosis, Sjogren's syndrome, progressive systemic sclerosis, scleroderma, acute coronary syndrome, ischemic reperfusion, Crohn's Disease, endometriosis, glomerulonephritis, myasthenia gravis, idiopathic pulmonary fibrosis, fibrotic diseases (e.g., pulmonary fibrosis, liver cirrhosis, atrial fibrosis, endomyocardial fibrosis, myelofibrosis, or retroperitoneal fibrosis), asthma, acute respiratory distress syndrome (ARDS), vasculitis, and inflammatory autoimmune myositis. In some embodiments, an antibody of the present disclosure is administered in combination with a therapeutic agent, such as an immunosuppressive, anti-inflammatory, or immunomodulatory agent. In some embodiments, an antibody provided herein is used in the treatment of an autoimmune disease or an inflammatory disease, e.g., multiple sclerosis, rheumatoid arthritis, a spondyloarthropathy, systemic lupus erythematosus, an antibody-mediated inflammatory or autoimmune disease, graft versus host disease, sepsis, diabetes, psoriasis, psoriatic arthritis, atherosclerosis, Sjogren's syndrome, progressive systemic sclerosis, scleroderma, acute coronary syndrome, ischemic reperfusion, Crohn's Disease, ulcerative colitis, endometriosis, glomerulonephritis, IgA nephropathy, polycystic kidney disease, myasthenia gravis, idiopathic pulmonary fibrosis, fibrotic disease (e.g., pulmonary fibrosis, liver cirrhosis, atrial fibrosis, endomyocardial fibrosis, myelofibrosis, or retroperitoneal fibrosis), asthma, atopic dermatitis, acute respiratory distress syndrome (ARDS), vasculitis, or inflammatory autoimmune myositis.

In some embodiments, an antibody of the present disclosure is part of a pharmaceutical formulation, e.g., including the antibody and one or more pharmaceutically acceptable carriers. Pharmaceutical compositions and formulations as described herein can be prepared by mixing the active ingredients (such as an antibody or a polypeptide) having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives; low molecular weight (less than about 10 residues) polypeptides; proteins, such as serum albumin, gelatin, or immunoglobulins; hydrophilic polymers such as polyvinylpyrrolidone; amino acids: monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). In some embodiments, an antibody of the present disclosure is lyophilized.

In some embodiments, an individual is administered a dose normalized to the body weight of the individual. In some embodiments, an individual is administered a dose of about 10 μg/kg, about 50 μg/kg, about 100 μg/kg, about 200 μg/kg, about 300 μg/kg, about 400 μg/kg, about 500 μg/kg, about 600 μg/kg, about 700 μg/kg, about 800 μg/kg, about 900 μg/kg, about 1,000 μg/kg, about 1,100 μg/kg, 1,200 μg/kg, 1,300 μg/kg, 1,400 μg/kg, 1,500 μg/kg, 1,600 μg/kg, 1.700 μg/kg, 1,800 μg/kg, 1,900 μg/kg, about 2,000 μg/kg, about 3000 μg/kg, about 4000 μg/kg, about 5000 μg/kg, about 6000 μg/kg, about 7000 μg/kg, about 8000 μg/kg, about 9000 μg/kg, about 10 mg/kg, about 20 mg/kg, about 30 mg/kg, about 40 mg/kg, about 50 mg/kg, about 60 mg/kg, about 70 mg/kg, about 80 mg/kg about 90 mg/kg, about 100 mg/kg, about 200 mg/kg, about 300 mg/kg, about 400 mg/kg, about 500 mg/kg, about 600 mg/kg, about 700 mg/kg, about 800 mg/kg, about 900 mg/kg, or about 1000 mg/kg of an antibody of the present disclosure.

In some embodiments, the period of time that an antibody of the present disclosure is administered to the individual is any suitable period as determined by the stage of the disease, the patient's medical history and the attending physician's discretion. Examples of such suitable periods include, but are not limited to, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months or longer. In particular aspects, the treatment period is continued for longer than 24 months, if desired, such as for 30 months, 31 months, 32 months, 33 months, 34 months, 35 months, 36 months, or longer than 36 months. In some embodiments, the period is 6 months, 1 year or 2 years. In another embodiment, the period of time of dosing for any of the methods described herein is for at least about 2 weeks, at least about 4 weeks, at least about 8 weeks, at least about 16 weeks, at least about 17 weeks, at least about 18 weeks, at least about 19 weeks, at least about 20 weeks, at least about 24 weeks, at least about 28 weeks, at least about 32 weeks, at least about 36 weeks, at least about 40 weeks, at least about 44 weeks, at least about 48 weeks, at least about 52 weeks, at least about 60 weeks, at least about 68 weeks, at least about 72 weeks, at least about 80 weeks, at least about 88 weeks, at least about 96 weeks, or at least about 104 weeks.

EXAMPLES

The present disclosure will be more fully understood by reference to the following examples. The examples should not, however, be construed as limiting the scope of the present disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Identification of Antibodies with Novel Binding Specificities to SIRP-α Proteins Methods
Antibody Production
The following proteins were used for immunization. Each includes a human or mouse SIRP-α peptide fused to a modified Fc region (either a human IgG4 Fc with a hinge region containing an S228P mutation, or an L234A/L235A/G1237A/N297A human IgG1 Fc designated as IgG1_AAA_N297A) for increased immunogenicity.

TABLE A

| | | |
|---|---|---|
| Immunogen sequences | | |
| Description | SEQ ID NO | Sequence |
| Human sirpa v1 (Fusion with Fc of IgG4_S228P) | 1 | EEELQVIQPDKSVLVAAGETATLRCTATSLIPV GPIQWFRGAGPGRELIYNQKEGHFPRVTTVSD LTKRINNMDFSIRIGNITPADAGTYYCVKFRKG SPDDVEFKSGAGTELSVRAKPSESKYGPPCPP CPAPEFLGGPSVFLFPPKPKDTLMISRTPEVTC VVVDVSQEDPEVQFNWYVDGVEVHNAKTKP |

TABLE A-continued

Immunogen sequences

| Description | SEQ ID NO | Sequence |
|---|---|---|
| | | REEQFNSTYRVVSVLTVLHQDWLNGKEYKCK<br>VSNKGLPSSIEKTISKAKGQPREPQVYTLPPSQ<br>EEMTKNQVSLTCLVKGFYPSDIAVEWESNGQ<br>PENNYKTTPPVLDSDGSFFLYSRLTVDKSRWQ<br>EGNVFSCSVMHEALHNHYTQKSLSLSLGK |
| Human sirpa v2<br>(Fusion with Fc of IgG4_S228P) | 2 | EEELQVIQPDKSVSVAAGESAILHCTVTSLIPV<br>GPIQWFRGAGPARELIYNQKEGHFPRVTTVSE<br>STKRENMDFSISISNITPADAGTYYCVKFRKGS<br>PDTEEKSGAGTELSVRAKPSESKYGPPCPPCPA<br>PEFLGGPSVFLFPPKPKDTLMISRTPEVTCVVV<br>DVSQEDPEVQFNWYVDGVEVHNAKTKPREE<br>QFNSTYRVVSVLTVLHQDWLNGKEYKCKVS<br>NKGLPSSIEKTISKAKGQPREPQVYTLPPSQEE<br>MTKNQVSLTCLVKGFYPSDIAVEWESNGQPE<br>NNYKTTPPVLDSDGSFFLYSRLTVDKSRWQE<br>GNVFSCSVMHEALHNHYTQKSLSLSLGK |
| Mouse 129 sirpa<br>(Fusion with Fc of<br>IgG1_AAA_N297A) | 3 | KELKVTQPEKSVSVAAGDSTVLNCTLTSLLPV<br>GPIKWYRGVGQSRLLIYSFTGEHFPRVTNVSD<br>ATKRNNMDFSIRISNVTPEDAGTYYCVKFQKG<br>PSEPDTEIQSGGGTEVYVLAKPSDKTHTCPPCP<br>APEAAGAPSVFLFPPKPKDTLMISRTPEVTCVV<br>VDVSHEDPEVKFNWYVDGVEVHNAKTKPRE<br>EQYASTYRVVSVLTVLHQDWLNGKEYKCKV<br>SNKALPAPIEKTISKAKGQPREPQVYTLPPSRE<br>EMTKNQVSLTCLVKGFYPSDIAVEWESNGQP<br>ENNYKTTPPVLDSDGSTFLYSKLTVDKSRWQ<br>QGNVFSCSVMHEALHNHYTQKSLSLSPGK |
| Mouse NOD sirpa<br>(Fusion with Fc of<br>IgG1_AAA_N297A) | 4 | TEVKVIQPEKSVSVAAGDSTVLNCTLTSLLPV<br>GPIRWYRGVGQSRQLIYSFTTEHFPRVTNVSD<br>ATKRSNEDFSIRISNNTPEDAGTYYCVKFQRG<br>SPDTEIQSGGGTEVYVLAKDKTHTCPPCPAPE<br>AAGAPSVFLFPPKPKDTLMISRTPEVTCVVVD<br>VSHEDPEVKFNWYVDGVEVHNAKTKPREEQ<br>YASTYRVVSVLTVLHQDWLNGKEYKCKVSN<br>KALPAPIEKTISKAKGQPREPQVYTLYPSREEM<br>TKNQVSLTCLVKGFYPSDIAVEWESNGQPEN<br>NYKTTPPVLDSDGSEFLYSKLTVDKSRWQQG<br>NVFSCSVMHEALHNHYTQKSLSLSPGK |

The above proteins were used to immunize wild-type chickens, SynVH chickens which are transgenic chickens containing VH from human and VL from chicken, or chickens with fully human "HuMAB" immunoglobulin loci (Crystal Bioscience; see. e.g., WO2012162422, WO2011019844, and WO2013059159). Chickens were immunized with varied schedules having alternating doses of antigen. An exemplary immunization schedule is as follows: initial immunization with 100 µg dose of antigen having the sequence of SEQ ID NO:1 at week 1, boost of 100 µg of antigen having the sequence of SEQ ID NO: 2 at week 3, draw at week 4, boost with 50 µg dose of antigen having the sequence of SEQ ID NO:1 at week 5, draw at week 6, boost with 50 µg of antigen having the sequence of SEQ ID NO: 2 at week 7, and draw at week 8. Additional descriptions of chicken immunization may be found, e.g., in Mettler Izquierdo, S. et al. (2016) Microscopy (Oxf) 1-16.

Compared with the mammalian SIRP-α sequences, the sequence of chicken SIPRα was found to be significantly more divergent. Without wishing to be bound to theory, it was thought that the divergence between mammalian and chicken SIRP-α sequences would provide unique opportunities to generate antibodies that cross-react across multiple mammalian SIRP-α proteins. For example, it may be difficult to generate anti-SIRP-α antibodies that cross-react with the murine sequence from a mouse host due to immune tolerance. Moreover, the greater divergence between the chicken and mammalian immune systems may lead to a greater diversity in antibody production.

Without wishing to be bound to theory, it is thought that antibodies with cross-reactive binding among human, cynomologus, and/or murine proteins may allow for characterization of antibodies in both animal models and clinical testing. Antibodies with isoform- and/or variant-specific binding may be useful for personalized medicine approaches to specific human populations and/or studies on specific variants of interest.

Determination of $K_{off}$

Binding of the antibody clones to various SIRP proteins was determined using surface plasmon resonance (SPR) detection on a ProteOn XPR36 instrument (Bio-Rad, Hercules, CA) using phosphate buffered saline (PBS, pH 7.4) supplemented with 0.01% Tween-20 (PBST) as running buffer. The pre-filtered media containing the secreted antibodies was used directly for the assay. First, anti-Human IgG Fc (BR-1008-39, GE Healthcare) was amine-coupled onto a GLC sensor chip to generate the capture surfaces for the antibodies. About 4000 RU per flow cell of immobilized anti-human IgG Fc is achieved. Each clone is screened using the same method as follows. The SIRP analytes used for the screen were SIRP-α from various species (human v1, human v2, cynomolgus, mouse 129, BL6, BALBc, NOD), human SIRP-β, and human SIRP-γ; SEQ ID NOs:5, 6, 11, 7, 9, 10, 8, 13, and 15, respectively.

~5-10 uL of pre-filtered media in 10 mM sodium acetate buffer (pH4.5) was injected for 2 mins at 30 ul/min, followed by buffer flow for 1 min at 100 uL/min. SIRP analyte (100 nM) was injected for 1 min at 100 uL/min, followed by a dissociation cycle of 10 mins. Regeneration of the chip surface was accomplished by flowing 3M Magnesium Chloride for 1 min at 25 uL/min in both orientations, followed by buffer flow for 1 min at 100 uL/min. Biosensor data were double-referenced by subtracting the interspot data (containing no immobilized anti-human IgG Fc) from the reaction spot data (immobilized anti-human IgG Fc) and then subtracting the response of a buffer "blank" analyte injection from that of an analyte injection. Binding was fitted using a 1:1 Langmuir and $K_{off}$ (1/S) values calculated. All SPR assays were performed at 25° C.

Determination of $K_D$

The interactions of anti-SIRPα antibodies with SIRPα from various species (human v1, human v2, cynomolgus, mouse 129, BL6, BALBc, NOD), SIRPβ and SIRPγ were analyzed using two methods, direct immobilization of the antibodies (via GLC chip) or capture via biotinylated Protein A (via NLC chip), according to the following protocols. All experiments were performed at 25° C. using a SPR-based ProteOn XPR36 biosensor (BioRad. Inc, Hercules, CA) equipped with GLC or NLC sensor chips. Antibodies were expressed using FreeStyle™ 293-FS cells (Thermo Fisher). Purification was carried out by standard Protein A affinity column chromatography and eluted antibodies were stored in PBS buffer.

The running buffer was PBS pH 7.4 with 0.01% Tween-20 (PBST+). All analytes were used at their nominal concentrations as determined by A280 Absorbance and using their molar calculated extinction coefficient. Analytes were injected in a "one-shot" kinetic mode as described elsewhere (see. e.g., Bravman, T. et al. (2006) *Anal. Biochem.* 358: 281-288).

For the method using GLC chip, the analytes were injected and flowed over anti-SIRPα antibodies immobilized (~1000 RUs) on GLC chips using Proteon Amine Coupling Kit. For the immobilization step, GLC chip was activated with EDAC/Sulpho-NHS 1:1 (Biorad) diluted 1/100 for 300s at 25 μL/min. Anti-SIRPα antibodies were diluted to 80 nM concentration in 10 mM sodium acetate buffer pH 4.5 and immobilized to the chip at 30 μL/min for 50s. Chip was inactivated with ethanolamine for 300s at 25 μL/min. The analytes (e.g., SIRP-α from different species, SIRP-β, SIRP-γ) were injected in a "one-shot" kinetic mode at nominal concentrations of 100, 33, 11, 3.7, 1.2 and 0 nM. Association times were monitored for 90s at 100 μL/min, and dissociation times were monitored for 1200s. The surfaces were regenerated with a 2:1 v/v blend of Pierce IgG elution buffer/4M NaCl.

Alternatively, $K_D$ determination was performed using antibody capture via an NLC chip. In this case, 15 ug/mL biotinylated protein A (Thermofisher) was injected at 30 uL/min for 120 s over the NLC chip to obtain an immobilization response of ~1000-1200 RUs. Next, anti-SIRPα antibodies (~160 nM) were injected for 80s at 30 uL/min. The analytes (SIRPα from different species, SIRP-β and SIPR-γ) were subsequently injected in a "one-shot" kinetic mode at nominal concentrations of 100, 33, 11, 3.7, 1.2 and 0 nM. Association times were monitored for 60s at 25 μl/min, and dissociation times were monitored for 120s. The surfaces were regenerated with a 2:1 v/v blend of Pierce IgG elution buffer/4M NaCl.

Biosensor data were double-referenced by subtracting the interspot data (containing no immobilized protein) from the reaction spot data (immobilized protein) and then subtracting the response of a buffer "blank" analyte injection from that of an analyte injection. Double-referenced data were fit globally to a simple Langmuir model and the $K_D$ value was calculated from the ratio of the apparent kinetic rate constants ($K_D=k_d/k_a$).

Results

The binding kinetics of various antibody clones to selected mouse SIRP-α proteins were determined. Mouse proteins that were tested include BALBc (SEQ ID NO:10), BL6 (SEQ ID N0:9), NOD (SEQ ID NO:8), and m129 (SEQ ID NO:7) SIRP-α proteins. The results are summarized in Tables B-E below. Variable domain sequences for AB21 and AB25 are shown in Table J1.

As used herein, antibody clones are referred to by clone ID number. In addition, the notation "S[clone number]" refers to an sc-Fv-Fc format; the notation "AB[clone number]" refers to a full IgG antibody format: the notation "AB[clone number]b" refers to a mouse IgG1 N297A format; and "AB[clone number]c" refers to a mouse IgG2a format.

TABLE B

Summary of kinetics for binding of selected antibodies to BALBc mouse SIRP-α protein (SEQ ID NO: 10)

| Antibody | $K_{on}$ (1/Ms) | $K_{off}$ (1/s) | $K_D$ (M) |
|---|---|---|---|
| AB21c | $4.62 \times 10^5$ | $6.18 \times 10^{-4}$ | $1.34 \times 10^{-9}$ |
| AB25c | $3.03 \times 10^5$ | $2.92 \times 10^{-3}$ | $9.64 \times 10^{-9}$ |

TABLE C

Summary of kinetics for binding of selected antibodies to BL6 mouse SIRP-α protein (SEQ ID NO: 9)

| Antibody | $K_{on}$ (1/Ms) | $K_{off}$ (1/s) | $K_D$ (M) |
|---|---|---|---|
| AB21c | $2.76 \times 10^5$ | $2.41 \times 10^{-4}$ | $8.76 \times 10^{-10}$ |
| AB25c | $1.42 \times 10^5$ | $3.99 \times 10^{-4}$ | $2.81 \times 10^{-9}$ |

TABLE D

Summary of kinetics for binding of selected antibodies to NOD mouse SIRP-α protein (SEQ ID NO: 8)

| Antibody | $K_{on}$ (1/Ms) | $K_{off}$ (1/s) | $K_D$ (M) |
|---|---|---|---|
| AB21c | $7.49 \times 10^5$ | $4.79 \times 10^{-4}$ | $6.40 \times 10^{-10}$ |
| AB25c | $3.66 \times 10^5$ | $1.43 \times 10^{-3}$ | $3.90 \times 10^{-9}$ |

TABLE E

Summary of kinetics for binding of selected antibodies to m129 mouse SIRP-α protein (SEQ ID NO: 7)

| Antibody | $K_{on}$ (1/Ms) | $K_{off}$ (1/s) | $K_D$ (M) |
|---|---|---|---|
| AB21c | $5.63 \times 10^5$ | $3.31 \times 10^{-5}$ | $5.88 \times 10^{-11}$ |
| AB25c | $3.52 \times 10^5$ | $2.07 \times 10^{-5}$ | $5.87 \times 10^{-11}$ |

These results demonstrate that the AB21 and AB25 antibody clones bound to all four mouse SIRP-α proteins, making these antibodies suitable for characterization in in vivo mouse models.

Example 2: Functional Properties of Anti-SIRP-α Antibodies

The previous Example describes the identification and characterization of anti-SIRP-α antibodies. These antibodies were next examined in animal models to explore SIRP-α's biological effects on tumor growth.

As noted above, antibody clones labeled as "b" were tested as full-length mouse IgG1 antibodies with an N297A mutation. Antibody clones labeled as "c" were tested as full-length mouse IgG2a antibodies.

Methods

In Vivo Anti-Tumor Activity

For the MC38 syngeneic mouse colon carcinoma model, MC38 cells were implanted subcutaneously in C57BL/6 mice and randomized into groups (8-10 mice/group). Treatment groups included vehicle (PBS), AB25b, AB25c, and AB27b. All anti-SIRPα antibodies had a mouse IgG1 Fc region bearing an N297A mutation except for AB25c, which had a mouse IgG2a. Treatment was initiated when tumors were an average of 60-65 mm$^3$, day 7 post implant. Mice were dosed intraperitoneally (IP) at 10 mg/kg twice a week for three weeks for anti-SIRPα. Animals were sacrificed when tumors reached a volume of ~2000 mm$^3$.

Results

The in vivo anti-tumor effects of various anti-SIRP-α antibodies were assayed in a syngeneic mouse colon carcinoma model. The anti-tumor activities of blocking anti-SIRP-α antibodies AB25b, AB25c, and AB27b were examined in an MC38 syngeneic mouse colon carcinoma model to assess their single agent activities. The blocking anti-SIRP-α antibodies AB25b, AB25c, and AB27b delayed tumor formation at 10 mg/kg as compared to vehicle alone (FIG. 1) in the MC38 syngeneic mouse model. On day 25, groups treated with anti-SIRPα antibodies had three mice below 600 mm$^3$ for AB25b, four mice below 600 mm$^3$ for AB25c, and 3 mice below 600 mm$^3$ for AB27b, while the vehicle-treated group had only two mice below 600 mm$^3$.

These results demonstrate the efficacy of anti-SIRP-α antibody treatment in inhibiting tumor growth in vivo. Blocking anti-SIRP-α antibodies were found to block in vivo tumor growth.

Example 3: Humanization of Anti-SIRP-α Antibodies

The Examples above describe the generation and characterization of anti-SIRP-α antibodies having a fully human heavy chain and a chicken light chain. In order to humanize the chicken-derived light chains, chicken HVRs of these antibodies were grafted onto various human lambda light chain frameworks.

Methods

Humanization

Antibodies were humanized using standard techniques. For measuring production yield, equal volume of Expi293 cultures expressing anti-SIRPα antibodies were purified by Protein A affinity chromatography. After buffer exchange into PBS, the protein concentration was determined by A280 and expressed in mg/mL.

Results

In order to design humanized light chains, each chicken light chain sequence was aligned to the closest human germline framework by IgBLAST (NCBI). Using this analysis, the closest match to the chicken lambda light chain framework is human IGLV3 (see SEQ ID NOs:27-30).

In another approach, a literature search was undertaken to determine the optimal human lambda light chain framework sequences to pair with a human VH3 sequences (the human heavy chain used for these antibodies). Based on these analyses, it was thought that human VH3 would pair well with human IGLV1 and IGLV2. See Glanville, J. et al. (2009) *Proc. Natl. Acad. Sci.* 106:20216-20221: Lloyd, C. et al. (2009) *Protein Eng. Des. Sel.* 22:159-168; and Jayaram, N. et al. (2012) *Protein Eng. Des. Sel.* 25:523-529.

Therefore, six humanized light chains were created: Hum1 (AB25 HVRs+ human IGLV3 framework; SEQ ID NO:25), Hum2 (AB25 HVRs+ human IGLV1 framework), Hum3 (AB66 HVRs+ human IGLV3 framework). Hum4 (AB66 HVRs+ human IGLV1 framework), Hum5 (AB25 HVRs+ human IGLV2 framework), and Hum6 (AB21 HVRs+ human IGLV1 framework).

Each of the 6 humanized light chains was paired with the AB21 heavy chain. Antibodies were expressed as described above. Surprisingly, human IGLV1 framework sequences resulted in decreased antibody expression regardless of the heavy chain. This refers to the heavy chain pairings with Hum2, Hum4 and Hum6. The results are summarized in FIG. 2 as "protein yield" (row 1). In contrast, antibodies with human IGLV2 and IGLV3 frameworks (Hum 1, Hum3, Hum5) in the light chain showed higher levels of expression.

Selected antibodies were also characterized for binding to a variety of SIRP proteins, e.g., to human SIRP-α v1 (SEQ ID NO:5), human SIRP-α v2 (SEQ ID NO:6), cynomolgus SIRP-α (SEQ ID NO:11), mouse BALB/c SIRP-α (SEQ ID NO:10), and human SIRP-γ (SEQ ID NO:15). These data are also summarized in FIG. 2. Selected humanized light chains caused a decrease in binding to one or more antigens. For instance, the human IGLV3 framework (represented by Hum1 and Hum3) was found to allow for superior levels of antibody production without perturbing binding affinity. For example, light chain variable domains with the IGLV3 frameworks and either the antibody 25 or antibody 66 HVR sequences (represented by Hum1 and Hum 3 respectively) combined well with the AB21 heavy chain and showed similar binding to different SIRP-α and SIRP-γ proteins. In contrast, IGLV1 and IGLV2 frameworks (represented by Hum2, Hum4, Hum5 and Hum6) were found to either lower expression and/or decrease binding to SIRP when paired with the AB21 heavy chain. Additional binding data from these experiments are provided in Table L infra. The human IGLV3 framework was selected for further testing.

Additional VL domains Hum9 and Hum8 were generated based on the Hum1 VL domain. Compared to Hum1, Hum9 contains 4 amino acid substitutions near or in HVR-L1 and -L2 that increase the humanness of the light chain to greater than or equal to 85% identity to human light chain sequence. Compared to Hum1, Hum8 contains 5 amino acid substitutions respectively near or in HVR-L1 and -L2 that increase the humanness of the light chain to greater than or equal to 85% identity to human light chain sequence. Hum1, Hum8 and Hum9 VLs when paired with heavy chain VH domain all_mut_AB21 (carrying germline mutations: SEQ ID NO:26) produced anti-SIRP-α antibodies that bind to human SIRP-α v1 with affinity equal or better than 10 pM (Table M).

Example 4: Induction of Phagocytosis and Dendritic Cell Activation by Anti-SIRP-α

Antibodies

Various anti-SIRP-α antibodies were next examined in phagocytosis and dendritic cell activation assays.

Methods

Tumor Cell Line Culturing

DLD-1 (human colorectal adenocarcinoma) cells were maintained in growth medium comprised of RPMI (Gibco) supplemented with 10 percent heat-inactivated Fetal Bovine Serum (Gibco), one percent penicillin/streptomycin (Gibco), and one percent Glutamax (Gibco).

Derivation and Culture of Human Monocyte-Derived Macrophages

Trima residuals were received from Blood Centers of the Pacific and diluted 1:4 with Phosphate Buffered Saline (PBS, Gibco). Diluted blood was split into four tubes and underlayed with 20 ml Ficoll-Paque Plus (GE Healthcare). Tubes were centrifuged for 30 minutes at 400×g. PBMCs were collected from the interface and resuspended in FACS buffer (PBS with 0.5 percent Bovine Serum Albumin (Gibco)). $CD14^+$ monocytes were purified by negative selection using the Monocyte Isolation Kit II (Miltenyi Biotec) and LS columns (Miltenyi Biotec) according to the manufacturer's protocol.

For nonpolarized macrophages, CD14+ monocytes were seeded into 15 cm tissue culture plates (Corning) at 10 million cells per dish in 25 ml IMDM (Gibco) supplemented with 10 percent human AB serum (Corning), one percent penicillin/streptomycin, and one percent Glutamax. Cells were cultured for seven to ten days.

For M2 polarized macrophages. $CD14^+$ monocytes were seeded into 15 cm tissue culture plates (Corning) at 6 million cells per dish in 25 ml RPMI(Gibco) supplemented with 10 fetal bovine serum (Thermo Fisher), one percent penicillin/streptomycin, and one percent Glutamax, and 50 ng/ml M-CSF (Miltenyi). Cells were cultured for seven to ten days.

In Vitro Phagocytosis Assays

DLD-1 cells were detached from culture plates by washing twice with 20 ml PBS and incubation in 10 ml TrypLE Select (Gibco) for 10 minutes at 37° C. Cells were centrifuged, washed in PBS, and resuspended in medium. Cells were labeled with the Celltrace CFSE Cell Proliferation kit (Thermo Fisher) according to the manufacturer's instructions and resuspended in IMDM. Macrophages were detached from culture plates by washing twice with 20 ml PBS and incubation in 10 ml TrypLE Select for 20 minutes at 37° C. Cells were removed with a cell scraper (Corning), washed in PBS, and resuspended in IMDM.

Phagocytosis assays were assembled in ultra-low attachment U-bottom 96 well plates (Corning) containing 100,000 DLD-1 cells, 50,000 macrophages, five-fold serial dilutions of anti-SIRP-α antibody from 100 nM to 6.4 pM, and cetuximab (Absolute Antibody) at 1 or 0.01 ug/ml or control antibody of the same isotype (Southern Biotech). Plates were incubated two hours at 37° C. in a humidified incubator with 5 percent carbon dioxide. Cells were pelleted by centrifugation for five minutes at 400×g and washed in 250 µl FACS buffer. Macrophages were stained on ice for 15 minutes in 50 µl FACS buffer containing 10 µl human FcR Blocking Reagent (Miltenyi Biotec). 0.5 µl anti-CD33 BV421 (Biolegend), and 0.5 µl anti-CD206 APC-Cy7 (Biolegend). Cells were washed in 200 µl FACS buffer, washed in 250 µl PBS, and stained on ice for 30 minutes in 50 µl Fixable Viability Dye eFluor 506 (ebioscience) diluted 1:1000 in PBS. Cells were washed twice in 250 µl FACS buffer and fixed for 30 minutes on ice in 75 µl Cytofix (BD Biosciences). Cells were washed in 175 µl FACS buffer and resuspended in 75 µl FACS buffer. Cells were analyzed on a FACS Canto 11 (BD Biosciences), with subsequent data analysis by Flowjo 10.7 (Treestar). Dead cells were excluded by gating on the e506-negative population. Macrophages that had phagocytosed tumor cells were identified as cells positive for CD33, CD206, and CFSE.

Dendritic Cell Activation Assays

Balb/c mice (n=3/group) were intravenously injected with a human IgG1 control, various anti-SIRP-α antibodies, mouse IgG control, or vehicle (PBS) at 10 mg/kg. Five hours post injection, spleens were harvested and processed into single cell suspension by mechanical dissociation. Activation marker CD86, MHCII and CCR7 level on CD4+ splenic dendritic cells was measured by flow cytometry.

Results

Figure 3A:
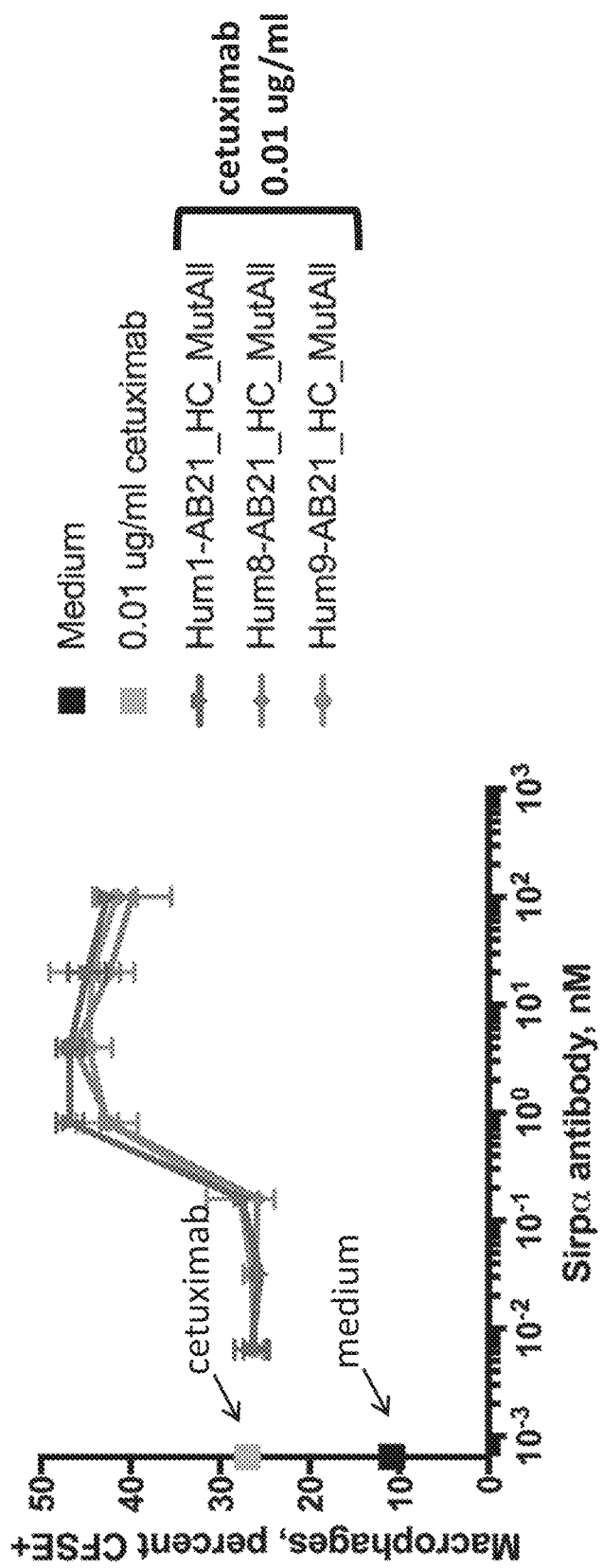
FIGS. 3A & 3D show the results of in vitro phagocytosis assays using EGFR(+) DLD-1 cells as the target and M2 macrophages as the phagocytosing cell. Anti-SIRP-α antibodies were tested at the indicated concentrations in combination with the anti-EGFR antibody cetuximab. Phagocytosis was measured by percentage of CFSE+ cells.
Figure 3B:
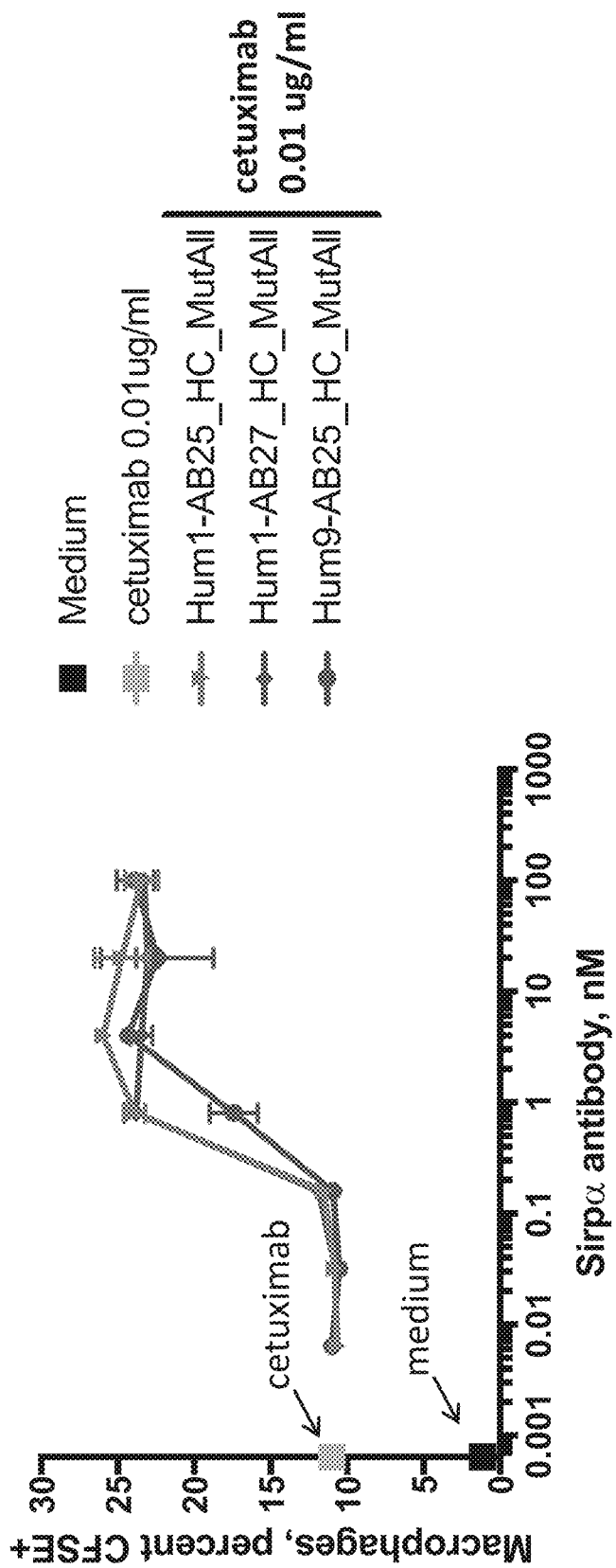

Humanized antibodies described above were tested for their effects on phagocytosis of EGFR(+) DLD-1 cells by M2 macrophages in combination with the anti-EGFR antibody cetuximab (FIG. 3A). All humanized antibodies were found to enhance cetuximab-induced phagocytosis. The humanized antibodies described above (antibody 25 heavy chain variant combined with Hum1 or Hum9 light chain and antibody 27 heavy chain variant combined with Hum1 light chain) were tested for their effects on phagocytosis of EGFR(+) DLD-1 cells by M2 macrophages in combination with the anti-EGFR antibody cetuximab (FIG. 3D). All humanized antibodies were found to enhance cetuximab-induced phagocytosis. All the antibodies tested were generated as full-length human IgG1 antibodies with L234A, L235A, G237A, and N297A mutations.

Next, various anti-SIRP-α antibodies were examined for their effects on in vivo dendritic cell activation (FIGS. 4A & 4B). Failure to engage mouse SIRP-α receptor on splenic dendritic cells via CD47 binding leads to splenic dendritic cell activation. Anti-SIRP-α antibodies Hum1/AB21mutall, Hum8/AB21mutall, and Hum9/AB21mutall were tested in vivo to determine if it leads to dendritic cell activation. As determined by CD86 and MHCII expression, these anti-SIRP-α blocking antibodies were able to induce activation of dendritic cells.

Example 5: Synergistic Anti-Tumor Effects of Combining Anti-SIRP-α Antibodies with Inhibition of the PD-L1/PD-1 Pathway Methods In Vivo Anti-Tumor Activity For the CT26 syngeneic mouse colon carcinoma model, CT26 cells were implanted subcutaneously in BALB/c mice and randomized into groups (8-9 mice/group). Treatment groups included vehicle (PBS), AB25b, anti-PD-L1, and AB25b/anti-PD-L1. Anti-PD-L 1 is generated by fusing the VH and VL domain of Atezolizumab with mouse IgG1 Fc region bearing an N297A mutation. All anti-SIRP-α antibodies also have a mouse IgG1 Fc region bearing an N297A mutation Treatment was initiated when tumors were an average of 75-80 $mm^3$, day 7 or 8 post implant. Mice were dosed intraperitoneally (IP) at 3 mg/kg or 10 mg/kg twice a week for three weeks for anti-SIRPα antibodies and three doses at 3 mg/kg, five days apart for anti-PD-L1. Animals were sacrificed when tumors reached a volume of ~2000 $mm^3$.

For the MC38 syngeneic mouse colon carcinoma model, MC38 cells were implanted subcutaneously in C57BL/6 mice and randomized into groups (8-10 mice/group). Treatment groups included vehicle (PBS), AB25b, anti-PD1 (clone RMP1-14, BioXCell), and AB25b/anti-PD1. All anti-SIRPα antibodies had a murine IgG1 Fc region bearing an N297A mutation except for AB25c. Treatment was initiated when tumors were an average of 60-65 mm³, day 7 post implant. Mice were dosed intraperitoneally (IP) at 10 mg/kg twice a week for three weeks for anti-SIRPα and three doses at 2 mg/kg for anti-PD1. Animals were sacrificed when tumors reached a volume of ~2000 mm³.

Results

Figure 5:
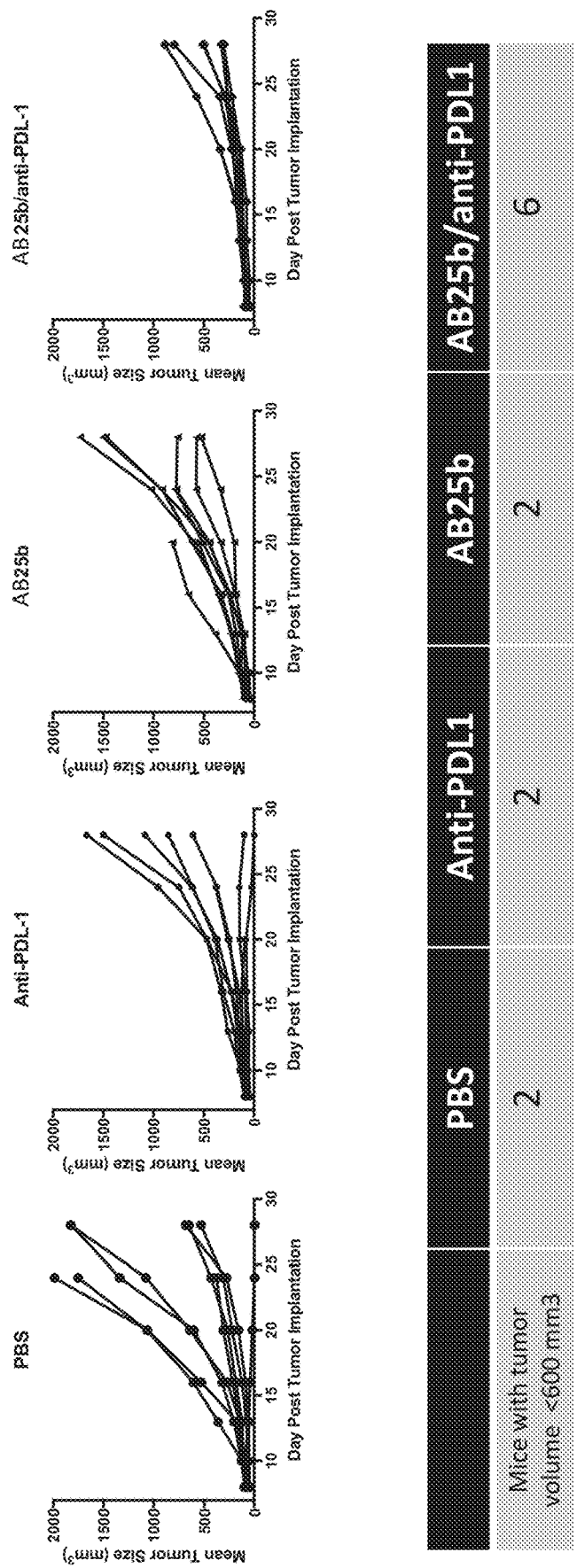
FIG. 5 shows the results of an in vivo syngeneic mouse colon carcinoma model to assess activity of combining anti-SIRP-α treatment with PD-L1/PD-1 pathway inhibition. CT26 cells were implanted subcutaneously in BALBc mice and randomized into groups (8 mice/group). Mice were treated with vehicle (PBS), anti-PD-L1 antibody, CD47 blocking anti-SIRP-α antibody AB25b, or AB25b and PD-L1. Treatment was initiated when tumors were an average of 60 mm³, day 7 post implant. Mice were dosed intraperitoneally (IP) at 10 mg/kg twice a week for three weeks and sacrificed when tumors reach a volume of ~2000 mm³.

Anti-tumor activity of the blocking AB25b anti-SIRP-α antibody was tested alone and in combination with an anti-PD-L1 antibody in the CT26 syngeneic mouse colon carcinoma model. As shown in FIG. 5, administration of AB25b at 10 mg/kg in combination with anti-PD-L1 at 3 mg/kg delayed tumor formation when compared to treatment with each single agent or vehicle control. On day 27 of the study, the combination treatment group had six mice with tumors below 600 mm³ in size, as compared to two, two, and two mice with tumors below 600 mm³ in size in the vehicle, anti-PD-L1 single agent, and anti-SIRP-α single agent treatment groups, respectively.

Figure 6:
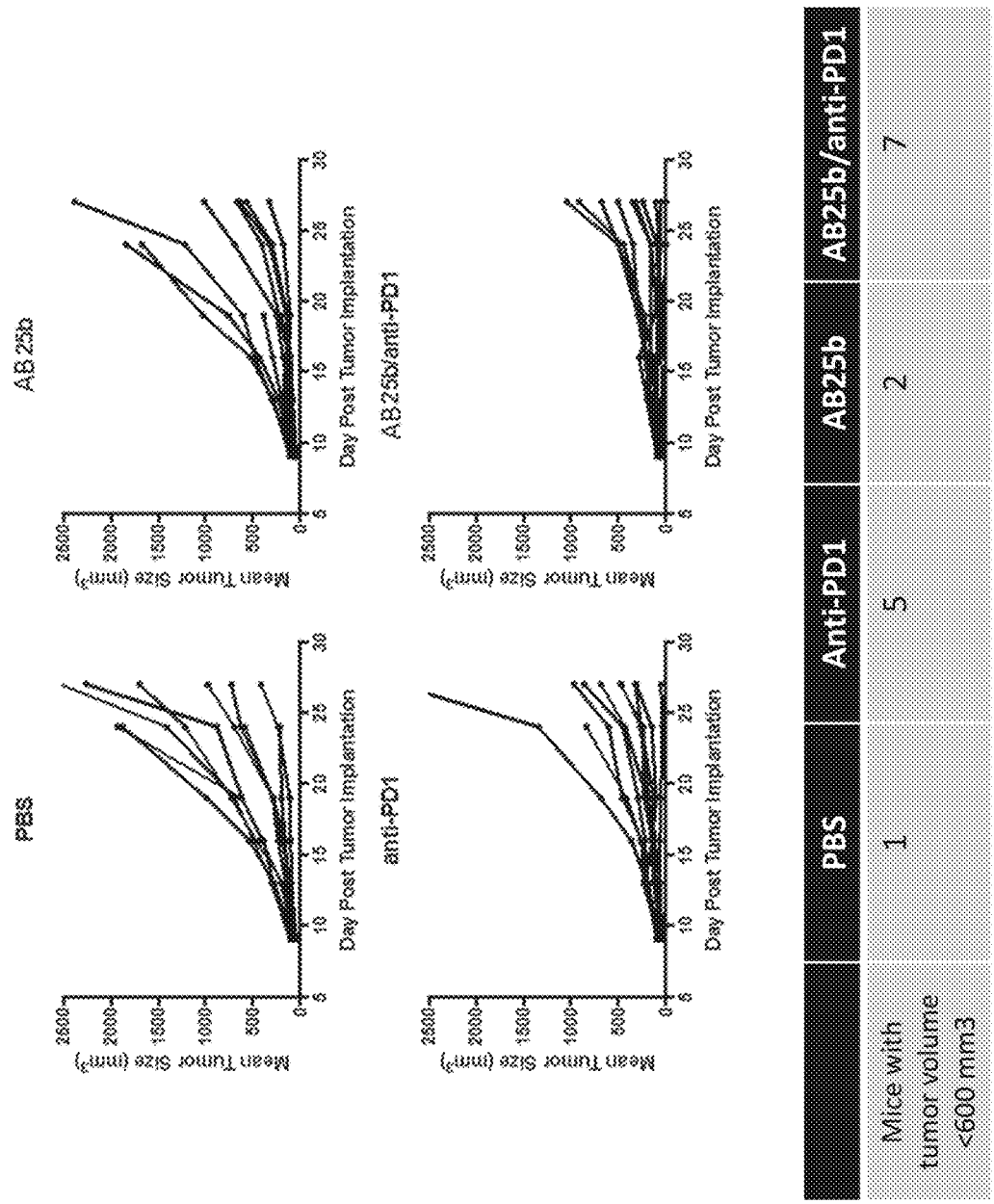
FIG. 6 shows the results of an in vivo syngeneic mouse colon carcinoma model to assess activity of combining anti-SIRP-α treatment with PD-L1/PD-1 pathway inhibition. MC38 cells were implanted subcutaneously in C57BL/6 mice and randomized into groups (8 mice/group). Mice were treated with vehicle (PBS), anti-PD-1 antibody, CD47 blocking anti-SIRP-α antibody AB25b, or AB25b and anti-PD-1. Treatment was initiated when tumors were an average of 60 mm³, day 7 post implant. Mice were dosed intraperitoneally (IP) at 10 mg/kg twice a week for three weeks and sacrificed when tumors reach a volume of ~2000 mm³.

Next, the anti-tumor activities of the AB25b anti-SIRP-α antibody were tested alone and in combination with an anti-PD-1 antibody in the MC38 syngeneic mouse colon carcinoma model. As shown in FIG. 6, combining AB25b (at 10 mg/kg) with anti-PD-1 at 5 mg/kg delayed tumor formation when compared to treatment with each single agent or vehicle control. On day 27 of the study, the AB25b/PD-1 combination treatment group had seven mice with tumors below 600 mm³ in size, as compared to one, five, and two mice with tumors below 600 mm³ in size in the vehicle, anti-PD-1 single agent, and AB25b single agent treatment groups, respectively.

A summary of antibodies described herein and their properties is provided in Table K. Additional binding data are provided in Tables L and N.

Example 6: Novel Anti-SIRP-α Antibody Light Chains Engineered to Remove Potential Liability Hot Spots Due to the properties of blocking anti-SIRP-α, antibodies AB21 and AB25 described above, an antibody comprising the variant AB21 VH domain (SEQ ID NO:26) and the humanized Hum1 VL domain (SEQ ID NO:25) was selected for analysis. The sequence of antibody light chains comprising the Hum1 humanized variable light chain domain described above was analyzed for potential liability hot spots, e.g., deamidation or glycation sites.

Protein deamidation is a post-translational modification in which the side chain amide of a glutamine or asparagine residue is converted into an acidic carboxylate group. Non-enzymatic deamidation of asparagine is faster than that of glutamine, and hence presents a higher physiological significance and greater potential liability risk in the manufacturing and storage of polypeptide-based therapeutics.

Glycation refers to the non-enzymatic glycosylation or Mallard reaction of proteins, which primarily occurs at the F-amino group of lysine, or a free amino group. The side chains of arginine, histidine, tryptophan, and cysteine residues represent additional potential glycation sites. Amadori-modified proteins are an early glycation product and undergo further reactions that give rise to advance glycation end products (AGEs).

The analyses of the Hum1-containing light chains identified sites where engineering may be desired to limit risk due, e.g., to modifications that may occur during manufacturing, storage, and/or drug development of anti-SIRP-α antibodies. This Example describes the testing and construction of Hum1 variants that remove these potential liabilities.

Methods

Peptide Mapping Analysis

For trypsin digests, samples were diluted in 6M Guanidine HCl and 1 mM EDTA. 10 mM DTT and 10 mM iodoacetamide were used to reduce and alkylate the samples, respectively. The buffer was than exchanged to 0.1M Tris-HCl and samples were incubated for 4 hours for digestion. For chymotrypsin digests, samples were diluted in 100 mM ammonium bicarbonate. 1% progenta anionic acid labile surfactant was added. Again, 10 mM DTT and 10 mM iodoacetamide were used to reduce and alkylate the samples respectively. Samples were incubated overnight.

The mass spectral data were acquired by Waters Acuity UHPLC in line with a Q Exactive Hybrid Quadrupole-Orbitrap (Thermo Scientific, San Jose CA). Column used is Agilent AdvanceBio Peptide Mapping (C18, 1×150 mm ID). Reversed phase solvents were used and the gradient used was 2% to 40% buffer over 41 minutes. Full MS scan range was 250-2000m/z. Peptide searches and relative abundance was analysed using Byonic and Byologic from Protein Metrics. Precursor Mass Accuracy of 10 ppm and fragment mass accuracy of 20 ppm was adopted.

Determination of $K_D$

The interactions of anti-SIRPa antibodies with SIPRa from various species (human v1, human v2, cynomolgus, mouse 129, BL6, BALBc, NOD), SIRPb and SIRPg were analyzed using direct immobilization of the antibodies. All experiments were performed at 25° C. using a SPR-based ProteOn XPR36 biosensor (BioRad, Inc, Hercules, CA) equipped with GLC sensor chips. Antibodies were expressed using FreeStyle™ 293-FS cells (Thermo Fisher). Purification was carried out by standard Protein A affinity column chromatography and eluted antibodies were stored in PBS buffer.

The running buffer was PBS pH 7.4 with 0.01% Tween-20 (PBST+). All analytes were used at their nominal concentrations as determined by A280 Absorbance and using their molar calculated extinction coefficient. Analytes were injected in a "one-shot" kinetic mode as described elsewhere (see. e.g., Bravman, T. et al. (2006) *Anal. Biochem.* 358: 281-288).

For immobilization using GLC chip, the analytes were injected and flowed over anti-SIRP-α antibodies immobilized (~1000 RUs) on GLC chips using Proteon Amine Coupling Kit. For the immobilization step, GLC chip was activated with EDAC/Sulpho-NHS 1:1 (Biorad) diluted 1/100 for 300s at 25 μL/min. Anti-SIRP-α antibodies were diluted to 80 nM concentration in 10 mM sodium acetate buffer pH 4.5 and immobilized to the chip at 30 μL/min for 50s. Chip was inactivated with ethanolamine for 300s at 25 μL/min. The analytes (e.g., SIRP-α from different species, SIRP-β, SIRP-γ) were injected in a "one-shot" kinetic mode at nominal concentrations of 100, 33, 11, 3.7, 1.2 and 0 nM. Association times were monitored for 90s at 100 uL/min, and dissociation times were monitored for 1200s. The surfaces were regenerated with a 2:1 v/v blend of Pierce IgG elution buffer/4M NaCl.

Biosensor data were double-referenced by subtracting the interspot data (containing no immobilized protein) from the reaction spot data (immobilized protein) and then subtracting the response of a buffer "blank" analyte injection from that of an analyte injection. Double-referenced data were fit globally to a simple Langmuir model and the $K_D$ value was calculated from the ratio of the apparent kinetic rate constants ($K_D=k_d/k_a$).

Results

An anti-SIRP-α antibody (antibody PC336) comprising a light chain (SEQ ID NO:47) with the Hum1 VL domain (SEQ ID NO:25) and a human IGLC1 lambda constant domain (SEQ ID NO:37), and a heavy chain (SEQ ID NO:61) with the AB21 MutAll VH domain (SEQ ID NO:26) and a constant region (SEQ ID NO:34) comprising a human IgG2 Da Fc region (comprising A330S and P331S mutations, amino acid position numbering according to EU) was carried out by trypsin and chymotrypsin digestion as described above. Overall sequence coverage of heavy chain was 100% (444 out of 444 amino acids), and light chain was 98.6% (211 out of 214 amino acids). Variable domain and full chain sequences for all antibodies are provided in Tables J1 and J2.

Figure 7:
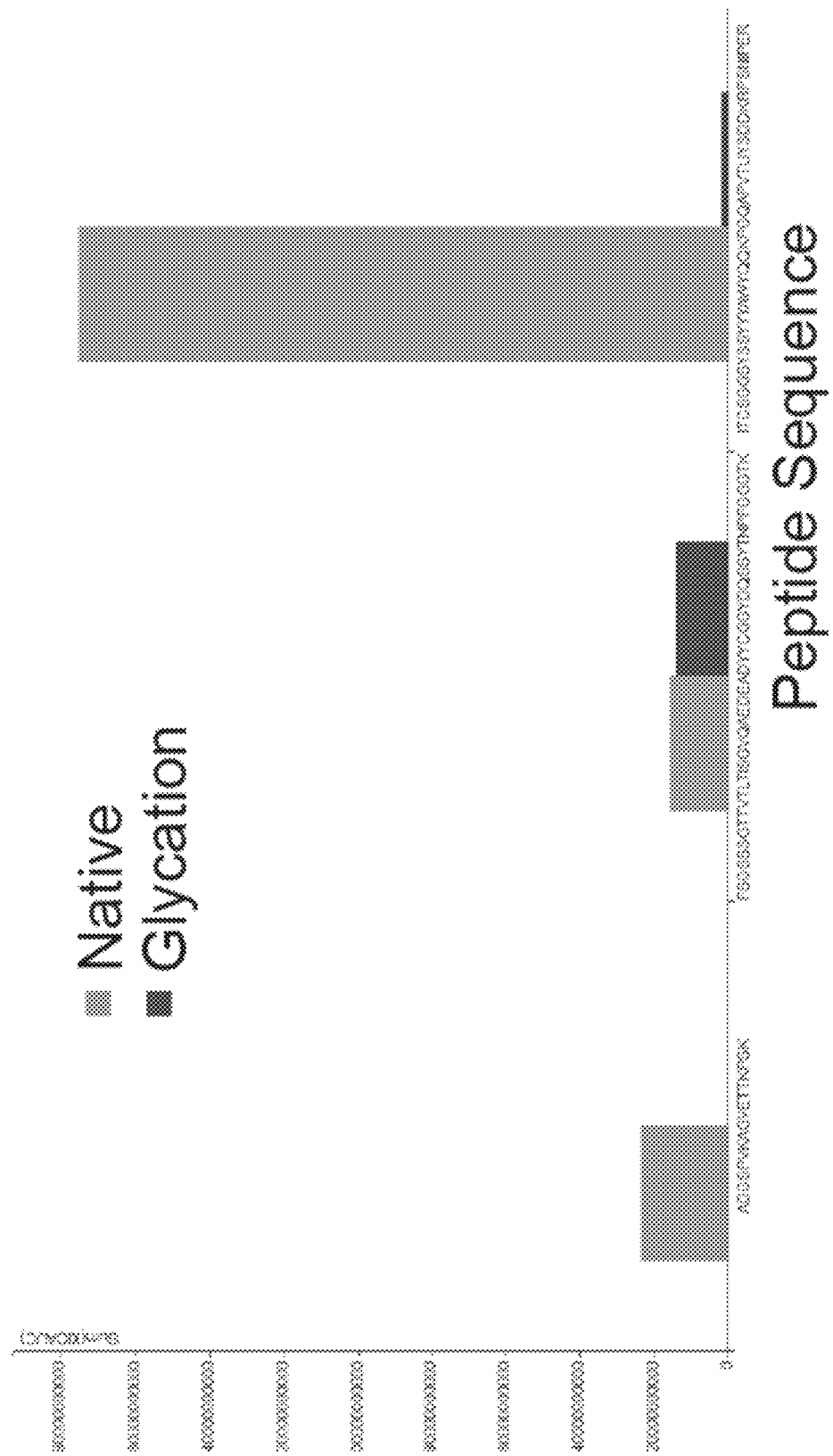
FIG. 7 shows the total extracted ion chromatography, area under the curve (XIC, AUC) of the glycated (black) versus unmodified form (grey) of peptides of antibody PC336, as analyzed by mass spectrometry. Sequences shown are SEQ ID NOs:64-66 (left to right).
Figure 8:
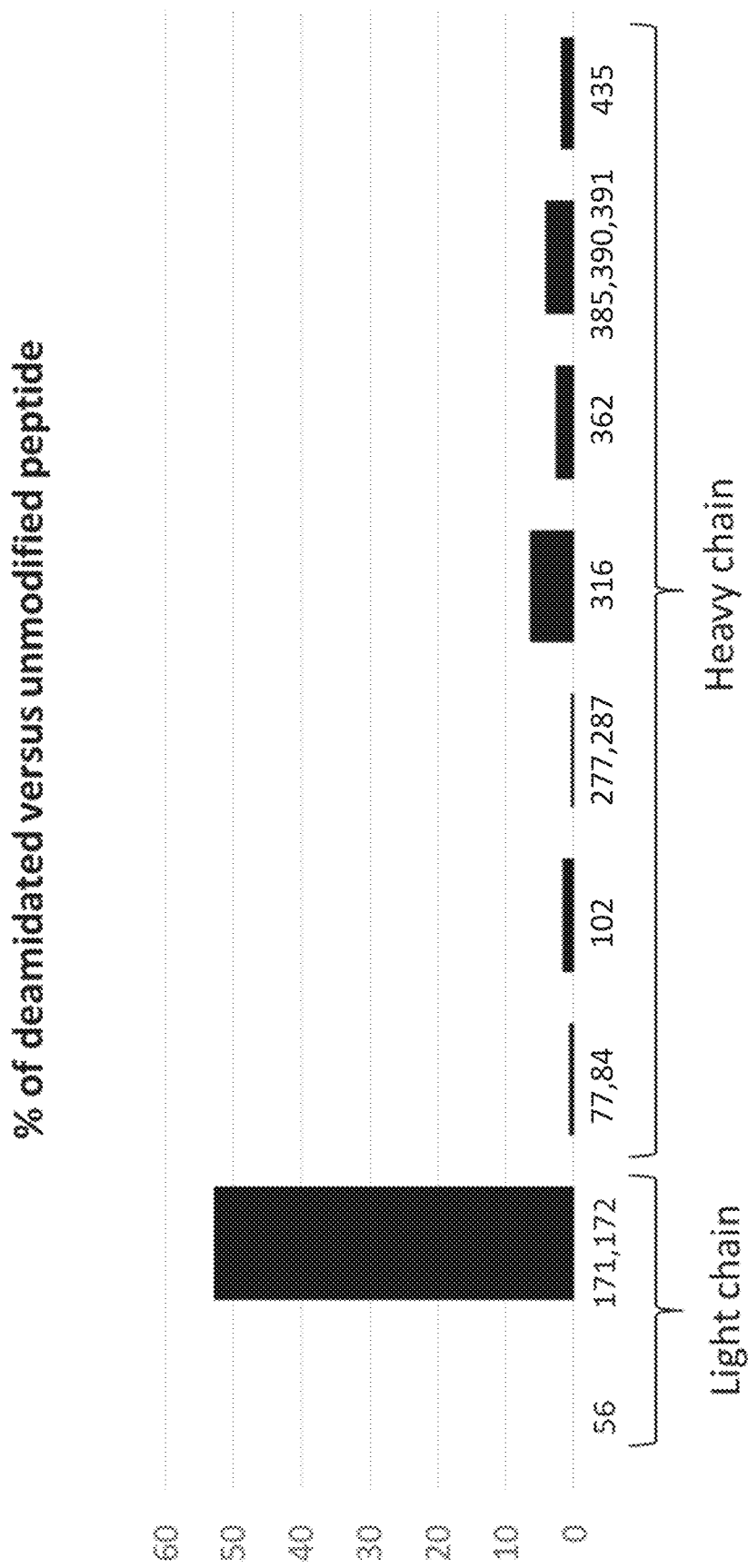
FIG. 8 shows the percentage of peptides modified by deamidation at the indicated residues of the light chain and heavy chain of anti-SIRP-α antibody PC301, as analyzed by mass spectrometry. Amino acid numbering is based on sequential numbering of residues in the light and heavy chain sequences of SEQ ID NOs: 63 and 59, respectively (not Kabat numbering).

These analyses revealed three light chain residues that were modified by glycation. Table F shows the glycation observed in the light chain. A total of 3 glycated peptides were isolated. Of these, it was observed that ~48% of the peptide with the sequence of SEQ ID NO:65 was glycated. The gly cation modification was assigned to K104 (numbering based on sequential numbering of amino acids for light chain, not Kabat). FIG. 7 shows the total extracted ion chromatography, area under the curve (XIC. AUC) of the glycated versus unmodified form of peptides of antibody PC336.

body PC301, which comprises a light chain (SEQ ID NO:63) with the Hum1 VL domain (SEQ ID NO:25) and a human IGLC2 lambda constant domain (SEQ ID NO:38), and a heavy chain (SEQ ID NO:59) with the AB21 MutAll VH domain (SEQ ID NO:26) and a constant region (SEQ ID NO:32) comprising a human IgG1 AAA N297A Fc region (comprising L234A, L235A, G237A, and N297A mutations, amino acid position numbering according to EU). As shown in FIG. 8, various sites in the light chain and heavy chain of antibody PC301 were observed to be deamidated. In particular, approximately 50% of peptides containing the N171 and N172 residues of the light chain constant domain were found to be modified by deamidation. From peptide mapping, it was not possible to determine whether N171, N172, or both residues were deamidated, since these two residues are adjacent to each other and isolated in the same peptide.

Post-translational modifications such as deamidation and glycation are undesirable for drug development. This is due to potential issues with product heterogeneity during drug manufacture. Therefore, it is desirable to limit modifications even though these modifications did not appear to affect binding affinities of the anti-SIRP-α antibodies.

TABLE F

Glycated peptides from Hum1-containing light chain of antibody PC336.

| Sequence of peptide | Modification/ Names | Modified AAs | AA position | Trypsin digested peptide | % |
|---|---|---|---|---|---|
| ADGSPVKAGVETTK PSK (SEQ ID NO: 64) | Hex/162.0528 | K | 158 | Unmodified Glycated | 99.5 0.521 |
| FSGSSSGTTVTLTISG VQAEDEADYYCGGY DQSSYTNPFGGGTK (SEQ ID NO: 65) | Hex/162.0528 | K | 104 | Unmodified Glycated | 52.1 47.9 |
| ITCSGGSYSSYYYAW YQQKPGQAPVTLIYS DDKRPSNIPER (SEQ ID NO: 66) | Hex/162.0528 | K | 38 | Unmodified Glycated | 99 1.03 |

Peptide mapping of a second anti-SIRP-α antibody (antibody PC333) comprising the same light chain (SEQ ID NO:47) and a heavy chain (SEQ ID NO:58) with the AB21 MutAll VH domain (SEQ ID NO:26) and a constant region (SEQ ID NO:31) comprising a wild-type human IgG1 Fc region was also carried out. Similar to what was observed for antibody 336, the lysine residue at position 104 of the light chain was also observed to be glycated in this antibody (~34% of peptides; see Table G).

TABLE G

Glycated peptide from Hum1-containing light chain of antibody PC333.

| Position | Modification/ Names | Modified AAs | Peptides | XIC | % |
|---|---|---|---|---|---|
| 104 | | | Native | 2.770E+8 | 66.02 |
| | Hex/162.0528 | K | Modified | 1.430E+8 | 33.98 |

Peptide mapping also revealed the presence of deamidated residues in the Hum1-containing light chain of anti- To remove the potentially deamidated residues (N171/N172), 4 deamidation site variants were first tested. Antibody PC334 contained the original Hum1 VL+IGLC1 light chain (SEQ ID NO:47). Antibody PC338 contained a light chain with the original Hum1 VL domain and the N172D variant constant domain (SEQ ID NO:48). Antibody PC339 contained a light chain with the original Hum1 VL domain and the N171D variant constant domain (SEQ ID NO:49). Antibody PC340 contained a light chain with the original Hum1 VL domain and the N171D,N172S deamidation site variant constant domain (SEQ ID NO:50). Antibody PC341 contained a light chain with the original Hum1 VL domain and the N171S,N172D deamidation site variant constant domain (SEQ ID NO:51). All antibodies had a heavy chain comprising the AB21HC mut all VH domain (SEQ ID NO:26) and a constant region (SEQ ID NO:32) comprising the human IgG1 AAA N297A Fc region (full heavy chain sequence as shown in SEQ ID NO:59). The results of the binding assay are shown in Table H. All four mutants bound with equivalent affinity to human SIRP-α v1, as compared with the wildtype antibody.

TABLE H

Binding of anti-SIRP-α antibodies with deamidation site variant
Hum1 light chains to human SIRP-α v1.

| Antibody | Light Chain | Fc | $K_D$ (M) for human SIRP v1 |
|---|---|---|---|
| PC334 | Hum1_IGLC1 | IgG1_AAA_dead* | <1E-12 |
| PC338 | Hum1_IGLC1_N172D | IgG1_AAA_dead | <1E-12 |
| PC339 | Hum1_IGLC1_N171D | IgG1_AAA_dead | <1E-12 |
| PC340 | Hum1_IGLC1_N171D, N172S | IgG1_AAA_dead | <1E-12 |
| PC341 | Hum1_IGLC1_N171S, N172D | IgG1_AAA_dead | <1E-12 |

*IgG1_AAA_dead refers to human IgG1 with L234A, L235A, G237A and N297A substitutions.

Next, the glycation site variants were tested. The region of the Hum1 VL domain with the glycation site is shown in FIG. 9. To remove this glycation site, three variants of this VL domain were created, labeled versions 1, 2, and 3 (v1, v2, and v3 are also used interchangeably herein). These variants mutate residues in and around the K104 glycation site. Versions 1 and 2 use sequences identical to the native human IGLJ1 and IGLJ7 sequence, respectively. Version 3 replaces the lysine with arginine to maintain the positive charge and size of residue. The glycation site variants were tested in the context of the N171S, N172D deamidation variants.

Antibody PC334 contained the original Hum1 VL+IGLC1 light chain (SEQ ID NO:47). Antibody PC341 contained a light chain with the original Hum1 VL domain and the N171S,N172D (abbreviated "SD") deamidation site variant constant domain (SEQ ID NO:51). Antibodies PC345, PC346, and PC347 also contained the SD deamidation site variant constant domain, but included the Hum1 variant 1, 2, and 3 VL domains, respectively (SEQ ID NOs:53, 55, and 57, respectively). All antibodies had a heavy chain comprising the AB21HC mut all VH domain (SEQ ID NO:26) and a constant region (SEQ ID NO:32) comprising the human IgG1 AAA N297A Fc region (full heavy chain sequence as shown in SEQ ID NO:59). The results of the binding assay are shown in Table I1.

TABLE I1

Binding of anti-SIRP-α antibodies with glycation site variant Hum1
light chains to human SIRP-α v1.

| Antibody | Light Chain | Fc | $K_D$ (M) for human SIRP v1 |
|---|---|---|---|
| PC334 | Hum1_IGLC1 | IgG1_AAA_dead* | <1.0E-12 |
| PC341 | Hum1_IGLC1_N171S, N172D | IgG1_AAA_dead | <1.0E-12 |
| PC345 | Hum1_IGLC1_version 1 + SD | IgG1_AAA_dead | <1.0E-12 |
| PC346 | Hum1_IGLC1_version 2 + SD | IgG1_AAA_dead | <1.0E-12 |
| PC347 | Hum1_IGLC1_version 3 + SD | IgG1_AAA_dead | <1.0E-12 |

*IgG1_AAA_dead refers to human IgG1 with L234A, L235A, G237A and N297A substitutions.

As shown in Tables H and I1, all antibodies bound with equivalent affinity to human SIRP-α v1, as compared with the wildtype antibody. These results demonstrate that the variants engineered to remove deamidation and glycation liability hot spots had no effect on binding to SIRP-α.

Based on the above results, 6 preferred light chain variants were generated, and the alignment of the respective sequences (SEQ ID NOs:52-57) are shown in FIGS. 10 & 11. They comprised combining two preferred deamidation site variants (N171D/N172S and N171S/N172D, abbreviated as "DS" and "SD," respectively) and the 3 glycation variants (v1, v2, v3). The original hum1 VL domain and human IGLC1 lambda constant region (SEQ ID NO:47) are also shown in the alignment.

Example 7: Effect of Constant Domain Sequence on Biological Activities of Anti-SIRP-α Antibodies Anti-SIRP-α antibodies with different Fc regions and light chain constant domains were tested for their effect on phagocytosis in order to understand how these sequences impact the biological properties of anti-SIRP-α antibodies.

Methods

For functional depletion of dendritic cells, peripheral blood mononuclear cells (PBMC) were isolated from Trima residuals of healthy individuals with Ficoll-Paque Plus. 500,000 PBMCs were incubated in u-bottom 96 well plates (coming) with anti-SIRP at a concentration of 10 ug/mL for 48 hrs at 37 C. For flow cytometry, cells were incubated in human FcR blocking reagent and stained with a cocktail of fluorochrome-labeled antibodies against lin– (CD3, CD14, CD16, CD19, CD56) and HLADR. Fixable viability dye was used to identify live cells. After staining, cells were washed and fixed with 0.5% paraformaldehyde in PBS. Prior to acquisition, absolute counting beads were added and samples were acquired with Canto II flow cytometer and analyzed using FlowJo software.

Phagocytosis was measured using the in vitro assay described in Example 4.

Results

Figure 12:
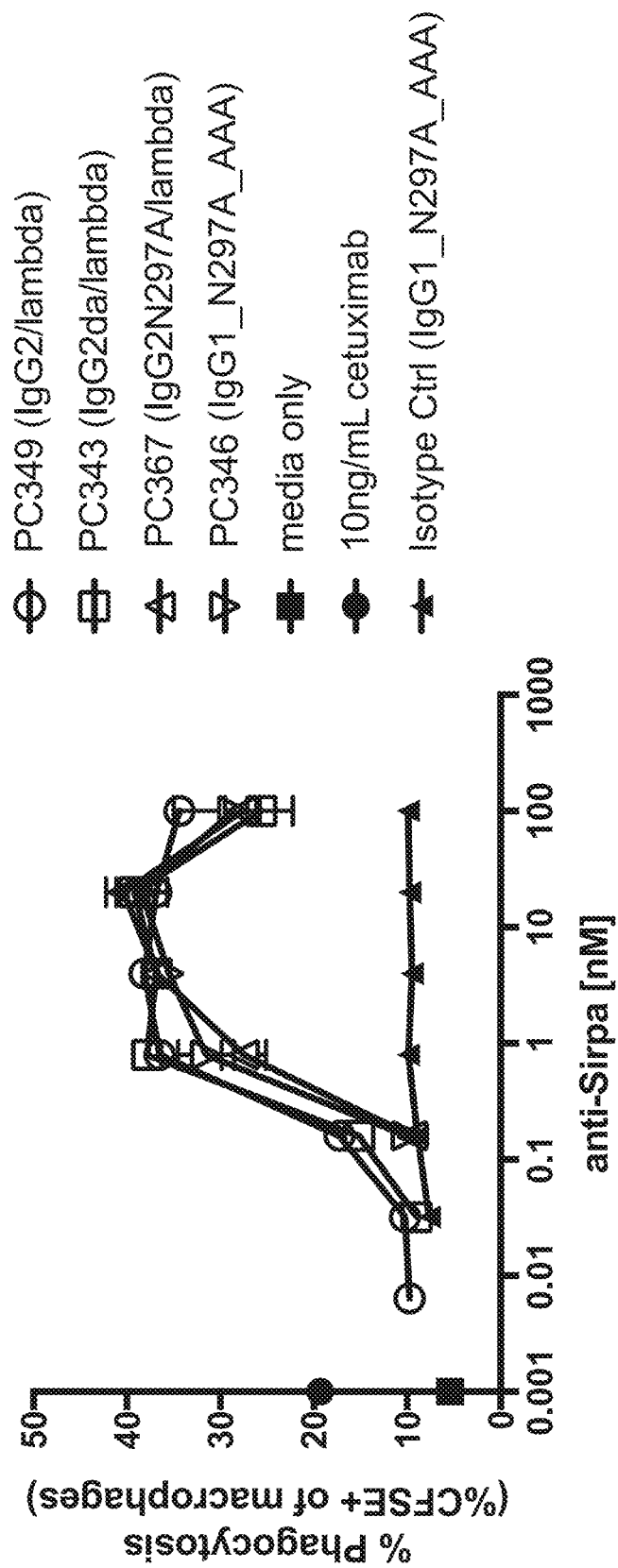
FIG. 12 shows the results of in vitro phagocytosis assays using EGFR(+) DLD-1 cells as the target and M2 macrophages as the phagocytosing cell. Anti-SIRP-α antibodies or isotype control with the indicated Fc regions were tested in combination with the anti-EGFR antibody cetuximab. Phagocytosis was measured by percentage of CFSE+ cells.

Humanized anti-SIRP-α antibodies with different Fc regions were tested for their effects on phagocytosis of EGFR(+) DLD-1 cells by M2 macrophages in combination with the anti-EGFR antibody cetuximab (FIG. 12). All antibodies had the light chain sequence of SEQ ID NO:55 and the VH domain sequence of SEQ ID NO:26. Fc regions tested included the IgG2 wild-type (as represented in the constant domain sequence of SEQ ID NO:33), IgG2 Da Fc region (comprising A330S and P331S mutations, amino acid position numbering according to EU; as represented in the constant domain sequence of SEQ ID NO:34), IgG2 Fc region comprising an N297A mutation (amino acid position numbering according to EU; as represented in the constant domain sequence of SEQ ID NO:137), and IgG1 Fc region comprising N297A. L234A, L235A, and G237A mutations (amino acid position numbering according to EU; as represented in the constant domain sequence of SEQ ID NO:32). All antibodies were found to have approximately equivalent activity in enhancing cetuximab-induced phagocytosis.

Figure 13A:
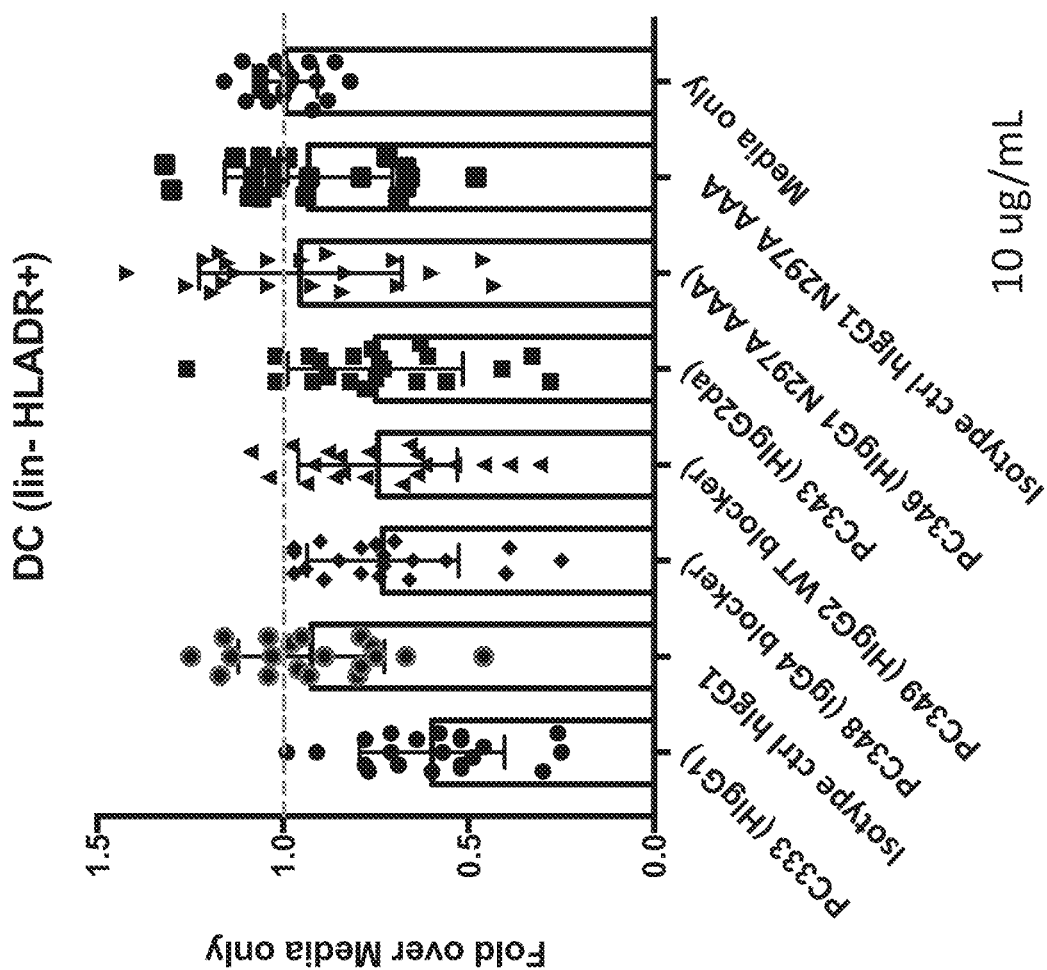
FIGS. 13A-13E show the results of depletion assays testing anti-SIRP-α antibodies with the indicated Fc regions for the ability to deplete various cell types from peripheral blood mononuclear cells (PBMCs).
Figure 13B:
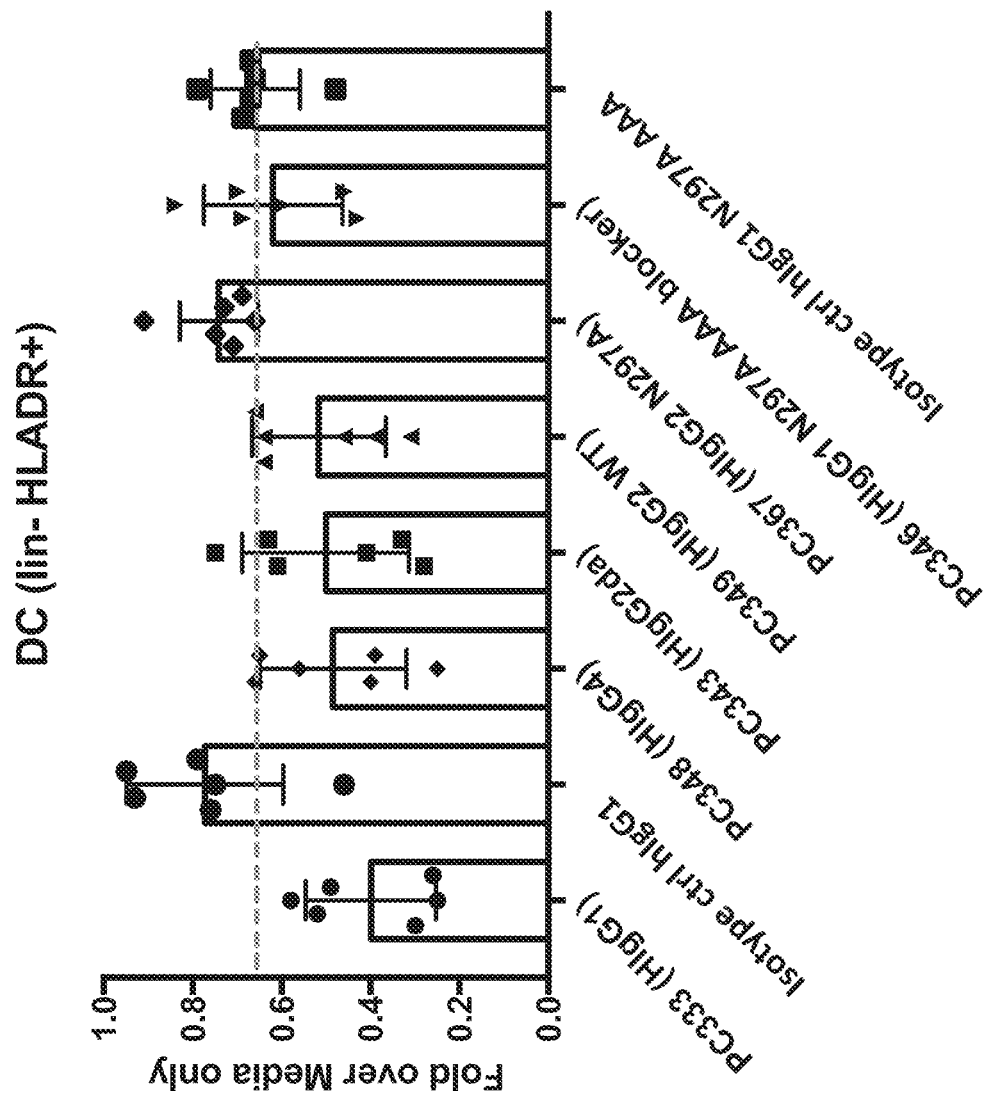
Figure 13C:
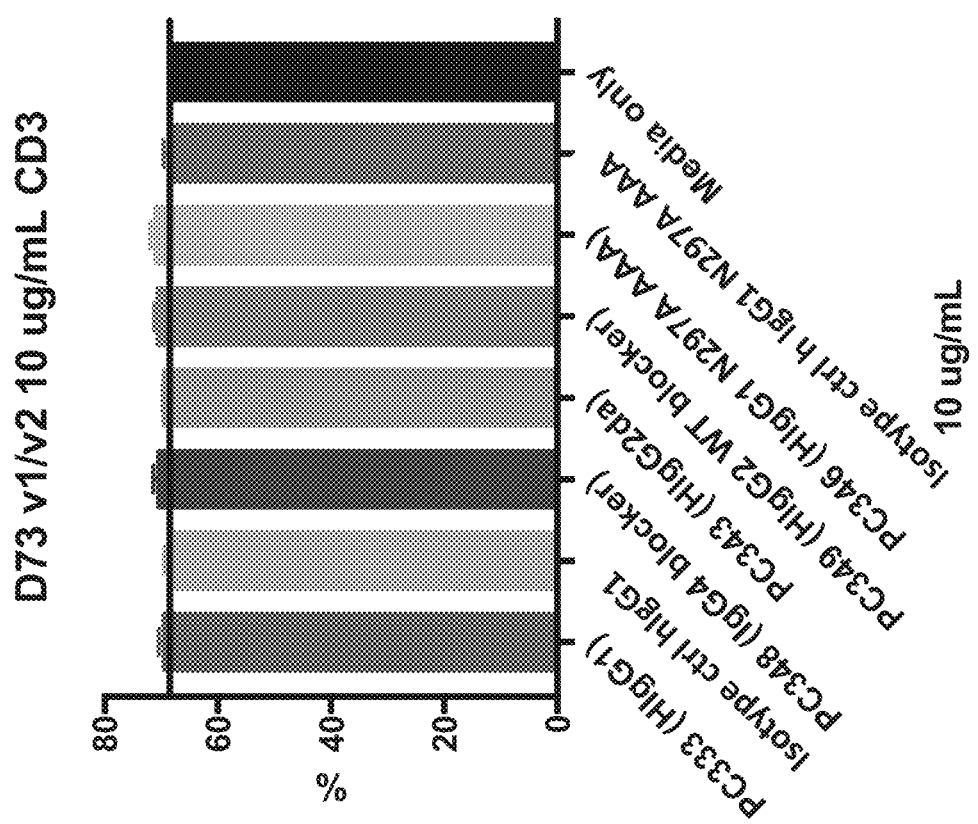
Figure 13D:
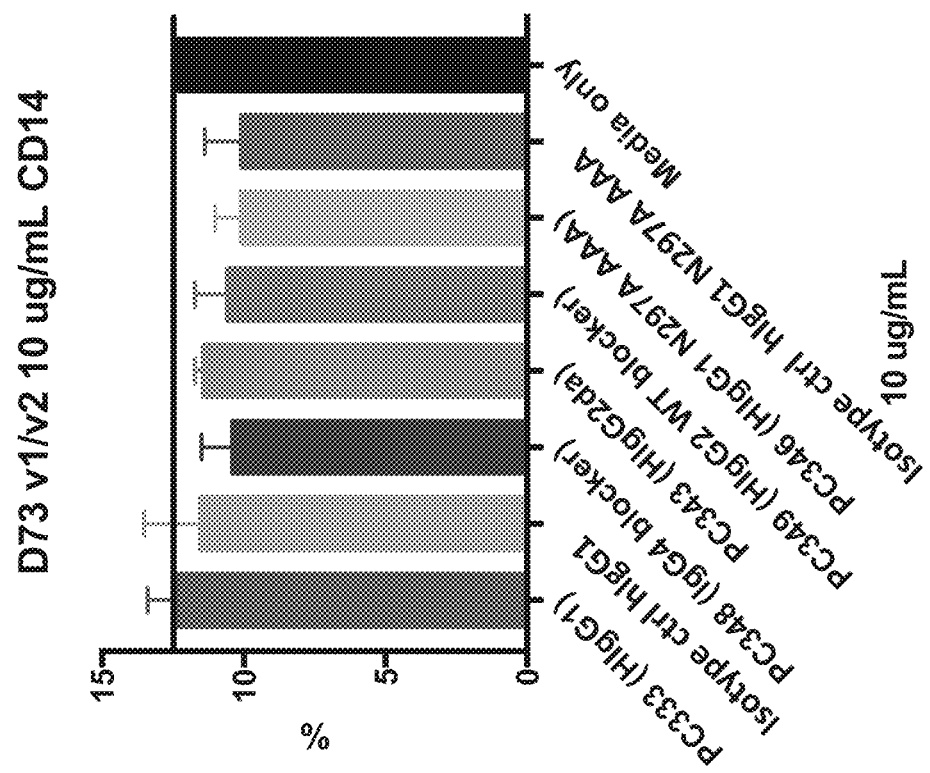
Figure 13E:
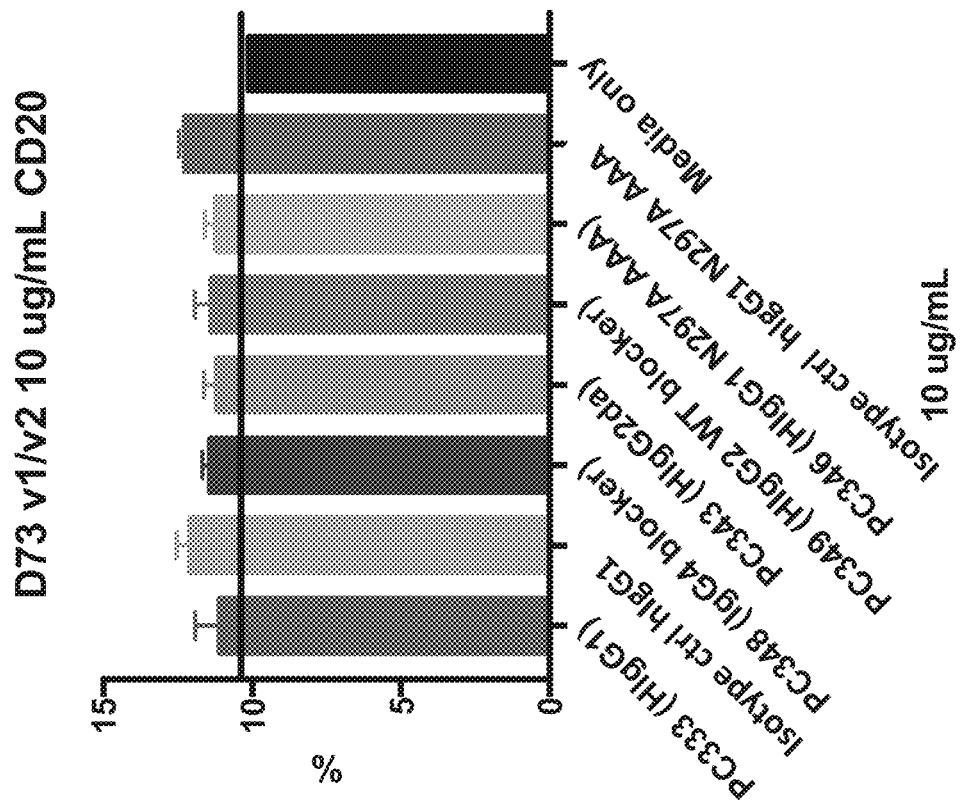

Next, anti-SIRP-α antibodies with different Fc regions (or corresponding isotype controls) were tested for their ability to deplete different cell types from donor PBMCs. All antibodies had the light chain sequence of SEQ ID NO:55 and the VH domain sequence of SEQ ID NO:26. As shown in FIGS. 13A & 13B, anti-SIRP-α antibodies with wild-type IgG1, wild-type IgG4, wild-type IgG2, or IgG2 Da Fc regions were able to deplete DCs from PBMCs obtained from two different donors. This indicates that these Fc regions have the ability to potentiate some DC depletion in the context of the PBMC assay (DCs are known to express SIRP-α). In contrast, only the L234A/L235A/G237A/N297A IgG1 and IgG2 N297A Fc regions did not show DC depletion. None of the antibodies tested led to significant depletion of T cells, monocytes, or B cells (FIGS. 13C-13E). Advantageously, the IgG2 N297A Fc region provides the same lack of depletion as the L234A/L235A/G237A/N297A IgG1 Fc region but with fewer mutations (and therefore potentially less immunogenicity).

Anti-SIRP-α antibodies were also tested for binding affinity to human SIRP-α v1; NOD, C57BL/6, and BALBc mouse SIRP-α; human SIRP-β; and human SIRP-γ. Antibodies tested included the following heavy and light chains: PC301: light chain of SEQ ID NO:63 and heavy chain of SEQ ID NO:59; PC334: light chain of SEQ ID NO:47 and heavy chain of SEQ ID NO:59, and PC367: light chain of SEQ ID NO:55 and heavy chain of SEQ ID NO:129.

TABLE I2

Binding affinities of anti-SIRP-α antibodies to SIRP proteins ($K_D$, M).

| | Protein | | | | | | | |
|---|---|---|---|---|---|---|---|---|
| | hSIRPa v1 | hSIRPa v2 | Cyno | NOD | C57BL/6 | BALBc | hSIRPb | hSIRPg |
| SEQ ID NO | 5 | 6 | 11 | 8 | 9 | 10 | 13 | 15 |
| PC301 | 2.06E-12 | 4.60E-12 | 3.89E-11 | 2.93E-09 | 9.25E-09 | 9.53E-09 | 1.22E-11 | <1.00E-12 |
| PC334 | 1.51E-11 | 4.38E-11 | 7.74E-11 | 8.19E-09 | 3.29E-09 | 6.75E-09 | 3.71E-11 | 4.52E-11 |
| PC367 | 2.11E-12 | 8.23E-11 | 5.01E-11 | 6.37E-09 | 1.97E-08 | 7.87E-09 | 3.27E-11 | 3.52E-11 |

Figure 14A:
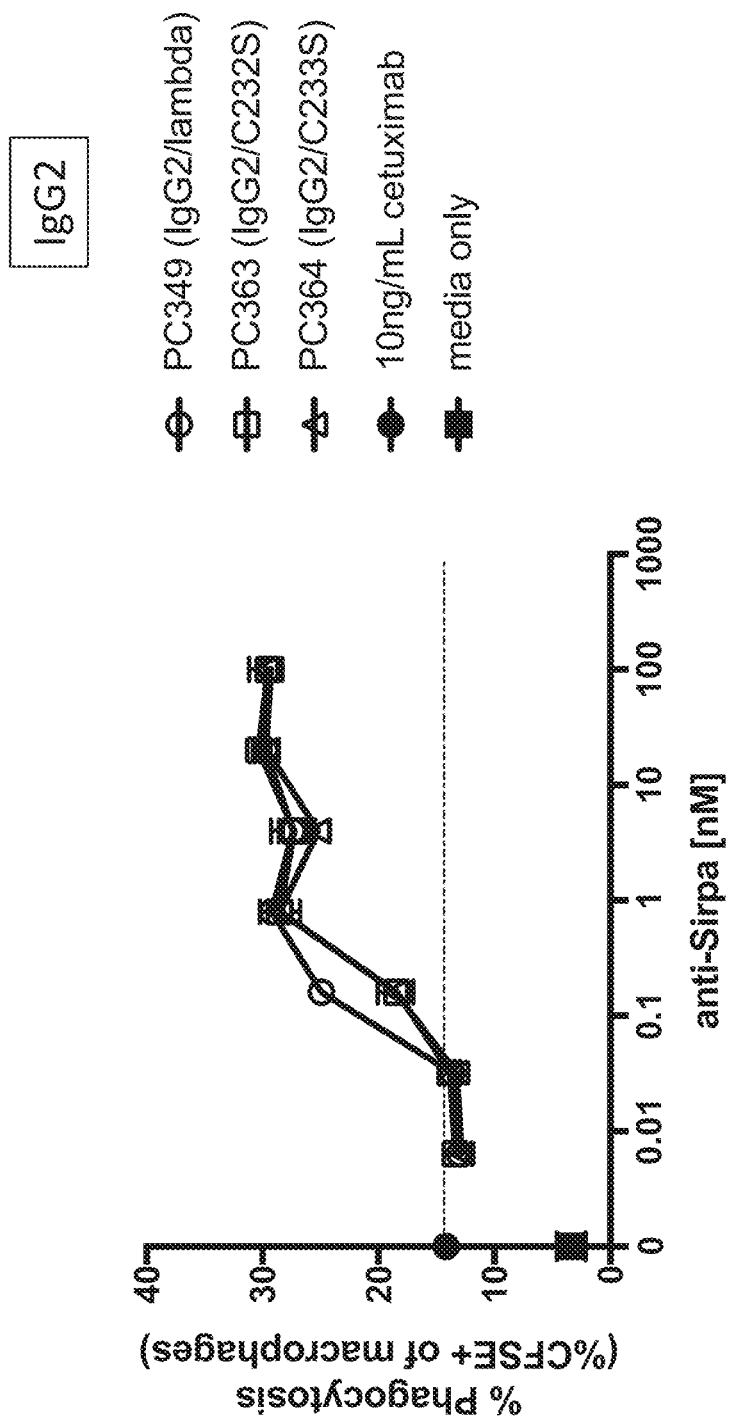
FIGS. 14A & 14B show the results of in vitro phagocytosis assays using EGFR(+) DLD-1 cells as the target and M2 macrophages as the phagocytosing cell. Anti-SIRP-α antibodies with the indicated Fc regions were tested in combination with the anti-EGFR antibody cetuximab. Phagocytosis was measured by percentage of CFSE+ cells.
Figure 14B:
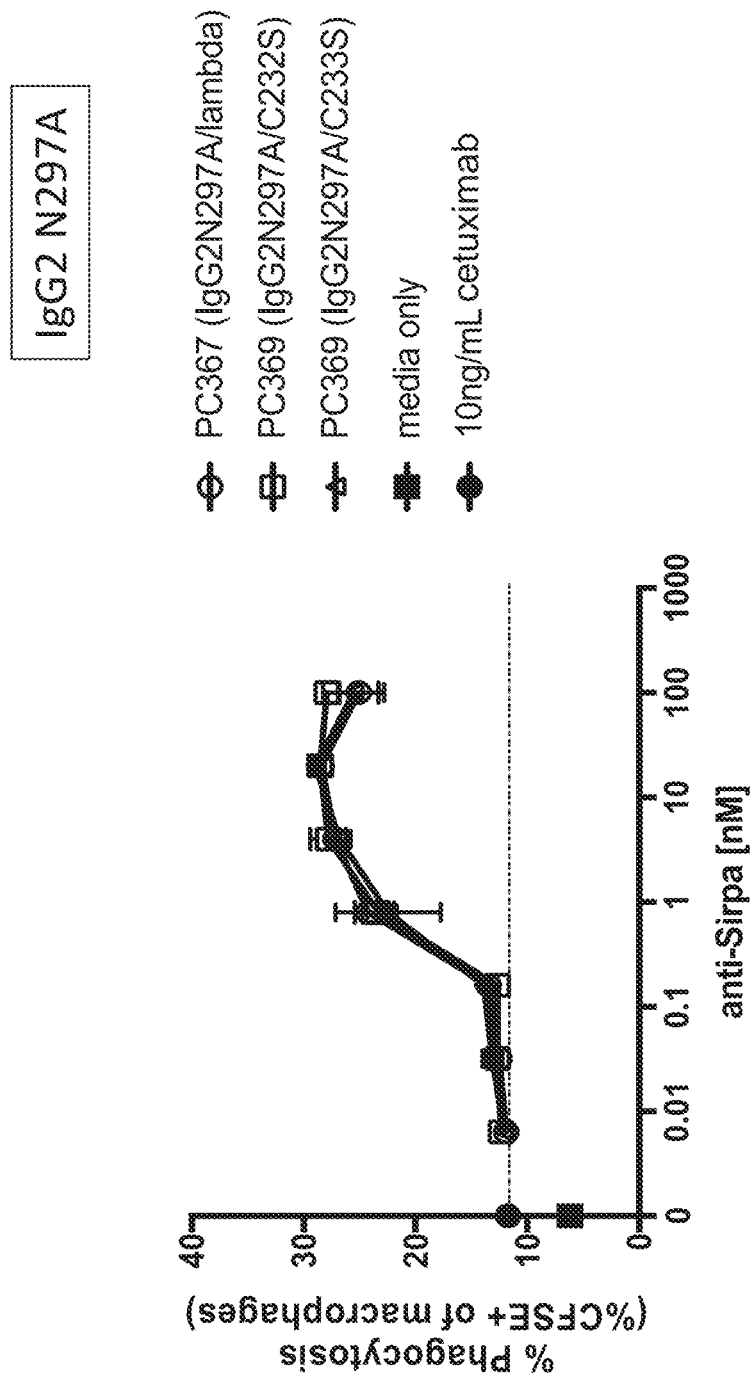

Human IgG2 antibodies are thought to exist in disulfide-based isoforms (A, B, and AB), and the introduction of C232S or C233S mutations into human IgG2 constant regions has been reported to reduce heterogeneity caused by disulfide shuffling (Lightle, S. et al. (2010) *Protein Sci.* 19:753-762). Each of these mutations is thought to force IgG2 antibodies into isoform A. In addition, the lambda light chain is also thought to promote isoform A abundance. Anti-SIRP-α antibodies with wild-type IgG2 (FIG. 14A) or IgG2 N297A (FIG. 14B) Fc regions comprising C232S or C233S mutations were tested for effects on phagocytosis of EGFR(+) DLD-1 cells by M2 macrophages in combination with the anti-EGFR antibody cetuximab. All antibodies had the light chain sequence of SEQ ID NO:55 and the VH domain sequence of SEQ ID NO:26. Wild-type and N297A Fc regions were tested using antibodies with the lambda light chain to drive isoform A predominance. IgG2 anti-SIRP-α antibodies comprising Fc regions with C232S or C233S mutations showed similar enhancement of phagocytosis, as compared to antibodies with wild-type IgG2 or IgG2 N297A Fc regions.

Figure 15A:
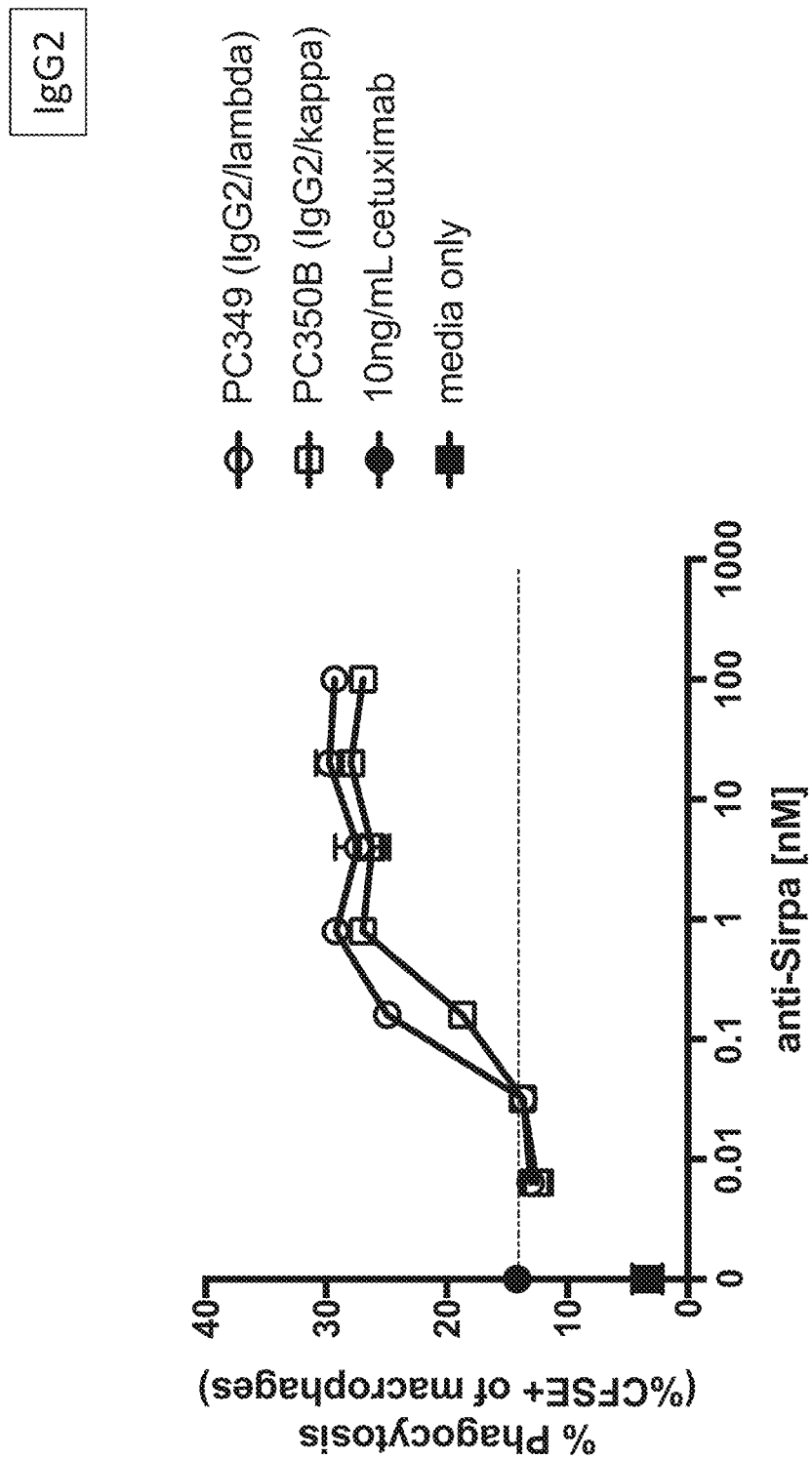
FIGS. 15A & 15B show the results of in vitro phagocytosis assays using EGFR(+) DLD-1 cells as the target and M2 macrophages as the phagocytosing cell. Anti-SIRP-α antibodies with the indicated light chain constant domains (lambda or kappa) were tested in combination with the anti-EGFR antibody cetuximab. Phagocytosis was measured by percentage of CFSE+ cells.
Figure 15B:
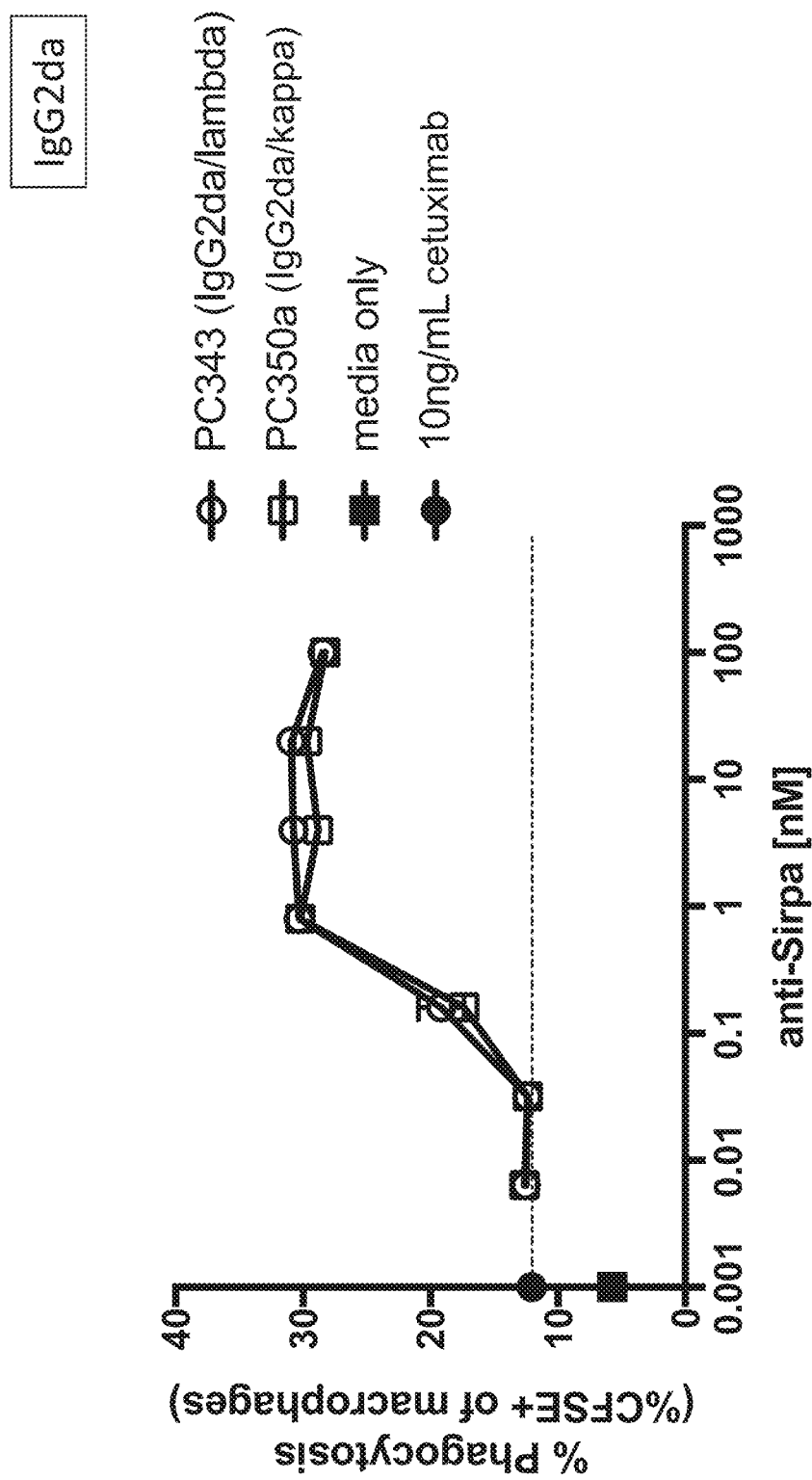

The effect of the light chain constant domain on the ability of anti-SIRP-α antibodies to enhance phagocytosis was also examined. All antibodies had the VH domain sequence of SEQ ID NO:26 and the VL domain sequence of SEQ ID NO:18. Anti-SIRP-α antibodies with lambda and kappa light chains showed similar enhancement of phagocytosis, both in the context of a wild-type IgG2 Fc– (FIG. 15A) or an IgG2da Fc– (FIG. 15B) containing heavy chain.

Although the foregoing disclosure has been described in some detail by way of illustration and example for purposes of clarity of understanding, the descriptions and examples should not be construed as limiting the scope of the present disclosure. The disclosures of all patent and scientific literature cited herein are expressly incorporated in their entirety by reference.

TABLE J1

Variable domain sequences for selected antibodies.

| Antibody | VH Domain | VL Domain |
|---|---|---|
| AB21 | DVQLVESGGGVVRPGESLRLSCAAS GETFSSNAMSWVRQAPGKGLEWLAG ISAGGSDTYYPASVKGRETISRDNSK NTLYLQMNTLTAEDTAVYYCARET WNHLFDYWGLGTLVTSS (SEQ ID NO: 73) | ALTPASVSANPGETVKIACSGGDYYSY YYGWYQQKAPGSALVTVIYSDDKRPSDI PSRFSGSASGSTATLTITGVRAEDEAVYY CGGYDYSTYANAFGAGYTTLTVL (SEQ ID NO: 74) |
| AB25 | DVQLVESGGGVVRPGESLRLSCEASG FTFSSNAMSWVRQAPGKGLEWVAGI SSGSDTYYGDSVKGRLTISRDNSKNIL YLQMNSLTAEDTAVYYCARETWNH LFDYWGLGTLVTSS (SEQ ID NO: 75) | ALTQPASVSANPGETVEITCSGGSYSSYY YAWYQQKSPGSAPVTLIYSDDKRPSNIP SRFSGSASGSTATLTITGVRAEDEAVYFC GGYDQSSYTNPFGAGTTLTVL (SEQ ID NO: 76) |
| PC301 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSGTTVTLTISGVQAEDEADYY CGGYDQSSYTNPFGGGTKLTVL (SEQ ID NO: 25) |
| PC333 | EVQLVESGGGVVQPGGSLRLSCAAS GFTFSSNAMSWVRQAPGKGLEWVA GISAGGSDTYYPASVKGRETISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTKLTVL (SEQ ID NO:25) |

TABLE J1-continued

Variable domain sequences for selected antibodies.

| Antibody | VH Domain | VL Domain |
| --- | --- | --- |
| PC334 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTKLTVL (SEQ ID NO: 25) |
| PC336 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCCSGGSYSS YYYAWYQQKPGQAPVTLIYSDDKRPSNI PERFSGSSSGTTVTLTISGVQAEDEADYY CGGYDQSSYTNPFGGGTKLTVL (SEQ ID NO: 25) |
| PC338 | EVQLVESGGGVVQPGGSLRESCAAS GFTFSSNAMSWVRQAPGKGLEWVA GISAGGSDTYYPASVKGRFTISRDNS KNTLYLQMNSLRAEDTAVYYCARET WNHLFDYWGTQGTLVTVSS (SEQ ID NO: 26) | SYELTQPPSVSVSPGQTARITCSGGSYSS YYYAWYQQKPGQAPVTLIYSDDKRPSNI PERFSGSSSGTTVILTISGVQAEDEADYY CGGYDQSSYTNPFGGGTKLTVL (SEQ ID NO: 25) |
| PC339 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPEGGGTKLTVL (SEQ ID NO: 25) |
| PC340 | EVQLVESGGGVVQPGGSLRLSCAAS GFTFSSNAMSWVRQAPGKGLEWVA GISAGGSDTYYPASVKGRETISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGYTTVTLTISGVQAEDEADYY CGGYDQSSYTNPFGGGTKLTVL (SEQ ID NO: 25) |
| PC341 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVITLIYSDDKRPSNI PERFSGSSSGTTVTLTISGVQAEDEADYY CGGYDQSSYTNPFGGGTKLTVL (SEQ ID NO: 25) |
| PC342 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYOQKPGQAPVTLIYSDDKRPSNI PERFSGSSSGTTVLTTISGVQAFDFADYY CGGYDQSSYTNPFGTGTKVCVL (SEQ ID NO: 39) |
| PC343 | EVQLVESGGGVVQPGGSLRLSCAAS GETFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |
| PC344 | EVQLVESGGGVVQPGGSLRLSCAAS GETFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQFPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTRLTVL (SEQ ID NO: 41) |
| PC345 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYNGQGTLVCVSS (SEQ ID NO: 26) | SYELTQPPSVSVSPGQTARITCSGGSYSS YYYAWYQQKPGQAPVTLIYSDDKRPSNI PERFSGSSSGTFVTLTISGVQAEDEADYY CGGYDQSSYTNPFGTGTKVTVL (SEQ ID NO: 39) |

TABLE J1-continued

Variable domain sequences for selected antibodies.

| Antibody | VH Domain | VL Domain |
| --- | --- | --- |
| PC346 | EVQLVESGGGVVQPGGSLRLSCAAS GETFSSNAMSWVRQAPGKGLEWVA GISAGGSDTYYPASVKGRFFISRDNS KNTLYLQMNSLRAEDTAVYYCARET WNHLFDYWGGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISQAEDEADYY CGGYDQSSYTNPFGGGTQLTVL (SEQ ID NO: 40) |
| PC347 | EVQLVESGGGVVQPGGSLRLSCAAS GFTESSNAMSWVRQAPGKGLEWVA GISAGGSDTYYPASVKGRETISRDNS KNTLYMNINSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTRLTVL (SEQ ID NO: 41) |
| AB21_HC_ mutAll + V1 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCCSGGSYSS YYYAWYQQKPGQAPVTLIYSDDKRPSNI PERFSGSSSGTTVTLTISGVQAEDEADYY CGGYDQSSYTNPFGTGTKVTVL (SEQ ID NO: 39) |
| AB21_HC_ mutAll + V2 | EVQLVESGGGVVQPGGSLRLSCAAS GFTSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |
| AB21HC mutAll + V3 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVFLTISGVQAEDEADYY CGGYDQSSYTNPFGGGTRLTVL (SEQ ID NO: 41) |
| PC348 | EVQLVESGGGVVQPGGSLRLSCAAS GFTFSSNAMSWVRQAPGKGLEWVA GISAGGSDTYYPASVKGRFTISRDNS KNTLYLQMNSLRAFDTANTYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |
| PC349 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARIFCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |
| PC350A | EVQLVESGGGVVQPCIGSLRESCAAS CIFTFSSNAMSWVRQAPGKEILEWVA GISAGGSDTYYPASVKGRETISRDNS KNTLYWNINSLRAEDTAVYYCARET WNFILEDYWCTQGTLVTVSS (SEQ ID NO: 26) | ALTQPASVSANPGETVEITCSGGSYSSYY YAWYQQKSPGSAPVTLIYSDDKRPSNIP SRESGSASGSTATLTITGVRAEDEAVYFC GGYDQSSYTNPFGAGTTLTVL (SEQ ID NO: 18) |
| PC350B | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | ALTQPASVSANPGETVEITCSGGSYSSYY YAWYQQKSPGSAPVTLIYSDDKRPSNIP SRFSGSASGSTATLTITGVRAEDEAVYFC GGYDQSSYTNPFGAGTTLTVL (SEQ ID NO: 18) |
| PC363 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |

TABLE J1-continued

Variable domain sequences for selected antibodies.

| Antibody | VH Domain | VL Domain |
| --- | --- | --- |
| PC364 | EVQLVESGGGVVQPGGSLRLSCAAS GFFSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTVL (SEQ ID NO: 40) |
| PC367 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYC RET WNHLFDYWWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTTISGVQAEDEADYY CGGYDQSSYTNPFGGGTQLTVL (SEQ ID NO: 40) |
| PC369 | EVQLVESGGGVVQPGGSLRLSCAAS GFTFYSSNAMSWVRQAPGKGLEWVA GISAGGSDTYYPASVKGRFTISRDNS KNTLYLQMNSLRAEDTAVYYCARET WNHLFDYWGQGTLVTVSS (SEQ ID NO: 26) | SYELTQPPSVSVSPGQTARITCSGGSYSS YYYAWYQQKPGQAPVTLIYSDDKRPSNI PERFSGSSSGTTVTLTISGVQAEDEADYY CGGYDQSSYTNPFGGGTQLTTVL (SEQ ID NO: 40) |

TABLE J2

Full chain sequences for selected antibodies.

| Antibody | Heavy chain | Light chain |
| --- | --- | --- |
| PC301 | EVQLVESGGGVVQPGGSLRLSCAAS GFTFSSNAMSWVRQAPGKGLEWVA GISAGGSDTYYPASVKGRFTISRDNS KNTLYQMNSLRAEDTAVYYCARET WNHLFDYWGQGTLVTVSSASTKGPS VFPLAPSSKSTSGGTAALGCLVKDYF PEPVTVSWNSGALCSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTTEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKAAPSVTLFPPSSEELQANK ATLVCLISDFYPGAVTVAWKADSSP VKAGVETTTPSKQSNNKYAASSYLS LTPEQWKSHRSYSCQVTHEGSTVEK TVAPTECS (SEQ ID NO: 63) |
| PC333 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSN TKVDKKVEPKSCDKTHTCP PCPAPELLGGPSVFLEPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 58) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKANPTVTLFPPSSEELQANK ATLVCLISDFYPGAVTVAWKADGSP VKAGVETTKPSKQSNNKYAASSYLS LTPEQWKSHRSYSCQVTHEGSTVEK TVAPTECS (SEQ ID NO: 47) |
| PC334 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAYYCARET WNHLFDYWGQGTLVTVSSASTKGPS | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKANPTVTLFPPSSEELQANK |

TABLE J2-continued

Full chain sequences for selected antibodies.

| Antibody | Heavy chain | Light chain |
|---|---|---|
| | VFPLAPSSKSTSGGTAALGCLVKDYF PEPVTVSWNSGALTSGVHTEPAVLQS SGLYSLSSVVTVPSSSLGTQTYICNV NHKPSNTKVDKKVEPKSCDKTHFCP PCPAPEAAGAPSVELEPPKTKDTLMIS RTPEVTCVVVDVSHEDPEVKFNWYV DGVEVHNAKTKPREEQYASTYRVVS VETVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | ATLVCLISDFYPGAVTVAWKADGSP VKAGVETTKPSKQSNNKYAASSYLS LTPEQWKSHRSYSCQVTHEGSTVEK TVAPTECS (SEQ ID NO: 47) |
| PC336 | EVQLVESGGGVVQPGGSLRLSCAAS GFTFSSNAMSWVRQAPGKGLEWVA GISAGGSDTYYPASVKGRFFISRDNS KNTLYLQMNSLRAEDTAVYYCARET WNHLFDYWGQGTLVTVSSASTKGPS VFPLAPCSRSTSESTAALGCLVKDYE PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTERVVSVLT VVHQDWLNGKEYKCKVSNKGLPSSI EKTISKTKGQPREPQVYTEPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKANPTVTLFPPSSEELQANK ATLVCLISDFYPGAVTVAWKADGSP VKAGVETTKPSKQSNNKYAASSYLS LTPEQWKSHRSYSCQVTHEGSTVEK TVAPTECS (SEQ ID NO: 47) |
| PC338 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLEPPKPKDTLMIS RTPEVTCVVVDVSHEDPEVKFNWYV DGVEVHNAKTKPREEQYASTYRVVS VETVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIAYSDDK RPSNIPERFSGSSSGTTVTLTISGVQAE DEADYYCGGYDQSSYTNPFGGGTKL TVLGQPKANPTVTLEPPSSEELQANK ATLVCLISDFYPGAVTVAWKADGSP VKAGVETTKPSKQSNDKYAASSYLS LTPEQWKSHRSYSCQVTHEGSTVEK TVAPTECS (SEQ ID NO 48) |
| PC339 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVELFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKANPTVTLFPPSSEELQANK ATLVCLISDFYPGAVTVAWKADGSP VKAGVETTKPSKQSNDKYAASSYLS LTPEQWKSHRSYSCQVTHEGSTVEK TVAPTECS (SEQ ID NO: 49) |

TABLE J2-continued

Full chain sequences for selected antibodies.

| Antibody | Heavy chain | Light chain |
|---|---|---|
| PC340 | EVQLVESGGGVVQPGGSLRLSCAAS GFTFSSNAMSWVRQAPGKGLEWVA GISAGGSDTYYPASVKGRFTISRDNS KNTLYLQMNSLRALDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV DGVEVHNAKTKPREEQYASTYRVVS VTTVLHQDWLNGKEYKCKVSNKAL PAPIEKTISKAKGQPREPQVYTLPPSR EEMTKNQVSLTCLVKGFYPSDIAVE WESNCQPENNYKTIPPVLDSDGSFEL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYGGYDQSSYFNPFGGGTKL TVLGQPKANPTVTLFPPSSEELQANK ATLVCLISDFYPGAVAWKADGSP VKAGVETTKPSKQSDSKYAASSYLSL TPEQWKSHRSYSCQVTHEGSTVEKT VAPTECS (SEQ ID NO: 50) |
| PC341 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSTFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTKL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 51) |
| PC342 | EVQLVESGGGVVQPGGSLRLSCAAS GFTFFSSNAMSWVRQAPGKGLEWVA GISAGGSDTYYPASVKGRFTISRDNS KNTLYLQMINSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPRMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVITLIYSDDK RPSNIPERFSGSSSGTTVTLTISGVQAE DEADYYCGGYDQSSYTNPFGTGTKV TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 53) |
| PC343 | EVQLVESGGGVVQPGGSLRLSCAAS GFTFSSNAMSWVRQAPGKGLEWVA GISAGGSDTYYPASVKGRFFISRDNS KNTLYQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGRSVFLFPPKPKDTLMISRTPE VTCVVVDVSHEDPEVQFNWYVDGV EVHNAKTKPREEQFNSTFRVVSVLT VVQDWLNGKEYKCKVSNKGLPSSI | SYELTQPPSVSVSPGQTARITCSGGSY SSYYYAWYQQKPGQAPVTLIYSDDK RPSNIPERESGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSSDKYAASSYLSL TPEQWKSHRSYSCQVFHEGSTVEKT VAPTECS (SEQ ID NO: 55) |

TABLE J2-continued

Full chain sequences for selected antibodies.

| Antibody | Heavy chain | Light chain |
|---|---|---|
| | EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | |
| PC344 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLFPPSSEELQANK ATLVVLISDFYPGAVTVAWKADGSP VKAGVETTKPSKQSSDKYAASSYLSL TPEQWKSHRSYSCQVTHEGSTVEKT VAPTECS (SEQ ID NO: 57) |
| PC345 | EVQLVESGGGVVQPGGSLRLSCAAS GFTFSSNAMSWVRQAPGKGLEWVA GISAGGSDTYYPASVKGRFTISRDNS KNTYLQMNSLRAEDTAVYYCARET WNFLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGEYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLFPPSSEELQANK ATLVCLISDFYPGAVTVAWKADGSP VKAGVETTKPSKQSSDKYAASSYLSI: TPEQWKSHRSYSCQVTHEGSTVEKT VAPTECS (SEQ ID NO: 53) |
| PC346 | EVQLVESGGGVVQPGGSLRLSCAAS GFTFSSNAMSWVRQAPGKGLEWVA GISAGGSDTYYPASVKGRFTISRDNS KNTLYLQMNSIRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVERKSCDKTHTCP PCPAPEAAGAPSVFLFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSESLSPG (SEQ ID NO: 59) | SELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGETTQL TVLGQPKANPTVTLFPPSSEELQANK ATLVCLTSDFYPGAVTVAWKADGSP VKAGVETTKPSKQSSDKYAASSYLSL TPEQWKSHRSYSCQVTHEGSTVEKT VAPTECS (SEQ ID NO: 55 ) |
| PC347 | EVQLVESGGGVVQPGGSLRLSCAAS GFTFSSNAMSATVRQAPGKGLEWVA GISAGGSDTYYPASKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV | SYELTQPPSVSVSPGQTARITCSGGSY SSYYYAWYQQKPCTQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSSDKYAASSYLSL TPEQWKSHRSYSCQVYHEGSTVEKT VAPTECS (SEQ ID NO: 57) |

TABLE J2-continued

Full chain sequences for selected antibodies.

| Antibody | Heavy chain | Light chain |
|---|---|---|
| | DGVEVHNAKTKPREEQYASTYRVVS VLTVLHQDWENGKEYKCKVSNKAL PAPIEKTISKAKWPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | |
| AB21_HC_mut All (IgG1 wt) + V1 + DS | EVQLVESGGGVVQPGGSLRLSCAAS GFTFSSNAMSWVRQAPGKGLEWVA GISAGGSDTYYPASVKGRFTISRDNS KNTLYLQMNSERAEDTAVYYCARET WNHLFDYWGQGTLVTVSSASTKGPS VFPLAPSSKSTSGGTAALGCLVKDYE PEPVTVSWNSGALTSGVHTFPAVEQS SGLYSLSSVVTVPSSSLGTQTYICNV NHKPSNTKVDKKVEPKSCDKTHTCP PCPAPELEGGPSVFLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGPYPSDIAVE WESNGQPENNYKTTPPVLDSDGSFFL YSKLTVDKSRWQQGNVFSCSVMHE ALHNHYTQKSLSLSPG (SEQ ID NO: 58) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLFPPSSEELQANK ATLVCLISDEYPGAVTVAWKADGSP VKAGVETTKPSKQSDSKYAASSYLSL TPEQWKSHRSYSCQVTHEGSTVEKT VAPTECS (SEQ ID NO: 52) |
| AB21_HC_mut All (IgG1 wt) + V1 + SD | EVQLVESGGGVVQPGGSLRLSCAAS GETFSSNAMSWVRQAPGKGLEWVA GISAGGSDTYYPASVKGRFFISRDNS KNTLYLQMNSERAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPELLGGPSVFLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 58) | SYELTQPPSVSVSPGQTARITCSGGSY SSYYYAWYQQKPGQAPVILIYSDDK RPSNIPERESGSSSGTTVTLTISGVQAE DEADYYCGGYDQSSYTNPFGTGTKV TVLGQPKANPTVTLEPPSSEELQANK ATLVCLISDFYPGAVTVAWKADGSP VKAGVETTKPSKQSDSKYAASSYLSE TPEQWKSHRSYSCQVTHEGSTVEKT VAPTECS (SEQ ID NO: 53) |
| AB21_HC_mut All (IgG1 wt) + V2 + DS | EVQLVESGGGVVQPGGSLRESCAAS GFTFSSNAMSWVRQAPGKGLEWVA GISAGGSDTYYPASVKGRFTISRDNS KNTLYQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPELLGGPSATLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREWY TLPPSR EEMTKNQVSLTCUVKGFYPSDIAVE WESNGQPENNYKTIPPVLDSDGSFEL YSKLTVDKSR WQQGNVESCSVMHE ALHNHYTQKSLSLSPG (SEQ ID NO: 58) | SYELTQPPSVSVSPGQTARITCSGGSY SSYYYAWYQQKPGQAPVTLIYSDDK RPSNIPERESGSSSGTTVTLTISGVQAE DEADYYCGGYDQSSYTNPFGGGTQL TVLGQPKANPTVTLFPPSSEELQANK ATLVCLISDFYPGATVAWKADGSP VKAGVETTKPSKQSDSKYAASSYLSL TPEQWKSHRSYSCQVTHEGSTVEKT VAPTECS (SEQ ID NO: 54) |
| AB21_HC_mut All (IgG1 wt) + V2H-SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYFNPFGGGTQL TVLGQPKANPTVTLEPPSSEELQANK |

TABLE J2-continued

Full chain sequences for selected antibodies.

| Antibody | Heavy chain | Light chain |
|---|---|---|
| | VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPELLGGPSVFLEPPKPKDTLMIS RTPEVTCVVVDVSHEDPEVFENWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVESCSVMHE ALHNHYTQKSLSLSPG (SEQ ID NO: 58) | ATLVCLISDFYPGAVTVAWKADGSP VKAGVETTKPSKQSSDKYAASSYLSL TPEQWKSHRSYSCQVTHEGSTVEKT VAPTECS (SEQ ID NO: 55) |
| AB21_HC_mut All (IgG1 wt) + V3 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPELLGGPSVFLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 58) | SYELTQPPSVSVSPGQTARITCSGGSY SSYYYAWYQQKPCQAPVTLIYSDDK RPSNIPERFSGSSSGTTVTLTISGVQAE DEADYYCGGYDQSSYTNPFGGGTRL TVLGQPKANPTLTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 58) |
| AB21_HC_mut All (IgGI wt) + V3 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLEDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSGDKTHFCP PCPAPELLGGPSATLFPPKPKDTLMIS RTPEVTCVVVDVSHEDPEVKFNWYV DGVEVHNAKTKPREEQYNSTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTIPPVLDSDGSFFL YSKLIVDKSRWQQGNVESCSVMHE ALHNHYTQKSLSLSPG (SEQ ID NO: 58) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLYPPSSEELQANK ATLVCLISDFYPGAVTVAWKADGSP VKAGVETTKPSKQSDSKYAASSYLSL TPEQWKSHRSYSCQVTHEGSTVEKT VAPFECS (SEQ ID NO: 57) |
| AB21_HC_mut All (IgGI AAA dead) + V1 + DS | EVQLVESGGGVVQPGGSLRLSGAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSGDKTHTCP PCPAPEAAGAPSVFLEPPKPKDTLMIS RTPEVTCVVVDVSHEDPEVKFNWYV DGVEVHNAKTKPREEQYASTYRVVS VLTVLHQDWLNGKEYKCKVSNKAL PAPIEKVISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 52) |

TABLE J2-continued

Full chain sequences for selected antibodies.

| Antibody | Heavy chain | Light chain |
| --- | --- | --- |
| A92_HC_mut All (IgG1 AAA dead) + V1 + SD | EVQLVESGGGVVQPGGSLRESCAAS GFTFSSNAMSWVRQAPGKGLEWVA GISAGGSDTYYPASVKGRFTISRDNS KNTLYLQMNSERAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLEPPKPKDTEMIS RTPEVTCVVVDVSHEDPEVKFNWYV DGVEVHNAKTKPREEQYASTYRVVS VETVLRQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVESCSVMHE ALHNHYTQKSLSLSPG (SEQ ID NO: 59) | SYFLTQPPSVSVSPGQTARITCSGGSY SSYYYAWYQQKPGQAPVTLIYSDDK RPSNIPERESGSSSGTTVTLTISGVQAE DEADYYCGGYDQSSYTNPFGTGTKV TVLGQPKANPTVTLEPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 53) |
| AB21__HC_mut All (IgG1 AAA dead) + V2 + DS | EVQLVESGGGVVQPGGSLRLSCAAS GFTFSSNAMSWVRQAPGKGLEWVA GISAGGSDTYYPASVKGRFITISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTILSKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 54) |
| A921_HC_mut All (IgG1 AAA dead) + V2 +SD | EVQLVESGGGVVQPGGSLRLSCAAS GETFSSNAMSWVRQAPGKGLEWVA GISAGGSDTYYPASVKGRFFISRDNS KNTLYLQMNSLRAEDTAVYCARET WNHLFDYWGQGLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLFPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGFYPSDIAVE WESNGQPENNYKTTPPVLDSDGSFFL YSKLTVDKSRWQQGNVFSCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERESGSSSGTTVTLTILSGVQAE DEADYYCGGYDQSSYTNPFGGGTQL TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 55) |
| AB21_HC_mut All (IgGI AAA dead) + V3 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVLQS SGLYSLSSVVTVPSSSLGTQTYICNV NHKPSNTKVDKKVEPKSCDKTHTCP PCPAPEAAGAPSVFLEPPKPKDTLMIS RTPEVTCVVVDVSHEDPEVKFNWYV DGVEVHNAKTKPREEQYASTYRVVS VLTVLHQDWLNGKEYKCKVSNKAL PAPIEKTISKAKWPREPQVYTLPPSR EEMTKNQVSLTCLVKGFYPSDIAVE | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 56) |

TABLE J2-continued

Full chain sequences for selected antibodies.

| Antibody | Heavy chain | Light chain |
|---|---|---|
| | WESNGQPENNYKTTPPVLDSDGSFFL YSKLTVDKSRWQQGNVFSCSVMHE ALHNHYTQKSLSLSPG (SEQ ID NO: 59) | |
| AB21_HC_mut All (IgGI AAA dead) + V3 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPSSKSTSGGTAALGCLVKDYF PEPVTVSWNSGALTSGVHTFPAVQS SGLYSLSSVVTVPSSSLGTQTYICNV NHKPSNTKVDKKVEPKSCDKTHTCP PCPAPEAAGAPSVFLFPPKPKDTLIMIS RTPEVTCVVVDVSHEDPEVKFNWYV DGVEVHNAKTKPREEQYASTYRVVS VLTVLHQDWLNGKEYKCKVSNKAL PAPIEKTISKAKGQPREPQVYTLPPSR EEMTKNQVSLTCLVKGPIPSDIAVE WESNGQPENNYKTTPPVLDSDGSFFL YSKLTVDKSRWQQGNVESCSVMHE ALHNHYTQKSLSLSPG (SEQ ID NO: 59) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 57) |
| A921_HC_mut All (IgG2 wt) + V1 + DS | EVQLVESGGGVVQPGGSLRLSCAAS GFTSSNAMSWVRQAPGKGLEWVA GISAGGSDTYYPASVKGRETISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKTLMISRTPE VTCVVVDVSHEDPEVQFNWYVDGV EVHNAKTKPREEQFNSTERVVSVLT VVHQDWLNGKEYKCKVSNKGLPAPI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 60) | SYELTQPPSVSVSPGQTARITCSGGSY SSYYYAWYQQKPGQAPVTLIYSDDK RPSNIPERESGSSSGTTVTLTISGVQAE DEADYYCGGYDQSSYTNPFGTGTKV TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 52) |
| AB21_HC_mut All (IgG2 wt) + V1 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPAPI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 60) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLEPPSSEELQANK ALTVCLISDFYPGAVTVAWKADGSP VKAGVETTKPSKQSSDKYAASSYLSL TPEQWKSHRSYSCQVTHEGSTVEKT VAPTECS (SEQ ID NO: 53) |
| AB21_HC_mut All (IgG2 wt) + V2 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYECKVSNKGLPAPI | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 54) |

TABLE J2-continued

Full chain sequences for selected antibodies.

| Antibody | Heavy chain | Light chain |
|---|---|---|
| | EKTISKTKGQPREPQVYTLPPSREEM<br>TKNQVSLTCLVKGFYPSDIAVEWES<br>NGQPENNYKTIPPMLDSIDGSFFLYS<br>KLTVDKSRWQQGNVFSCSVNMHEAL<br>HNHYTQKSLSLSPG (SEQ ID NO: 60) | |
| AB21_HC_mut<br>All (IgG2 wt) +<br>V2 + SD | EVQLVESGGGVVQPGGSLRLSCAAS<br>GFTFSSNAMSWVRQAPGKGLEWVA<br>GISAGGSDTYYPASVKGRFTISRDNS<br>KNTLYLQMNSLRAEDTAVYYCARET<br>WNHLFDYWGQGTLVTVSSASTKGPS<br>VFPLAPCSRSTSESTAALGCLVKDYF<br>PEPVTVSWNSGALTSGVHTFPAVLQS<br>SGLYSLSSVVTVPSSNFGTQTYTCNV<br>DHKPSNTKVDKTVERKCCVECPPCP<br>APPVAGPSATLFPPKPKDTLMISRTPE<br>VTCVVVDVSHEDPEVQFNWYVDGV<br>EVHNAKTKPREEQFNSTFRVVSVLT<br>VVHQDWLNGKEYKCKVSNKGLPAPI<br>EKTISKTKGQPREPQVYTLPPSREEM<br>TKNQVSLTCLVKGFYPSDIAVEWES<br>NGQPENNYKTTPPMLDSDGSFFLYS<br>KLTVDKSRWQQGNVFSCSVMHEAL<br>HNHYTQKSLSLSPG (SEQ ID NO: 60) | SYELTQPPSVSVSPGQTARITCSGGSY<br>SSYYYAWYQQKPGQAPVTLIYSDDK<br>RPSNIPERFSGSSSGTTVTLTISGVQAE<br>DEADYYCGGYDQSSYTNPFGGGTQL<br>TVLGQPKANPTVTLEPPSSEELQANK<br>ATLVCLISDFYPGAVTVAWKADGSP<br>VKAGVETTKPSKQSSDKYAASSYLSL<br>TPEQWKSHRSYSCQVTHEGSTVEKT<br>VAPTECS (SEQ ID NO: 55) |
| AB21_HC_mut<br>All (IgG2 wt) +<br>V3 + DS | EVQLVESGGGVVQPGGSLRLSCAAS<br>GFTFSSNAMSWVRQAPGKGLEWVA<br>GISAGGSDTYYPASVKGRFTISRDNS<br>KNTLYLQMNSLRAEDTAVYYCARET<br>WNHLFDYWGQGTLVTVSSASTKGPS<br>VFPLAPCSRSTSESTAALGCLVKDYF<br>PEPVTVSWNSGALTSGVHTFPAVLQS<br>SGLYSLSSVVTVPSSNFGTQTYTCNV<br>DHKPSNTKVDKTVERKCCVECPPCP<br>APPVAGPSVFLFPPKPKDTLMISRTPE<br>VTCVVVDVSHEDPEVQFNWYVDGV<br>EVHNAKTKPREEQFNSTFRVVSVLT<br>VVHQDWLNGKEYKCKVSNKGLPAPI<br>EKTISKTKGQPREPQVYTLPPSREEM<br>TKNQVSLTCLVKGFYPSDIAVEWES<br>NCQPENNYKTTPPMLDSDGSFFLYS<br>KLTVDKSRWQQGNVFSCSVMHEAL<br>HNHYTQKSLSLSPG (SEQ ID NO: 60) | SYELTQPPSVSVSPGQTARITCSGGSY<br>SSYYYAWYQQKPGQAPVTLIYSDDK<br>RPSNIPERFSGSSSGTTVTLTISGVQAE<br>DEADYYCGGYDQSSYTNPFGGGTRL<br>TVLGQPKANPTVTLEPPSSEELQANK<br>ATLVCLISDFYPGAVTVAWKADGSP<br>VKAGVETTKPSKQSDSKYAASSYLSL<br>TPEQWKSHRSYSCQVTHEGSTVEKT<br>VAPTECS (SEQ ID NO: 56) |
| AB21_HC_mut<br>All (IgG2 wt) +<br>V3 + SD | EVQLVESGGGVVQPGGSLRLSCAAS<br>GFTFSSNAMSWVRQAPGKGLEWVA<br>GISAGGSDTYYPASVKGRFTISRDNS<br>KNTLYLQMNSLRAEDTAVYYCARET<br>WNHLFDYWGQGTLNTVSSASTKGPS<br>VFPLAPCSRSTSESTAALGCLVKDYF<br>PEPVTVSWNSGALTSGVHTFPAVLQS<br>SGLYSLSSVVTVPSSNEGTQTYTCNV<br>DHKPSNTKVDKTVERKCCVECPPCP<br>APPVAGPSVFLFPPKPKDTLMISRTPE<br>VTCVVVDVSHEDPEVQFNWYVDGV<br>EVHNAKTKPREEQFNSTERVVSVLT<br>VVHQDWLNGKEYKEKVSNKGLPAPI<br>EKTISKTKGQPREPQVYTLPPSREEM<br>TKNQVSLTCLNKGFYPSDIAVEWES<br>NGQPENNYKTTPPMLDSDGSFFLYS<br>KLTVDKSRWQQGNVFSCSVMHEAL<br>HNHYTQKSLSLSPG (SEQ ID NO: 60) | SYELTQPPSVSVSPGQTARITCSGGSY<br>SSYYAWYQQKPGQAPVTLIYSDDK<br>RPSNIPERFSGSSSGTTVTLTISGVQAE<br>DEADYYCGGYDQSSYTNPFGGGTRL<br>TVLGQPKANPTVTLEPPSSEELQANK<br>ATLVCLISDFYPGAVTVAWKADGSP<br>VKAGVETTKPSKQSSDKYAASSYLSL<br>TPEQWKSHRSYSCQVTHEGSTVEKT<br>VAPTECS (SEQ ID NO: 57) |
| AB21_HC_mut<br>All (IgG2 Da)+<br>V1 + DS | EVQLVESGGGVVQPGGSLRLSCAAS<br>GFTESSNAMSWVRQAPGKGLEWVA<br>GISAGGSDTYYPASVKGRFTISRDNS<br>KNTLYLQMNSLRAEDTAVYYCARET<br>WNHLFDYWGQGTLVTVSSASTKGPS<br>VFPLAPCSRSTSESTAALGCLVKDYF<br>PEPVTVSWNSGALTSGVHTFPAVLQS<br>SGLYSLSSVVTVPSSNFGTQTYI<br>DHKPSNTKVDKTVERKCCVECPPCP<br>APPVAGPSVFLFPPKPKDTLMISRTPE<br>EVHNAKTKPREEQFNSTFRVVSVLT<br>VVHQDWLNGKEYKCKVSNKGLPSSI<br>EKTISKTKGQPREPQVYTLPPSREEM | SYELTQPPSVSVSPGQTARITCSGGSY<br>SSYYAWYQQKPGQAPVTLIYSDDK<br>RPSNIPERFSGSSSGTTVTLTISGVQAE<br>DEADYYCGGYDQSSYTNPFGTGTKV<br>TVLGQPKANPTVTLFPPSSEELQANK<br>ATLVCLISDFYPGAVTVAWKADGSP<br>VKAGVETTKPSKQSDSKYAASSYLSL<br>TPEQWKSHRSYSCQVTHEGSTVEKT<br>VAPTECS (SEQ ID NO: 52) |

TABLE J2-continued

Full chain sequences for selected antibodies.

| Antibody | Heavy chain | Light chain |
|---|---|---|
| | TKNQVSLTCLVKGEYPSDIAVEWES NGQPENNYKTTPPMLDSDGSFFLYS KLTVDKSRWQQGNVFSCSVMHEAL HNHYTQKSLSLSPG (SEQ ID NO: 61) | |
| AB21_HC_mut All (IgG2 Da) + V1 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLEDYWGQGTLVTVSSASTKGPS VEPLAPCSRSTSESTAALGCLVKDYF PEPVTVSWNSGALTSGVHTFPAVLQS SGLYSLSSVVTVPSSNEGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLEPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 53) |
| AB21_HC_mut All (1gG2 Da) + V2 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSDSKYAASSYLSL TPEQWKSERSYSCQVTHEGSTVEKT VAPTECS (SEQ ID NO: 54) |
| AB21_HC_mut All (IgG2 Da) + V2 +SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNEGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPGQAPVITLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 55) |
| AB21_HC_mut All (IgG2 Da) + V3 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTSSASTKGPS VFPLAPCSRSTSESTAALGCLVKDYE PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM | SYELTQPPSVSVSPGQTARITCSGGSY SSYYYAWYQQKPGQAPVTLIYSDDK RPSNIPERFSGSSSGTTVTLTISGVAE DEADYYCGGYDQSSYTNPFGGGTRL TVEGQPKANPTVTLFPPSSEELQANK ATLVCLISDFYPGAVTVAWKADGSP VKAGVETIKPSKQSDSKYAASSYLSL TPEQWKSHRSYSCQVTHEGSTVEKT VAPTECS (SEQ ID NO: 56) |

TABLE J2-continued

Full chain sequences for selected antibodies.

| Antibody | Heavy chain | Light chain |
|---|---|---|
| | TKNQVSLTCLVKGFYPSDIAVEWES NCQPENNYKTTPPMLDSDGSFFLYS KLTVDKSRWQQGNVFSCSVMHEAL HNHYTQKSLSLSPG (SEQ ID NO: 61) | |
| AB21_HC_mut All (IgG2 Da) + V3 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | SYELTQPPSVSVSPGQTARITCSGGSY SSYYYAWYQQKPCQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 57) |
| AB21_HC_mut All (IgG4 S228P) + V1 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG (SEQ ID NO: 62) | SYELTQPPSVSVSPGQTARITCSGGSY SSYYYAWYQQKPGQAPVTLFYSDDK RPSNIPERFSGSSSGTTVTLTISGVQAE DEADYYCGGYDQSSYTNPFGTGTKV TVLGQPKANPTVTLEFPSSEELQANK ATLVCLISDFYPGAVTVAWKADGSP VKAGVETTKPSKQSDSKYAASSYLSL TPEQWKSHRSYSCQVTHEGSTVEKT VAPTECS (SEQ ID NO: 52) |
| AB21_HC_mut All (IgG4 S228P) + V1 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLEPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG (SEQ ID NO: 62) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGTGTKV TVLGQPKANPTVTLFPPSSEELQANK ATLVCLISDFYPGAVTVAWKADGSP VKAGVETTKPSKQSSDKYAASSLSL TPEQWKSHRSYSCQVTHEGSTVEKT VAPTECS (SEQ ID NO: 53) |
| AB21_HC_mut All (IgG4 S228P) + V2 + DS | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKUGLPSS IEKTISKAKGQPREPQVVTLPPSQEE | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 54) |

TABLE J2-continued

Full chain sequences for selected antibodies.

| Antibody | Heavy chain | Light chain |
|---|---|---|
| | MTKNQVSLTCLVKGFYPSDIAVEWE SNGQPENNYKTTPPVLDSDGSFFLYS RLTVDKSRWQEGNVESCSVMHEAL HNHYTQKSLSLSLG (SEQ ID NO: 62) | |
| AB21_HC_mut All (IgG4 S228P) + V2 + SD | EVQLVESGGGVVQPGGSLRLSCAAS GFTFSSNAMSWVRQAPGKGLEWVA GISAGGSDTYYPASVKGRFTISRDNS KNTLYQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE MTKNQVSLTCLVKGFYPSDIAVEWE SNGQPENNYKYTTPPVLDSDGSFFLYS RLTVDKSRWQEGNVFSCSVMHEAL HNHYTQKSLSISLG (SEQ ID NO: 62) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPEFGGGTQL TVLGQPKANPTVTLFPPSSEELQANK ATLVCLISDEYPGAVTVAWKADGSP VKAGVETTKPSKQSSDKYAASSYLSL TPEQWKSHRSYSCQVPHEGSTVEKT VAPTECS (SEQ ID NO: 55) |
| AB21_HC_mut All (IgG4 S228P) + V3 + DS | EVQLVESGGGVVQPGGSLRLSCAAS GFTSSNAMSWVRQAPGKGLEWVA GISAGGSDTYYPASVKGRFTLSRDNS KNTLYLQMNSLRAEDTAVYYCARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG (SEQ ID NO: 62) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 56) |
| AB21_HC_mut All (IgG4 S228P) + V3 + SD | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYWARET WNHLFDYWGQGTLVTVSSASTKGPS VFPLAPCSRSTSESTAALGCLVKDYF PEPVTVSWNSGALTSGVHTFPAVLQS SGLYSLSSVVTVPSSSLGTKTYTCNV DHKPSNTKVDKRVESKYGPPCPPCP APEFLGGPSVFLFPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE MTKNQVSLTCLVKGFYPSDIAVEWE SNGQPENNYKTTPPVLDSDGSFFLYS RLTVDKSRWQEGNVFSCSVMHEAL HNHYTQKSLSLSLG (SEQ ID NO: 62) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTRL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 57) |
| PC348 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAVYYCARET WNHLFDYWGQGTLVTVSSASTKGPS VFPLAPCSRSTSESTAALGCLVKDYF PEPVFVSWNSGALTSGVHTEPAVLQS SGLYSLSSVVTVPSSSLGTKTYTCNV DHKPSNTKVDKRVESKYGPPCPPCP APEFLGGPSVELFPPKPKDTLMISRTP EVTCVVVDVSQEDPEVQFNWYVDG VEVHNAKTKPREEQFNSTYRVVSVL TVLHQDWLNGKEYKCKVSNKGLPSS IEKTISKAKGQPREPQVYTLPPSQEE | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 55) |

TABLE J2-continued

Full chain sequences for selected antibodies.

| Antibody | Heavy chain | Light chain |
|---|---|---|
| | MTKNQVSLTCLVKGFYPSDIAVEWE SNGQPENNYKTTPPVLDSDGSFFLYS RLTVDKSRWQEGNVESCSVMHEAL HNHYTQKSLSLSLG (SEQ ID NO: 62) | |
| PC349 | EVQLVESGGGVVQPGGSLRLSCAAS GFTFSSNAMSWVRQAPGKGLEWVA GISAGGSDTYYPASVKGRFTISRDNS KNTLYLQMNSLRAEDTAPNCARET WNHLFDYWGQGTLVTVSSASTKGPS VEPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE VTCVVVDVSHEDPEVQFNWYVDGV EVHNAKTKPREEQFNSTFRVVSVLT VVHQDWLNGKEYKCKVSNKGLPAPI EKTISKTKGQPREPQVYTLPPSREEM TKNQVSLICLVKGFYPSDIAVEWES NGQPENNYKTTPPMLDSDGSFELYS KLTVDKSRWQQGNVFSCSVMHEAL HNHYTQKSLSLSPG (SEQ ID NO: 60) | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLEPPSSEELQANK ATLVCLISDFYPGAVTVAWKADGSP VKAGVETTKPSKQSSDKYAASSYLSL TPEQWKSHRSYSCQVTHEGSTVEKT VAPTECS (SEQ ID NO: 55) |
| PC350A | EVQLVESGGGVVQPGGSLRLSCAAS GFTFSSNAMSWVRQAPGKGLEWVA GISAGGSDTYYPASVKGRFTISRDNS KNTLYLQMNSLRAEDTAWYCARET WNHLFDYWGQGTLvTVSSASTKGPS VFPLAPCSRSTSESTAALGCLVKDYF PEPVTVSWNSGALTSGVHTEPAVLQS SGLYSLSSVVTVPSSNEGTQTYTCNV DHKPSNTKVDKTVERKCCVECPPCP APPVAGPSVELEPPKPKDTLMISRTPE VTCVVVDVSHEDPEVQFNWYVDGV EVHNAKTKPREEQFNSTFRVVSVLT VVHQDWLNGKEYKCKVSNKGLPSSI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 61) | ALTQPASVSANPGETVEITCSGGSYSS YYYAWYQQKSPGSAPVTLIYSDDKR PSNIPSRFSGSASGSTATLTITGVRAE DEAVYFCGGYDQSSYTNPFGAGTTL TVLRTVAAPSVFIPPPSDEQLKSGTAS VVCLLNNFYPREAKVQWKVDNALQ SGNSQESVTEQDSKDSTYSLSSTLTLS KADYEKHKVYACEVTHQGLSSPVTK SFNRGEC (SEQ ID NO: 140) |
| PC350B | EVQLVESGGGVVQPGGSLRLSCAAS GFTFSSNAMSWVRQAPGKGLEWVA GISAGGSDTYYPASVKGRFTISRDNS KNTLYLQMNSIRAEDTAVYYCARET WNHLFDYWGQGTLVFVSSASTKGPS VEPLAPCSRSTSESTAALGCLVKDYF PEPVTVSWNSGALTSGVHTFPAVLQS SGLYSLSSVVTVPSSNFGTQTYTCNV DHKPSNTKVDKTVERKCCVECPPCP APPVAGPSVFLFPPKPKDTLMISRTPE EVHNAKTKPREEQFNSTFRVVSVLT VVHQDWLNGKEYKCKVSNKGLPAPI EKTISKTKGQPREPQVYTLPPSREEM TKNQVSLTCLVKGFYPSDIAVEWES NGQPENNYKTTPPMLDSDGSFFLYS KLTVDKSRWQQGNVFSCSVMHEAL HNHYTQKSLSLSPG (SEQ ID NO: 60) | ALTQPASVSANPGETVEITCSGGSYSS YYYAWYQQKSPGSAPVTLIYSDDKR PSNIPSRFSGSASGSTATLTITGVRAI DEAVYFCGGYDQSSYTNPFGAGTTL TVLRTVAAPSVFIPPPSDEQLKSGTAS VVCLLNNFYPREAKVQWKVDNALQ SGNSQESVTEQDSKDSTYSLSSTLTLS KADYEKHKVYACEVTHQGLSSPVTK SFNRGEC (SEQ ID NO: 140) |
| PC363 | EVQLVESGGGVVQPGGSLRLSCA ASGFTFSSNAMSWVRQAPGKGLE WVAGISAGGSDTYYPASVKGRFT ISRDNSKNTLYLQMNSLRAEDTA VYYCARETWNHLFDYWGQGTLV TVSSASTKGPSVFPLAPCSRSTSES TAALGCLVKDYFPEPVTVSWNSG ALTSGVHTFPAVLQSSGLYSLSSV VTVPSSNFGTQTYTCNVDHKPSN TKVDKTVERKSCVECPPCPAPPV AGPSVFLFPPKPKDTLMISRTPEV TCVVVDVSHEDPEVQFNWYVDG VEVHNAKTKPREEQFNSTERVVS VLTVVHQDWLNGKEYKCKVSNK GLPAPIEKTISKTKGQPREPQVYT | SYELTQPPSVSVSPGQTARITCSGGSY SSYYYAWYQQKPGQAPVTLIYSDDK RPSNIPERFSGSSSGTTVTLTISGVQAE DEADYYCGGYDQSSYTNPFGGGTQL TVLGQPKANPTVTLFPPSSEELQANK ATLVCLISDEYPGAVTVAWKADCSP VKAGVETTKPSKQSSDKYAASSYLSL TPEQWKSHRSYSCQVTHEGSTVEKT VAPTECS (SEQ ID NO: 55) |

TABLE J2-continued

Full chain sequences for selected antibodies.

| Antibody | Heavy chain | Light chain |
|---|---|---|
| | LPPSREEMTKNQVSLTCLVKGFY<br>PSDIAVEWESNGQPENNYKTTPP<br>MLDSDGSFFLYSKLTVDKSRWQQ<br>GNVFSCSVMHEALEINHYTQKSLS<br>LSPG (SEQ ID NO: 125) | |
| PC364 | EVQLVESGGGVVQPGGSLRLSCA<br>ASGFTFSSNAMSWVRQAPGKGLE<br>WVAGISAGGSDTYYPASVKGRFT<br>ISRDNSKNTLYLQMNSLRAEDTA<br>VYYCARETWNHLFDYWGQGTLV<br>TVSSASTKGPSVFPLAPCSRSTSES<br>TAALGCLVKDYFPEPVTVSWNSG<br>ALTSGVHTFPAVLQSSGLYSLSSV<br>VTVPSSNFGTQYTCNVDHKPSN<br>TKVDKTVERKCSVECPPCPAPPV<br>AGPSVFLFPPKPKDTLMISRTPEV<br>TCVVVDVSHEDPEVQFNWYVDG<br>VEVHNAKTKPREEQFNSTFRVVS<br>VLTVVHQDWLNGKEYKEKVSNK<br>GLPAPIEKTISKTKGQPREPQVYT<br>LPPSREEMIKNQVSLTCLVKGFY<br>PSDIAVEWESNGQPENNYKTTPP<br>MLDSDGSFFLYSKLIVDKSRWQQ<br>GNVFSCSVMHEALHNHYTQKSLS<br>LSPG (SEQ ID NO: 126) | SYELTQPPSVSVSPGQTARITCSGGSY<br>SSYYYAWYQQKPGQAPVTLIYSDDK<br>RPSNIPERFSGSSSGTTVTLTISGVQAE<br>DEADYYCGGYDQSSYTNPFGGGTQL<br>TVLGQPKANPTVTLEPPSSEELQANK<br>ATLVCLISDFYPGAVTVAWKADGSP<br>VKAGVETTKPSKQSSDKYAASSYLSL<br>TPEQWKSHRSYSCQVTHEGSTVEKT<br>VAPTECS (SEQ ID NO: 55) |
| PC367 | EVQLVESGGGVVQPGGSLRLSCA<br>ASGFTFSSNAMSWVRQAPGKGLE<br>WVAGISAGGSDTYYPASVKGRFT<br>ISRDNSKNTLYLQMNSLRAEDTA<br>VYYCARETWNHLFDYWGQGTLV<br>TVSSASTKGPSVFPLAPCSRSTSES<br>TAALGCLVKDYFPEPVTVSWNSG<br>ALTSGVHTFPAVLQSSGLYSLSSV<br>VTVPSSNFGTQYTCNVDHKPSN<br>TKVDKTVERKCCVECPPCPAPPV<br>AGPSVFLEPPKPKDTLMISRTPEV<br>TCVVVDVSHEDPEVQFNWYVDG<br>VEVHNAKTKPREEQFASTFRVVS<br>VLTVVHQDWLNGKEYKCKVSNK<br>GLPAPIEKTISKTKGQPREPQVYT<br>LPPSREEMTKNQVSLTCLVKGFY<br>PSDIAVEWESNGQPENNYKTTPP<br>MLDSDGSFFLYSKLTVDKSRWQQ<br>GNVFSCSVMHEALHNHYTQKSLS<br>LSPG (SEQ ID NO: 129) | SYELTQPPSVSVSPGQTARITCSGGSY<br>SSYYYAWYQQKPGQAPVFLIYSDDK<br>RPSNIPERFSGSSSGTTVTLTISGVQAE<br>DEADYYCGGYDQSSYTNPFGGGTQL<br>TVLGQPKANPTVTLFPPSSEELQANK<br>ATLVCLISDFYPGAVTVAWKADGSP<br>VKAGVETTKPSKQSSDKYAASSYLSL<br>TPEQWKSHRSYSCQVTHEGSTVEKT<br>VAPTECS (SEQ ID NO: 55) |
| PC369 | EVQLVESGGGVVQPGGSLRLSCA<br>ASGFTFSSNAMSWVRQAPGKGLE<br>WVAGISAGGSDTYYPASVKGRFT<br>ISRDNSKTLYLQMNSLRAEDTA<br>VVYCARETWNHLFDYWGQGTLV<br>TVSSASTKGPSVFPLAPCSRSTSES<br>TAALGCLVKDYFPEPVTVSWNSG<br>ALTSGVHTFPAVLQSSGLYSLSSV<br>VTVPSSNEGTQYTCNVDHKPSN<br>TKVDKTVERKCSVECPPCPAPPV<br>AGPSVFLFPPKPKDTLMISRTPEV<br>TCVVVDVSHEDPEVQFNWYVDG<br>VEVHNAKTKPREEQFASTFRVVS<br>VLTVVHQDWLNGKEYKCKVSNK<br>GLPAPIEKTISKTKGQPREPQVYT<br>LPPSREEMTKNQVSLTCLVKGFY<br>PSDIAVEWESNGQPENNYKTTPP<br>MLD (SEQ ID NO: 130) | SYELTQPPSVSVSPGQTARITCSGGSY<br>SSYYYAWYQQKPCTQAPVTLIYSDDK<br>RPSNIPERFSGSSSGTTVLTISGVQAE<br>DEADYYCGGYDQSSYTNPFGGGTQL<br>TVLGQPKANPTVTLFPPSSEELQANK<br>ATLVCLISDFYPGAVTVAWKADGSP<br>VKAGVETTKPSKQSSDKYAASSYLSL<br>TPEQWKSHRSYSCQVTHEGSTVEKT<br>VAPTECS (SEQ ID NO: 55) |

TABLE K

Anti-SIRP-α antibody summary.

| Antibody | Type of Binding | In vitro phago (+/−) | In vivo mouse (+/−) | Species Binding (+/−) (Koff) | | | Human Isoforms (+/−) (Koff) | | $K_D$ | $K_D$ | Heavy Chain | Light Chain |
|---|---|---|---|---|---|---|---|---|---|---|---|---|
| | | | | Human v1 (SEQ ID NO: 5) | Cyno (SEQ ID NO: 11) | Mouse 129 SEQ ID (NO: 7) | Beta SEQ ID (NO: 13) | Gamma SEQ ID (NO: 15) | Human V1 SEQ ID (NO: 5) | Human V2 SEQ ID (NO: 6) | (Human/ Chicken) | (Human/ Chicken) |
| 21 | Blocker | + | + | + | + | + | + | + | <1.0E−12 | <1.0E−12 | Human | Chicken |
| 25 | Blocker | + | + | + | + | + | + | + | <1.0E−12 | <1.0E−12 | Human | Chicken |

TABLE L

Anti-SIRP-α antibody humanization summary (round 1).

| Antibody Designation | VL | VH | Koff (1/s) | | | | | In vitro phago (+/−) | In vivo mouse (+/−) |
|---|---|---|---|---|---|---|---|---|---|
| | | | SEQ ID NO: 5 Human V1 | SEQ ID NO: 6 Human V2 | SEQ ID NO: 11 Cyno | SEQ ID NO: 10 BALBc | SEQ ID NO: 15 SIRPg | | |
| Parental Antibodies | | | | | | | | | |
| AB21 | Chicken (AB21_LC_wt) | Human (AB21_HC_wt) | 7.07E−04 | 1.92E−03 | 2.29E−03 | 2.41E−03 | 9.02E−04 | NT | + |
| AB25 | Chicken (AB25_LC_wt) | Human (AB25_HC_wt) | 1.65E−04 | 3.53E−04 | 3.94E−04 | 1.78E−03 | 2.03E−04 | + | + |
| Humanization of chicken light chain of AB25, AB66—replaced with human IGLV3 framework | | | | | | | | | |
| Hum1/ AB21_HC_wt | Hum1_ Humanized (AB25_IGLV3) | Human (AB21_HC_wt) | 1.93E−04 | 3.03E−04 | 3.95E−04 | 2.91E−03 | 1.88E−04 | + | |
| Hum1/ AB25_HC_wt | Hum1_ Humanized (AB25_IGLV3) | Human (AB25_HC_wt) | 1.33E−04 | 2.67E−04 | 3.30E−04 | 3.74E−03 | 2.03E−04 | + | |
| Hum3/ AB21_HC_wt | Hum3_ Humanized (AB66_IGLV3) | Human (AB21_HC_wt) | 1.37E−04 | 4.38E−04 | 4.32E−04 | 2.31E−03 | 2.10E−04 | NT | |
| Hum3/ AB25_HC_wt | Hum3_ Humanized (AB66_IGLV3) | Human (AB25_HC_wt) | 5.94E−05 | 3.53E−04 | 3.75E−04 | 2.27E−04 | 1.69E−04 | NT | |

NT or blank = not tested.

TABLE M

Anti-SIRP-α antibody humanization summary (round 2).

| Antibody Designation | VL | VH | KD (M) | | | | | | | | In vitro phago (+/−) |
|---|---|---|---|---|---|---|---|---|---|---|---|
| | | | SEQ ID NO: 5 Human V1 | SEQ ID NO: 6 Human V2 | SEQ ID NO: 11 Cyno | SEQ ID NO: 8 NOD | SEQ ID NO: 9 BL6 | SEQ ID NO: 10 BALBc | SEQ ID NO: 13 SIRPb | SEQ ID NO: 15 SIRPg | |
| Pairing of humanized light chain with heavy chain (Germline mut) | | | | | | | | | | | |
| Hum1/ AB21_HC_ Mutal1 | Hum1_ Humanized SEQ ID NO: 25 | Human (AB21_HC_ Mutal1) SEQ ID NO: 26 | 5.32E−12 | 4.60E−12 | 2.91E−11 | 3.70E−09 | 9.50E−09 | 7.91E−09 | 6.7E−12 | >1.0E−12 | + |
| Mutation of humanized light chain to increase % humaness | | | | | | | | | | | |
| Hum8/ AB21_HC_ Mutal1 | Hum8_ Humanized (AB25_ IGLV3) + 5aa in CDR | Human (AB21_HC_ Mutal1) SEQ ID NO: 26 | 2.01E−11 | | | 2.78E−08 | 4.15E−04 | 7.12E−08 | | | + |

TABLE M-continued

Anti-SIRP-α antibody humanization summary (round 2).

| Antibody Designation | VL | VH | KD (M) | | | | | | | | In vitro phago (+/−) |
|---|---|---|---|---|---|---|---|---|---|---|---|
| | | | SEQ ID NO: 5 Human V1 | SEQ ID NO: 6 Human V2 | SEQ ID NO: 11 Cyno | SEQ ID NO: 8 NOD | SEQ ID NO: 9 BL6 | SEQ ID NO: 10 BALBc | SEQ ID NO: 13 SIRPb | SEQ ID NO: 15 SIRPg | |
| Hum9/ AB21_HC_ Mutal1 | Hum9_ Humanized (AB25_ IGLV3) + 4aa in CDR | Human (AB21_HC_ Mutal1) | 1.19E−11 | 1.19E−10 | 2.22E−10 | 2.41E−08 | 5.33E−04 | 1.36E−07 | 5.69E−11 | 3.45E−11 | + |

NT or blank = not tested

TABLE N

Anti-SIRP-α antibody binding data summary. Values indicated are tested by SPR ($K_{off}$ 1/s).

| Antibody | CV1-3 SEQ ID NO: 18 | v1 SEQ ID NO: 5 | v2 SEQ ID NO: 6 | cyno1 SEQ ID NO: 11 | cyno2 SEQ ID NO: 12 | m129 SEQ ID NO: 7 | NOD SEQ ID NO: 8 | BL6 SEQ ID NO: 9 | SIRPb SEQ ID NO: 13 | SIRPg SEQ ID NO: 15 | CD47 blocking |
|---|---|---|---|---|---|---|---|---|---|---|---|
| S21 | 1.95E−04 | 1.80E−04 | 2.07E−04 | 2.33E−04 | 2.52E−04 | 2.81E−04 | 2.64E−03 | 8.06E−04 | 1.90E−04 | 1.84E−04 | block |
| S25 | 1.40E−04 | 1.12E−04 | 2.09E−04 | 2.19E−04 | 2.12E−04 | 1.33E−04 | 7.79E−04 | 2.90E−04 | 1.71E−04 | 1.41E−04 | block |

What is claimed is:

1. An isolated antibody that binds an extracellular domain of a human SIRP-a polypeptide, wherein the antibody comprises:
   (a) a heavy chain that comprises the amino acid sequence of SEQ ID NO:58, 62, or 124; and
   (b) a light chain comprising a light chain variable (VL) domain that comprises the amino acid sequence of SEQ ID NO:25 or 40.

2. The antibody of claim 1, wherein the light chain further comprises a lambda constant light chain (CL) domain that comprises the amino acid sequence of SEQ ID NO:37 or 46.

3. The antibody of claim 1, wherein the light chain comprises the amino acid sequence of SEQ ID NO:47 or 55.

4. The antibody of claim 1, wherein:
   (a) the heavy chain comprises the amino acid sequence of SEQ ID NO:58, and the light chain comprises the amino acid sequence of SEQ ID NO:47;
   (b) the heavy chain comprises the amino acid sequence of SEQ ID NO:62, and the light chain comprises the amino acid sequence of SEQ ID NO:47;
   (c) the heavy chain comprises the amino acid sequence of SEQ ID NO:124, and the light chain comprises the amino acid sequence of SEQ ID NO:47;
   (d) the heavy chain comprises the amino acid sequence of SEQ ID NO:58, and the light chain comprises the amino acid sequence of SEQ ID NO:55;
   (e) the heavy chain comprises the amino acid sequence of SEQ ID NO:62, and the light chain comprises the amino acid sequence of SEQ ID NO:55; or
   (f) the heavy chain comprises the amino acid sequence of SEQ ID NO:124, and the light chain comprises the amino acid sequence of SEQ ID NO:55.

5. The antibody of claim 1, wherein the antibody enhances phagocytosis by a macrophage expressing a human SIRP-α polypeptide.

6. The antibody of claim 1, wherein the antibody enhances activation of a dendritic cell expressing a human SIRP-α polypeptide.

7. The antibody of claim 1, wherein the antibody inhibits in vivo growth of a tumor that expresses CD47.

8. A polynucleotide encoding the antibody of claim 1.

9. A vector comprising the polynucleotide of claim 8.

10. A host cell comprising the polynucleotide of claim 8.

11. A method of producing an antibody, the method comprising culturing the host cell of claim 10 such that the antibody is produced.

12. The method of claim 11, further comprising recovering the antibody from the host cell.

13. A method of treating or delaying progression of cancer in an individual, the method comprising administering to the individual an effective amount of the antibody of claim 1.

14. The method of claim 13, further comprising administering to the individual an effective amount of a second antibody that binds an antigen expressed by the cancer.

15. The method of claim 14, wherein the antigen expressed by the cancer is selected from the group consisting of CD19, CD20, CD22, CD30, CD33, CD38, CD52, CD56, CD70, CD74, CD79b, CD123, CD138, CS1/SLAMF7, Trop-2, 5T4, EphA4, BCMA, PTK7, STEAP1, Endothelin B Receptor, mesothelin, ENPP3, SLC44A4, GNMB, nectin 4, NaPi2b, LIV-1A, Guanylyl cyclase C, DLL3, EGFR, HER2, VEGF, VEGFR, integrin αVβ3, integrin α5β1, MET, IGF1R, TRAILR1, TRAILR2, RANKL, FAP, Tenascin, Leg, EpCAM, CEA, gpA33, PSMA, TAG72, a mucin, CAIX, EPHA3, folate receptor α, GD2, GD3, and an MHC/peptide complex comprising a peptide from NY-ESO-1/LAGE, SSX-2, a MAGE family protein, gp100/pme117, Melan-A/MART-1, gp75/TRP1, tyrosinase, TRP2, CEA, PSA, TAG-72, immature laminin receptor, MOK/RAGE-1, WT-1, SAP-1, BING-4, EpCAM, MUC1, PRAME, survivin, BRCA1, BRCA2, CDK4, CML66, MART-2, p53, Ras, β-catenin, TGF-βRII, HPV E6, or HPV E7.

16. The method of claim 13, further comprising administering to the individual an effective amount of an immunotherapeutic agent.

17. The method of claim 16, wherein the immunotherapeutic agent comprises a second antibody.

18. The method of claim 17, wherein the second antibody binds to an antigen selected from the group consisting of BDCA2, BDCA4, ILT7, LILRB1, LILRB2, LILRB3, LILRB4, CSF-1R, CD40, CD40L, CD163, CD206, DEC205, CD47, CD123, IDO, TDO, 41BB, CTLA4, PD1, PD-L1, PD-L2, TIM-3, BTLA, VISTA, LAG-3, CD28, OX40, GITR, CD137, CD27, HVEM, CCR4, CD25, CD103, KIrg1, Nrp1, CD278, Gpr83, TIGIT, CD154, CD160, PVRIG, DNAM, and ICOS.

19. The method of claim 18, wherein the second antibody binds to PD-1.

20. The method of claim 18, wherein the second antibody binds to PD-L1.

21. The method of claim 16, wherein the immunotherapeutic agent comprises a vaccine, oncolytic virus, adoptive cell therapy, cytokine, or small molecule agent.

22. The method of claim 15, wherein the mucin is Mucin 1 or Mucin 16.

23. The method of claim 15, wherein the EGFR is EGFRvIII.

24. The method of claim 15, wherein the MAGE family protein is MAGE A3.

* * * * *

SEQUENCE LISTING

```
<160> NUMBER OF SEQ ID NOS: 140

<210> SEQ ID NO 1
<211> LENGTH: 348
<212> TYPE: PRT
<213> ORGANISM: Artificial Sequence
<220> FEATURE:
<223> OTHER INFORMATION: Synthetic Construct

<400> SEQUENCE: 1
```

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Glu Ser Lys Tyr Gly Pro Pro Cys Pro
        115                 120                 125

Pro Cys Pro Ala Pro Glu Phe Leu Gly Gly Pro Ser Val Phe Leu Phe
    130                 135                 140

Pro Pro Lys Pro Lys Asp Thr Leu Met Ile Ser Arg Thr Pro Glu Val
145                 150                 155                 160

Thr Cys Val Val Val Asp Val Ser Gln Glu Asp Pro Glu Val Gln Phe

```
                    165                 170                 175
Asn Trp Tyr Val Asp Gly Val Glu Val His Asn Ala Lys Thr Lys Pro
            180                 185                 190

Arg Glu Glu Gln Phe Asn Ser Thr Tyr Arg Val Val Ser Val Leu Thr
            195                 200                 205

Val Leu His Gln Asp Trp Leu Asn Gly Lys Glu Tyr Lys Cys Lys Val
            210                 215                 220

Ser Asn Lys Gly Leu Pro Ser Ser Ile Glu Lys Thr Ile Ser Lys Ala
225                 230                 235                 240

Lys Gly Gln Pro Arg Glu Pro Gln Val Tyr Thr Leu Pro Pro Ser Gln
                245                 250                 255

Glu Glu Met Thr Lys Asn Gln Val Ser Leu Thr Cys Leu Val Lys Gly
            260                 265                 270

Phe Tyr Pro Ser Asp Ile Ala Val Glu Trp Glu Ser Asn Gly Gln Pro
            275                 280                 285

Glu Asn Asn Tyr Lys Thr Thr Pro Pro Val Leu Asp Ser Asp Gly Ser
            290                 295                 300

Phe Phe Leu Tyr Ser Arg Leu Thr Val Asp Lys Ser Arg Trp Gln Glu
305                 310                 315                 320

Gly Asn Val Phe Ser Cys Ser Val Met His Glu Ala Leu His Asn His
                325                 330                 335

Tyr Thr Gln Lys Ser Leu Ser Leu Ser Leu Gly Lys
            340                 345

<210> SEQ ID NO 2
<211> LENGTH: 347
<212> TYPE: PRT
<213> ORGANISM: Artificial Sequence
<220> FEATURE:
<223> OTHER INFORMATION: Synthetic Construct

<400> SEQUENCE: 2

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
            35                  40                  45

Ile Tyr Asn Gln Lys Glu Gly His Phe Pro Arg Val Thr Thr Val Ser
            50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Glu Ser Lys Tyr Gly Pro Pro Cys Pro Pro
            115                 120                 125

Cys Pro Ala Pro Glu Phe Leu Gly Gly Pro Ser Val Phe Leu Phe Pro
            130                 135                 140

Pro Lys Pro Lys Asp Thr Leu Met Ile Ser Arg Thr Pro Glu Val Thr
145                 150                 155                 160

Cys Val Val Val Asp Val Ser Gln Glu Asp Pro Glu Val Gln Phe Asn
                165                 170                 175

Trp Tyr Val Asp Gly Val Glu Val His Asn Ala Lys Thr Lys Pro Arg
```

180                 185                     190
Glu Glu Gln Phe Asn Ser Thr Tyr Arg Val Val Ser Val Leu Thr Val
                    195                 200                 205
Leu His Gln Asp Trp Leu Asn Gly Lys Glu Tyr Lys Cys Lys Val Ser
                210                 215                 220
Asn Lys Gly Leu Pro Ser Ser Ile Glu Lys Thr Ile Ser Lys Ala Lys
225                 230                 235                 240
Gly Gln Pro Arg Glu Pro Gln Val Tyr Thr Leu Pro Pro Ser Gln Glu
                245                 250                 255
Glu Met Thr Lys Asn Gln Val Ser Leu Thr Cys Leu Val Lys Gly Phe
                260                 265                 270
Tyr Pro Ser Asp Ile Ala Val Glu Trp Glu Ser Asn Gly Gln Pro Glu
                275                 280                 285
Asn Asn Tyr Lys Thr Thr Pro Pro Val Leu Asp Ser Asp Gly Ser Phe
                290                 295                 300
Phe Leu Tyr Ser Arg Leu Thr Val Asp Lys Ser Arg Trp Gln Glu Gly
305                 310                 315                 320
Asn Val Phe Ser Cys Ser Val Met His Glu Ala Leu His Asn His Tyr
                325                 330                 335
Thr Gln Lys Ser Leu Ser Leu Ser Leu Gly Lys
                340                 345

<210> SEQ ID NO 3
<211> LENGTH: 346
<212> TYPE: PRT
<213> ORGANISM: Artificial Sequence
<220> FEATURE:
<223> OTHER INFORMATION: Synthetic Construct

<400> SEQUENCE: 3

Lys Glu Leu Lys Val Thr Gln Pro Glu Lys Ser Val Ser Val Ala Ala
1               5                   10                  15
Gly Asp Ser Thr Val Leu Asn Cys Thr Leu Thr Ser Leu Leu Pro Val
                20                  25                  30
Gly Pro Ile Lys Trp Tyr Arg Gly Val Gly Gln Ser Arg Leu Leu Ile
                35                  40                  45
Tyr Ser Phe Thr Gly Glu His Phe Pro Arg Val Thr Asn Val Ser Asp
                50                  55                  60
Ala Thr Lys Arg Asn Asn Met Asp Phe Ser Ile Arg Ile Ser Asn Val
65                  70                  75                  80
Thr Pro Glu Asp Ala Gly Thr Tyr Tyr Cys Val Lys Phe Gln Lys Gly
                85                  90                  95
Pro Ser Glu Pro Asp Thr Glu Ile Gln Ser Gly Gly Gly Thr Glu Val
                100                 105                 110
Tyr Val Leu Ala Lys Pro Ser Asp Lys Thr His Thr Cys Pro Pro Cys
                115                 120                 125
Pro Ala Pro Glu Ala Ala Gly Ala Pro Ser Val Phe Leu Phe Pro Pro
                130                 135                 140
Lys Pro Lys Asp Thr Leu Met Ile Ser Arg Thr Pro Glu Val Thr Cys
145                 150                 155                 160
Val Val Val Asp Val Ser His Glu Asp Pro Glu Val Lys Phe Asn Trp
                165                 170                 175
Tyr Val Asp Gly Val Glu Val His Asn Ala Lys Thr Lys Pro Arg Glu
                180                 185                 190
Glu Gln Tyr Ala Ser Thr Tyr Arg Val Val Ser Val Leu Thr Val Leu

```
                195                 200                 205
His Gln Asp Trp Leu Asn Gly Lys Glu Tyr Lys Cys Lys Val Ser Asn
            210                 215                 220
Lys Ala Leu Pro Ala Pro Ile Glu Lys Thr Ile Ser Lys Ala Lys Gly
225                 230                 235                 240
Gln Pro Arg Glu Pro Gln Val Tyr Thr Leu Pro Pro Ser Arg Glu Glu
                245                 250                 255
Met Thr Lys Asn Gln Val Ser Leu Thr Cys Leu Val Lys Gly Phe Tyr
            260                 265                 270
Pro Ser Asp Ile Ala Val Glu Trp Glu Ser Asn Gly Gln Pro Glu Asn
                275                 280                 285
Asn Tyr Lys Thr Thr Pro Pro Val Leu Asp Ser Asp Gly Ser Phe Phe
            290                 295                 300
Leu Tyr Ser Lys Leu Thr Val Asp Lys Ser Arg Trp Gln Gln Gly Asn
305                 310                 315                 320
Val Phe Ser Cys Ser Val Met His Glu Ala Leu His Asn His Tyr Thr
                325                 330                 335
Gln Lys Ser Leu Ser Leu Ser Pro Gly Lys
            340                 345

<210> SEQ ID NO 4
<211> LENGTH: 342
<212> TYPE: PRT
<213> ORGANISM: Artificial Sequence
<220> FEATURE:
<223> OTHER INFORMATION: Synthetic Construct

<400> SEQUENCE: 4

Thr Glu Val Lys Val Ile Gln Pro Glu Lys Ser Val Ser Val Ala Ala
1               5                   10                  15
Gly Asp Ser Thr Val Leu Asn Cys Thr Leu Thr Ser Leu Leu Pro Val
            20                  25                  30
Gly Pro Ile Arg Trp Tyr Arg Gly Val Gly Gln Ser Arg Gln Leu Ile
            35                  40                  45
Tyr Ser Phe Thr Thr Glu His Phe Pro Arg Val Thr Asn Val Ser Asp
        50                  55                  60
Ala Thr Lys Arg Ser Asn Leu Asp Phe Ser Ile Arg Ile Ser Asn Val
65                  70                  75                  80
Thr Pro Glu Asp Ala Gly Thr Tyr Tyr Cys Val Lys Phe Gln Arg Gly
                85                  90                  95
Ser Pro Asp Thr Glu Ile Gln Ser Gly Gly Gly Thr Glu Val Tyr Val
            100                 105                 110
Leu Ala Lys Asp Lys Thr His Thr Cys Pro Pro Cys Pro Ala Pro Glu
            115                 120                 125
Ala Ala Gly Ala Pro Ser Val Phe Leu Phe Pro Pro Lys Pro Lys Asp
        130                 135                 140
Thr Leu Met Ile Ser Arg Thr Pro Glu Val Thr Cys Val Val Val Asp
145                 150                 155                 160
Val Ser His Glu Asp Pro Glu Val Lys Phe Asn Trp Tyr Val Asp Gly
                165                 170                 175
Val Glu Val His Asn Ala Lys Thr Lys Pro Arg Glu Glu Gln Tyr Ala
            180                 185                 190
Ser Thr Tyr Arg Val Val Ser Val Leu Thr Val Leu His Gln Asp Trp
            195                 200                 205
Leu Asn Gly Lys Glu Tyr Lys Cys Lys Val Ser Asn Lys Ala Leu Pro
```

```
                210                 215                 220
Ala Pro Ile Glu Lys Thr Ile Ser Lys Ala Lys Gly Gln Pro Arg Glu
225                 230                 235                 240

Pro Gln Val Tyr Thr Leu Pro Pro Ser Arg Glu Glu Met Thr Lys Asn
                245                 250                 255

Gln Val Ser Leu Thr Cys Leu Val Lys Gly Phe Tyr Pro Ser Asp Ile
            260                 265                 270

Ala Val Glu Trp Glu Ser Asn Gly Gln Pro Glu Asn Asn Tyr Lys Thr
        275                 280                 285

Thr Pro Pro Val Leu Asp Ser Asp Gly Ser Phe Phe Leu Tyr Ser Lys
    290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 5
<211> LENGTH: 119
<212> TYPE: PRT
<213> ORGANISM: Homo sapiens

<400> SEQUENCE: 5

Glu Glu Glu Leu Gln Val Ile Gln Pro Asp Lys Ser Val Leu Val Ala
1               5                   10                  15

Ala Gly Glu Thr Ala Thr Leu Arg Cys Thr Ala Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Gly Asn
65                  70                  75                  80

Ile Thr Pro Ala Asp Ala Gly Thr Tyr Tyr Cys Val Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 6
<211> LENGTH: 118
<212> TYPE: PRT
<213> ORGANISM: Homo sapiens

<400> SEQUENCE: 6

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
    50                  55                  60

Glu Ser Thr Lys Arg Glu Asn Met Asp Phe Ser Ile Ser Ile Ser Asn
```

```
                 65                  70                  75                  80
Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser
            115

<210> SEQ ID NO 7
<211> LENGTH: 119
<212> TYPE: PRT
<213> ORGANISM: Mus musculus

<400> SEQUENCE: 7

Lys Glu Leu Lys Val Thr Gln Pro Glu Lys Ser Val Ser Val Ala Ala
1               5                  10                  15

Gly Asp Ser Thr Val Leu Asn Cys Thr Leu Thr Ser Leu Leu Pro Val
                20                  25                  30

Gly Pro Ile Lys Trp Tyr Arg Gly Val Gly Gln Ser Arg Leu Leu Ile
            35                  40                  45

Tyr Ser Phe Thr Gly Glu His Phe Pro Arg Val Thr Asn Val Ser Asp
        50                  55                  60

Ala Thr Lys Arg Asn Asn Met Asp Phe Ser Ile Arg Ile Ser Asn Val
65                  70                  75                  80

Thr Pro Glu Asp Ala Gly Thr Tyr Tyr Cys Val Lys Phe Gln Lys Gly
                85                  90                  95

Pro Ser Glu Pro Asp Thr Glu Ile Gln Ser Gly Gly Gly Thr Glu Val
                100                 105                 110

Tyr Val Leu Ala Lys Pro Ser
            115

<210> SEQ ID NO 8
<211> LENGTH: 115
<212> TYPE: PRT
<213> ORGANISM: Mus musculus

<400> SEQUENCE: 8

Thr Glu Val Lys Val Ile Gln Pro Glu Lys Ser Val Ser Val Ala Ala
1               5                  10                  15

Gly Asp Ser Thr Val Leu Asn Cys Thr Leu Thr Ser Leu Leu Pro Val
                20                  25                  30

Gly Pro Ile Arg Trp Tyr Arg Gly Val Gly Gln Ser Arg Gln Leu Ile
            35                  40                  45

Tyr Ser Phe Thr Thr Glu His Phe Pro Arg Val Thr Asn Val Ser Asp
        50                  55                  60

Ala Thr Lys Arg Ser Asn Leu Asp Phe Ser Ile Arg Ile Ser Asn Val
65                  70                  75                  80

Thr Pro Glu Asp Ala Gly Thr Tyr Tyr Cys Val Lys Phe Gln Arg Gly
                85                  90                  95

Ser Pro Asp Thr Glu Ile Gln Ser Gly Gly Gly Thr Glu Val Tyr Val
                100                 105                 110

Leu Ala Lys
        115

<210> SEQ ID NO 9
<211> LENGTH: 117
<212> TYPE: PRT
```

<213> ORGANISM: Mus musculus

<400> SEQUENCE: 9

Lys Glu Leu Lys Val Thr Gln Pro Glu Lys Ser Val Ser Val Ala Ala
1               5                   10                  15

Gly Asp Ser Thr Val Leu Asn Cys Thr Leu Thr Ser Leu Leu Pro Val
            20                  25                  30

Gly Pro Ile Arg Trp Tyr Arg Gly Val Gly Pro Ser Arg Leu Leu Ile
        35                  40                  45

Tyr Ser Phe Ala Gly Glu Tyr Val Pro Arg Ile Arg Asn Val Ser Asp
    50                  55                  60

Thr Thr Lys Arg Asn Asn Met Asp Phe Ser Ile Arg Ile Ser Asn Val
65                  70                  75                  80

Thr Pro Ala Asp Ala Gly Ile Tyr Tyr Cys Val Lys Phe Gln Lys Gly
                85                  90                  95

Ser Ser Glu Pro Asp Thr Glu Ile Gln Ser Gly Gly Gly Thr Glu Val
            100                 105                 110

Tyr Val Leu Ala Lys
        115

<210> SEQ ID NO 10
<211> LENGTH: 117
<212> TYPE: PRT
<213> ORGANISM: Mus musculus

<400> SEQUENCE: 10

Thr Glu Val Lys Val Thr Gln Pro Glu Lys Ser Val Ser Val Ala Ala
1               5                   10                  15

Gly Asp Ser Thr Ile Leu Asn Cys Thr Val Thr Ser Leu Leu Pro Val
            20                  25                  30

Gly Pro Ile Arg Trp Tyr Arg Gly Val Gly Gln Ser Arg Leu Leu Ile
        35                  40                  45

Tyr Ser Phe Thr Gly Glu His Phe Pro Arg Ile Arg Asn Val Ser Asp
    50                  55                  60

Thr Thr Lys Arg Asn Asn Met Asp Phe Ser Ile Arg Ile Ser Asn Val
65                  70                  75                  80

Thr Pro Glu Asp Ala Gly Thr Tyr Tyr Cys Val Lys Phe Gln Arg Gly
                85                  90                  95

Ser Ser Glu Pro Asp Thr Glu Ile Gln Ser Gly Gly Gly Thr Glu Val
            100                 105                 110

Tyr Val Leu Ala Lys
        115

<210> SEQ ID NO 11
<211> LENGTH: 118
<212> TYPE: PRT
<213> ORGANISM: Macaca fascicularis

<400> SEQUENCE: 11

Glu Glu Glu Leu Gln Val Ile Gln Pro Glu Lys Ser Val Ser Val Ala
1               5                   10                  15

Ala Gly Glu Ser Ala Thr Leu Asn Cys Thr Ala Thr Ser Leu Ile Pro
            20                  25                  30

Val Gly Pro Ile Gln Trp Phe Arg Gly Val Gly Pro Gly Arg Glu Leu
        35                  40                  45

Ile Tyr His Gln Lys Glu Gly His Phe Pro Arg Val Thr Pro Val Ser
    50                  55                  60

```
Asp Pro Thr Lys Arg Asn Asn Met Asp Phe Ser Ile Arg Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Val Glu Leu Lys Ser Gly Ala Gly Thr Glu Leu Ser
            100                 105                 110

Val Arg Ala Lys Pro Ser
        115

<210> SEQ ID NO 12
<211> LENGTH: 118
<212> TYPE: PRT
<213> ORGANISM: Macaca fascicularis

<400> SEQUENCE: 12

Glu Glu Glu Leu Gln Val Ile Gln Pro Glu Lys Ser Val Ser Val Ala
  1               5                  10                  15

Ala Gly Asp Ser Ala Thr Leu Asn Cys Thr Val Ser Ser Leu Ile Pro
             20                  25                  30

Val Gly Pro Ile Gln Trp Phe Arg Gly Ala Gly Pro Gly Arg Glu Leu
         35                  40                  45

Ile Tyr Asn Leu Lys Glu Gly His Phe Pro Arg Val Thr Ala Val Ser
     50                  55                  60

Asp Pro Thr Lys Arg Asn Asn Met Asp Phe Ser Ile Arg Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Val Glu Leu Lys Ser Gly Ala Gly Thr Glu Leu Ser
            100                 105                 110

Val Arg Ala Lys Pro Ser
        115

<210> SEQ ID NO 13
<211> LENGTH: 119
<212> TYPE: PRT
<213> ORGANISM: Homo sapiens

<400> SEQUENCE: 13

Glu Asp Glu Leu Gln Val Ile Gln Pro Glu Lys Ser Val Ser Val Ala
  1               5                  10                  15

Ala Gly Glu Ser Ala Thr Leu Arg Cys Ala Met Thr Ser Leu Ile Pro
             20                  25                  30

Val Gly Pro Ile Met Trp Phe Arg Gly Ala Gly Ala Gly Arg Glu Leu
         35                  40                  45

Ile Tyr Asn Gln Lys Glu Gly His Phe Pro Arg Val Thr Thr Val Ser
     50                  55                  60

Glu Leu Thr Lys Arg Asn Asn Leu Asp Phe Ser Ile Ser Ile Ser Asn
 65                  70                  75                  80

Ile Thr Pro Ala Asp Ala Gly Thr Tyr Tyr Cys Val Lys Phe Arg Lys
                 85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 14
```

```
<211> LENGTH: 119
<212> TYPE: PRT
<213> ORGANISM: Homo sapiens

<400> SEQUENCE: 14

Glu Glu Glu Leu Gln Val Ile Gln Pro Asp Lys Ser Ile Ser Val Ala
1               5                   10                  15

Ala Gly Glu Ser Ala Thr Leu His Cys Thr Val Thr Ser Leu Ile Pro
            20                  25                  30

Val Gly Pro Ile Gln Trp Phe Arg Gly Ala Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp His Val Glu Phe Lys Ser Gly Ala Gly Thr Glu Leu
            100                 105                 110

Ser Val Arg Ala Lys Pro Ser
        115

<210> SEQ ID NO 15
<211> LENGTH: 119
<212> TYPE: PRT
<213> ORGANISM: Homo sapiens

<400> SEQUENCE: 15

Glu Glu Glu Leu Gln Met Ile Gln Pro Glu Lys Leu Leu Leu Val Thr
1               5                   10                  15

Val Gly Lys Thr Ala Thr Leu His Cys Thr Val Thr Ser Leu Leu Pro
            20                  25                  30

Val Gly Pro Val Leu Trp Phe Arg Gly Val Gly Pro Gly Arg Glu Leu
        35                  40                  45

Ile Tyr Asn Gln Lys Glu Gly His Phe Pro Arg Val Thr Thr Val Ser
    50                  55                  60

Asp Leu Thr Lys Arg Asn Asn Met Asp Phe Ser Ile Arg Ile Ser Ser
65                  70                  75                  80

Ile Thr Pro Ala Asp Val Gly Thr Tyr Tyr Cys Val Lys Phe Arg Lys
                85                  90                  95

Gly Ser Pro Glu Asn Val Glu Phe Lys Ser Gly Pro Gly Thr Glu Met
            100                 105                 110

Ala Leu Gly Ala Lys Pro Ser
        115

<210> SEQ ID NO 16
<211> LENGTH: 117
<212> TYPE: PRT
<213> ORGANISM: Artificial Sequence
<220> FEATURE:
<223> OTHER INFORMATION: Synthetic Construct

<400> SEQUENCE: 16

Gln Leu Leu Phe Asn Lys Thr Lys Ser Val Glu Phe Thr Phe Ser Asn
1               5                   10                  15

Asp Thr Val Val Ile Pro Cys Phe Val Thr Asn Met Glu Ala Gln Asn
            20                  25                  30

Thr Thr Glu Val Tyr Val Lys Trp Lys Phe Lys Gly Arg Asp Ile Tyr
```

```
                35                  40                  45

Thr Phe Asp Gly Ala Leu Asn Lys Ser Thr Val Pro Thr Asp Phe Ser
 50                  55                  60

Ser Ala Lys Ile Glu Val Ser Gln Leu Leu Lys Gly Asp Ala Ser Leu
65                  70                  75                  80

Lys Met Asp Lys Ser Asp Ala Val Ser His Thr Gly Asn Tyr Thr Cys
                85                  90                  95

Glu Val Thr Glu Leu Thr Arg Glu Gly Glu Thr Ile Ile Glu Leu Lys
                100                 105                 110

Tyr Arg Val Val Ser
        115

<210> SEQ ID NO 17
<211> LENGTH: 118
<212> TYPE: PRT
<213> ORGANISM: Artificial Sequence
<220> FEATURE:
<223> OTHER INFORMATION: Synthetic Construct

<400> SEQUENCE: 17

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
                20                  25                  30

Ala Met Ser Trp Val Arg Gln Ala Pro Gly Lys Gly Leu Glu Trp Leu
                35                  40                  45

Ala Gly Ile Ser Ala Gly Gly Ser Asp Thr Tyr Tyr Pro Ala Ser Val
 50                  55                  60

Lys Gly Arg Phe Thr Ile Ser Arg Asp Asn Ser Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
                100                 105                 110

Leu Val Thr Val Ser Ser
        115

<210> SEQ ID NO 18
<211> LENGTH: 107
<212> TYPE: PRT
<213> ORGANISM: Artificial Sequence
<220> FEATURE:
<223> OTHER INFORMATION: Synthetic Construct

<400> SEQUENCE: 18

Ala Leu Thr Gln Pro Ala Ser Val Ser Ala Asn Pro Gly Glu Thr Val
1               5                   10                  15

Glu Ile Thr Cys Ser Gly Gly Ser Tyr Ser Ser Tyr Tyr Tyr Ala Trp
                20                  25                  30

Tyr Gln Gln Lys Ser Pro Gly Ser Ala Pro Val Thr Leu Ile Tyr Ser
                35                  40                  45

Asp Asp Lys Arg Pro Ser Asn Ile Pro Ser Arg Phe Ser Gly Ser Ala
 50                  55                  60

Ser Gly Ser Thr Ala Thr Leu Thr Ile Thr Gly Val Arg Ala Glu Asp
65                  70                  75                  80

Glu Ala Val Tyr Phe Cys Gly Tyr Asp Gln Ser Ser Tyr Thr Asn
                85                  90                  95
```

Pro Phe Gly Ala Gly Thr Thr Leu Thr Val Leu
            100                 105

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Ser Asn Ala Met Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Construct

<400> SEQUENCE: 20

Gly Ile Ser Ala Gly Gly Ser Asp Thr Tyr Tyr Pro Ala Ser Val Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: Synthetic Construct

<400> SEQUENCE: 21

Glu Thr Trp Asn His Leu Phe Asp Tyr
1               5

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Ser Gly Gly Ser Tyr Ser Tyr Tyr Tyr Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic Construct

<400> SEQUENCE: 23

Ser Asp Asp Lys Arg Pro Ser
1               5

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

```
Gly Gly Tyr Asp Gln Ser Ser Tyr Thr Asn Pro
1               5                   10
```

<210> SEQ ID NO 25
<211> LENGTH: 108
<212> TYPE: PRT
<213> ORGANISM: Artificial Sequence
<220> FEATURE:
<223> OTHER INFORMATION: Synthetic Construct

<400> SEQUENCE: 25

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
                20                  25                  30

Ala Trp Tyr Gln Gln Lys Pro Gly Gln Ala Pro Val Thr Leu Ile Tyr
            35                  40                  45

Ser Asp Asp Lys Arg Pro Ser Asn Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu
            100                 105
```

<210> SEQ ID NO 26
<211> LENGTH: 118
<212> TYPE: PRT
<213> ORGANISM: Artificial Sequence
<220> FEATURE:
<223> OTHER INFORMATION: Synthetic Construct

<400> SEQUENCE: 26

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Asn
                20                  25                  30

Ala Met Ser Trp Val Arg Gln Ala Pro Gly Lys Gly Leu Glu Trp Val
            35                  40                  45

Ala Gly Ile Ser Ala Gly Gly Ser Asp Thr Tyr Tyr Pro Ala Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser
        115
```

<210> SEQ ID NO 27
<211> LENGTH: 22
<212> TYPE: PRT
<213> ORGANISM: Artificial Sequence
<220> FEATURE:
<223> OTHER INFORMATION: Synthetic Construct

<400> SEQUENCE: 27

Ser Tyr Glu Leu Thr Gln Pro Pro Ser Val Ser Val Ser Pro Gly Gln
1               5                   10                  15

Thr Ala Arg Ile Thr Cys
            20

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Trp Tyr Gln Gln Lys Pro Gly Gln Ala Pro Val Thr Leu Ile Tyr
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Asn Ile Pro Glu Arg Phe Ser Gly Ser Ser Ser Gly Thr Thr Val Thr
1               5                   10                  15

Leu Thr Ile Ser Gly Val Gln Ala Glu Asp Glu Ala Asp Tyr Tyr Cys
            20                  25                  30

<210> SEQ ID NO 30
<211> LENGTH: 10
<212> TYPE: PRT
<213> ORGANISM: Artificial Sequence
<220> FEATURE:
<223> OTHER INFORMATION: Synthetic Construct

<400> SEQUENCE: 30

Phe Gly Gly Gly Thr Lys Leu Thr Val Leu
1               5                   10

<210> SEQ ID NO 31
<211> LENGTH: 329
<212> TYPE: PRT
<213> ORGANISM: Artificial Sequence
<220> FEATURE:
<223> OTHER INFORMATION: Synthetic Construct

<400> SEQUENCE: 31

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

```
Pro Ala Pro Glu Leu Leu Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 32
<211> LENGTH: 329
<212> TYPE: PRT
<213> ORGANISM: Artificial Sequence
<220> FEATURE:
<223> OTHER INFORMATION: Synthetic Construct

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
            115                 120                 125

Lys Pro Lys Asp Thr Leu Met Ile Ser Arg Thr Pro Glu Val Thr Cys
130                 135                 140
```

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 33
<211> LENGTH: 325
<212> TYPE: PRT
<213> ORGANISM: Artificial Sequence
<220> FEATURE:
<223> OTHER INFORMATION: Synthetic Construct

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 34
<211> LENGTH: 325
<212> TYPE: PRT
<213> ORGANISM: Artificial Sequence
<220> FEATURE:
<223> OTHER INFORMATION: Synthetic Construct

<400> SEQUENCE: 34

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

```
Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 35
<211> LENGTH: 326
<212> TYPE: PRT
<213> ORGANISM: Artificial Sequence
<220> FEATURE:
<223> OTHER INFORMATION: Synthetic Construct

<400> SEQUENCE: 35

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240
```

```
Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 37
<211> LENGTH: 106
<212> TYPE: PRT
<213> ORGANISM: Artificial Sequence
<220> FEATURE:
<223> OTHER INFORMATION: Synthetic Construct

<400> SEQUENCE: 37

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 38
<211> LENGTH: 106
<212> TYPE: PRT
<213> ORGANISM: Artificial Sequence
<220> FEATURE:
<223> OTHER INFORMATION: Synthetic Construct

<400> SEQUENCE: 38

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 39
<211> LENGTH: 108
<212> TYPE: PRT
<213> ORGANISM: Artificial Sequence
<220> FEATURE:
<223> OTHER INFORMATION: Synthetic Construct

<400> SEQUENCE: 39

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Thr Gly Thr Lys Val Thr Val Leu
            100                 105

<210> SEQ ID NO 40
<211> LENGTH: 108
<212> TYPE: PRT
<213> ORGANISM: Artificial Sequence
<220> FEATURE:
<223> OTHER INFORMATION: Synthetic Construct

<400> SEQUENCE: 40

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
         35                  40                  45

Ser Asp Asp Lys Arg Pro Ser Asn Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                 85                  90                  95

Asn Pro Phe Gly Gly Gly Thr Gln Leu Thr Val Leu
            100                 105

<210> SEQ ID NO 41
<211> LENGTH: 108
<212> TYPE: PRT
<213> ORGANISM: Artificial Sequence
<220> FEATURE:
<223> OTHER INFORMATION: Synthetic Construct

<400> SEQUENCE: 41

Ser Tyr Glu Leu Thr Gln Pro Pro Ser Val Ser Val Ser Pro Gly Gln
 1                5                  10                  15

Thr Ala Arg Ile Thr Cys Ser Gly Gly Ser Tyr Ser Ser Tyr Tyr Tyr
             20                  25                  30

Ala Trp Tyr Gln Gln Lys Pro Gly Gln Ala Pro Val Thr Leu Ile Tyr
         35                  40                  45

Ser Asp Asp Lys Arg Pro Ser Asn Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                 85                  90                  95

Asn Pro Phe Gly Gly Gly Thr Arg Leu Thr Val Leu
            100                 105

<210> SEQ ID NO 42
<211> LENGTH: 106
<212> TYPE: PRT
<213> ORGANISM: Artificial Sequence
<220> FEATURE:
<223> OTHER INFORMATION: Synthetic Construct

<400> SEQUENCE: 42

Gly Gln Pro Lys Ala Asn Pro Thr Val Thr Leu Phe Pro Pro Ser Ser
 1                5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Gly Ser Pro
         35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 43

```
<211> LENGTH: 106
<212> TYPE: PRT
<213> ORGANISM: Artificial Sequence
<220> FEATURE:
<223> OTHER INFORMATION: Synthetic Construct

<400> SEQUENCE: 43

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asp
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 44
<211> LENGTH: 106
<212> TYPE: PRT
<213> ORGANISM: Artificial Sequence
<220> FEATURE:
<223> OTHER INFORMATION: Synthetic Construct

<400> SEQUENCE: 44

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asp Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 45
<211> LENGTH: 106
<212> TYPE: PRT
<213> ORGANISM: Artificial Sequence
<220> FEATURE:
<223> OTHER INFORMATION: Synthetic Construct

<400> SEQUENCE: 45

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45
```

Val Lys Ala Gly Val Glu Thr Thr Lys Pro Ser Lys Gln Ser Asp Ser
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 46
<211> LENGTH: 106
<212> TYPE: PRT
<213> ORGANISM: Artificial Sequence
<220> FEATURE:
<223> OTHER INFORMATION: Synthetic Construct

<400> SEQUENCE: 46

Gly Gln Pro Lys Ala Asn Pro Thr Val Thr Leu Phe Pro Pro Ser Ser
  1               5                  10                  15

Glu Glu Leu Gln Ala Asn Lys Ala Thr Leu Val Cys Leu Ile Ser Asp
                 20                  25                  30

Phe Tyr Pro Gly Ala Val Thr Val Ala Trp Lys Ala Asp Gly Ser Pro
             35                  40                  45

Val Lys Ala Gly Val Glu Thr Thr Lys Pro Ser Lys Gln Ser Ser Asp
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 47
<211> LENGTH: 214
<212> TYPE: PRT
<213> ORGANISM: Artificial Sequence
<220> FEATURE:
<223> OTHER INFORMATION: Synthetic Construct

<400> SEQUENCE: 47

Ser Tyr Glu Leu Thr Gln Pro Pro Ser Val Ser Val Ser Pro Gly Gln
  1               5                  10                  15

Thr Ala Arg Ile Thr Cys Ser Gly Gly Ser Tyr Ser Tyr Tyr Tyr
                 20                  25                  30

Ala Trp Tyr Gln Gln Lys Pro Gly Gln Ala Pro Val Thr Leu Ile Tyr
             35                  40                  45

Ser Asp Asp Lys Arg Pro Ser Asn Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                 85                  90                  95

Asn Pro Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

```
Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asn Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 48
<211> LENGTH: 214
<212> TYPE: PRT
<213> ORGANISM: Artificial Sequence
<220> FEATURE:
<223> OTHER INFORMATION: Synthetic Construct

<400> SEQUENCE: 48

```
Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asp Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 49
<211> LENGTH: 214
<212> TYPE: PRT
<213> ORGANISM: Artificial Sequence
<220> FEATURE:
<223> OTHER INFORMATION: Synthetic Construct

<400> SEQUENCE: 49

Ser Tyr Glu Leu Thr Gln Pro Pro Ser Val Ser Val Ser Pro Gly Gln

```
1               5                   10                  15
Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
            35                  40                  45

Ser Asp Asp Lys Arg Pro Ser Asn Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asp Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 50
<211> LENGTH: 214
<212> TYPE: PRT
<213> ORGANISM: Artificial Sequence
<220> FEATURE:
<223> OTHER INFORMATION: Synthetic Construct

<400> SEQUENCE: 50

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
            35                  40                  45

Ser Asp Asp Lys Arg Pro Ser Asn Ile Pro Glu Arg Phe Ser Gly Ser
        50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
        130                 135                 140

Ala Val Thr Val Ala Trp Lys Ala Asp Gly Ser Pro Val Lys Ala Gly
```

```
                145                 150                 155                 160
Val Glu Thr Thr Lys Pro Ser Lys Gln Ser Asp Ser Lys Tyr Ala Ala
                    165                 170                 175

Ser Ser Tyr Leu Ser Leu Thr Pro Glu Gln Trp Lys Ser His Arg Ser
                    180                 185                 190

Tyr Ser Cys Gln Val Thr His Glu Gly Ser Thr Val Glu Lys Thr Val
                    195                 200                 205

Ala Pro Thr Glu Cys Ser
            210

<210> SEQ ID NO 51
<211> LENGTH: 214
<212> TYPE: PRT
<213> ORGANISM: Artificial Sequence
<220> FEATURE:
<223> OTHER INFORMATION: Synthetic Construct

<400> SEQUENCE: 51

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Tyr Tyr Tyr
                20                  25                  30

Ala Trp Tyr Gln Gln Lys Pro Gly Gln Ala Pro Val Thr Leu Ile Tyr
                35                  40                  45

Ser Asp Asp Lys Arg Pro Ser Asn Ile Pro Glu Arg Phe Ser Gly Ser
            50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Lys Leu Thr Val Leu Gly Gln Pro Lys
                100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asp Lys Tyr Ala Ala
                    165                 170                 175

Ser Ser Tyr Leu Ser Leu Thr Pro Glu Gln Trp Lys Ser His Arg Ser
                    180                 185                 190

Tyr Ser Cys Gln Val Thr His Glu Gly Ser Thr Val Glu Lys Thr Val
                    195                 200                 205

Ala Pro Thr Glu Cys Ser
            210

<210> SEQ ID NO 52
<211> LENGTH: 214
<212> TYPE: PRT
<213> ORGANISM: Artificial Sequence
<220> FEATURE:
<223> OTHER INFORMATION: Synthetic Construct

<400> SEQUENCE: 52

Ser Tyr Glu Leu Thr Gln Pro Pro Ser Val Ser Val Ser Pro Gly Gln
1               5                   10                  15
```

```
Thr Ala Arg Ile Thr Cys Ser Gly Gly Ser Tyr Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Thr Gly Thr Lys Val Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asp Ser Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 53
<211> LENGTH: 214
<212> TYPE: PRT
<213> ORGANISM: Artificial Sequence
<220> FEATURE:
<223> OTHER INFORMATION: Synthetic Construct

<400> SEQUENCE: 53

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Thr Gly Thr Lys Val Thr Val Leu Gly Gln Pro Lys
            100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160
```

```
Val Glu Thr Thr Lys Pro Ser Lys Gln Ser Asp Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 54
<211> LENGTH: 214
<212> TYPE: PRT
<213> ORGANISM: Artificial Sequence
<220> FEATURE:
<223> OTHER INFORMATION: Synthetic Construct

<400> SEQUENCE: 54

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Gln Leu Thr Val Leu Gly Gln Pro Lys
            100                 105                 110

Ala Asn Pro Thr Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asp Ser Lys Tyr Ala Ala
            165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 55
<211> LENGTH: 214
<212> TYPE: PRT
<213> ORGANISM: Artificial Sequence
<220> FEATURE:
<223> OTHER INFORMATION: Synthetic Construct

<400> SEQUENCE: 55

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30
```

Ala Trp Tyr Gln Gln Lys Pro Gly Gln Ala Pro Val Thr Leu Ile Tyr
            35                  40                  45

Ser Asp Asp Lys Arg Pro Ser Asn Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Gln Leu Thr Val Leu Gly Gln Pro Lys
                100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asn Asp Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
            195                 200                 205

Ala Pro Thr Glu Cys Ser
            210

<210> SEQ ID NO 56
<211> LENGTH: 214
<212> TYPE: PRT
<213> ORGANISM: Artificial Sequence
<220> FEATURE:
<223> OTHER INFORMATION: Synthetic Construct

<400> SEQUENCE: 56

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
                20                  25                  30

Ala Trp Tyr Gln Gln Lys Pro Gly Gln Ala Pro Val Thr Leu Ile Tyr
            35                  40                  45

Ser Asp Asp Lys Arg Pro Ser Asn Ile Pro Glu Arg Phe Ser Gly Ser
 50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                85                  90                  95

Asn Pro Phe Gly Gly Gly Thr Arg Leu Thr Val Leu Gly Gln Pro Lys
                100                 105                 110

Ala Asn Pro Thr Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Asp Ser Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 57
<211> LENGTH: 214
<212> TYPE: PRT
<213> ORGANISM: Artificial Sequence
<220> FEATURE:
<223> OTHER INFORMATION: Synthetic Construct

<400> SEQUENCE: 57

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
    50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
            85                  90                  95

Asn Pro Phe Gly Gly Gly Thr Arg Leu Thr Val Leu Gly Gln Pro Lys
        100                 105                 110

Ala Asn Pro Thr Val Thr Leu Phe Pro Pro Ser Ser Glu Glu Leu Gln
    115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Gly Ser Pro Val Lys Ala Gly
145                 150                 155                 160

Val Glu Thr Thr Lys Pro Ser Lys Gln Ser Ser Asp Lys Tyr Ala Ala
            165                 170                 175

Ser Ser Tyr Leu Ser Leu Thr Pro Glu Gln Trp Lys Ser His Arg Ser
        180                 185                 190

Tyr Ser Cys Gln Val Thr His Glu Gly Ser Thr Val Glu Lys Thr Val
    195                 200                 205

Ala Pro Thr Glu Cys Ser
    210

<210> SEQ ID NO 58
<211> LENGTH: 447
<212> TYPE: PRT
<213> ORGANISM: Artificial Sequence
<220> FEATURE:
<223> OTHER INFORMATION: Synthetic Construct

<400> SEQUENCE: 58

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val

```
                35                  40                  45
Ala Gly Ile Ser Ala Gly Ser Asp Thr Tyr Tyr Pro Ala Ser Val
 50                  55                  60
Lys Gly Arg Phe Thr Ile Ser Arg Asp Asn Ser Lys Asn Thr Leu Tyr
 65                      70                  75                  80
Leu Gln Met Asn Ser Leu Arg Ala Glu Asp Thr Ala Val Tyr Tyr Cys
                 85                  90                  95
Ala Arg Glu Thr Trp Asn His Leu Phe Asp Tyr Trp Gly Gln Gly Thr
             100                 105                 110
Leu Val Thr Val Ser Ser Ala Ser Thr Lys Gly Pro Ser Val Phe Pro
         115                 120                 125
Leu Ala Pro Ser Ser Lys Ser Thr Ser Gly Gly Thr Ala Ala Leu Gly
 130                 135                 140
Cys Leu Val Lys Asp Tyr Phe Pro Glu Pro Val Thr Val Ser Trp Asn
 145                 150                 155                 160
Ser Gly Ala Leu Thr Ser Gly Val His Thr Phe Pro Ala Val Leu Gln
                 165                 170                 175
Ser Ser Gly Leu Tyr Ser Leu Ser Ser Val Val Thr Val Pro Ser Ser
             180                 185                 190
Ser Leu Gly Thr Gln Thr Tyr Ile Cys Asn Val Asn His Lys Pro Ser
         195                 200                 205
Asn Thr Lys Val Asp Lys Lys Val Glu Pro Lys Ser Cys Asp Lys Thr
 210                 215                 220
His Thr Cys Pro Pro Cys Pro Ala Pro Glu Leu Leu Gly Gly Pro Ser
 225                 230                 235                 240
Val Phe Leu Phe Pro Pro Lys Pro Lys Asp Thr Leu Met Ile Ser Arg
                 245                 250                 255
Thr Pro Glu Val Thr Cys Val Val Val Asp Val Ser His Glu Asp Pro
             260                 265                 270
Glu Val Lys Phe Asn Trp Tyr Val Asp Gly Val Glu Val His Asn Ala
         275                 280                 285
Lys Thr Lys Pro Arg Glu Glu Gln Tyr Asn Ser Thr Tyr Arg Val Val
 290                 295                 300
Ser Val Leu Thr Val Leu His Gln Asp Trp Leu Asn Gly Lys Glu Tyr
 305                 310                 315                 320
Lys Cys Lys Val Ser Asn Lys Ala Leu Pro Ala Pro Ile Glu Lys Thr
                 325                 330                 335
Ile Ser Lys Ala Lys Gly Gln Pro Arg Glu Pro Gln Val Tyr Thr Leu
             340                 345                 350
Pro Pro Ser Arg Glu Glu Met Thr Lys Asn Gln Val Ser Leu Thr Cys
         355                 360                 365
Leu Val Lys Gly Phe Tyr Pro Ser Asp Ile Ala Val Glu Trp Glu Ser
 370                 375                 380
Asn Gly Gln Pro Glu Asn Asn Tyr Lys Thr Thr Pro Pro Val Leu Asp
 385                 390                 395                 400
Ser Asp Gly Ser Phe Phe Leu Tyr Ser Lys Leu Thr Val Asp Lys Ser
                 405                 410                 415
Arg Trp Gln Gln Gly Asn Val Phe Ser Cys Ser Val Met His Glu Ala
             420                 425                 430
Leu His Asn His Tyr Thr Gln Lys Ser Leu Ser Leu Ser Pro Gly
         435                 440                 445

<210> SEQ ID NO 59
```

```
<211> LENGTH: 447
<212> TYPE: PRT
<213> ORGANISM: Artificial Sequence
<220> FEATURE:
<223> OTHER INFORMATION: Synthetic Construct

<400> SEQUENCE: 59

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380
```

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
        435                 440                 445

<210> SEQ ID NO 60
<211> LENGTH: 443
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300
```

```
Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
            325                 330                 335

Lys Gly Gln Pro Arg Glu Pro Gln Val Tyr Thr Leu Pro Pro Ser Arg
        340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
            405                 410                 415

Gly Asn Val Phe Ser Cys Ser Val Met His Glu Ala Leu His Asn His
        420                 425                 430

Tyr Thr Gln Lys Ser Leu Ser Leu Ser Pro Gly
        435                 440

<210> SEQ ID NO 61
<211> LENGTH: 443
<212> TYPE: PRT
<213> ORGANISM: Artificial Sequence
<220> FEATURE:
<223> OTHER INFORMATION: Synthetic Construct

<400> SEQUENCE: 61

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Glu Thr Trp Asn His Leu Phe Asp Tyr Trp Gly Gln Gly Thr
        100                 105                 110

Leu Val Thr Val Ser Ser Ala Ser Thr Lys Gly Pro Ser Val Phe Pro
    115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Asn Phe Gly Thr Gln Thr Tyr Thr Cys Asn Val Asp His Lys Pro Ser
    195                 200                 205

Asn Thr Lys Val Asp Lys Thr Val Glu Arg Lys Cys Cys Val Glu Cys
    210                 215                 220
```

```
Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
        290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 62
<211> LENGTH: 444
<212> TYPE: PRT
<213> ORGANISM: Artificial Sequence
<220> FEATURE:
<223> OTHER INFORMATION: Synthetic Construct

<400> SEQUENCE: 62

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 63
<211> LENGTH: 214
<212> TYPE: PRT
<213> ORGANISM: Artificial Sequence
<220> FEATURE:
<223> OTHER INFORMATION: Synthetic Construct

<400> SEQUENCE: 63

Ser Tyr Glu Leu Thr Gln Pro Pro Ser Val Ser Val Ser Pro Gly Gln
1               5                   10                  15

Thr Ala Arg Ile Thr Cys Ser Gly Gly Ser Tyr Ser Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
50                  55                  60

Ser Ser Gly Thr Thr Val Thr Leu Thr Ile Ser Gly Val Gln Ala Glu
 65                  70                  75                  80

Asp Glu Ala Asp Tyr Tyr Cys Gly Gly Tyr Asp Gln Ser Ser Tyr Thr
                 85                  90                  95

Asn Pro Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 64
<211> LENGTH: 17
<212> TYPE: PRT
<213> ORGANISM: Artificial Sequence
<220> FEATURE:
<223> OTHER INFORMATION: Synthetic Construct

<400> SEQUENCE: 64

Ala Asp Gly Ser Pro Val Lys Ala Gly Val Glu Thr Thr Lys Pro Ser
1               5                   10                  15

Lys

<210> SEQ ID NO 65
<211> LENGTH: 44
<212> TYPE: PRT
<213> ORGANISM: Artificial Sequence
<220> FEATURE:
<223> OTHER INFORMATION: Synthetic Construct

<400> SEQUENCE: 65

Phe Ser Gly Ser Ser Ser Gly Thr Thr Val Thr Leu Thr Ile Ser Gly
1               5                   10                  15

Val Gln Ala Glu Asp Glu Ala Asp Tyr Tyr Cys Gly Gly Tyr Asp Gln
            20                  25                  30

Ser Ser Tyr Thr Asn Pro Phe Gly Gly Gly Thr Lys
        35                  40

<210> SEQ ID NO 66
<211> LENGTH: 41
<212> TYPE: PRT
<213> ORGANISM: Artificial Sequence
<220> FEATURE:
<223> OTHER INFORMATION: Synthetic Construct

<400> SEQUENCE: 66

Ile Thr Cys Ser Gly Gly Ser Tyr Ser Ser Tyr Tyr Tyr Ala Trp Tyr
1               5                   10                  15

Gln Gln Lys Pro Gly Gln Ala Pro Val Thr Leu Ile Tyr Ser Asp Asp

```
                20                  25                  30

Lys Arg Pro Ser Asn Ile Pro Glu Arg
        35                  40

<210> SEQ ID NO 67
<211> LENGTH: 10
<212> TYPE: PRT
<213> ORGANISM: Artificial Sequence
<220> FEATURE:
<223> OTHER INFORMATION: Synthetic Construct

<400> SEQUENCE: 67

Phe Gly Gly Gly Thr Lys Leu Thr Val Leu
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Synthetic Construct

<400> SEQUENCE: 68

Phe Gly Thr Gly Thr Lys Val Thr Val Leu
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthetic Construct

<400> SEQUENCE: 69

Phe Gly Gly Gly Thr Gln Leu Thr Val Leu
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthetic Construct

<400> SEQUENCE: 70

Phe Gly Gly Gly Thr Arg Leu Thr Val Leu
1               5                   10

<210> SEQ ID NO 71
<211> LENGTH: 108
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 101
<223> OTHER INFORMATION: Xaa = Gly or Thr
<220> FEATURE:
<221> NAME/KEY: VARIANT
<222> LOCATION: 104
<223> OTHER INFORMATION: Xaa = Lys, Gln, or Arg
<220> FEATURE:
<221> NAME/KEY: VARIANT
<222> LOCATION: 105
<223> OTHER INFORMATION: Xaa = Leu or Val

<400> SEQUENCE: 71
```

```
Ser Tyr Glu Leu Thr Gln Pro Pro Ser Val Ser Pro Gly Gln
1               5                   10                  15

Thr Ala Arg Ile Thr Cys Ser Gly Gly Ser Tyr Ser Tyr Tyr Tyr
            20                  25                  30

Ala Trp Tyr Gln Gln Lys Pro Gly Gln Ala Pro Val Thr Leu Ile Tyr
        35                  40                  45

Ser Asp Asp Lys Arg Pro Ser Asn Ile Pro Glu Arg Phe Ser Gly Ser
50                  55                  60

Ser Ser Gly Thr Thr Val Thr Leu Thr Ile Ser Gly Val Gln Ala Glu
65                  70                  75                  80

Asp Glu Ala Asp Tyr Tyr Cys Gly Gly Tyr Asp Gln Ser Ser Tyr Thr
                85                  90                  95

Asn Pro Phe Gly Xaa Gly Thr Xaa Xaa Thr Val Leu
            100                 105
```

<210> SEQ ID NO 72
<211> LENGTH: 106
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 63
<223> OTHER INFORMATION: Xaa = Asn, Asp, or Ser
<220> FEATURE:
<221> NAME/KEY: VARIANT
<222> LOCATION: 64
<223> OTHER INFORMATION: Xaa = Asp, Asn, or Ser

<400> SEQUENCE: 72

```
Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Xaa Xaa
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 73
<211> LENGTH: 118
<212> TYPE: PRT
<213> ORGANISM: Artificial Sequence
<220> FEATURE:
<223> OTHER INFORMATION: Synthetic Construct

<400> SEQUENCE: 73

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45
```

```
Ala Gly Ile Ser Ala Gly Gly Ser Asp Thr Tyr Tyr Pro Ala Ser Val
 50                  55                  60
Lys Gly Arg Phe Thr Ile Ser Arg Asp Asn Ser Lys Asn Thr Leu Tyr
 65                  70                  75                  80
Leu Gln Met Asn Thr Leu Thr Ala Glu Asp Thr Ala Val Tyr Tyr Cys
                 85                  90                  95
Ala Arg Glu Thr Trp Asn His Leu Phe Asp Tyr Trp Gly Leu Gly Thr
                100                 105                 110
Leu Val Thr Val Ser Ser
            115

<210> SEQ ID NO 74
<211> LENGTH: 107
<212> TYPE: PRT
<213> ORGANISM: Artificial Sequence
<220> FEATURE:
<223> OTHER INFORMATION: Synthetic Construct

<400> SEQUENCE: 74

Ala Leu Thr Gln Pro Ala Ser Val Ser Ala Asn Pro Gly Glu Thr Val
 1               5                  10                  15
Lys Ile Ala Cys Ser Gly Gly Asp Tyr Tyr Ser Tyr Tyr Tyr Gly Trp
                 20                  25                  30
Tyr Gln Gln Lys Ala Pro Gly Ser Ala Leu Val Thr Val Ile Tyr Ser
                 35                  40                  45
Asp Asp Lys Arg Pro Ser Asp Ile Pro Ser Arg Phe Ser Gly Ser Ala
 50                  55                  60
Ser Gly Ser Thr Ala Thr Leu Thr Ile Thr Gly Val Arg Ala Glu Asp
 65                  70                  75                  80
Glu Ala Val Tyr Tyr Cys Gly Gly Tyr Asp Tyr Ser Thr Tyr Ala Asn
                 85                  90                  95
Ala Phe Gly Ala Gly Thr Thr Leu Thr Val Leu
                100                 105

<210> SEQ ID NO 75
<211> LENGTH: 117
<212> TYPE: PRT
<213> ORGANISM: Artificial Sequence
<220> FEATURE:
<223> OTHER INFORMATION: Synthetic Construct

<400> SEQUENCE: 75

Asp Val Gln Leu Val Glu Ser Gly Gly Val Val Arg Pro Gly Glu
 1               5                  10                  15
Ser Leu Arg Leu Ser Cys Glu Ala Ser Gly Phe Thr Phe Ser Ser Asn
                 20                  25                  30
Ala Met Ser Trp Val Arg Gln Ala Pro Gly Lys Gly Leu Glu Trp Val
                 35                  40                  45
Ala Gly Ile Ser Ser Gly Ser Asp Thr Tyr Tyr Gly Asp Ser Val Lys
 50                  55                  60
Gly Arg Leu Thr Ile Ser Arg Asp Asn Ser Lys Asn Ile Leu Tyr Leu
 65                  70                  75                  80
Gln Met Asn Ser Leu Thr Ala Asp Thr Ala Val Tyr Tyr Cys Ala
                 85                  90                  95
Arg Glu Thr Trp Asn His Leu Phe Asp Tyr Trp Gly Leu Gly Thr Leu
                100                 105                 110
Val Thr Val Ser Ser
            115
```

<210> SEQ ID NO 76
<211> LENGTH: 107
<212> TYPE: PRT
<213> ORGANISM: Artificial Sequence
<220> FEATURE:
<223> OTHER INFORMATION: Synthetic Construct

<400> SEQUENCE: 76

```
Ala Leu Thr Gln Pro Ala Ser Val Ser Ala Asn Pro Gly Glu Thr Val
1               5                   10                  15

Glu Ile Thr Cys Ser Gly Gly Ser Tyr Ser Tyr Tyr Tyr Ala Trp
            20                  25                  30

Tyr Gln Gln Lys Ser Pro Gly Ser Ala Pro Val Thr Leu Ile Tyr Ser
        35                  40                  45

Asp Asp Lys Arg Pro Ser Asn Ile Pro Ser Arg Phe Ser Gly Ser Ala
    50                  55                  60

Ser Gly Ser Thr Ala Thr Leu Thr Ile Thr Gly Val Arg Ala Glu Asp
65                  70                  75                  80

Glu Ala Val Tyr Phe Cys Gly Tyr Asp Gln Ser Ser Tyr Thr Asn
                85                  90                  95

Pro Phe Gly Ala Gly Thr Thr Leu Thr Val Leu
            100                 105
```

<210> SEQ ID NO 77
<211> LENGTH: 118
<212> TYPE: PRT
<213> ORGANISM: Artificial Sequence
<220> FEATURE:
<223> OTHER INFORMATION: Synthetic Construct

<400> SEQUENCE: 77

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115
```

<210> SEQ ID NO 78
<211> LENGTH: 117
<212> TYPE: PRT
<213> ORGANISM: Artificial Sequence
<220> FEATURE:
<223> OTHER INFORMATION: Synthetic Construct

<400> SEQUENCE: 78

```
Asp Val Gln Leu Val Glu Ser Gly Gly Gly Val Val Arg Pro Gly Glu
1               5                   10                  15
```

```
Ser Leu Arg Leu Ser Cys Glu Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Leu Thr Ile Ser Arg Asp Asn Ser Lys Asn Ile Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 79
<211> LENGTH: 117
<212> TYPE: PRT
<213> ORGANISM: Artificial Sequence
<220> FEATURE:
<223> OTHER INFORMATION: Synthetic Construct

<400> SEQUENCE: 79

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 80
<211> LENGTH: 118
<212> TYPE: PRT
<213> ORGANISM: Artificial Sequence
<220> FEATURE:
<223> OTHER INFORMATION: Synthetic Construct

<400> SEQUENCE: 80

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Pro Lys Asn Ser Leu Tyr
65                  70                  75                  80
```

```
Leu Gln Met Ser Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 81
<211> LENGTH: 117
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

<210> SEQ ID NO 82
<211> LENGTH: 117
<212> TYPE: PRT
<213> ORGANISM: Artificial Sequence
<220> FEATURE:
<223> OTHER INFORMATION: Synthetic Construct

<400> SEQUENCE: 82

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Val Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115
```

```
<210> SEQ ID NO 83
<211> LENGTH: 117
<212> TYPE: PRT
<213> ORGANISM: Artificial Sequence
<220> FEATURE:
<223> OTHER INFORMATION: Synthetic Construct

<400> SEQUENCE: 83
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

```
<210> SEQ ID NO 84
<211> LENGTH: 117
<212> TYPE: PRT
<213> ORGANISM: Artificial Sequence
<220> FEATURE:
<223> OTHER INFORMATION: Synthetic Construct

<400> SEQUENCE: 84
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Val Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser
        115

```
<210> SEQ ID NO 85
<211> LENGTH: 118
<212> TYPE: PRT
<213> ORGANISM: Artificial Sequence
<220> FEATURE:
<223> OTHER INFORMATION: Synthetic Construct

<400> SEQUENCE: 85
```

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Val Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser
            115

<210> SEQ ID NO 86
<211> LENGTH: 118
<212> TYPE: PRT
<213> ORGANISM: Artificial Sequence
<220> FEATURE:
<223> OTHER INFORMATION: Synthetic Construct

<400> SEQUENCE: 86

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Leu Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser
            115

<210> SEQ ID NO 87
<211> LENGTH: 117
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Leu Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu

```
                65                  70                  75                  80
Gln Met Asn Ser Leu Thr Ala Glu Asp Thr Ala Val Tyr Tyr Cys Ala
                    85                  90                  95

Arg Glu Thr Trp Asn His Leu Phe Asp Tyr Trp Gly Gln Gly Thr Leu
                100                 105                 110

Val Thr Val Ser Ser
        115

<210> SEQ ID NO 88
<211> LENGTH: 117
<212> TYPE: PRT
<213> ORGANISM: Artificial Sequence
<220> FEATURE:
<223> OTHER INFORMATION: Synthetic Construct

<400> SEQUENCE: 88

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
                20                  25                  30

Ala Leu Ser Trp Val Arg Gln Ala Pro Gly Lys Gly Leu Glu Trp Val
                35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                    85                  90                  95

Arg Glu Thr Trp Asn His Leu Phe Asp Tyr Trp Gly Gln Gly Thr Leu
                100                 105                 110

Val Thr Val Ser Ser
        115

<210> SEQ ID NO 89
<211> LENGTH: 117
<212> TYPE: PRT
<213> ORGANISM: Artificial Sequence
<220> FEATURE:
<223> OTHER INFORMATION: Synthetic Construct

<400> SEQUENCE: 89

Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
                20                  25                  30

Ala Met Ser Trp Val Arg Gln Ala Pro Gly Lys Gly Leu Glu Trp Val
                35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                    85                  90                  95

Arg Glu Thr Trp Asn His Leu Phe Asp Tyr Trp Gly Leu Gly Thr Leu
                100                 105                 110

Val Thr Val Ser Ser
        115
```

-continued

```
<210> SEQ ID NO 90
<211> LENGTH: 118
<212> TYPE: PRT
<213> ORGANISM: Artificial Sequence
<220> FEATURE:
<223> OTHER INFORMATION: Synthetic Construct

<400> SEQUENCE: 90

Asp Val Gln Leu Val Glu Ser Gly Gly Ala Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Glu Asn Ser Leu Tyr
65                  70                  75                  80

Leu Gln Met Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 91
<211> LENGTH: 119
<212> TYPE: PRT
<213> ORGANISM: Artificial Sequence
<220> FEATURE:
<223> OTHER INFORMATION: Synthetic Construct

<400> SEQUENCE: 91

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Arg Gln Phe Gln Glu Gln Ser Leu
65                  70                  75                  80

Ser Pro Asn Glu Pro Ala Leu Thr Ala Glu Asp Thr Ala Val Tyr Tyr
                85                  90                  95

Cys Ala Arg Glu Thr Trp Asn His Leu Phe Asp Tyr Trp Gly Leu Gly
            100                 105                 110

Thr Leu Val Thr Val Ser Ser
        115

<210> SEQ ID NO 92
<211> LENGTH: 118
<212> TYPE: PRT
<213> ORGANISM: Artificial Sequence
<220> FEATURE:
<223> OTHER INFORMATION: Synthetic Construct

<400> SEQUENCE: 92

Asp Val Gln Leu Val Glu Ser Gly Gly Gly Val Val Arg Pro Gly Glu
```

```
            1               5                  10                  15
         Ser Leu Arg Leu Ser Cys Ala Ala Ser Gly Phe Thr Phe Ser Ser His
                     20                  25                  30

Ala Met Ser Trp Val Arg Gln Ala Pro Gly Lys Gly Leu Glu Trp Leu
                     35                  40                  45

Ala Gly Ile Ser Ala Gly Gly Ser Asp Thr Tyr Tyr Ile Asp Ser Val
                     50                  55                  60

Lys Gly Arg Phe Thr Ile Ser Arg Asp Asn Ser Lys Ser Ser Leu Tyr
         65                  70                  75                  80

Leu Arg Met Asn Ser Leu Thr Ala Glu Asp Thr Ala Val Tyr Tyr Cys
                             85                  90                  95

Ala Arg Glu Thr Trp Asn His Leu Phe Asp Tyr Trp Gly Leu Gly Thr
                         100                 105                 110

Leu Val Thr Val Ser Ser
                         115

<210> SEQ ID NO 93
<211> LENGTH: 118
<212> TYPE: PRT
<213> ORGANISM: Artificial Sequence
<220> FEATURE:
<223> OTHER INFORMATION: Synthetic Construct

<400> SEQUENCE: 93

Asp Val Gln Leu Val Glu Ser Gly Gly Gly Val Val Arg Pro Gly Glu
         1               5                  10                  15

Ser Leu Arg Leu Ser Cys Ala Ala Ser Gly Phe Thr Phe Ser Ser Asn
                     20                  25                  30

Ala Met Ser Trp Val Arg Gln Ala Pro Gly Lys Gly Leu Glu Trp Leu
                     35                  40                  45

Ala Gly Ile Ser Ala Gly Gly Ser Asp Thr Tyr Tyr Pro Ala Ser Val
                     50                  55                  60

Lys Gly Arg Phe Thr Ile Ser Arg Asp Asn Pro Lys Asn Thr Leu Tyr
         65                  70                  75                  80

Leu Gln Met Asn Thr Leu Thr Ala Glu Asp Thr Ala Val Tyr Tyr Cys
                             85                  90                  95

Ala Arg Glu Thr Trp Asn His Leu Phe Asp Tyr Trp Gly Leu Gly Thr
                         100                 105                 110

Leu Val Thr Val Ser Ser
                         115

<210> SEQ ID NO 94
<211> LENGTH: 118
<212> TYPE: PRT
<213> ORGANISM: Artificial Sequence
<220> FEATURE:
<223> OTHER INFORMATION: Synthetic Construct

<400> SEQUENCE: 94

Asp Val Gln Leu Val Glu Ser Gly Gly Gly Val Val Arg Pro Gly Glu
         1               5                  10                  15

Ser Leu Arg Leu Ser Cys Ala Ala Ser Gly Phe Thr Phe Ser Thr Tyr
                     20                  25                  30

Ala Met Ser Trp Val Arg Gln Ala Pro Gly Lys Gly Leu Glu Trp Val
                     35                  40                  45

Ser Gly Ile Ser Ala Ser Gly Ser Gly Thr Tyr Tyr Gly Asp Ser Val
                     50                  55                  60
```

```
Lys Gly Arg Phe Thr Met Ser Arg Asp Asn Ser Lys Asn Thr Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
            100                 105                 110

Leu Val Thr Val Ser Ser
            115
```

<210> SEQ ID NO 95
<211> LENGTH: 117
<212> TYPE: PRT
<213> ORGANISM: Artificial Sequence
<220> FEATURE:
<223> OTHER INFORMATION: Synthetic Construct

<400> SEQUENCE: 95

```
Asp Val Gln Leu Val Glu Ser Gly Gly Gly Val Val Arg Pro Gly Glu
  1               5                  10                  15

Ser Leu Arg Leu Ser Cys Ala Ala Ser Gly Phe Ser Phe Ser Ser Asn
                 20                  25                  30

Ala Met Ser Trp Val Arg Gln Ala Pro Gly Lys Gly Leu Glu Trp Val
             35                  40                  45

Ala Gly Ile Ser Ala Ser Gly Asp Thr Tyr Tyr Ser Gly Ser Met Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Thr Ala Glu Asp Thr Ala Val Tyr Tyr Cys Ala
                 85                  90                  95

Arg Glu Thr Trp Asn His Leu Phe Asp Tyr Trp Gly Leu Gly Thr Leu
            100                 105                 110

Val Thr Val Ser Ser
            115
```

<210> SEQ ID NO 96
<211> LENGTH: 117
<212> TYPE: PRT
<213> ORGANISM: Artificial Sequence
<220> FEATURE:
<223> OTHER INFORMATION: Synthetic Construct

<400> SEQUENCE: 96

```
Asp Val Gln Leu Val Glu Ser Gly Gly Gly Val Val Arg Pro Gly Glu
  1               5                  10                  15

Ser Leu Arg Leu Ser Cys Ala Val Ser Gly Phe Arg Phe Ser Ser Tyr
                 20                  25                  30

Ala Met Ser Trp Val Arg Gln Ala Pro Gly Lys Gly Leu Glu Trp Val
             35                  40                  45

Ser Gly Ile Ser Ser Asp Ser Asp Ala Tyr Tyr Val Asp Ser Val Lys
 50                  55                  60

Gly Arg Phe Thr Ile Ser Arg Asp Asn Ser Lys Asn Thr Leu Tyr Leu
 65                  70                  75                  80

Gln Val Asn Ser Leu Thr Ala Glu Asp Thr Ala Val Tyr Tyr Cys Ala
                 85                  90                  95

Arg Glu Thr Trp Asn His Leu Phe Asp Tyr Trp Gly Leu Gly Thr Met
            100                 105                 110

Val Thr Val Ser Ser
            115
```

<210> SEQ ID NO 97
<211> LENGTH: 117
<212> TYPE: PRT
<213> ORGANISM: Artificial Sequence
<220> FEATURE:
<223> OTHER INFORMATION: Synthetic Construct

<400> SEQUENCE: 97

```
Asp Val Gln Leu Val Glu Ser Gly Gly Gly Val Val Arg Pro Gly Glu
1               5                   10                  15

Ser Leu Arg Leu Ser Cys Glu Ala Ser Gly Phe Thr Phe Ser Ser Asp
            20                  25                  30

Ala Met Ser Trp Val Arg Gln Ala Pro Gly Lys Gly Leu Glu Trp Val
        35                  40                  45

Ser Gly Ile Ser Ser Gly Ser Thr Tyr Tyr Gly Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115
```

<210> SEQ ID NO 98
<211> LENGTH: 117
<212> TYPE: PRT
<213> ORGANISM: Artificial Sequence
<220> FEATURE:
<223> OTHER INFORMATION: Synthetic Construct

<400> SEQUENCE: 98

```
Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115
```

<210> SEQ ID NO 99
<211> LENGTH: 118
<212> TYPE: PRT
<213> ORGANISM: Artificial Sequence
<220> FEATURE:
<223> OTHER INFORMATION: Synthetic Construct

<400> SEQUENCE: 99

```
Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Lys Asn Ser Leu Tyr
65                  70                  75                  80

Leu Gln Val Asn Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
            115
```

<210> SEQ ID NO 100
<211> LENGTH: 117
<212> TYPE: PRT
<213> ORGANISM: Artificial Sequence
<220> FEATURE:
<223> OTHER INFORMATION: Synthetic Construct

<400> SEQUENCE: 100

```
Asp Val Gln Leu Val Glu Ser Gly Gly Gly Val Val Arg Pro Gly Glu
1               5                   10                  15

Ser Leu Arg Leu Ser Cys Ala Val Ser Gly Phe Arg Phe Ser Ser His
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Val Asn Ser Leu Thr Ala Glu Asp Thr Ala Ile Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
            115
```

<210> SEQ ID NO 101
<211> LENGTH: 118
<212> TYPE: PRT
<213> ORGANISM: Artificial Sequence
<220> FEATURE:
<223> OTHER INFORMATION: Synthetic Construct

<400> SEQUENCE: 101

```
Asp Val Gln Leu Val Asp Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60
```

```
Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 102
<211> LENGTH: 118
<212> TYPE: PRT
<213> ORGANISM: Artificial Sequence
<220> FEATURE:
<223> OTHER INFORMATION: Synthetic Construct

<400> SEQUENCE: 102

Asp Val Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 103
<211> LENGTH: 118
<212> TYPE: PRT
<213> ORGANISM: Artificial Sequence
<220> FEATURE:
<223> OTHER INFORMATION: Synthetic Construct

<400> SEQUENCE: 103

Asp Leu Gln Leu Val Glu Ser Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
    50                  55                  60

Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
            100                 105                 110

Leu Val Thr Val Ser Ser
```

<210> SEQ ID NO 104
<211> LENGTH: 118
<212> TYPE: PRT
<213> ORGANISM: Artificial Sequence
<220> FEATURE:
<223> OTHER INFORMATION: Synthetic Construct

<400> SEQUENCE: 104

Asp Val Gln Leu Val Glu Ser Gly Gly Gly Val Val Arg Pro Gly Glu
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Leu
        35                  40                  45
Ala Gly Ile Ser Ala Gly Gly Ser Asp Ala Tyr Tyr Ile Asp Ser Val
    50                  55                  60
Lys Gly Arg Phe Thr Ile Ser Arg Asp Asn Ser Lys Asn Ser Leu Tyr
65                  70                  75                  80
Leu Gln Met Asn Ser Leu Thr Ala Glu Asp Thr Ala Val Tyr Tyr Cys
                85                  90                  95
Ala Arg Glu Thr Trp Asn His Leu Phe Asp Tyr Trp Gly Leu Gly Thr
            100                 105                 110
Leu Val Thr Val Ser Ser
        115

<210> SEQ ID NO 105
<211> LENGTH: 118
<212> TYPE: PRT
<213> ORGANISM: Artificial Sequence
<220> FEATURE:
<223> OTHER INFORMATION: Synthetic Construct

<400> SEQUENCE: 105

Asp Val Gln Leu Val Glu Ser Gly Gly Gly Val Val Arg Pro Gly Glu
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Leu
        35                  40                  45
Ala Gly Ile Ser Ala Gly Gly Ser Asp Thr Tyr Tyr Ile Asp Ser Val
    50                  55                  60
Lys Gly Arg Phe Thr Ile Ser Arg Asp Asn Ser Lys Asn Ser Leu Tyr
65                  70                  75                  80
Leu Gln Met Asn Ser Leu Thr Ala Glu Asp Thr Ala Val Tyr Tyr Cys
                85                  90                  95
Ala Arg Glu Thr Trp Asn His Leu Phe Asp Tyr Trp Gly Leu Gly Thr
            100                 105                 110
Leu Val Thr Val Ser Ser
        115

<210> SEQ ID NO 106
<211> LENGTH: 117
<212> TYPE: PRT
<213> ORGANISM: Artificial Sequence
<220> FEATURE:
<223> OTHER INFORMATION: Synthetic Construct

<400> SEQUENCE: 106

```
Asp Val Gln Leu Val Glu Ser Gly Gly Gly Val Val Arg Pro Gly Glu
1               5                   10                  15

Ser Leu Arg Leu Ser Cys Glu Ala Ser Gly Phe Thr Phe Ser Ser Asn
            20                  25                  30

Ala Met Ser Trp Ala Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Leu Thr Ile Ser Arg Asp Asn Ser Lys Asn Ile Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Leu Gly Thr Leu
            100                 105                 110

Val Thr Val Ser Ser
        115

<210> SEQ ID NO 107
<211> LENGTH: 118
<212> TYPE: PRT
<213> ORGANISM: Artificial Sequence
<220> FEATURE:
<223> OTHER INFORMATION: Synthetic Construct

<400> SEQUENCE: 107

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Leu
        35                  40                  45

Ala Gly Ile Ser Ala Gly Asp Ser Asp Thr Tyr Tyr Pro Ala Ser Val
    50                  55                  60

Lys Gly Arg Phe Thr Ile Ser Arg Asp Asn Pro Lys Asn Thr Leu Tyr
65                  70                  75                  80

Leu Gln Met Asn Thr Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Val Ser Ser
        115

<210> SEQ ID NO 108
<211> LENGTH: 118
<212> TYPE: PRT
<213> ORGANISM: Artificial Sequence
<220> FEATURE:
<223> OTHER INFORMATION: Synthetic Construct

<400> SEQUENCE: 108

Asp Val Gln Leu Val Glu Ser Gly Gly Gly Val Val Arg Pro Gly Glu
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Leu
        35                  40                  45

Ala Gly Ile Ser Ala Gly Gly Ser Asp Thr Tyr Tyr Ile Asp Ser Val
```

```
                50                  55                  60
Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
                100                 105                 110

Leu Val Thr Val Ser Ser
            115

<210> SEQ ID NO 109
<211> LENGTH: 118
<212> TYPE: PRT
<213> ORGANISM: Artificial Sequence
<220> FEATURE:
<223> OTHER INFORMATION: Synthetic Construct

<400> SEQUENCE: 109

Asp Val Gln Leu Val Glu Ser Gly Gly Ala Val Val Arg Pro Gly Glu
 1               5                  10                  15

Thr Leu Arg Leu Ser Cys Thr Ala Ser Gly Phe Thr Phe Ser Ser Tyr
                 20                  25                  30

Ala Met Ser Trp Val Arg Gln Ala Pro Gly Lys Gly Leu Glu Trp Val
             35                  40                  45

Ser Gly Ile Ser Ala Ser Gly Ser Asp Thr Tyr Tyr Ala Asp Ser Val
         50                  55                  60

Lys Gly Arg Ser Thr Ile Ser Arg Asp Asn Ser Lys Asn Thr Leu Tyr
 65                  70                  75                  80

Leu Arg Met Ser Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
                100                 105                 110

Leu Val Thr Val Ser Ser
            115

<210> SEQ ID NO 110
<211> LENGTH: 118
<212> TYPE: PRT
<213> ORGANISM: Artificial Sequence
<220> FEATURE:
<223> OTHER INFORMATION: Synthetic Construct

<400> SEQUENCE: 110

Asp Val Gln Leu Val Glu Ser Gly Gly Gly Val Val Arg Pro Gly Glu
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Leu
             35                  40                  45

Ala Gly Ile Ser Ala Gly Gly Ser Asp Thr Tyr Tyr Ile Asp Ser Val
         50                  55                  60

Lys Gly Arg Phe Thr Ile Ser Arg Asp Asn Ser Lys Asn Ser Leu Tyr
 65                  70                  75                  80

Leu Gln Met Asn Ser Leu Thr Ala Glu Asp Thr Ala Val Tyr Tyr Cys
                 85                  90                  95

Ala Arg Glu Thr Trp Asn His Leu Phe Asp Tyr Trp Gly Leu Gly Thr
                100                 105                 110
```

Leu Val Thr Val Ser Ser
        115

<210> SEQ ID NO 111
<211> LENGTH: 118
<212> TYPE: PRT
<213> ORGANISM: Artificial Sequence
<220> FEATURE:
<223> OTHER INFORMATION: Synthetic Construct

<400> SEQUENCE: 111

Asp Val Gln Leu Val Glu Ser Gly Gly Ala Val Val Arg Pro Gly Glu
1               5                   10                  15

Thr Leu Arg Leu Ser Cys Thr Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ala Ser Gly Ser Asp Thr Tyr Tyr Ala Asp Ser Val
    50                  55                  60

Lys Gly Arg Ser Thr Ile Ser Arg Asp Asn Ser Lys Asn Thr Leu Tyr
65                  70                  75                  80

Leu Arg Met Ser Ser Leu Thr Ala Glu Asp Thr Ala Val Tyr Tyr Cys
                85                  90                  95

Ala Arg Glu Thr Trp Asn His Leu Phe Asp Tyr Trp Gly Leu Gly Thr
            100                 105                 110

Leu Val Thr Leu Ser Ser
        115

<210> SEQ ID NO 112

<400> SEQUENCE: 112

000

<210> SEQ ID NO 113

<400> SEQUENCE: 113

000

<210> SEQ ID NO 114
<211> LENGTH: 446
<212> TYPE: PRT
<213> ORGANISM: Artificial Sequence
<220> FEATURE:
<223> OTHER INFORMATION: Synthetic Construct

<400> SEQUENCE: 114

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
    195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
    435                 440                 445

<210> SEQ ID NO 115
<211> LENGTH: 446
<212> TYPE: PRT
<213> ORGANISM: Artificial Sequence
<220> FEATURE:
<223> OTHER INFORMATION: Synthetic Construct

<400> SEQUENCE: 115

Glu Val Gln Leu Val Glu Ser Gly Gly Gly Val Val Gln Pro Gly Gly
1               5                   10                  15

```
Ser Leu Arg Leu Ser Cys Ala Ala Ser Gly Phe Thr Phe Ser Ser Asn
         20                  25                  30

Ala Met Ser Trp Val Arg Gln Ala Pro Gly Lys Gly Leu Glu Trp Val
     35                  40                  45

Ala Gly Ile Ser Ser Gly Ser Asp Thr Tyr Tyr Gly Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Thr Ala Glu Asp Thr Ala Val Tyr Tyr Cys Ala
                 85                  90                  95

Arg Glu Thr Trp Asn His Leu Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
```

435                 440                 445

<210> SEQ ID NO 116
<211> LENGTH: 442
<212> TYPE: PRT
<213> ORGANISM: Artificial Sequence
<220> FEATURE:
<223> OTHER INFORMATION: Synthetic Construct

<400> SEQUENCE: 116

Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe

```
                 355                 360                 365
Tyr Pro Ser Asp Ile Ala Val Glu Trp Glu Ser Asn Gly Gln Pro Glu
            370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
                420                 425                 430

Thr Gln Lys Ser Leu Ser Leu Ser Pro Gly
            435                 440

<210> SEQ ID NO 117
<211> LENGTH: 442
<212> TYPE: PRT
<213> ORGANISM: Artificial Sequence
<220> FEATURE:
<223> OTHER INFORMATION: Synthetic Construct

<400> SEQUENCE: 117

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ser Gly Ser Asp Thr Tyr Tyr Gly Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Thr Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
```

```
                275                 280                 285
Glu Glu Gln Phe Asn Ser Thr Phe Arg Val Val Ser Val Leu Thr Val
        290                 295                 300
Val His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Thr Lys
                325                 330                 335
Gly Gln Pro Arg Glu Pro Gln Val Tyr Thr Leu Pro Pro Ser Arg Glu
        340                 345                 350
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly
            435                 440

<210> SEQ ID NO 118
<211> LENGTH: 443
<212> TYPE: PRT
<213> ORGANISM: Artificial Sequence
<220> FEATURE:
<223> OTHER INFORMATION: Synthetic Construct

<400> SEQUENCE: 118

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Thr Phe Ser Ser Asn
            20                  25                  30
Ala Met Ser Trp Val Arg Gln Ala Pro Gly Lys Gly Leu Glu Trp Val
        35                  40                  45
Ala Gly Ile Ser Ser Gly Ser Asp Thr Tyr Tyr Gly Asp Ser Val Lys
    50                  55                  60
Gly Arg Phe Thr Ile Ser Arg Asp Asn Ser Lys Asn Thr Leu Tyr Leu
65                  70                  75                  80
Gln Met Asn Ser Leu Thr Ala Glu Asp Thr Ala Val Tyr Tyr Cys Ala
                85                  90                  95
Arg Glu Thr Trp Asn His Leu Phe Asp Tyr Trp Gly Gln Gly Thr Leu
            100                 105                 110
Val Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Lys Thr Tyr Thr Cys Asn Val Asp His Lys Pro Ser Asn
```

```
                 195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 119
<211> LENGTH: 446
<212> TYPE: PRT
<213> ORGANISM: Artificial Sequence
<220> FEATURE:
<223> OTHER INFORMATION: Synthetic Construct

<400> SEQUENCE: 119

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
```

```
            115                 120                 125
Ala Pro Ser Ser Lys Ser Thr Ser Gly Gly Thr Ala Ala Leu Gly Cys
        130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
210                 215                 220
Thr Cys Pro Pro Cys Pro Ala Pro Glu Leu Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

<210> SEQ ID NO 120
<211> LENGTH: 446
<212> TYPE: PRT
<213> ORGANISM: Artificial Sequence
<220> FEATURE:
<223> OTHER INFORMATION: Synthetic Construct

<400> SEQUENCE: 120

Glu Val Gln Leu Val Glu Ser Gly Gly Gly Val Val Gln Pro Gly Gly
1               5                   10                  15
Ser Leu Arg Leu Ser Cys Ala Ala Ser Gly Phe Arg Phe Ser Ser Tyr
            20                  25                  30
Ala Met Ser Trp Val Arg Gln Ala Pro Gly Lys Gly Leu Glu Trp Val
```

```
             35                  40                  45
Ser Gly Ile Ser Ser Gly Gly Asp Thr Tyr Tyr Val Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Glu Thr Trp Asn His Leu Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Ala Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 121
```

<211> LENGTH: 442
<212> TYPE: PRT
<213> ORGANISM: Artificial Sequence
<220> FEATURE:
<223> OTHER INFORMATION: Synthetic Construct

<400> SEQUENCE: 121

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

```
Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
            420                 425                 430

Thr Gln Lys Ser Leu Ser Leu Ser Pro Gly
            435                 440

<210> SEQ ID NO 122
<211> LENGTH: 442
<212> TYPE: PRT
<213> ORGANISM: Artificial Sequence
<220> FEATURE:
<223> OTHER INFORMATION: Synthetic Construct

<400> SEQUENCE: 122

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
            35                  40                  45

Ser Gly Ile Ser Ser Gly Gly Asp Thr Tyr Tyr Val Asp Ser Val Lys
        50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
            85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300
```

Val His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Thr Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly
        435                 440

<210> SEQ ID NO 123
<211> LENGTH: 443
<212> TYPE: PRT
<213> ORGANISM: Artificial Sequence
<220> FEATURE:
<223> OTHER INFORMATION: Synthetic Construct

<400> SEQUENCE: 123

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Arg Phe Ser Ser Tyr
            20                  25                  30

Ala Met Ser Trp Val Arg Gln Ala Pro Gly Lys Gly Leu Glu Trp Val
        35                  40                  45

Ser Gly Ile Ser Ser Gly Gly Asp Thr Tyr Tyr Val Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Thr Trp Asn His Leu Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
            245                 250                 255

Thr Cys Val Val Val Asp Val Ser Gln Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Tyr Arg Val Val Ser Val Leu Thr
        290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly
        435                 440

<210> SEQ ID NO 124
<211> LENGTH: 447
<212> TYPE: PRT
<213> ORGANISM: Artificial Sequence
<220> FEATURE:
<223> OTHER INFORMATION: Synthetic Construct

<400> SEQUENCE: 124

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Ala Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
        260                 265                 270

Glu Val Lys Phe Asn Trp Tyr Val Asp Gly Val Glu Val His Asn Ala
    275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
        340                 345                 350

Pro Pro Ser Arg Glu Glu Met Thr Lys Asn Gln Val Ser Leu Thr Cys
    355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly
    435                 440                 445

<210> SEQ ID NO 125
<211> LENGTH: 443
<212> TYPE: PRT
<213> ORGANISM: Artificial Sequence
<220> FEATURE:
<223> OTHER INFORMATION: Synthetic Construct

<400> SEQUENCE: 125

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Ser Cys Val Glu Cys
210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 126
<211> LENGTH: 443
<212> TYPE: PRT
<213> ORGANISM: Artificial Sequence
<220> FEATURE:
```

-continued

<223> OTHER INFORMATION: Synthetic Construct

<400> SEQUENCE: 126

```
Glu Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Ser Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400
```

```
Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440
```

<210> SEQ ID NO 127
<211> LENGTH: 443
<212> TYPE: PRT
<213> ORGANISM: Artificial Sequence
<220> FEATURE:
<223> OTHER INFORMATION: Synthetic Construct

<400> SEQUENCE: 127

```
Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Ser Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320
```

```
Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 128
<211> LENGTH: 443
<212> TYPE: PRT
<213> ORGANISM: Artificial Sequence
<220> FEATURE:
<223> OTHER INFORMATION: Synthetic Construct

<400> SEQUENCE: 128

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Ser Val Glu Cys
    210                 215                 220

Pro Pro Cys Pro Ala Pro Pro Val Ala Gly Pro Ser Val Phe Leu Phe
225                 230                 235                 240
```

Pro Pro Lys Pro Lys Asp Thr Leu Met Ile Ser Arg Thr Pro Glu Val
                245                 250                 255

Thr Cys Val Val Val Asp Val Ser His Glu Asp Pro Val Gln Phe
        260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
        290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
            435                 440

<210> SEQ ID NO 129
<211> LENGTH: 443
<212> TYPE: PRT
<213> ORGANISM: Artificial Sequence
<220> FEATURE:
<223> OTHER INFORMATION: Synthetic Construct

<400> SEQUENCE: 129

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Val Val Thr Val Pro Ser Ser
        180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Cys Val Glu Cys
    210                 215                 220

Pro Pro Cys Pro Ala Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Ala Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 130
<211> LENGTH: 443
<212> TYPE: PRT
<213> ORGANISM: Artificial Sequence
<220> FEATURE:
<223> OTHER INFORMATION: Synthetic Construct

<400> SEQUENCE: 130

Glu Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                 85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Ser Cys Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Ala Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
            420                 425                 430

Tyr Thr Gln Lys Ser Leu Ser Leu Ser Pro Gly
        435                 440

<210> SEQ ID NO 131
<211> LENGTH: 443
<212> TYPE: PRT
<213> ORGANISM: Artificial Sequence
<220> FEATURE:
<223> OTHER INFORMATION: Synthetic Construct

<400> SEQUENCE: 131

-continued

```
Glu Val Gln Leu Val Glu Ser Gly Gly Gly Val Gln Pro Gly Gly
1               5                   10                  15

Ser Leu Arg Leu Ser Cys Ala Ala Ser Gly Phe Thr Phe Ser Ser Asn
            20                  25                  30

Ala Met Ser Trp Val Arg Gln Ala Pro Gly Lys Gly Leu Glu Trp Val
        35                  40                  45

Ala Gly Ile Ser Ala Gly Gly Ser Asp Thr Tyr Tyr Pro Ala Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Thr Trp Asn His Leu Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Arg Lys Cys Ser Val Glu Cys
    210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Ala Ser Thr Phe Arg Val Val Ser Val Leu Thr
    290                 295                 300

Val Val His Gln Asp Trp Leu Asn Gly Lys Glu Tyr Lys Cys Lys Val
305                 310                 315                 320

Ser Asn Lys Gly Leu Pro Ala Pro Ile Glu Lys Thr Ile Ser Lys Thr
                325                 330                 335

Lys Gly Gln Pro Arg Glu Pro Gln Val Tyr Thr Leu Pro Pro Ser Arg
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
```

```
                420                 425                 430
Tyr Thr Gln Lys Ser Leu Ser Leu Ser Pro Gly
            435                 440

<210> SEQ ID NO 132
<211> LENGTH: 329
<212> TYPE: PRT
<213> ORGANISM: Artificial Sequence
<220> FEATURE:
<223> OTHER INFORMATION: Synthetic Construct

<400> SEQUENCE: 132

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 133
<211> LENGTH: 325
<212> TYPE: PRT
<213> ORGANISM: Artificial Sequence
<220> FEATURE:
<223> OTHER INFORMATION: Synthetic Construct

<400> SEQUENCE: 133

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 134
<211> LENGTH: 325
<212> TYPE: PRT
<213> ORGANISM: Artificial Sequence
<220> FEATURE:
<223> OTHER INFORMATION: Synthetic Construct
```

<400> SEQUENCE: 134

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325
```

<210> SEQ ID NO 135
<211> LENGTH: 325
<212> TYPE: PRT
<213> ORGANISM: Artificial Sequence
<220> FEATURE:
<223> OTHER INFORMATION: Synthetic Construct

<400> SEQUENCE: 135

```
Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 136
<211> LENGTH: 325
<212> TYPE: PRT
<213> ORGANISM: Artificial Sequence
<220> FEATURE:
<223> OTHER INFORMATION: Synthetic Construct

<400> SEQUENCE: 136

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Ser Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 137
<211> LENGTH: 325
<212> TYPE: PRT
<213> ORGANISM: Artificial Sequence
<220> FEATURE:
<223> OTHER INFORMATION: Synthetic Construct

<400> SEQUENCE: 137

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80
```

Tyr Thr Cys Asn Val Asp His Lys Pro Ser Asn Thr Lys Val Asp Lys
            85                  90                  95

Thr Val Glu Arg Lys Cys Cys Val Glu Cys Pro Pro Cys Pro Ala Pro
        100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 138
<211> LENGTH: 325
<212> TYPE: PRT
<213> ORGANISM: Artificial Sequence
<220> FEATURE:
<223> OTHER INFORMATION: Synthetic Construct

<400> SEQUENCE: 138

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
        100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 139
<211> LENGTH: 325
<212> TYPE: PRT
<213> ORGANISM: Artificial Sequence
<220> FEATURE:
<223> OTHER INFORMATION: Synthetic Construct

<400> SEQUENCE: 139

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Ala
            165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly
            325

<210> SEQ ID NO 140
<211> LENGTH: 214
<212> TYPE: PRT
<213> ORGANISM: Artificial Sequence
<220> FEATURE:
<223> OTHER INFORMATION: Synthetic Construct

<400> SEQUENCE: 140

Ala Leu Thr Gln Pro Ala Ser Val Ser Ala Asn Pro Gly Glu Thr Val
1               5                   10                  15

Glu Ile Thr Cys Ser Gly Gly Ser Tyr Ser Ser Tyr Tyr Tyr Ala Trp
            20                  25                  30

Tyr Gln Gln Lys Ser Pro Gly Ser Ala Pro Val Thr Leu Ile Tyr Ser
        35                  40                  45

Asp Asp Lys Arg Pro Ser Asn Ile Pro Ser Arg Phe Ser Gly Ser Ala
    50                  55                  60

Ser Gly Ser Thr Ala Thr Leu Thr Ile Thr Gly Val Arg Ala Glu Asp
65                  70                  75                  80

Glu Ala Val Tyr Phe Cys Gly Tyr Asp Gln Ser Ser Tyr Thr Asn
            85                  90                  95

Pro Phe Gly Ala Gly Thr Thr Leu Thr Val Leu Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

```
                    -continued
Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```